United States Patent
Lorenz et al.

[11] Patent Number: 5,925,596
[45] Date of Patent: Jul. 20, 1999

[54] SUBSTITUTED AMINOMETHYLPHENYLSULFONYLUREAS THEIR PREPARATION AND THEIR USE AS HERBICIDES AND PLANT GROWTH REGULATORS

[75] Inventors: Klaus Lorenz, Weiterstadt; Lothar Willms, Hofheim; Klaus Bauer, Hanua; Hermann Bieringer, Eppstein; Christopher Rosinger, Hofheim, all of Germany

[73] Assignee: Hoechst-Schering AgrEvo GmbH, Berlin, Germany

[21] Appl. No.: 08/842,490

[22] Filed: Apr. 24, 1997

[30] Foreign Application Priority Data

Apr. 25, 1996 [DE] Germany ............ 196 16 445

[51] Int. Cl.$^6$ .......... A01N 43/66; A01N 43/54; A01N 43/40; A01N 43/82; C07D 211/72; C07D 251/100

[52] U.S. Cl. .......... 504/134; 504/136; 504/139; 504/220; 504/228; 504/231; 504/233; 504/227; 504/239; 504/240; 504/241; 504/243; 504/244; 504/259; 504/262; 544/199; 544/205; 544/213; 544/280; 544/278; 544/320; 544/298; 544/220; 544/311; 546/288; 546/289; 548/255

[58] Field of Search .......... 546/288, 289; 548/255; 544/199, 205, 213, 280, 278, 320, 298, 220, 311; 504/134, 136, 139, 220, 228, 231, 233, 227, 239, 240, 241, 243, 244, 259, 262

[56] References Cited

U.S. PATENT DOCUMENTS 4,786,314 11/1988 Artz ............ 71/93
4,927,453 5/1990 Gee ............ 71/92

FOREIGN PATENT DOCUMENTS 0205348 12/1986 European Pat. Off. .
43 35 297 4/1995 Germany .
WO 89/10921 11/1989 WIPO .
WO 95/10507 4/1995 WIPO .

*Primary Examiner*—S. Mark Clardy
*Assistant Examiner*—Alton Pryor
*Attorney, Agent, or Firm*—Frommer Lawrence & Haug LLP

[57] ABSTRACT

Substituted aminomethylphenylsulfonylureas, their preparation, and their use as herbicides and plant growth regulators Compounds of the formula (I) and salts thereof

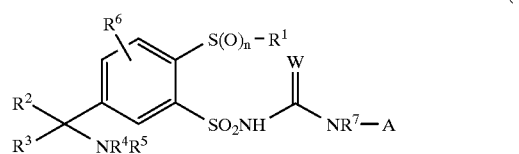

(I)

where $R^1$ to $R^7$ and A are as defined in claim 1 and, inter alia, $R^5$ is an acyl radical or $NR^4R^5$ together are a heterocyclic radical, are useful as herbicides and plant growth regulators. They can be prepared by the methods of known processes, using novel intermediates of the formula (II), (IV), (VI) or (VII) (cf. claim 5).

7 Claims, No Drawings

SUBSTITUTED AMINOMETHYLPHENYLSULFONYLUREAS THEIR PREPARATION AND THEIR USE AS HERBICIDES AND PLANT GROWTH REGULATORS

DESCRIPTION

Substituted aminomethylphenylsulfonylureas, their preparation, and their use as herbicides and plant growth regulators Some phenylsulfonylureas are known to have herbicidal and plant growth regulating properties; cf. U.S. Pat. Nos. 4,786,314, 4,927,453, WO 89/10921 and WO 951/10507 (=ZA 94/8063). However, some of these compounds have practical disadvantages, for example a high persistency or insufficient selectivity in important crop plants or a very limited spectrum of harmful plants which can be controlled.

There have now been found novel phenylsulfonylureas having specific radicals at the phenyl ring which can advantageously be employed as herbicides and plant growth regulators.

The present invention relates to a compound of the formula (I) or a salt thereof

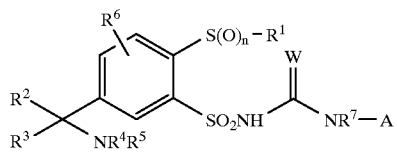

(I)

where $R^1$ is $NR^8R^9$ or an unsubstituted or substituted hydrocarbon radical preferably containing inclusive of substituents 1 to 20 carbon atoms, n is 0, 1 or 2, excluding n=0 or 1 if $R^1=NR^8R^9$, $R^2$ and $R^3$ are each independently of the other H or (1–4)alkyl, $R^4$ is H, OH, formyl, or a radical of the formula R, R—O—, R—CO— or R—$SO_2$—, R being an unsubstituted or substituted hydrocarbon radical preferably having inclusive of substituents 1 to 20 carbon atoms, $R^5$ is an acyl radical or $NR^4R^5$ together are an unsubstituted or substituted heterocyclic radical preferably containing inclusive of substituents 2 to 12 carbon atoms and in particular an electron-withdrawing radical owing to substituents of the heterocycle at the nitrogen atom of the group $NR^4R^5$, W is an oxygen or sulfur atom, $R^6$ is H, (1–4)alkyl, (1–4)alkoxy, (1–4)alkylthio, [(1–4)alkyl]-carbonyl or [(1–4)alkoxy]carbonyl, each of the last radicals being unsubstituted or substituted by one or more halogen atoms, or halogen, $NO_2$, CN or mono- or disubstituted amino, $R^7$ is H or (1–4)alkyl, $R^8$ and $R^9$ are each independently of the other H, (1–4)alkyl,, (1–4)alkoxy, [(1–4)alkyl]carbonyl or (1–4)alkylsulfonyl, A is a radical of the formula

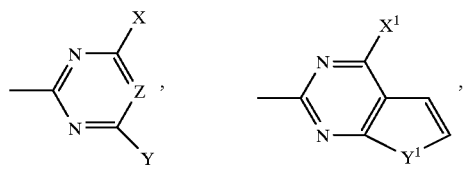

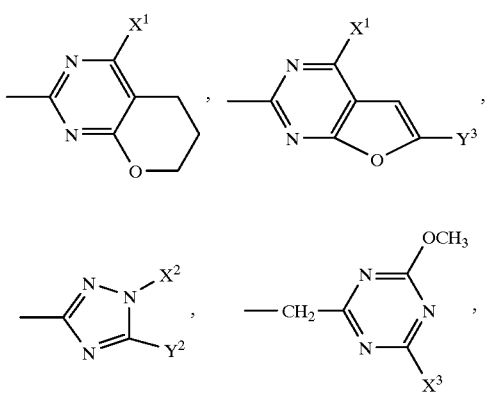

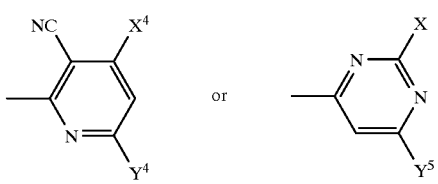

one of the radicals X and Y being hydrogen, (1–3)alkyl or (1–3)alkoxy, the last two radicals being unsubstituted or mono- or polysubstituted by halogen or monosubstituted by (1–3)alkoxy, and the other of the radicals X and Y being hydrogen, halogen, (1–3)alkyl, (1–3)alkoxy or (1–3)alkylthio, the last three alkyl-containing radicals being unsubstituted or mono- or polysubstituted by halogen or mono- or disubstituted by (1–3)alkoxy or (1–3)alkylthio, or a radical of the formula $NR^aR^b$, where $R^a$ and $R^b$, independently of each other, are H, (1–3)alkyl or (1–3)alkenyl, or (3–6)cycloalkyl, (2–4) alkenyl, (2–4)alkynyl, (3–4)-alkenyloxy or (3–4) alkynyloxy, Z isCH or N, $X^1$ is $CH_3$, $OCH_3$, $OC_2H_5$ or $OCHF_2$, $Y^1$ is —O— or —$CH_2$—, $X^2$ is $CH_3$, $C_2H_5$ or $CH_2CF_3$, $Y^2$ is $OCH_3$, $OC_2H_5$, $SCH_2CH_3$, $CH_3$ or $C_2H_5$, $X^3$ is $CH_3$ or $OCH_3$, $Y^3$ is H or $CH_3$, $X^4$ is $CH_3$, $OCH_3$, $OC_2H_5$, $CH_2OCH_3$ or Cl, $Y^4$ is $CH_3$, $OCH_3$, $OC_2H_5$ or Cl and $Y^5$ is $CH_3$, $C_2H_5$, $OCH_3$ or Cl.

The definitions of general radicals having carbon atoms in formula (I) often contain ranges or specific numbers for the number of possible carbon atoms. The range or number of carbon atoms is stated as a prefix in brackets prior to the term of the general chemical group; thus, for example, (1–4)alkyl is an alkyl radical having 1 to 4 carbon atoms; or (1–4) haloalkyl is a haloalkyl having 1 to 4 carbon atoms in the alkyl moiety or alkyl skeleton; (1)alkyl is synonymous to methyl; and the general definition unsubstituted (3) alkyl thus includes n-propyl and i-propyl.

The compounds of the formula (I) can form salts where the hydrogen of the —SO$_2$—NH— group is replaced by an agriculturally useful cation. These salts are, for example, metal salts, in particular alkali metal salts or alkaline earth metal salts, in particular sodium salts and potassium salts, or else ammonium salts or salts with organic amines. Salt formation can also be carried out by addition of an acid to basic groups, such as amino and alkyamino. Suitable acids in this context are strong inorganic and organic acids, for example HCl, HBr, H$_2$SO$_4$ or HNO$_3$.

In formula (I) and all subsequent formulae, the radicals alkyl, alkoxy, haloalkyl, haloalkoxy, alkylamino and alkylthio and the corresponding unsaturated and/or substituted radicals can be in each case straight-chain or branched in the carbon skeleton. Unless specifically indicated, the lower carbon skeletons, for example those having 1 to 6 carbon atoms or, in the case of unsaturated groups, 2 to 6 carbon atoms, are preferred for these radicals. Alkyl radicals, also in the composite meanings such as alkoxy, haloalkyl and the like, are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, i -methylhexyl and 1,4-dimethylpentyl; alkenyl and alkynyl radicals have the meanings of the unsaturated radicals which are possible and which correspond to the alkyl radicals; alkeanyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Cycloalkyl is a carbocyclic saturated ring system having for example 3–8 carbon atoms, for example cycopropyl, cyclopantyl or cyclohexyl.

Alkenyl in the form of "(3–4)alkenyl" or "(3–6)alkenyl" is preferably an alkenyl radical having 3 to 4 or 3 to 6 carbon atoms in which the double bond is not positioned at the carbon atom attached to the remainder of the molecule of the compound (I) ("yl" position). The same applies analogously to (3–4)-alkynyl, etc.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example CF$_3$, CHF$_2$, CH$_2$F, CF$_3$CF$_2$, CH$_2$FCHCl, CCl$_3$, CHCl$_2$, CH$_2$CH$_2$Cl; haloalkoxy is, for example, OCF3, OCHF$_2$, OCH$_2$F, CF$_3$CF$_2$O, OCH$_2$CF$_3$ and OCH$_2$CH$_2$Cl; the same applies analogously to haloalkenyl and other halogen-substituted radicals.

A hydrocarbon radical is a straight-chain, branched or cyclic saturated or unsaturated aliphatic or aromatic hydrocarbon radical, for example alkyl, alkenyl, alkynyl, cycloalkyl, cycloalkenyl or aryl; aryl is, in this context, a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms, or phenyl; the same applies analogously to a hydrocarbon radical in a hydrocarbon-oxy radical.

A heterocyclic radical or ring (heterocyclyl) may be saturated, unsaturated or heteroaromatic; it preferably contains one or more hetero units in the ring, preferably selected from the group consisting of N, O, S, SO, SO$_2$; it is preferably an aliphatic heterocyclyl radical having 3 to 7 ring atoms or a heteroaromatic radical having 5 or 6 ring atoms and contains 1, 2 or 3 hetero units. For example, the heterocyclic radical may be a heteroaromatic radical or ring (heteroaryl), for example a mono-, bi- or polycyclic aromatic system in which at least 1 ring contains one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or it is a partially or fully hydrogenated radical such as oxiranyl, pyrrolidyl, piperidyl, piperazinyl, dioxolanyl, morpholinyl, tetrahydrofuryl. Suitable substituents for a substituted heterocyclic radical are the substituents mentioned further below, and additionally also oxo. The oxo group may also be located on the hetero ring atoms which can exist at various oxidation levels, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl; and unsaturated aliphatic radicals, such as alkenyl, alkynyl, alkenyloxy, alkynyloxy and the like, corresponding to the abovementioned saturated hydrocarbon-containing radicals. Amongst radicals having carbon atoms, those having 1 to 4 carbon atoms, in particular 1 or 2 carbon atoms are preferred. Preferred are, as a rule, substituents selected from the group consisting of halogen, for example fluorine and chlorine, (1–4)alkyl, preferably methyl or ethyl, (1–4)haloalkyl, preferably trifluoromethyl, (1–4)alkoxy, preferably methoxy or ethoxy, (1–4) haloalkoxy, nitro and cyano. Especially preferred in this context are the substituents methyl, methoxy and chlorine.

Mono- or disubstituted amino is a chemically stable radical selected from the group consisting of the substituted amino radicals which are H-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred in this context are alkyl radicals having 1 to 4 carbon atoms; aryl is, in this context, preferably phenyl or substituted phenyl; acyl is as defined further below, preferably (1–4)alkanoyl. The same applies analogously to substituted hydroxylamino or hydrazino.

Optionally substituted phenyl is preferably phenyl which is unsubstituted or mono- or polysubstituted, preferably up to trisubstituted, by identical or different radicals selected from the group consisting of halogen, (1–4)alkyl, (1–4) alkoxy, (1–4)haloalkyl, (1–4)haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid, for example the radical of a carbonylic acid and radicals of acids derived therefrom, such as thiocarboxylic acid, optionally N-substituted iminocarboxylic acids or the radical of carboxylic monoesters, or of optionally N-substituted carbamic acid, of sulfonic acids, sulfinic acids, phosphonic acids and phosphinic acids. Acyl is, for example, formyl, alkylcarbonyl such as [(1–4)alkyl]-carbonyl, phenylcarbonyl, it being possible for the phenyl ring to be substituted as demonstrated above for example for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The invention also relates to all stereoisomers which are embraced by formula (I) and to their mixtures. Such compounds of the formula (I) contain one or more asymmetric carbon atoms or else double bonds which are not separately indicated in formula (I). The sterecisomers which are possible and which are defined by their specific spatial form, such as enantiomers, diastereomers and Z and E isomers, are all embraced by formula (I) and can be obtained from mixtures of the sterecisomers by customary methods, or else prepared by stereoselective reactions in combination with the use of stereochemically pure starting materials.

The abovementioned examples of radicals or ranges of radicals included in general terms such as "alkyl", "acy", "substituted radicals", etc. are not a complete enumeration. The general terms include in particular also the definitions of ranges of radicals in groups of preferred compounds listed further below, in particular ranges of radicals including specific radicals from the examples in the tables.

Compounds of the formula (I) or salts thereof according to the invention which are of particular interest, mainly because of more potent herbicidal activity, better selectivity and/or because they can be prepared more easily, are those in which $R^1$ is $NR^8R^9$, (1–6)alkyl, (2–6)alkenyl, (2–6)alkynyl, (3–6)cycloalkyl, (3–6)cycloalkenyl or phenyl, each of the last 6 radicals being unsubstituted or substituted by one or more radicals from the group consisting of halogen, CN, (1–4)alkoxy, (1–4)haloalkoxy, (1–4)alkoxy(1–4)alkoxy, (1–4)alkylthio, (1–4)alkylsulfinyl, (1–4)-alkylsulfonyl, formyl, [(1–4)alkyl]-carbonyl, [(1–4)alkoxy]carbonyl, [(1–4)alkyl]carbonyloxy and in the case of cyclic radicals also (1–4)alkyl, (1–4)haloalkyl and (1–4)alkoxy-(1–4)alkyl, n is 0, 1 or 2, excluding n=0 or 1 if $R^1=NR^8R^9$, $R^2$ and $R^3$ are each independently of the other H or (1–4)alkyl, $R^4$ is H, OH, formyl, (1–6)alkyl, (2–6)alkenyl, (2–6)alkynyl, (1–6)alkoxy, (2–5)alkenyloxy, (2–5)alkynyloxy, [(1–6)alkyl]-carbonyl, (1–6)alkylsulfonyl, [(2–6)alkenyl]carbonyl, (2–6)alkenylsulfonyl, [(2–6)alkynyl]carbonyl, (2–6)alkynylsulfonyl, (3–6)cycloalkyl, (3–6)cycloalkenyl, [(3–6)cycloalkyl]carbonyl, (3–6)cycloalkylsulfonyl, [(3–6)cycloalkenyl]carbonyl or (3–6)cycloalkenylsulfonyl, each of the last 18 radicals being unsubstituted or substituted by one or more radicals from the group consisting of halogen, (1–4)alkoxy, (1–4)alkylthio, (1–4)alkylsulfinyl, (1–4)alkylsulfonyl, [(1–4)alkoxyl]carbonyl, [(1–4)alkyl]carbonyl, [(1–4)alkylicarbonyloxy and CN and in the case of cyclic radicals also (1–4)alkyl and (1–4)haloalkyl, or phenylcarbonyl or phenylsulfonyl, the phenyl ring in the two last radicals being unsubstituted or substituted by one or more radicals from the group consisting of halogen, CN, $NO_2$, (1–4)alkyl, (1–4)haloalkyl, (1–4)alkoxy and (1–4)haloalkoxy, and $R^5$ is CHO, [(1–6)alkyl]carbonyl, [(2–6)alkenyl]carbonyl, [(2–6)alkynyl]carbonyl, (1–6)alkylsulfonyl, (2–6)alkenylsulfonyl, (2–6)alkynysulfonyl, [(3–6)cycloalkyl]carbonyl, [(3–6)cycloalkenyl]carbonyl, (3–6)cycloalkylsulfonyl or (3–6)cycloalkenylsulfonyl, each of the last 10 radicals being unsubstituted or substituted by one or more radicals from the group consisting of halogen, (1–4)alkoxy, (1–4)alkylthio, (1–4)alkylsulfinyl (1–4)alkylsulfonyl, [(1–4)alkyl]-carbonyl, [(1–4)alkoxy]carbonyl, [(1–4)alkyl]carbonyloxy and CN and in the case of cyclic radicals also (1–4)alkyl and (1–4)haloalkyl, or phenylcarbonyl or phenylsulfonyl, each of the last two radicals being unsubstituted in the phenyl ring or substituted by one or more radicals from the group consisting of halogen, CN, $NO_2$, (1–4)alkyl, (1–4)haloalkyl, (1–4)alkoxy and (1–4)haloalkoxy, or mono- or di-[(1–4)alkyl]aminosulfonyl which is unsubstituted in the alkyl moiety or substituted by one or more radicals from the group consisting of halogen, (1–4)alkoxy, (1–4)alkylthio, (1–4)alkylsulfinyl, [(1–4)alkyl]-carbonyl, [(1–4)alkyl]carbonyloxy, [(1–4)alkoxylcarbonyl and CN or a group of the formula COCOR' where R'=H, OH, (1–4)alkoxy or (1–4)alkyl, or a group of the formula

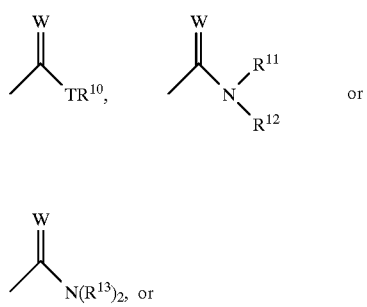

$R^4$ and $R^5$ together are a chain of the formula $(-CH_2)_{m1}B^1-$ or $-B^1-(CH_2)_{m2}B^2$ where individual groups $CH_2$ may be replaced by oxygen atoms and where the chain is unsubstituted or substituted by one or more (1–3)alkyl radicals or halogen and m1=3, 4 or 5 or m2=2, 3 or 4, and W is O or S, $B^1$ and $B^2$ are each independently of the other $SO_2$ or CO, T is O or S, $R^6$ is H, (1–4)alkyl, (1–4)alkoxy, (1–4)alkylthio, [(1–4)alkyl]-carbonyl or [(1–4)alkoxy]carbonyl, each of the last 5 radicals being unsubstituted or substituted in the alkyl moiety by one or more halogen atoms, or halogen, $NO_2$, CN or mono- or di-[(1–4)alkyl]amino, $R^7$ H or (1–4)alkyl, preferably H or $CH_3$, $R^8$ is (1–4)alkyl, (1–4)alkoxy, (3–6)cycloalkyl or (3–6)cycloalkenyl, $R^9$ is H or (1–4)alkyl, $R^{10}$ is (1–4)alkyl, (3–4)alkenyl or (3–4)alkynyl, each of the last three radicals being unsubstituted or substituted by one or more radicals from the group consisting of halogen, (1–4)alkoxy, (1–4)alkylthio, [(1–4)alkyl]carbonyl and [(1–4)alkoxyl]carbonyl, $R^{11}$ and $R^{12}$ are each independently of the other H, (1–4)alkyl, (3–4)alkenyl or (3–4)alkynyl, each of the last three radicals being unsubstituted or substituted by one or more radicals from the group consisting of halogen, (1–4)alkoxy, (1–4)alkylthio, (1–4)alkyl]carbonyl and [(1–4)alkoxy]carbonyl, the radicals $R^{13}$ together with the nitrogen atom are a 5- to 6-membered heterocyclic ring which may contain further hetero atoms from the group consisting of N, O and S in the possible oxidation states and is unsubstituted or substituted by (1–4)alkyl or the oxo group or is benzo-fused.

Further of interest are compounds of the formula (I) and salts thereof according to the invention in which $R^1$ is $NR^8R^9$, (1–4)alkyl, (3–6)cycloalkyl or phenyl, each of the last 3 radicals being unsubstituted or substituted by one or more radicals from the group consisting of halogen, CN, (1–4)alkoxy, (1–4)haloalkoxy, (1–4) alkylthio, (1–4)-alkylsulfonyl, formyl, [(1–4)alkoxy] carbonyl, [(1–4)alkyl]carbonyloxy and In the case of cyclic radicals also (1–4)alkyl, (1–4)haloalkyl and (1–4) alkoxy-(1–4)alkyl, or (2–4)alkenyl or (2–4)alkynyl, n is 0, 1 or 2, excluding n=0 or 1 if $R^1$=$NR^8R^9$, $R^2$ and $R^3$ are each independently of the other H or (1–4) alkyl, $R^4$ H, OH, formyl, (1–4)alkyl, (2–4)alkenyl, (2–4)alkynyl, (1–4)alkoxy, [(1–4)alkyl]carbonyl, (1–4)alkylsulfonyl, each of the last 6 radicals being unsubstituted or substituted by one or more radicals from the group consisting of halogen and (1–4)alkoxy, or phenylcarbonyl or phenylsulfonyl, the phenyl ring of the last two radicals being unsubstituted or substituted by one or more radicals from the group consisting of halogen, (1–4)alkyl, (1–4) haloalkyl, (1–4)alkoxy and (1–4)haloalkoxy, and $R^5$ is CHO, [(1–4)alkyl]carbonyl, [(2–4)alkenyl]carbonyl, [(2–4)alkynyl]carbonyl, (1–4)alkylsulfonyl, (2–4) alkenylsulfonyl, (2–4)alkynylsulfonyl, [(3–6)cycloalkyl] carbonyl, each of the last 7 radicals being unsubstituted or substituted by one or more radicals from the group consisting of halogen, (1–4)alkoxy, (1–4)alkylthio, [(1–4) alkoxy]carbonyl, [(1–4)alkyl]-carbonyloxy and CN and in the case of cyclic radicals also (1–4)alkyl and (1–4) haloalkyl, or phenylcarbonyl or phenylsulfonyl, each of the last two radicals being unsubstituted in the phenyl ring or substituted by one or more radicals from the group consisting of halogen, CN, $NO_2$, (1–4)alkyl, (1–4) haloalkyl, (1–4)alkoxy and (1–4)haloalkoxy, or mono- or di-[(–4)alkyl]aminosulfonyl which is unsubstituted in the alkyl moiety or substituted by one or more halogen atoms, or a group of the formula COCOR' where R'=H, OH, (1–4)alkoxy or (1–4)alkyl, or a group of the formula

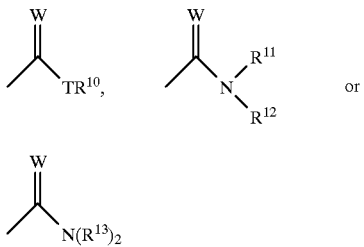

or $R^4$ and $R^5$ together are a chain of the formula (—$CH_2$)$_{m1}$$B^1$— or —$B^1$—($CH_2$)$_{m2}$$B^2$—, where the chain is unsubstituted or substituted by one or more (1–3)alkyl radicals or halogen and m1=3, 4 or 5 or m2=2, 3 or 4, and W is O or S, $B^1$ and $B^2$ are each independently of the other $SO_2$ or CO, T O is or S, $R^6$ is H, (1–4)alkyl, (1–4)alkoxy or halogen, $R^7$ is H or $CH_3$, $R^8$ is (1–4)alkyl, $R^9$ is H or (1–4)alkyl, $R^{10}$ is (1–4)alkyl, (1–4)haloalkyl, (3–4)alkenyl or (3–4) alkynyl, $R^{11}$ and $R^{12}$ are each independently of the other H or (1–4)alkyl or an alkylene chain having 4 or 5 carbon atoms, the radicals $R^{13}$ together are an alkeanylene chain having 4 or 5 carbon atoms, A is a radical of the formula

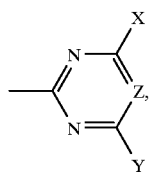

one of the radicals X and Y being halogen, (1–3)alkyl, halo(1–3)alkyl, (1–3)alkoxy or halo(1–3)alkoxy and the other of the radicals X and Y being (1–3)alkyl, halo(1–3) alkyl, (1–3)alkoxy, halo(1–3)alkoxy, halogen, mono- or di-[(1–3)alkyl]amino and Z is CH or N.

Preferred compounds of the formula (I) and salts thereof according to the invention are those in which $R^1$ is mono- or di-[(1–4)alkyl]amino or (1–4)alkyl, preferably $CH_3$, $C_2H_5$, n—$C_3H_7$, i—$C_3H_7$ or N($CH_3$)$_2$, n is 2, $R^2$ and $R^3$ are each hydrogen, $R^4$ is H or (1–4)alkyl, $R^5$ is CHO, [(1–4)alkyl]carbonyl, [(1–4)haloalkyl]carbonyl, (1–4)alkylsulfonyl, (1–4)haloalkylsulfonyl, [(1–4) alkoxy]-carbonyl, mono- or di-[(1–4)alkyl] aminocarbonyl, mono- or di-[(1–4)alkyl]aminosulfonyl or $R^4$ and $R^5$ together are a chain of the formula (—$CH_2$)$_{m1}$ $B^1$— or —$B^1$—($CH_2$)$_{m2}$$B^2$— where $B^1$ and $B^2$ independently of each other are $SO_2$ or CO, W and T are each O, $R^6$ is H and $R^7$ is H or $CH_3$.

The present invention also relates to a process for preparing the compounds of the formula (I) or salts thereof, which comprises a) reacting a compound of the formula (II)

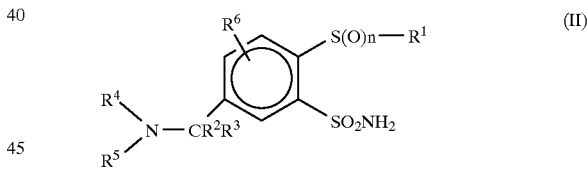

with a heterocyclic carbamate of the formula (III),

where R* is unsubstituted or substituted phenyl or (1–4) alkyl, or b) reacting an arylsulfonylcarbamate of the formula (IV)

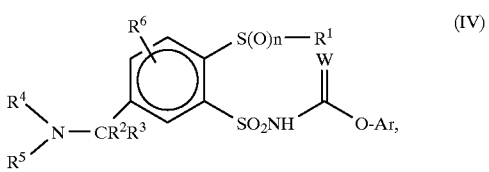

where Ar is an aryl radical, preferably unsubstituted or substituted phenyl, with an amino heterocycle of the formula (V)

H—NR⁷—A         (V)

or
c) reacting a sulfonyl isocyanate of the formula (VI)

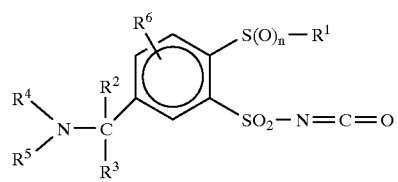

with an amino heterocycle of the formula H—NR⁷—A (V), or
d) reacting in a one-pot reaction first an amino heterocycle of the formula H-NR⁷—A (V) in the presence of a base with phosgene and then the intermediate formed with a phenylsulfonamide of the formula (II), or
e) reacting a sulfonyl chloride of the formula (VII)

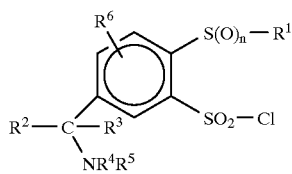

with a cyanate M—OCN where M=a cation, for example NH₄, Na or K, and with an amino heterocycle of the formula H—NR⁷—A (V) in the presence of a base, or
f) reacting a sulfonamide of the formula (II) mentioned with a (thio)isocyanate of the formula (V')

W=C=N—A         (V')

in the presence of a base where the radicals or symbols R¹ to R⁷, A, W and n in the formulae (II)–(VII) and (V') are as defined in formula (I) and where the compounds initially obtained in variants a) and c)–e) are compounds of the formula (I) where W=O.

The reaction of the compounds of the formulae (II) and (III) is preferably carried out under base catalysis in an inert organic solvent, for example dichloromethane, acetonitrile, dioxane or THF, at temperatures between 0° C. and the boiling point of the solvent. Suitable bases in this context are, for example, organic amine bases, such as 1,8-diazabicyclo[5.4.0]undec-7-ene (DBU), in particular if R*= (substituted) phenyl (cf. EP-A44807), or trimethylaluminum or triethylaluminum, the latter in particular if R*=alkyl (cf. EP-A-166516).

The sulfonamides (I) are novel compounds. They and their preparation are also part of the subject matter of this invention.

The preparation of the sulfonamides (II) can as a rule be carried out in the following manner:

Starting from unsubstituted or substituted 4-chloro-3-nitrotoluenes (VIII), the chlorine is, in the cases where R¹ is not NR⁸R⁹, initially substituted by reaction with a mercaptan of the formula R¹—SH. Reduction of the nitro group in (IX) to give the aniline derivative (X) and subsequent diazotization and coupling with SO₂/CuCl (cf. H. Meerwein at al., Chem. Ber. 90, 841–1178 (1957)) and aminolysis with tert-butylamine affords sulfonamide (XI) (see Scheme 1).

Scheme 1:

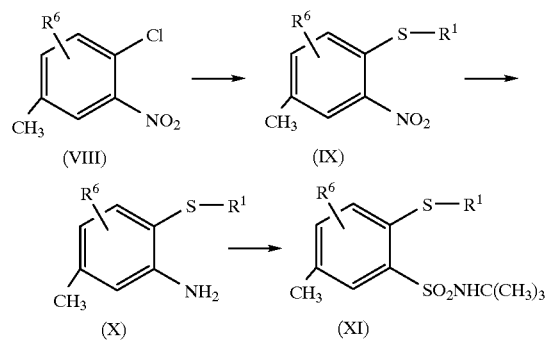

To prepare the sulfonamides (II), the compounds of the formula (XI) are then, if appropriate after prior oxidation to (XII), converted into the sulfonamides (II) via side chain halogenation to (XIII), subsequent substitution of the halogen atom in (XIII) by amines, or by azide with successive reduction to the benzylamines (XIV), and further functionalization of the amino group and cleavage of the tert-butyl protecting group by known procedures (for example with CF₃COOH) (see Scheme 2).

Scheme 2:

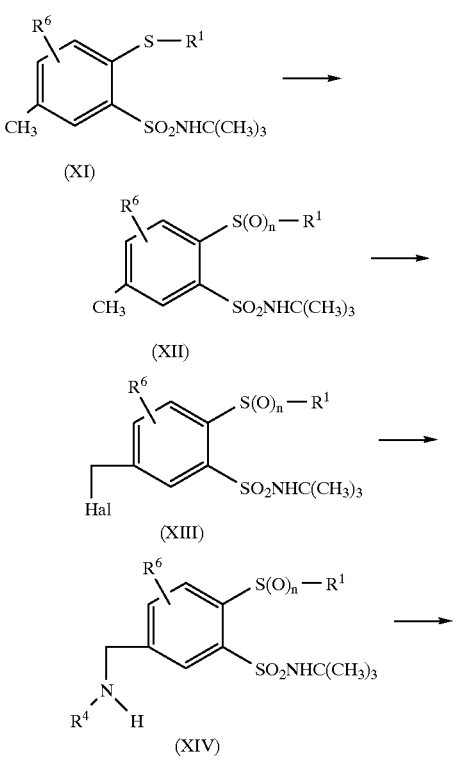

-continued

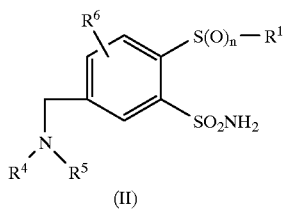

(II)

In compounds of the formula (II) wherein $R^1=NR^8R^9$ (see Scheme 3), for example, the chlorine in unsubstituted or substituted 4-chloro-3-nitrotoluenes (VIII) is initially exchanged with alkyl mercaptans or preferably with benzyl mercaptans to give (IX'). After oxidation and aminolysis of the sulfochloride intermediates with $HNR^8R^9$, sulfonamides (XV) are obtained which, after reduction to (XVI), are converted into the corresponding sulfonamides (II) where $R^1=NR^8R^9$ as described in Schemes 1 and 2 for (X).

Scheme 3:

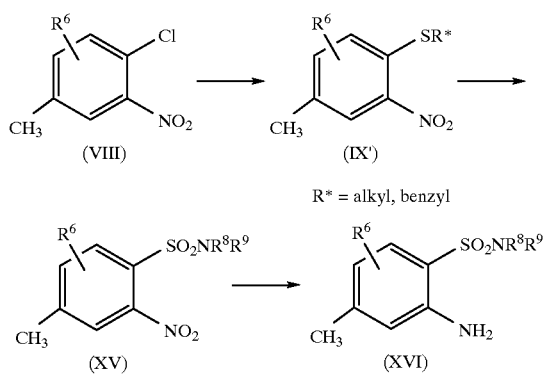

The carbamates of the formula (III) can be prepared by methods described in the South African Patent applications 8215671 and 8215045 or EP-A-70804 (U.S. Pat. No. 4,480, 101) or RD 275056.

The reaction of the compounds (IV) with the amino heterocycles (V) is preferably carried out in inert aprotic solvents, such as dioxane, acetonitrile or tetrahydrofuran, at temperatures between 0° C. and the boiling temperature of the solvent. The starting materials (V) required are known from the literature or can be prepared by processes known from the literature. The arylsulfonylcarbamates of the formula (IV) can be obtained by the methods of U.S. Pat. No. 4,684,393 or U.S. Pat. No. 4,743,290.

The phenylsulfonyl isocyanates of the formula (VI) can be prepared by the method of U.S. Pat. No. 4,481,029 and reacted with the amino heterocycles (V).

The phosgenation of the compounds of the formula (V) according to variant d) car preferably be carried out in the presence of bases, such as sterically hindered organic amine bases, for example triethylamine. The subsequent reaction with compounds of the formula (II) according to variant d) can be carried out by known procedures (cf. EP-A-232 067).

The sulfochlorides (VII) can be obtained from the corresponding sulfonic acids, for example by standard methods such as the reaction of the potassium salt with phosphorus oxychloride or thionyl chloride in inert solvents such as acetonitrile and/or sulfolane or without a solvent by heating under reflux (cf. Houben-Weyl-Klamann, "Methoden der organischen Chemie", 4th edition Vol. 3 XI/2, pp. 1067–1073, Thieme Verlag Stuttgart, 1985).

The corresponding sulfonic acids can be obtained from the corresponding nitro compounds similarly to the reaction of compounds (IX).

Alternatively, in some cases the sulfochlorides (VII) can be prepared by sulfonation (+chlorination) or sulfochlorination of suitable substituted benzoic esters; sulfochlorination according to Houben-Weyl-Klamann, "Methoden der organischen Chemie", 4th edition Vol. E XI/2, p. 1067 ff., Thieme Verlag Stuttgart, 1985; Houben-Weyl-Müller, "Methoden der organischen Chemie", 4th edition Vol. IX, p. 563ff., Thieme Verlag Stuttgart, 1955; sulfonation according to Houbean-Weyl-Klamann, "Methoden der organischean Chemie, 4th edition Vol. E XI/2, p. 1055ff., Thieme Verlag Stuttgart, 1985; Houben-Weyl-Müller, "Methoden der organischen Chemie", 4th edition Vol. IX, p. 435 ff., Thieme Verlag Stuttgart, 1955.

The (thio)isocyanates of the formula (V') can be obtained by literature methods (EP-A-232067, EP-A-166516). The reaction of the (thio)isocyanates (V') with the compounds (II) is carried out at −10° C. to 100° C., preferably 20 to 100° C., in an inert aprotic solvent, such as acetone or acetonitrile, in the presence of a suitable base, for example $N(C_2H_5)_3$ or $K_2CO_3$.

The salts of the compounds of the formula (I) are preferably prepared in inert polar solvents such as water, methanol or acetone at temperatures of 0–100° C. Suitable bases for preparing the salts according to the invention are, for example, alkali metal carbonates, such as potassium carbonate, alkali metal hydroxides and alkaine earth metal hydroxides, for example NaOH or KOH, or ammonia or ethanolamine.

Solvents which have been termed "inert solvents" in the above process variants are to be understood as meaning in each case solvents which are inert under the prevailing reaction conditions, but which do not have to be inert under any selected reaction conditions.

The compounds of the formula (I) according to the invention have an outstanding herbicidal activity against a broad spectrum of economically important monocotyledonous and dicotyledonous harmful plants. The active substances also act efficiently on perennial broad-leaved weeds which produce shoots from rhizomes, rootstocks or other perennial organs and which are difficult to control. In this context, it does not matter whether the substances are applied before sowing, pre-emergence or post-emergence.

Specifically, examples may be mentioned of some representatives of the monocotyledonous and dicotyledonous weed flora which can be controlled by the compounds according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the range of action extends to species such as, for example, Galium, Viola, Veronica, Lamium, Stellaria, Amaranthus, Sinapis, Ipomosa, Matricaria, Abutilon and Sida from amongst the annuals, and Convolvuius, Cirsium, Rumex and Artemisia in the case of the perennial weeds.

The active substances according to the invention also effect outstanding control of weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

Of the active substances are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledonous and dicotyledonous weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in areas under agricultural crops.

In addition, the substances according to the invention have outstanding growth-regulatory properties in crop plants. They engage in the plant metabolism in a regulating manner and can thus be employed for the targeted control of plant constituents and for facilitating harvesting, for example by triggering desiccation and stunted growth. Moreover, they are also suitable for the general control and inhibition of undesirable vegetative growth without destroying the plants in the process. The inhibition of vegetative growth is very important in a large number of monocotyledonous and dicotyledonous crops since it can reduce, or completely prevent, lodging.

The compounds according to the invention can be applied in the form of wettable powders, emulsifiable concentrates, sprayable solutions, dusts or granules in the customary preparations. The invention therefore also relates to herbicidal and plant-growth-regulating compositions which comprise the compounds of the formula (I).

The compounds of the formula (I) can be formulated in various ways, depending on the prevailing biological and/or chemico-physical parameters. The following possibilities are suitable formulations: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, solutions which are miscible with oils, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], Volume 7, C. Heuser Verlag Munich, 4th Ed. 19856, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active substances, such as, for example, insecticides, acaricides, herbicides, fungicides, and also with safeners, fertilizers and/or growth regulators, for example in the form of a ready mix or a tank mix.

Wettable powders are preparations which are uniformly dispersible in water and which, besides the active substance, also comprise ionic and/or non-ionic surfactants (wetting agents, dispersants), for example polyoxethylated alkylphenols, polyoxethylated fatty alcohols, polyoxethylated fatty amines, fatty alcohol polyglycol ether sulfates, alkanesulfonates, alkylbenzeanesufonates, sodium lignosulfonate, sodium 2,2'-dinaphthylmethane6,6'-sulfonate, sodium dibutylnaphthalenesulfonate or else sodium oleoylmethyltaurinate, in addition to a diluent or inert substance. To prepare the wettable powders, the herbicidally active substances are ground finely, for example in customary equipment such as hammer mills, blower mills and air-jet mills, and simultaneously or subsequently mixed with the formulation auxiliaries.

Emulsifiable concentrates are prepared, for example, by dissolving the active substance in an organic solvent, for example butanol, cyclohexanone, dimethylformamide, xylene, or else higher-boiling aromatics or hydrocarbons or mixtures of the organic solvents with the addition of one or more ionic and/or non-ionic surfactants (emulsifiers). Examples of emulsifiers which can be used are: calcium salts of alkylarysulfonic acids such as calcium dodecylbenzenesulfonate, or non-ionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active substance with finely divided solid substances, for example talc, natural clays such as kaolin, bentonite and pyrophyllite, or diatomaceous earth.

Suspension concentrates can be water- or oil-based. They can be prepared, for example, by wet grinding using commercially available bead mills with an optional addition of surfactants as they have already been mentioned above for example in the case of the other types of formulation.

Emulsions, for example oil-in-water emulsions (EW), can be prepared for example by means of stirrers, colloid mills and/or static mixers using aqueous organic solvents and, if appropriate, surfactants as they have already been mentioned above for example in the case of the other types of formulation.

Granules can be prepared either by spraying the active substance onto adsorptive granulated inert material or by applying active substance concentrates to the surface of carriers such as sand, kaolinites or of granulated inert material by means of binders, for example polyvinyl alcohol, sodium polyacrylate or else mineral oils. Suitable active substances can also be granulated in the manner which is conventional for the production of fertilizer granules, if desired as a mixture with fertilizers.

Water-dispersible granules are generally prepared by the customary processes such as spray drying, fluidized-bed granulation, disk granulation, mixing with high-speed mixers and extrusion without solid inert material.

For the preparation of disk, fluidized-bed, extruder and spray granules, see, for example, the processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, N.Y. 1973, pp. 8–57.

For further details on the formulation of crop protection products see, for example, G. C. Klingman, "Weed Control as a Science", John Wiley and Sons, Inc., N.Y., 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). The active substance concentration in wettable powders is, for example, approximately 10 to 90% by weight, the remainder to 100% by weight being composed of customary formulation components. In the case of emulsifiable concentrates, the active substance concentration may amount to approximately 1 to 90, preferably 5 to 80%, by weight. Formulations in the form of dusts comprise 1 to 30% by weight of active substance, in most cases preferably 5 to 20% by weight of active substance, and sprayable solutions comprise approximately 0.05 to 80, preferably 2 to 50%, by weight of active substance. The active substance content of water-dispersible granules depends partly on whether the active compound is in liquid or solid form and on which granulation auxiliaries, fillers and the like are being used. The active substance content of the water-dispersible granules amounts to, for example, between 1 and 95% by weight, preferably between 10 and 80% by weight.

In addition, the abovementioned formulations of active substances comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the active substances according to the invention in mixed formulations or in the tank mix are, for example, known active substances as they are described, for example, in Weed Research 26, 441–445 (1986), or "The Pesticide Manual", 10th edition, The British Crop Protection Council and the Royal Soc. of Chemistry, 1994, and the literature cited therein. Examples of active substances which may be mentioned as herbicides which are known from the literature and which can be combined with the compounds of the formula (I) are the following (note: either the common names in accordance with the International Organization for Standardization (ISO) or the chemical names, if appropriate together with a customary code number, of the compounds are given): acetochlor; acifluorfen; aclonifen; AKH 7088, ie. [[[1-[5-[2-chloro-4-(trifluoromethyl)phenoxy]-2-nitrophenyl ]-2-methoxyethylidene]amino]oxy]acetic acid and its methyl ester; alachlor; alloxydim; ametryn; amidosulfuron; amitrol; AMS, ie. ammonium sulfamate; anilofos; asulam; atrazine; azimsulfurone (DPX-A8947); aziprotryn; barban; BAS 516 H, ie. 5-fluoro-2-phenyl-4H-3,1-benzoxazin-4-one; benazolin; benfluralin; benfuresate; bensulfuron-methyl; bensulide; bentazone; benzofenap; benzofluor; benzoyloprop-ethyl; benzthiazuron, bialaphos; bifenox; bromacil; bromobutide; bromofenoxim; bromoxynil; bromuron; burinafos; busoxinone; butachlor; butamifos; butenachlor; buthidazole; butralin; butylate; cafenstrole (CH-900); carbetamide; cafentrazone (ICI-A0051); CDAA, ie. 2-chloro-N,N-di-2-propenylacetamide; CDEC, ie. 2-chloroallyl diethyldithiocarbamate; chlormethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron, (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters, such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, ie. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, ie. N-[2-chloro-4-fluoro-5-[4-(3-fluoropropyl)-4,5-dihydro-5-oxo-1H-tetrazol-1-yl]phenyl ]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazapyr; imazaquin and salts, such as the ammonium salt; imazethamethapyr; imazethapyr; imazosulfuron; ioxynil; isocarbamid; isopropalin; isoproturon; isouron; isoxaben; isoxapyrifop, karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, ie. 6-chloro-N-(3-chloro-2-propenyl)-5-methyl-N-phenyl-3-pyridazinamine; MT 5950, ie. N-[3-chloro-4-(1-methylethyl)phenyl]-2-methylpentanamide; naproanilide; napropamide; naptalam; NC 310 ie. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham;

picloram; piperophos; piributicarb; pirifenop-butyl; pretilachlor; primsulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivates, for example quizalofop-ethyl; quizalofop-P-tefuryl and -ethyl; renriduron; rimsulfuron (DPX-E 9636); S 275, ie. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, ie. 2-[[7-[2-chloro-4-(trifluoromethyl)phenoxyl]-2-naphthalenyl]oxy]propanoic acid and its methyl ester; sulfentrazone (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, ie. N,N-diethyl-3-[(2-ethyl-6-methylphenyl)sulfonyl]-1H-1,2,4-triazole-1-carboxamide; thenylchlor (NSK-850); thiazafluron, thiazopyr (Mon-13200); thidiazimine (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, ie. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application or for broadcasting and sprayable solutions are conventionally not diluted any further with inert substances prior to use.

The application rate required, of the compounds of the formula (I), varies with the external factors such as, inter alia, temperature, humidity and nature of the herbicide used. It can vary within wide limits, for example between 0.001 and 10.0 kg/ha or more of active substance, but it is preferably between 0.005 and 5 kg/ha.

A. Chemical examples

Abbreviations:
If not further specified, the % details and molar ratios are based on weight.
in vacuo=under reduced pressure
h=hour(s)
DMF=dimethylformamide
EtOH=$C_2H_5OH$ Example A1
4-Methylthio-3-nitrotoluene 138 g (1 mol) of $K_2CO_3$ are added to a solution of 171.6 g (1 mol) of 4-chloro-3-nitrotoluene in 500 ml of DMF. 1 molar equivalent of methyl mercaptan is passed through, and stirring is continued at 50° C. for 3 h. The reaction mixture is poured on a large amount of ice-water and the precipitate is filtered off under suction, washed with water and dried; 146.3 g (80%) of 4-methylthio-3-nitrotoluene of melting point 71–73° C. are obtained.

Example A2
3-Amino-4-methylthiotoluene

A solution of 146 g (0.8 mol) of 4-methylthio-3-nitrotoluene in a mixture of 1000 ml of EtOH and 700 ml of glacial acetic acid is heated to 65–80° C. and, over a period of about 8 h, admixed with a total of 122.9 g (2.2 mol) of powdered iron, a little at a time. After the reaction has ended, the mixture is filtered off under suction through $Na_2SO_4$, washed thoroughly with EtOH and concentrated in vacuo. 122 g (99%) of 3-amino4-methylthiotoluens are obtained as a dark brown oil.

$^1$H—NMR (300 MHz, $CDCl_3$):
δ=2.24 (s, 3H, $SCH_3$)
2.30 (s, 3H, Ar—$CH_3$)
4.25 (bs, 2H, $NH_2$)
6.52 (m, 2H, Ar—H)
7.25 (d, 1H, Ar—H)

Example A3
N-tert-Butyl-2-methylthio-5-methylbenzenesulfonamide

At 0–10° C., 24.3 g (0.352 mol) of $NaNO_2$ dissolved in 50 ml of $H_2O$ are added dropwise to a suspension of 49 g (0.32 mol) of 3-amino-4-methylthiotoluene in 180 ml of conc. HCl, and stirring is continued for half an hour. The diazonium salt suspension obtained is added a little at a time to a mixture of $SO_2$-saturated glacial acetic acid (450 ml), 9.5 g (0.096 mol) of CuCl and $CH_2Cl_2$ (450 ml) which has been warmed to 30° C. After the addition, stirring is continued at 30° C. for 1–2 h and the mixture is poured into ice-water. The phases are separated and the aqueous phase is extracted two more times with $CH_2Cl_2$. The combined organic extracts are washed, dried over $Na_2SO_4$ and completely evaporated in vacuo.

The crude product obtained (66.5 g, 0.28 mol) is dissolved in 650 ml of $CH_2Cl_2$ and treated with 73 ml (0.7 mol, 2.5 equivalents) of tert-butylamine at 0° C.

For work-up, the mixture is poured into ice-water after about 1 h, the phases are separated and the aqueous phase is extracted two more times with $CH_2Cl_2$. The combined organic extracts are washed, dried over $Na_2SO_4$ and concentrated in vacuo. The solid obtained on digesting the residue with a mixture of diisopropyl etherlethyl acetate is filtered off and dried. 41.5 g (47.4%) of N-tert-butyl-2-methylthio-5-methylbenzenesulfonamide of melting point 119–121° C. are obtained.

Example A4
N-tert-Butyl-2-methanesulfonyl-5-methylbenzenesulfonamide

A solution of 41.5 g (0.152 mol) of N-tert-butyl-2-methylthio-5-methylbenzenesulfonamide in 470 ml of MeOH and 190 ml of $H_2O$ is heated to 50° C. and, over a period of 7 h, admixed with 140.2 g (0.228 mol) of sodium peroxomonosulfate (®Oxone), a little at a time. After the reaction has ended, the mixture is poured into a large volume of ice-water and the precipitated product is filtered off. After drying, 46.0 g (99%) of N-tert-butyl-2-methanesulfonyl-5-methylbenzenesulfonamide of melting point 129–133° C. are obtained.

Example A5
N-tert-Butyl-5-bromomethyl-2-methanesulfonylbenzenesulfonamide

A solution of 46 g (0.152 mol) of N-tert-butyl-2-methanesulfonyl-5-methyl-benzenesulfonamide in 450 ml of $CCl_4$ is, after the addition of 27.0 g (0.152 mol) of NBS (N-bromosuccinimide) and 1 g of AIBN (azobisisobutyronitrile), heated under reflux for 7 h using a daylight lamp. The reaction mixture is then filtered and washed successively with NaHSO₃ solution, NaHCO₃ solution and water, dried over MgSO₄ and completely concentrated in vacuo. 51.2 g of a crude mixture containing 55% by weight of N-tert-butyl-5-bromomethyl-2-methanesulfonylbenzenesulfonamide are obtained.

¹H-NMR (300 MHz, CDCl₃):
δ=1.25 (s, 9H, tert-butyl)
3.40 (s, 3H, SO₂CH₃)
4.52 (s, 2H, ArCH₂)
6.26 (s, 1H, NH)
7.75 (dd, 1H, Ar—H, J=2 Hz, 8 Hz)
8.25 (d, 1H, Ar—H, J=8 Hz)
8.31 (d, 1H, Ar—H, J=2 Hz)

Example A6

At 0° C., 51 g of N-tert-butyl-5-bromomethyl-2-methanesulfonylbenzenesulfonamide (55% by weight $^A$28.05 g=0.669 mol) dissolved in 250 ml of THF are added to a solution of 59.5 ml (0.69 mol) of a 40% strength aqueous methylamine solution in 150 ml of THF. Stirring is continued at 0–5° C. for 2–3 h. For work-up, the solution is completely concentrated, the residue is taken up in plenty of 2N HCl and extracted with diethyl ether (2×200 ml). The acidic aqueous phase is adjusted to pH 9 with 4N NaOH and extracted with ethyl acetate (3×200 ml). The combined ethyl acetate extracts are washed with water, dried over Na₂SO₄ and evaporated in vacuo. 17 g (73.7%) of N-tert-butyl-5-methylaminomethyl-2-methanesulfonylbenzenesulfonamide of melting point 76–78° C. are obtained as residue.

Example A7
N-tert-Butyl-5-(N-methyl-N-methanesulfonylaminomethyl)-2-methanesulfonylbenzenesulfonamide 0.39 ml (5 mmol) of methenesulfonyl chloride dissolved in 5 ml of dichloromethane are added dropwise to a solution of 1.67 g (5 mmol) of N-tert-butyl-5-methylaminomethyl-2-methanesulfonylbenzenesulfonamide and 0.73 ml (5.3 mmol) of triethylamine in 20 ml of dichloromethane which had been cooled to 0° C. After 30 min at room temperature, the reaction solution is washed with water, dried and completely evaporated in vacuo. 1.85 g (89.7%) of N-tert-butyl-5-(N-methyl-N-methanesulfonylaminomethyl)-2-methanesulfonylbenzenesulfonamide are obtained as a viscous oil.

¹H—NMR (300 MHz, CDCl₃):
δ=1.23 (s, 9H, tert-butyl)

2.82 (s, 3H, N—CH₃)
2.94 (s, 3H, N—SO₂CH₃)
3.40 (s, 3H, Ar—SC₂CH₃)
4.46 (s, 2H, Ar—CH₂)
6.30 (s, 1H, NH)
7.83 (dd, 1H, Ar—H, J=2 Hz, 8 Hz)
8.20 (d, 1H, Ar—H, J=2 Hz)
8.30 (d, 1H, Ar—H, J=8 Hz)

Example A8
5-(N-Methyl-N-methanesulfonylaminomethyl)-2-methanesulfonylbenzenesulfonamide A solution of 1.85 g (4.5 mmol) of N-tert-butyl-5-(N-methyl-N-methanesulfonylaminomethyl)-2-methanesulfonylbenzenesulfonamide in 20 ml of trifluoroacetic acid is stirred at room temperature for 8 h. The mixture is evaporated to dryness and then coevaporated with toluene, and the residue obtained is crystallized from ethyl acetate/diisopropyl ether. 1.32 g (83%) of 5-(N-methyl-N-methanesulfonylaminomethyl)-2-methanesulfonylbenzenesulfonamide of melting point 165–169° C. are obtained.

Example A9
N-(4,6-Dimethoxypyrimidin-2-ylaminocarbonyl)-5-(N-methyl-N-methanesulfonylaminomethyl)-2-methanesulfonylbenzenesulfonamide 0.56 ml (3.7 mmol) of DBU is added dropwise to a suspension of 1.33 g (3.7 mmol) of 5-(N-methyl-N-methanesulfonylaminomethyl)-2-methanesulfonylbenzenesulfonamide and 1.03 g (3.7 mmol) of phenyl N-(4,6-dimethoxypyrimidin-2-yl)carbamate in 20 ml of acetonitrile. After 2 h, the mixture is diluted with water and diethyl ether and acidified to pH 1–2 with HCl and the precipitated product is filtered off, washed with water and diethyl ether and dried; yield: 1.78 g (89.5%) of N-(4,6-dimethoxypyrimidin-2-ylaminocarbonyl)-5-(N-methyl-N-methanesulfonylamiinomethyl)-2-methanesulfonylbenzenesulfonamide of melting point 205–210° C. (decomposition).

The compounds according to the invention listed in the tables below are obtained by or analogously to Examples A1 to A8 or by the processes mentioned in the general part.

Abbreviations in the Tables:
No.=Example number, Example compound number
mp.=melting point
n-, i-, s-, t-C₄H₉=n-, iso-, secondary-, tertiary-butyl
n-C₃H₇=n-propyl
i-C₃H₇=isopropyl

TABLE 1

Compound of the formula (1a)

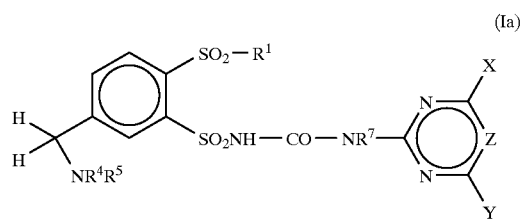

(Ia)

| No. | R¹ | R⁴ | R⁵ | R⁷ | X | Y | Z | mp.(°C.) |
|---|---|---|---|---|---|---|---|---|
| 1 | CH₃ | H | CHO | H | OCH₃ | OCH₃ | CH | 142–148 |
| 2 | CH₃ | H | CHO | H | OCH₃ | CH₃ | CH | |

TABLE 1-continued

Compound of the formula (Ia)

(Ia)

| No. | R¹ | R⁴ | R⁵ | R⁷ | X | Y | Z | mp.(°C.) |
|---|---|---|---|---|---|---|---|---|
| 3 | $CH_3$ | H | CHO | H | $CH_3$ | $CH_3$ | CH | |
| 4 | $CH_3$ | H | CHO | H | $CH_3$ | $OC_2H_5$ | CH | |
| 5 | $CH_3$ | H | CHO | H | $C_2H_5$ | $OCH_3$ | CH | |
| 6 | $CH_3$ | H | CHO | H | $OC_2H_5$ | $OC_2H_5$ | CH | |
| 7 | $CH_3$ | H | CHO | H | $OCHF_2$ | $OCHF_2$ | CH | |
| 8 | $CH_3$ | H | CHO | H | $CH_3$ | $OCHF_2$ | CH | |
| 9 | $CH_3$ | H | CHO | H | Cl | $OCH_3$ | CH | |
| 10 | $CH_3$ | H | CHO | H | $OCH_3$ | $OCH_3$ | N | |
| 11 | $CH_3$ | H | CHO | H | $OCH_3$ | $CH_3$ | N | |
| 12 | $CH_3$ | H | CHO | H | $CH_3$ | $CH_3$ | N | |
| 13 | $CH_3$ | H | CHO | H | $N(CH_3)_2$ | $OCH_2CF_3$ | N | |
| 14 | $CH_3$ | H | CHO | H | $OCH_3$ | $CF_3$ | N | |
| 15 | $CH_3$ | H | CHO | H | $OC_2H_5$ | $NHCH_3$ | N | |
| 16 | $CH_3$ | H | CHO | $CH_3$ | $OCH_3$ | $OCH_3$ | CH | |
| 17 | $CH_3$ | H | CHO | $CH_3$ | $OCH_3$ | $CH_3$ | N | |
| 18 | $CH_3$ | H | $COCH_3$ | H | $OCH_3$ | $OCH_3$ | CH | 195–200 |
| 19 | $CH_3$ | H | $COCH_3$ | H | $OCH_3$ | $CH_3$ | CH | |
| 20 | $CH_3$ | H | $COCH_3$ | H | $CH_3$ | $CH_3$ | CH | |
| 21 | $CH_3$ | H | $COCH_3$ | H | $CH_3$ | $OC_2C_5$ | CH | |
| 22 | $CH_3$ | H | $COCH_3$ | H | $C_2H_5$ | $OCH_3$ | CH | |
| 23 | $CH_3$ | H | $COCH_3$ | H | $OC_2H_5$ | $OC_2H_5$ | CH | |
| 24 | $CH_3$ | H | $COCH_3$ | H | $OCHF_2$ | $OCHF_2$ | CH | |
| 25 | $CH_3$ | H | $COCH_3$ | H | $CH_3$ | $OCHF_2$ | CH | |
| 26 | $CH_3$ | H | $COCH_3$ | H | Cl | $OCH_3$ | CH | |
| 27 | $CH_3$ | H | $COCH_3$ | H | $OCH_3$ | $OCH_3$ | N | |
| 28 | $CH_3$ | H | $COCH_3$ | H | $OCH_3$ | $CH_3$ | N | |
| 29 | $CH_3$ | H | $COCH_3$ | H | $CH_3$ | $CH_3$ | N | |
| 30 | $CH_3$ | H | $COCH_3$ | H | $N(CH_3)_2$ | $OCH_2CF_3$ | N | |
| 31 | $CH_3$ | H | $COCH_3$ | H | $OCH_3$ | $CF_3$ | N | |
| 32 | $CH_3$ | H | $COCH_3$ | H | $OC_2H_5$ | $NHCH_3$ | N | |
| 33 | $CH_3$ | H | $COCH_3$ | $CH_3$ | $OCH_3$ | $OCH_3$ | CH | |
| 34 | $CH_3$ | H | $COCH_3$ | $CH_3$ | $OCH_3$ | $CH_3$ | N | |
| 35 | $CH_3$ | H | $COC_2H_5$ | H | $OCH_3$ | $OCH_3$ | CH | 196–200 |
| 36 | $CH_3$ | H | $COC_2H_5$ | H | $OCH_3$ | $CH_3$ | CH | |
| 37 | $CH_3$ | H | $COC_2H_5$ | H | $CH_3$ | $CH_3$ | CH | |
| 38 | $CH_3$ | H | $COC_2H_5$ | H | $CH_3$ | $OC_2H_5$ | CH | |
| 39 | $CH_3$ | H | $COC_2H_5$ | H | $C_2H_5$ | $OCH_3$ | CH | |
| 40 | $CH_3$ | H | $COC_2H_5$ | H | $OC_2H_5$ | $OC_2H_5$ | CH | |
| 41 | $CH_3$ | H | $COC_2H_5$ | H | $OCHF_2$ | $OCHF_2$ | CH | |
| 42 | $CH_3$ | H | $COC_2H_5$ | H | $CH_3$ | $OCHF_2$ | CH | |
| 43 | $CH_3$ | H | $COC_2H_5$ | H | Cl | $OCH_3$ | CH | |
| 44 | $CH_3$ | H | $COC_2H_5$ | H | $OCH_3$ | $OCH_3$ | N | |
| 45 | $CH_3$ | H | $COC_2H_5$ | H | $OCH_3$ | $CH_3$ | N | |
| 46 | $CH_3$ | H | $COC_2H_5$ | H | $CH_3$ | $CH_3$ | N | |
| 47 | $CH_3$ | H | $COC_2H_5$ | H | $N(CH_3)_2$ | $OCH_2CF_3$ | N | |
| 48 | $CH_3$ | H | $COC_2H_5$ | H | $OCH_3$ | $CF_3$ | N | |
| 49 | $CH_3$ | H | $COC_2H_5$ | H | $OC_2H_5$ | $NHCH_3$ | N | |
| 50 | $CH_3$ | H | $COC_2H_5$ | H | $OCH_3$ | $OCH_3$ | CH | |
| 51 | $CH_3$ | H | $COC_2H_5$ | H | $OCH_3$ | $CH_3$ | N | |
| 52 | $CH_3$ | H | $CO$-n-$C_3H_7$ | H | $OCH_3$ | $OCH_3$ | CH | |
| 53 | $CH_3$ | H | $CO$-n-$C_3H_7$ | H | $OCH_3$ | $CH_3$ | CH | |
| 54 | $CH_3$ | H | $CO$-n-$C_3H_7$ | H | $CH_3$ | $CH_3$ | CH | |
| 55 | $CH_3$ | H | $CO$-n-$C_3H_7$ | H | $CH_3$ | $OC_2H_5$ | CH | |
| 56 | $CH_3$ | H | $CO$-n-$C_3H_7$ | H | $C_2H_5$ | $OCH_3$ | CH | |
| 57 | $CH_3$ | H | $CO$-n-$C_3H_7$ | H | $OC_2H_5$ | $OC_2H_5$ | CH | |
| 58 | $CH_3$ | H | $CO$-n-$C_3H_7$ | H | $OCHF_2$ | $OCHF_2$ | CH | |
| 59 | $CH_3$ | H | $CO$-n-$C_3H_7$ | H | $CH_3$ | $OCHF_2$ | CH | |
| 60 | $CH_3$ | H | $CO$-n-$C_3H_7$ | H | Cl | $OCH_3$ | CH | |
| 61 | $CH_3$ | H | $CO$-n-$C_3H_7$ | H | $OCH_3$ | $OCH_3$ | N | |
| 62 | $CH_3$ | H | $CO$-n-$C_3H_7$ | H | $OCH_3$ | $CH_3$ | N | |
| 63 | $CH_3$ | H | $CO$-n-$C_3H_7$ | H | $CH_3$ | $CH_3$ | N | |
| 64 | $CH_3$ | H | $CO$-n-$C_3H_7$ | H | $N(CH_3)_2$ | $OCH_2CF_3$ | N | |
| 65 | $CH_3$ | H | $CO$-n-$C_3H_7$ | H | $OCH_3$ | $CF_3$ | N | |

TABLE 1-continued

Compound of the formula (Ia)

| No. | R¹ | R⁴ | R⁵ | R⁷ | X | Y | Z | mp.(°C.) |
|---|---|---|---|---|---|---|---|---|
| 66 | $CH_3$ | H | $CO$-n-$C_3H_7$ | H | $OC_2H_5$ | $NHCH_3$ | N | |
| 67 | $CH_3$ | H | $CO$-n-$C_3H_7$ | $CH_3$ | $OCH_3$ | $OCH_3$ | CH | |
| 68 | $CH_3$ | H | $CO$-n-$C_3H_7$ | $CH_3$ | $OCH_3$ | $CH_3$ | N | |
| 69 | $CH_3$ | H | $CO$-i-$C_3H_7$ | H | $OCH_3$ | $OCH_3$ | CH | 80–89 |
| 70 | $CH_3$ | H | $CO$-i-$C_3H_7$ | H | $OCH_3$ | $CH_3$ | CH | |
| 71 | $CH_3$ | H | $CO$-i-$C_3H_7$ | H | $CH_3$ | $CH_3$ | CH | |
| 72 | $CH_3$ | H | $CO$-i-$C_3H_7$ | H | $CH_3$ | $OC_2H_5$ | CH | |
| 73 | $CH_3$ | H | $CO$-i-$C_3H_7$ | H | $C_2H_5$ | $OCH_3$ | CH | |
| 74 | $CH_3$ | H | $CO$-i-$C_3H_7$ | H | $OC_2H_5$ | $OC_2H_5$ | CH | |
| 75 | $CH_3$ | H | $CO$-i-$C_3H_7$ | H | $OCHF_2$ | $OCHF_2$ | CH | |
| 76 | $CH_3$ | H | $CO$-i-$C_3H_7$ | H | $CH_3$ | $OCHF_2$ | CH | |
| 77 | $CH_3$ | H | $CO$-i-$C_3H_7$ | H | Cl | $OCH_3$ | CH | |
| 78 | $CH_3$ | H | $CO$-i-$C_3H_7$ | H | $OCH_3$ | $OCH_3$ | N | |
| 79 | $CH_3$ | H | $CO$-i-$C_3H_7$ | H | $OCH_3$ | $CH_3$ | N | |
| 80 | $CH_3$ | H | $CO$-i-$C_3H_7$ | H | $CH_3$ | $CH_3$ | N | |
| 81 | $CH_3$ | H | $CO$-i-$C_3H_7$ | H | $N(CH_3)_2$ | $OCH_2CF_3$ | N | |
| 82 | $CH_3$ | H | $CO$-i-$C_3H_7$ | H | $OCH_3$ | $CF_3$ | N | |
| 83 | $CH_3$ | H | $CO$-i-$C_3H_7$ | H | $OC_2H_5$ | $NHCH_3$ | N | |
| 84 | $CH_3$ | H | $CO$-i-$C_3H_7$ | $CH_3$ | $OCH_3$ | $OCH_3$ | CH | |
| 85 | $CH_3$ | H | $CO$-i-$C_3H_7$ | $CH_3$ | $OCH_3$ | $CH_3$ | N | |
| 86 | $CH_3$ | H | $COCF_3$ | H | $OCH_3$ | $OCH_3$ | CH | 138–141 |
| 87 | $CH_3$ | H | $COCF_3$ | H | $OCH_3$ | $CH_3$ | CH | |
| 88 | $CH_3$ | H | $COCF_3$ | H | $CH_3$ | $CH_3$ | CH | |
| 89 | $CH_3$ | H | $COCF_3$ | H | $CH_3$ | $OC_2H_5$ | CH | |
| 90 | $CH_3$ | H | $COCF_3$ | H | $C_2H_5$ | $OCH_3$ | CH | |
| 91 | $CH_3$ | H | $COCF_3$ | H | $OC_2H_5$ | $OC_2H_5$ | CH | |
| 92 | $CH_3$ | H | $COCF_3$ | H | $OCHF_2$ | $OCHF_2$ | CH | |
| 93 | $CH_3$ | H | $COCF_3$ | H | $CH_3$ | $OCHF_2$ | CH | |
| 94 | $CH_3$ | H | $COCF_3$ | H | Cl | $OCH_3$ | CH | |
| 95 | $CH_3$ | H | $COCF_3$ | H | $OCH_3$ | $OCH_3$ | N | |
| 96 | $CH_3$ | H | $COCF_3$ | H | $OCH_3$ | $CH_3$ | N | |
| 97 | $CH_3$ | H | $COCF_3$ | H | $CH_3$ | $CH_3$ | N | |
| 98 | $CH_3$ | H | $COCF_3$ | H | $N(CH_3)_2$ | $OCH_2CF_3$ | N | |
| 99 | $CH_3$ | H | $COCF_3$ | H | $OCH_3$ | $CF_3$ | N | |
| 100 | $CH_3$ | H | $COCF_3$ | H | $OC_2H_5$ | $NHCH_3$ | N | |
| 101 | $CH_3$ | H | $COCF_3$ | $CH_3$ | $OCH_3$ | $OCH_3$ | CH | |
| 102 | $CH_3$ | H | $COCF_3$ | $CH_3$ | $OCH_3$ | $CH_3$ | N | |
| 103 | $CH_3$ | H | $COOCH_3$ | H | $OCH_3$ | $OCH_3$ | CH | 150–154 |
| 104 | $CH_3$ | H | $COOCH_3$ | H | $OCH_3$ | $CH_3$ | CH | |
| 105 | $CH_3$ | H | $COOCH_3$ | H | $CH_3$ | $CH_3$ | CH | |
| 106 | $CH_3$ | H | $COOCH_3$ | H | $CH_3$ | $OC_2H_5$ | CH | |
| 107 | $CH_3$ | H | $COOCH_3$ | H | $C_2H_5$ | $OCH_3$ | CH | |
| 108 | $CH_3$ | H | $COOCH_3$ | H | $OC_2H_5$ | $OC_2H_5$ | CH | |
| 109 | $CH_3$ | H | $COOCH_3$ | H | $OCHF_2$ | $OCHF_2$ | CH | |
| 110 | $CH_3$ | H | $COOCH_3$ | H | $CH_3$ | $OCHF_2$ | CH | |
| 111 | $CH_3$ | H | $COOCH_3$ | H | Cl | $OCH_3$ | CH | |
| 112 | $CH_3$ | H | $COOCH_3$ | H | $OCH_3$ | $OCH_3$ | N | |
| 113 | $CH_3$ | H | $COOCH_3$ | H | $OCH_3$ | $CH_3$ | N | |
| 114 | $CH_3$ | H | $COOCH_3$ | H | $CH_3$ | $CH_3$ | N | |
| 115 | $CH_3$ | H | $COOCH_3$ | H | $N(CH_3)_2$ | $OCH_2CF_3$ | N | |
| 116 | $CH_3$ | H | $COOCH_3$ | H | $OCH_3$ | $CF_3$ | N | |
| 117 | $CH_3$ | H | $COOCH_3$ | H | $OC_2H_5$ | $NHCH_3$ | N | |
| 118 | $CH_3$ | H | $COOCH_3$ | $CH_3$ | $OCH_3$ | $OCH_3$ | CH | |
| 119 | $CH_3$ | H | $COOCH_3$ | $CH_3$ | $OCH_3$ | $CH_3$ | N | |
| 120 | $CH_3$ | H | $COOC_2H_5$ | H | $OCH_3$ | $OCH_3$ | CH | 151–156 |
| 121 | $CH_3$ | H | $COOC_2H_5$ | H | $OCH_3$ | $CH_3$ | CH | |
| 122 | $CH_3$ | H | $COOC_2H_5$ | H | $CH_3$ | $CH_3$ | CH | |
| 123 | $CH_3$ | H | $COOC_2H_5$ | H | $CH_3$ | $OC_2H_5$ | CH | |
| 124 | $CH_3$ | H | $COOC_2H_5$ | H | $C_2H_5$ | $OCH_3$ | CH | |
| 125 | $CH_3$ | H | $COOC_2H_5$ | H | $OC_2H_5$ | $OC_2H_5$ | CH | |
| 126 | $CH_3$ | H | $COOC_2H_5$ | H | $OCHF_2$ | $OCHF_2$ | CH | |
| 127 | $CH_3$ | H | $COOC_2H_5$ | H | $CH_3$ | $OCHF_2$ | CH | |
| 128 | $CH_3$ | H | $COOC_2H_5$ | H | Cl | $OCH_3$ | CH | |

TABLE 1-continued

Compound of the formula (1a)

$$\text{(Ia)}$$

| No. | $R^1$ | $R^4$ | $R^5$ | $R^7$ | X | Y | Z | mp.(°C.) |
|---|---|---|---|---|---|---|---|---|
| 129 | $CH_3$ | H | $COOC_2H_5$ | H | $OCH_3$ | $OCH_3$ | N | |
| 130 | $CH_3$ | H | $COOC_2H_5$ | H | $OCH_3$ | $CH_3$ | N | |
| 131 | $CH_3$ | H | $COOC_2H_5$ | H | $CH_3$ | $CH_3$ | N | |
| 132 | $CH_3$ | H | $COOC_2H_5$ | H | $N(CH_3)_2$ | $OCH_2CF_3$ | N | |
| 133 | $CH_3$ | H | $COOC_2H_5$ | H | $OCH_3$ | $CF_3$ | N | |
| 134 | $CH_3$ | H | $COOC_2H_5$ | H | $OC_2H_5$ | $NHCH_3$ | N | |
| 135 | $CH_3$ | H | $COOC_2H_5$ | $CH_3$ | $OCH_3$ | $OCH_3$ | CH | |
| 136 | $CH_3$ | H | $COOC_2H_5$ | $CH_3$ | $OCH_3$ | $CH_3$ | CH | |
| 137 | $CH_3$ | H | $COOC_2H_5$ | $CH_3$ | $OCH_3$ | $CH_3$ | N | |
| 138 | $CH_3$ | H | $SO_2CH_3$ | H | $OCH_3$ | $OCH_3$ | CH | 208–210 |
| 139 | $CH_3$ | H | $SO_2CH_3$ | H | $OCH_3$ | $CH_3$ | CH | |
| 140 | $CH_3$ | H | $SO_2CH_3$ | H | $CH_3$ | $CH_3$ | CH | |
| 141 | $CH_3$ | H | $SO_2CH_3$ | H | $CH_3$ | $OC_2H_5$ | CH | |
| 142 | $CH_3$ | H | $SO_2CH_3$ | H | $C_2H_5$ | $OCH_3$ | CH | |
| 143 | $CH_3$ | H | $SO_2CH_3$ | H | $OC_2H_5$ | $OC_2H_5$ | CH | |
| 144 | $CH_3$ | H | $SO_2CH_3$ | H | $OCHF_2$ | $OCHF_2$ | CH | |
| 145 | $CH_3$ | H | $SO_2CH_3$ | H | $CH_3$ | $OCHF_2$ | CH | |
| 146 | $CH_3$ | H | $SO_2CH_3$ | H | Cl | $OCH_3$ | CH | |
| 147 | $CH_3$ | H | $SO_2CH_3$ | H | $OCH_3$ | $OCH_3$ | N | |
| 148 | $CH_3$ | H | $SO_2CH_3$ | H | $OCH_3$ | $CH_3$ | N | |
| 149 | $CH_3$ | H | $SO_2CH_3$ | H | $CH_3$ | $CH_3$ | N | |
| 150 | $CH_3$ | H | $SO_2CH_3$ | H | $N(CH_3)_2$ | $OCH_2CF_3$ | N | |
| 151 | $CH_3$ | H | $SO_2CH_3$ | H | $OCH_3$ | $CF_3$ | N | |
| 152 | $CH_3$ | H | $SO_2CH_3$ | H | $OC_2H_5$ | $NHCH_3$ | N | |
| 153 | $CH_3$ | H | $SO_2CH_3$ | $CH_3$ | $OCH_3$ | $OCH_3$ | CH | |
| 154 | $CH_3$ | H | $SO_2CH_3$ | $CH_3$ | $OCH_3$ | $CH_3$ | N | |
| 155 | $CH_3$ | H | $C_2H_5SO_2$ | H | $OCH_3$ | $OCH_3$ | CH | 157–160 |
| 156 | $CH_3$ | H | $C_2H_5SO_2$ | H | $OCH_3$ | $CH_3$ | CH | |
| 157 | $CH_3$ | H | $C_2H_5SO_2$ | H | $CH_3$ | $CH_3$ | CH | |
| 158 | $CH_3$ | H | $C_2H_5SO_2$ | H | $CH_3$ | $OC_2H_5$ | CH | |
| 159 | $CH_3$ | H | $C_2H_5SO_2$ | H | $C_2H_5$ | $OCH_3$ | CH | |
| 160 | $CH_3$ | H | $C_2H_5SO_2$ | H | $OC_2H_5$ | $OC_2H_5$ | CH | |
| 161 | $CH_3$ | H | $C_2H_5SO_2$ | H | $OCHF_2$ | $OCHF_2$ | CH | |
| 162 | $CH_3$ | H | $C_2H_5SO_2$ | H | $CH_3$ | $OCHF_2$ | CH | |
| 163 | $CH_3$ | H | $C_2H_5SO_2$ | H | Cl | $OCH_3$ | CH | |
| 164 | $CH_3$ | H | $C_2H_5SO_2$ | H | $OCH_3$ | $OCH_3$ | N | |
| 165 | $CH_3$ | H | $C_2H_5SO_2$ | H | $OCH_3$ | $CH_3$ | N | |
| 166 | $CH_3$ | H | $C_2H_5SO_2$ | H | $CH_3$ | $CH_3$ | N | |
| 167 | $CH_3$ | H | $C_2H_5SO_2$ | H | $N(CH_3)_2$ | $OCH_2CF_3$ | N | |
| 168 | $CH_3$ | H | $C_2H_5SO_2$ | H | $OCH_3$ | $CF_3$ | N | |
| 169 | $CH_3$ | H | $C_2H_5SO_2$ | H | $OC_2H_5$ | $NHCH_3$ | N | |
| 170 | $CH_3$ | H | $C_2H_5SO_2$ | $CH_3$ | $OCH_3$ | $OCH_3$ | CH | |
| 171 | $CH_3$ | H | $C_2H_5SO_2$ | $CH_3$ | $OCH_3$ | $CH_3$ | N | |
| 172 | $CH_3$ | H | $n-C_3H_7SO_2$ | H | $OCH_3$ | $OCH_3$ | CH | |
| 173 | $CH_3$ | H | $n-C_3H_7SO_2$ | H | $OC_2H_5$ | $OCH_3$ | CH | |
| 174 | $CH_3$ | H | $n-C_3H_7SO_2$ | H | $OCH_3$ | $CH_3$ | CH | |
| 175 | $CH_3$ | H | $n-C_3H_7SO_2$ | H | $CH_3$ | $CH_3$ | CH | |
| 176 | $CH_3$ | H | $n-C_3H_7SO_2$ | H | $CH_3$ | $OC_2H_5$ | CH | |
| 177 | $CH_3$ | H | $n-C_3H_7SO_2$ | H | $C_2H_5$ | $OCH_3$ | CH | |
| 178 | $CH_3$ | H | $n-C_3H_7SO_2$ | H | $OC_2H_5$ | $OC_2H_5$ | CH | |
| 179 | $CH_3$ | H | $n-C_3H_7SO_2$ | H | $OCHF_2$ | $OCHF_2$ | CH | |
| 180 | $CH_3$ | H | $n-C_3H_7SO_2$ | H | $CH_3$ | $OCHF_2$ | CH | |
| 181 | $CH_3$ | H | $n-C_3H_7SO_2$ | H | Cl | $OCH_3$ | CH | |
| 182 | $CH_3$ | H | $n-C_3H_7SO_2$ | H | $OCH_3$ | $OCH_3$ | N | |
| 183 | $CH_3$ | H | $n-C_3H_7SO_2$ | H | $OCH_3$ | $CH_3$ | N | |
| 184 | $CH_3$ | H | $n-C_3H_7SO_2$ | H | $CH_3$ | $CH_3$ | N | |
| 185 | $CH_3$ | H | $n-C_3H_7SO_2$ | H | $N(CH_3)_2$ | $OCH_2CF_3$ | N | |
| 186 | $CH_3$ | H | $n-C_3H_7SO_2$ | H | $OCH_3$ | $CF_3$ | N | |
| 187 | $CH_3$ | H | $n-C_3H_7SO_2$ | H | $OC_2H_5$ | $NHCH_3$ | N | |
| 188 | $CH_3$ | H | $n-C_3H_7SO_2$ | $CH_3$ | $OCH_3$ | $OCH_3$ | CH | |
| 189 | $CH_3$ | H | $n-C_3H_7SO_2$ | $CH_3$ | $OCH_3$ | $CH_3$ | N | |
| 190 | $CH_3$ | H | $i-C_3H_7SO_2$ | H | $OCH_3$ | $OCH_3$ | CH | |
| 191 | $CH_3$ | H | $i-C_3H_7SO_2$ | H | $OCH_3$ | $CH_3$ | CH | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 192 | CH₃ | H | i-C₃H₇SO₂ | H | CH₃ | CH₃ | CH | |
| 193 | CH₃ | H | i-C₃H₇SO₂ | H | CH₃ | OC₂H₅ | CH | |
| 194 | CH₃ | H | i-C₃H₇SO₂ | H | C₂H₅ | OCH₃ | CH | |
| 195 | CH₃ | H | i-C₃H₇SO₂ | H | OC₂H₅ | OC₂H₅ | CH | |
| 196 | CH₃ | H | i-C₃H₇SO₂ | H | OCHF₂ | OCHF₂ | CH | |
| 197 | CH₃ | H | i-C₃H₇SO₂ | H | CH₃ | OCHF₂ | CH | |
| 198 | CH₃ | H | i-C₃H₇SO₂ | H | Cl | OCH₃ | CH | |
| 199 | CH₃ | H | i-C₃H₇SO₂ | H | OCH₃ | OCH₃ | N | |
| 200 | CH₃ | H | i-C₃H₇SO₂ | H | OCH₃ | CH₃ | N | |
| 201 | CH₃ | H | i-C₃H₇SO₂ | H | CH₃ | CH₃ | N | |
| 202 | CH₃ | H | i-C₃H₇SO₂ | H | N(CH₃)₂ | OCH₂CF₃ | N | |
| 203 | CH₃ | H | i-C₃H₇SO₂ | H | OCH₃ | CF₃ | N | |
| 204 | CH₃ | H | i-C₃H₇SO₂ | H | OC₂H₅ | NHCH₃ | N | |
| 205 | CH₃ | H | i-C₃H₇SO₂ | CH₃ | OCH₃ | OCH₃ | CH | |
| 206 | CH₃ | H | i-C₃H₇SO₂ | CH₃ | OCH₃ | CH₃ | N | |
| 207 | CH₃ | H | ClCH₂CO | H | OCH₃ | OCH₃ | CH | |
| 208 | CH₃ | H | ClCH₂CO | H | OCH₃ | CH₃ | CH | |
| 209 | CH₃ | H | ClCH₂CO | H | CH₃ | CH₃ | CH | |
| 210 | CH₃ | H | ClCH₂CO | H | Cl | OCH₃ | CH | |
| 211 | CH₃ | H | ClCH₂CO | H | OCH₃ | OCH₃ | N | |
| 212 | CH₃ | H | ClCH₂CO | H | OCH₃ | CH₃ | N | |
| 213 | CH₃ | H | ClCH₂CO | H | OCH₃ | CF₃ | N | |
| 214 | CH₃ | H | ClCH₂CO | CH₃ | OCH₃ | OCH₃ | CH | |
| 215 | CH₃ | H | ClCH₂CO | CH₃ | OCH₃ | CH₃ | N | |
| 216 | CH₃ | H | Cl₂CHCO | H | OCH₃ | OCH₃ | CH | |
| 217 | CH₃ | H | Cl₂CHCO | H | OCH₃ | CH₃ | CH | |
| 218 | CH₃ | H | Cl₂CHCO | H | CH₃ | CH₃ | CH | |
| 219 | CH₃ | H | Cl₂CHCO | H | Cl | OCH₃ | CH | |
| 220 | CH₃ | H | Cl₂CHCO | H | OCH₃ | OCH₃ | N | |
| 221 | CH₃ | H | Cl₂CHCO | H | OCH₃ | CH₃ | N | |
| 222 | CH₃ | H | Cl₂CHCO | H | OCH₃ | CF₃ | N | |
| 223 | CH₃ | H | Cl₂CHCO | CH₃ | OCH₃ | OCH₃ | CH | |
| 224 | CH₃ | H | Cl₂CHCO | CH₃ | OCH₃ | CH₃ | N | |
| 225 | CH₃ | H | Cl₃CCO | H | OCH₃ | OCH₃ | CH | 125–130 |
| 226 | CH₃ | H | Cl₃CCO | H | OCH₃ | CH₃ | CH | |
| 227 | CH₃ | H | Cl₃CCO | H | CH₃ | CH₃ | CH | |
| 228 | CH₃ | H | Cl₃CCO | H | Cl | OCH₃ | CH | |
| 229 | CH₃ | H | Cl₃CCO | H | OCH₃ | OCH₃ | N | |
| 230 | CH₃ | H | Cl₃CCO | H | OCH₃ | CH₃ | N | |
| 231 | CH₃ | H | Cl₃CCO | H | OCH₃ | CF₃ | N | |
| 232 | CH₃ | H | Cl₃CCO | CH₃ | OCH₃ | OCH₃ | CH | |
| 233 | CH₃ | H | Cl₃CCO | CH₃ | OCH₃ | CH₃ | N | |
| 234 | CH₃ | H | CH₃OCH₂CO | H | OCH₃ | OCH₃ | CH | |
| 235 | CH₃ | H | CH₃OCH₂CO | H | OCH₃ | CH₃ | CH | |
| 236 | CH₃ | H | CH₃OCH₂CO | H | CH₃ | CH₃ | CH | |
| 237 | CH₃ | H | CH₃OCH₂CO | H | Cl | OCH₃ | CH | |
| 238 | CH₃ | H | CH₃OCH₂CO | H | OCH₃ | OCH₃ | N | |
| 239 | CH₃ | H | CH₃OCH₂CO | H | OCH₃ | CH₃ | N | |
| 240 | CH₃ | H | CH₃OCH₂CO | H | OCH₃ | CF₃ | N | |
| 241 | CH₃ | H | CH₃OCH₂CO | CH₃ | OCH₃ | OCH₃ | CH | |
| 242 | CH₃ | H | CH₃OCH₂CO | CH₃ | OCH₃ | CH₃ | N | |
| 243 | CH₃ | H | CH₂=CHCO | H | OCH₃ | OCH₃ | CH | |
| 244 | CH₃ | H | CH₂=CHCO | H | OCH₃ | CH₃ | CH | |
| 245 | CH₃ | H | CH₂=CHCO | H | CH₃ | CH₃ | CH | |
| 246 | CH₃ | H | CH₂=CHCO | H | Cl | OCH₃ | CH | |
| 247 | CH₃ | H | CH₂=CHCO | H | OCH₃ | OCH₃ | N | |
| 248 | CH₃ | H | CH₂=CHCO | H | OCH₃ | CH₃ | N | |
| 249 | CH₃ | H | CH₂=CHCO | H | OCH₃ | CF₃ | N | |
| 250 | CH₃ | H | CH₂=CHCO | CH₃ | OCH₃ | OCH₃ | CH | |
| 251 | CH₃ | H | CH₂=CHCO | CH₃ | OCH₃ | CH₃ | N | |
| 252 | CH₃ | H | CH≡CCO | H | OCH₃ | OCH₃ | CH | |
| 253 | CH₃ | H | CH≡CCO | H | OCH₃ | CH₃ | CH | |
| 254 | CH₃ | H | CH≡CCO | H | OCH₃ | CH₃ | CH | |

TABLE 1-continued

Compound of the formula (1a)

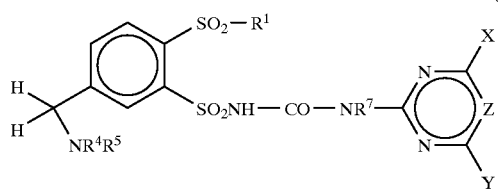

| No. | R¹ | R⁴ | R⁵ | R⁷ | X | Y | Z | mp.(°C.) |
|---|---|---|---|---|---|---|---|---|
| 255 | CH₃ | H | CH≡CCO | H | Cl | OCH₃ | CH | |
| 256 | CH₃ | H | CH≡CCO | H | OCH₃ | OCH₃ | N | |
| 257 | CH₃ | H | CH≡CCO | H | OCH₃ | CH₃ | N | |
| 258 | CH₃ | H | CH≡CCO | H | OCH₃ | CF₃ | N | |
| 259 | CH₃ | H | CH≡CCO | CH₃ | OCH₃ | OCH₃ | CH | |
| 260 | CH₃ | H | CH≡CCO | CH₃ | OCH₃ | CH₃ | N | |
| 261 | CH₃ | H | CO—▷ | H | OCH₃ | OCH₃ | CH | |
| 262 | CH₃ | H | CO—▷ | H | OCH₃ | CH₃ | CH | |
| 263 | CH₃ | H | CO—▷ | H | CH₃ | CH₃ | CH | |
| 264 | CH₃ | H | CO—▷ | H | Cl | OCH₃ | CH | |
| 265 | CH₃ | H | CO—▷ | H | OCH₃ | OCH₃ | N | |
| 266 | CH₃ | H | CO—▷ | H | OCH₃ | CH₃ | N | |
| 267 | CH₃ | H | CO—▷ | H | OCH₃ | CF₃ | N | |
| 268 | CH₃ | H | CO—▷ | CH₃ | OCH₃ | OCH₃ | CH | |
| 269 | CH₃ | H | CO—▷ | CH₃ | OCH₃ | CH₃ | N | |
| 270 | CH₃ | H | CO—◇ | H | OCH₃ | OCH₃ | CH | |

TABLE 1-continued

Compound of the formula (1a)

(Ia)

| No. | R¹ | R⁴ | R⁵ | R⁷ | X | Y | Z | mp.(°C.) |
|-----|-----|-----|-----|-----|-----|-----|-----|-----|
| 271 | CH₃ | H | CO—(cyclobutyl) | H | OCH₃ | CH₃ | CH | |
| 272 | CH₃ | H | CO—(cyclobutyl) | H | CH₃ | CH₃ | CH | |
| 273 | CH₃ | H | CO—(cyclobutyl) | H | Cl | OCH₃ | CH | |
| 274 | CH₃ | H | CO—(cyclobutyl) | H | OCH₃ | OCH₃ | N | |
| 275 | CH₃ | H | CO—(cyclobutyl) | H | OCH₃ | CH₃ | N | |
| 276 | CH₃ | H | CO—(cyclobutyl) | H | OCH₃ | CF₃ | N | |
| 277 | CH₃ | H | CO—(cyclobutyl) | CH₃ | OCH₃ | OCH₃ | CH | |
| 278 | CH₃ | H | CO—(cyclobutyl) | CH₃ | OCH₃ | CH₃ | N | |
| 279 | CH₃ | H | CO—(cyclopentyl) | H | OCH₃ | OCH₃ | CH | |
| 280 | CH₃ | H | CO—(cyclopentyl) | H | OCH₃ | CH₃ | CH | |

TABLE 1-continued

Compound of the formula (1a)

(Ia)

[Structure: benzene ring with SO₂—R¹ substituent, SO₂NH—CO—NR⁷— linked to pyrimidine ring bearing X, Y, Z; and CH₂—NR⁴R⁵ substituent]

| No. | R¹ | R⁴ | R⁵ | R⁷ | X | Y | Z | mp.(°C.) |
|-----|-----|-----|-----|-----|-----|-----|-----|-----|
| 281 | CH₃ | H | CO-cyclopentyl | H | CH₃ | CH₃ | CH | |
| 282 | CH₃ | H | CO-cyclopentyl | H | Cl | OCH₃ | CH | |
| 283 | CH₃ | H | CO-cyclopentyl | H | OCH₃ | OCH₃ | N | |
| 283 | CH₃ | H | CO-cyclopentyl | H | OCH₃ | OCH₃ | N | |
| 284 | CH₃ | H | CO-cyclopentyl | H | OCH₃ | CH₃ | N | |
| 285 | CH₃ | H | CO-cyclopentyl | H | OCH₃ | CF₃ | N | |
| 286 | CH₃ | H | CO-cyclopentyl | CH₃ | OCH₃ | OCH₃ | CH | |
| 287 | CH₃ | H | CO-cyclopentyl | CH₃ | OCH₃ | CH₃ | N | |
| 288 | CH₃ | H | CO-cyclohexyl | H | OCH₃ | OCH₃ | CH | |
| 289 | CH₃ | H | CO-cyclohexyl | H | OCH₃ | CH₃ | CH | |

TABLE 1-continued

Compound of the formula (1a)

(Ia)

[Structure: benzene ring with SO₂-R¹ substituent, SO₂NH-CO-NR⁷ linked to a pyrimidine/triazine ring bearing X, Y, Z substituents; and a CH₂-NR⁴R⁵ group on the benzene ring]

| No. | R¹ | R⁴ | R⁵ | R⁷ | X | Y | Z | mp.(°C.) |
|---|---|---|---|---|---|---|---|---|
| 290 | CH₃ | H | CO-cyclohexyl | H | CH₃ | CH₃ | CH | |
| 291 | CH₃ | H | CO-cyclohexyl | H | Cl | OCH₃ | CH | |
| 292 | CH₃ | H | CO-cyclohexyl | H | OCH₃ | OCH₃ | N | |
| 293 | CH₃ | H | CO-cyclohexyl | H | OCH₃ | CH₃ | N | |
| 294 | CH₃ | H | CO-cyclohexyl | H | OCH₃ | CF₃ | N | |
| 295 | CH₃ | H | CO-cyclohexyl | CH₃ | OCH₃ | OCH₃ | CH | |
| 296 | CH₃ | H | CO-cyclohexyl | CH₃ | OCH₃ | CH₃ | N | |
| 297 | CH₃ | H | CF₃SO₂ | H | OCH₃ | OCH₃ | CH | |
| 298 | CH₃ | H | CF₃SO₂ | H | OCH₃ | CH₃ | CH | |
| 299 | CH₃ | H | CF₃SO₂ | H | CH₃ | CH₃ | CH | |
| 300 | CH₃ | H | CF₃SO₂ | H | Cl | OCH₃ | CH | |
| 301 | CH₃ | H | CF₃SO₂ | H | OCH₃ | OCH₃ | N | |
| 302 | CH₃ | H | CF₃SO₂ | H | OCH₃ | CH₃ | N | |
| 303 | CH₃ | H | CF₃SO₂ | H | OCH₃ | CF₃ | N | |
| 304 | CH₃ | H | CF₃SO₂ | CH₃ | OCH₃ | OCH₃ | CH | |
| 305 | CH₃ | H | CF₃SO₂ | CH₃ | OCH₃ | CH₃ | N | |
| 306 | CH₃ | H | FCH₂SO₂ | H | OCH₃ | OCH₃ | CH | |
| 307 | CH₃ | H | FCH₂SO₂ | H | OCH₃ | CH₃ | CH | |
| 308 | CH₃ | H | FCH₂SO₂ | H | CH₃ | CH₃ | CH | |
| 309 | CH₃ | H | FCH₂SO₂ | H | Cl | OCH₃ | CH | |
| 310 | CH₃ | H | FCH₂SO₂ | H | OCH₃ | OCH₃ | N | |
| 311 | CH₃ | H | FCH₂SO₂ | H | OCH₃ | CH₃ | N | |

TABLE 1-continued

Compound of the formula (1a)

| No. | R¹ | R⁴ | R⁵ | R⁷ | X | Y | Z | mp.(°C.) |
|---|---|---|---|---|---|---|---|---|
| 312 | $CH_3$ | H | $FCH_2SO_2$ | H | $OCH_3$ | $CF_3$ | N | |
| 313 | $CH_3$ | H | $FCH_2SO_2$ | $CH_3$ | $OCH_3$ | $OCH_3$ | CH | |
| 314 | $CH_3$ | H | $FCH_2SO_2$ | $CH_3$ | $OCH_3$ | $CH_3$ | N | |
| 315 | $CH_3$ | H | $ClCH_2SO_2$ | H | $OCH_3$ | $OCH_3$ | CH | |
| 316 | $CH_3$ | H | $ClCH_2SO_2$ | H | $OCH_3$ | $CH_3$ | CH | |
| 317 | $CH_3$ | H | $ClCH_2SO_2$ | H | $CH_3$ | $CH_3$ | CH | |
| 318 | $CH_3$ | H | $ClCH_2SO_2$ | H | Cl | $OCH_3$ | CH | |
| 319 | $CH_3$ | H | $ClCH_2SO_2$ | H | $OCH_3$ | $OCH_3$ | N | |
| 320 | $CH_3$ | H | $ClCH_2SO_2$ | H | $OCH_3$ | $CH_3$ | N | |
| 321 | $CH_3$ | H | $ClCH_2SO_2$ | H | $OCH_3$ | $CF_3$ | N | |
| 322 | $CH_3$ | H | $ClCH_2SO_2$ | $CH_3$ | $OCH_3$ | $OCH_3$ | CH | |
| 323 | $CH_3$ | H | $ClCH_2SO_2$ | $CH_3$ | $OCH_3$ | $CH_3$ | N | |
| 324 | $CH_3$ | H | $ClCH_2SO_2$ | H | $OCH_3$ | $OCH_3$ | CH | |
| 325 | $CH_3$ | H | $ClCH_2SO_2$ | H | $OCH_3$ | $CH_3$ | CH | |
| 326 | $CH_3$ | H | $ClCH_2SO_2$ | H | $CH_3$ | $CH_3$ | CH | |
| 327 | $CH_3$ | H | $ClCH_2SO_2$ | H | Cl | $OCH_3$ | CH | |
| 328 | $CH_3$ | H | $ClCH_2SO_2$ | H | $OCH_3$ | $OCH_3$ | N | |
| 329 | $CH_3$ | H | $ClCH_2SO_2$ | H | $OCH_3$ | $CH_3$ | N | |
| 330 | $CH_3$ | H | $Cl_2CHSO_2$ | H | $OCH_3$ | $CF_3$ | N | |
| 331 | $CH_3$ | H | $Cl_2CHSO_2$ | $CH_3$ | $OCH_3$ | $OCH_3$ | CH | |
| 332 | $CH_3$ | H | $Cl_2CHSO_2$ | $CH_3$ | $OCH_3$ | $CH_3$ | N | |
| 333 | $CH_3$ | H | $Cl_3CSO_2$ | H | $OCH_3$ | $OCH_3$ | CH | |
| 334 | $CH_3$ | H | $Cl_3CSO_2$ | H | $OCH_3$ | $CH_3$ | CH | |
| 335 | $CH_3$ | H | $Cl_3CSO_2$ | H | $CH_3$ | $CH_3$ | CH | |
| 336 | $CH_3$ | H | $Cl_3CSO_2$ | H | Cl | $OCH_3$ | CH | |
| 337 | $CH_3$ | H | $Cl_3CSO_2$ | H | $OCH_3$ | $OCH_3$ | N | |
| 338 | $CH_3$ | H | $Cl_3CSO_2$ | H | $OCH_3$ | $CH_3$ | N | |
| 339 | $CH_3$ | H | $Cl_3CSO_2$ | H | $OCH_3$ | $CF_3$ | N | |
| 340 | $CH_3$ | H | $Cl_3CSO_2$ | $CH_3$ | $OCH_3$ | $OCH_3$ | CH | |
| 341 | $CH_3$ | H | $Cl_3CSO_2$ | $CH_3$ | $OCH_3$ | $CH_3$ | N | |
| 342 | $CH_3$ | H | $nC_4H_9SO_2$ | H | $OCH_3$ | $OCH_3$ | CH | |
| 343 | $CH_3$ | H | $nC_4H_9SO_2$ | H | $OCH_3$ | $CH_3$ | CH | |
| 344 | $CH_3$ | H | $nC_4H_9SO_2$ | H | $CH_3$ | $CH_3$ | CH | |
| 345 | $CH_3$ | H | $nC_4H_9SO_2$ | H | Cl | $OCH_3$ | CH | |
| 346 | $CH_3$ | H | $nC_4H_9SO_2$ | H | $OCH_3$ | $OCH_3$ | N | |
| 347 | $CH_3$ | H | $nC_4H_9SO_2$ | H | $OCH_3$ | $CH_3$ | N | |
| 348 | $CH_3$ | H | $nC_4H_9SO_2$ | H | $OCH_3$ | $CF_3$ | N | |
| 349 | $CH_3$ | H | $nC_4H_9SO_2$ | $CH_3$ | $OCH_3$ | $OCH_3$ | CH | |
| 350 | $CH_3$ | H | $nC_4H_9SO_2$ | $CH_3$ | $OCH_3$ | $CH_3$ | N | |
| 351 | $CH_3$ | H | $CF_3CH_2SO_2$ | H | $OCH_3$ | $OCH_3$ | CH | |
| 352 | $CH_3$ | H | $CF_3CH_2SO_2$ | H | $OCH_3$ | $CH_3$ | CH | |
| 353 | $CH_3$ | H | $CF_3CH_2SO_2$ | H | $CH_3$ | $CH_3$ | CH | |
| 354 | $CH_3$ | H | $CF_3CH_2SO_2$ | H | Cl | $OCH_3$ | CH | |
| 355 | $CH_3$ | H | $CF_3CH_2SO_2$ | H | $OCH_3$ | $OCH_3$ | N | |
| 356 | $CH_3$ | H | $CF_3CH_2SO_2$ | H | $OCH_3$ | $CH_3$ | N | |
| 357 | $CH_3$ | H | $CF_3CH_2SO_2$ | H | $OCH_3$ | $CF_3$ | N | |
| 358 | $CH_3$ | H | $CF_3CH_2SO_2$ | $CH_3$ | $OCH_3$ | $OCH_3$ | CH | |
| 359 | $CH_3$ | H | $CF_3CH_2SO_2$ | $CH_3$ | $OCH_3$ | $CH_3$ | N | |
| 360 | $CH_3$ | H | $CH_3NHSO_2$ | H | $OCH_3$ | $OCH_3$ | CH | |
| 361 | $CH_3$ | H | $CH_3NHSO_2$ | H | $OCH_3$ | $CH_3$ | CH | |
| 362 | $CH_3$ | H | $CH_3NHSO_2$ | H | $CH_3$ | $CH_3$ | CH | |
| 363 | $CH_3$ | H | $CH_3NHSO_2$ | H | Cl | $OCH_3$ | CH | |
| 364 | $CH_3$ | H | $CH_3NHSO_2$ | H | $OCH_3$ | $OCH_3$ | N | |
| 365 | $CH_3$ | H | $CH_3NHSO_2$ | H | $OCH_3$ | $CH_3$ | N | |
| 366 | $CH_3$ | H | $CH_3NHSO_2$ | H | $OCH_3$ | $CF_3$ | N | |
| 367 | $CH_3$ | H | $CH_3NHSO_2$ | $CH_3$ | $OCH_3$ | $OCH_3$ | CH | |
| 368 | $CH_3$ | H | $CH_3NHSO_2$ | $CH_3$ | $OCH_3$ | $CH_3$ | N | |
| 369 | $CH_3$ | H | $Me_2NSO_2$ | H | $OCH_3$ | $OCH_3$ | CH | |
| 370 | $CH_3$ | H | $Me_2NSO_2$ | H | $OCH_3$ | $CH_3$ | CH | |
| 371 | $CH_3$ | H | $Me_2NSO_2$ | H | $CH_3$ | $CH_3$ | CH | |
| 372 | $CH_3$ | H | $Me_2NSO_2$ | H | Cl | $OCH_3$ | CH | |
| 373 | $CH_3$ | H | $Me_2NSO_2$ | H | $OCH_3$ | $OCH_3$ | N | |
| 374 | $CH_3$ | H | $Me_2NSO_2$ | H | $OCH_3$ | $CH_3$ | N | |

TABLE 1-continued

Compound of the formula (1a)

$$\text{(Ia)}$$

Structure: benzene ring with SO$_2$-R$^1$ group, SO$_2$NH-CO-NR$^7$- linked to a pyrimidine ring bearing X, Y, Z substituents, and a CH$_2$-NR$^4$R$^5$ group.

| No. | R$^1$ | R$^4$ | R$^5$ | R$^7$ | X | Y | Z | mp.(°C.) |
|-----|-------|-------|-------|-------|---|---|---|----------|
| 375 | CH$_3$ | H | Me$_2$NSO$_2$ | H | OCH$_3$ | CF$_3$ | N | |
| 376 | CH$_3$ | H | Me$_2$NSO$_2$ | CH$_3$ | OCH$_3$ | OCH$_3$ | CH | |
| 377 | CH$_3$ | H | Me$_2$NSO$_2$ | CH$_3$ | OCH$_3$ | CH$_3$ | N | |
| 378 | CH$_3$ | H | Me$_3$C—OCO | H | OCH$_3$ | OCH$_3$ | CH | |
| 379 | CH$_3$ | H | Me$_3$C—OCO | H | OCH$_3$ | CH$_3$ | CH | |
| 380 | CH$_3$ | H | Me$_3$C—OCO | H | CH$_3$ | CH$_3$ | CH | |
| 381 | CH$_3$ | H | Me$_3$C—OCO | H | Cl | OCH$_3$ | CH | |
| 382 | CH$_3$ | H | Me$_3$C—OCO | H | OCH$_3$ | OCH$_3$ | N | |
| 383 | CH$_3$ | H | Me$_3$C—OCO | H | OCH$_3$ | CH$_3$ | N | |
| 384 | CH$_3$ | H | Me$_3$C—OCO | H | OCH$_3$ | CF$_3$ | N | |
| 385 | CH$_3$ | H | Me$_3$C—OCO | H | OCH$_3$ | OCH$_3$ | CH | |
| 386 | CH$_3$ | H | Me$_3$C—OCO | H | OCH$_3$ | CH$_3$ | N | |
| 387 | CH$_3$ | H | PhCO | H | OCH$_3$ | OCH$_3$ | CH | |
| 388 | CH$_3$ | H | PhCO | H | OCH$_3$ | CH$_3$ | CH | |
| 389 | CH$_3$ | H | PhCO | H | CH$_3$ | CH$_3$ | CH | |
| 390 | CH$_3$ | H | PhCO | H | Cl | OCH$_3$ | CH | |
| 391 | CH$_3$ | H | PhCO | H | OCH$_3$ | OCH$_3$ | N | |
| 392 | CH$_3$ | H | PhCO | H | OCH$_3$ | CH$_3$ | N | |
| 393 | CH$_3$ | H | PhCO | H | OCH$_3$ | CF$_3$ | N | |
| 394 | CH$_3$ | H | PhCO | CH$_3$ | OCH$_3$ | OCH$_3$ | CH | |
| 395 | CH$_3$ | H | PhCO | CH$_3$ | OCH$_3$ | CH$_3$ | N | |
| 396 | CH$_3$ | H | PhSO$_2$ | H | OCH$_3$ | OCH$_3$ | CH | |
| 397 | CH$_3$ | H | PhSO$_2$ | H | OCH$_3$ | CH$_3$ | CH | |
| 398 | CH$_3$ | H | PhSO$_2$ | H | CH$_3$ | CH$_3$ | CH | |
| 399 | CH$_3$ | H | PhSO$_2$ | H | Cl | OCH$_3$ | CH | |
| 400 | CH$_3$ | H | PhSO$_2$ | H | OCH$_3$ | OCH$_3$ | N | |
| 401 | CH$_3$ | H | PhSO$_2$ | H | OCH$_3$ | CH$_3$ | N | |
| 402 | CH$_3$ | H | PhSO$_2$ | H | OCH$_3$ | CF$_3$ | N | |
| 403 | CH$_3$ | H | PhSO$_2$ | CH$_3$ | OCH$_3$ | OCH$_3$ | CH | |
| 404 | CH$_3$ | H | PhSO$_2$ | CH$_3$ | OCH$_3$ | CH$_3$ | N | |
| 405 | CH$_3$ | H | MeNHCO | H | OCH$_3$ | OCH$_3$ | CH | |
| 406 | CH$_3$ | H | MeNHCO | H | OCH$_3$ | CH$_3$ | CH | |
| 407 | CH$_3$ | H | MeNHCO | H | CH$_3$ | CH$_3$ | CH | |
| 408 | CH$_3$ | H | MeNHCO | H | Cl | OCH$_3$ | CH | |
| 409 | CH$_3$ | H | MeNHCO | H | OCH$_3$ | OCH$_3$ | N | |
| 410 | CH$_3$ | H | MeNHCO | H | OCH$_3$ | CH$_3$ | N | |
| 411 | CH$_3$ | H | MeNHCO | H | OCH$_3$ | CF$_3$ | N | |
| 412 | CH$_3$ | H | MeNHCO | CH$_3$ | OCH$_3$ | OCH$_3$ | CH | |
| 413 | CH$_3$ | H | MeNHCO | CH$_3$ | OCH$_3$ | CH$_3$ | N | |
| 414 | CH$_3$ | H | EtNHCO | H | OCH$_3$ | OCH$_3$ | CH | |
| 415 | CH$_3$ | H | EtNHCO | H | OCH$_3$ | CH$_3$ | CH | |
| 416 | CH$_3$ | H | EtNHCO | H | CH$_3$ | CH$_3$ | CH | |
| 417 | CH$_3$ | H | EtNHCO | H | Cl | OCH$_3$ | CH | |
| 418 | CH$_3$ | H | EtNHCO | H | OCH$_3$ | OCH$_3$ | N | |
| 419 | CH$_3$ | H | EtNHCO | H | OCH$_3$ | CH$_3$ | N | |
| 420 | CH$_3$ | H | EtNHCO | H | OCH$_3$ | CF$_3$ | N | |
| 421 | CH$_3$ | H | EtNHCO | CH$_3$ | OCH$_3$ | OCH$_3$ | CH | |
| 422 | CH$_3$ | H | EtNHCO | CH$_3$ | OCH$_3$ | CH$_3$ | N | |
| 423 | CH$_3$ | H | MeNHCS | H | OCH$_3$ | OCH$_3$ | CH | |
| 424 | CH$_3$ | H | MeNHCS | H | OCH$_3$ | CH$_3$ | CH | |
| 425 | CH$_3$ | H | MeNHCS | H | CH$_3$ | CH$_3$ | CH | |
| 426 | CH$_3$ | H | MeNHCS | H | Cl | OCH$_3$ | CH | |
| 427 | CH$_3$ | H | MeNHCS | H | OCH$_3$ | OCH$_3$ | N | |
| 428 | CH$_3$ | H | MeNHCS | H | OCH$_3$ | CH$_3$ | N | |
| 429 | CH$_3$ | H | MeNHCS | H | OCH$_3$ | CF$_3$ | N | |
| 430 | CH$_3$ | H | MeNHCS | CH$_3$ | OCH$_3$ | OCH$_3$ | CH | |
| 431 | CH$_3$ | H | MeNHCS | CH$_3$ | OCH$_3$ | CH$_3$ | N | |
| 432 | CH$_3$ | H | EtNHCS | H | OCH$_3$ | OCH$_3$ | CH | |
| 433 | CH$_3$ | H | EtNHCS | H | OCH$_3$ | CH$_3$ | CH | |
| 434 | CH$_3$ | H | EtNHCS | H | CH$_3$ | CH$_3$ | CH | |
| 435 | CH$_3$ | H | EtNHCS | H | Cl | OCH$_3$ | CH | |
| 436 | CH$_3$ | H | EtNHCS | H | OCH$_3$ | OCH$_3$ | N | |
| 437 | CH$_3$ | H | EtNHCS | H | OCH$_3$ | CH$_3$ | N | |

TABLE 1-continued

Compound of the formula (1a)

$$\text{(Ia)}$$

Structure: benzene ring with $SO_2-R^1$, $SO_2NH-CO-NR^7-$ (pyrimidine with X, Y, Z substituents), and $CH_2-NR^4R^5$ group.

| No. | R¹ | R⁴ | R⁵ | R⁷ | X | Y | Z | mp.(°C.) |
|---|---|---|---|---|---|---|---|---|
| 438 | CH₃ | H | EtNHCS | H | OCH₃ | CF₃ | N | |
| 439 | CH₃ | H | EtNHCS | CH₃ | OCH₃ | OCH₃ | CH | |
| 440 | CH₃ | H | EtNHCS | CH₃ | OCH₃ | CH₃ | N | |
| 441 | CH₃ | \multicolumn{2}{c}{cyclohexanoyl} | H | OCH₃ | OCH₃ | CH | |
| 442 | CH₃ | \multicolumn{2}{c}{cyclohexanoyl} | H | OCH₃ | CH₃ | CH | |
| 443 | CH₃ | \multicolumn{2}{c}{cyclohexanoyl} | H | CH₃ | CH₃ | CH | |
| 444 | CH₃ | \multicolumn{2}{c}{cyclohexanoyl} | H | Cl | OCH₃ | CH | |
| 445 | CH₃ | \multicolumn{2}{c}{cyclohexanoyl} | H | OCH₃ | OCH₃ | N | |
| 446 | CH₃ | \multicolumn{2}{c}{cyclohexanoyl} | H | OCH₃ | CH₃ | N | |
| 447 | CH₃ | \multicolumn{2}{c}{cyclohexanoyl} | H | OCH₃ | CF₃ | N | |
| 448 | CH₃ | \multicolumn{2}{c}{cyclohexanoyl} | CH₃ | OCH₃ | OCH₃ | CH | |
| 449 | CH₃ | \multicolumn{2}{c}{cyclohexanoyl} | CH₃ | OCH₃ | CH₃ | N | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 450 | CH₃ | | cycloheptanone | H | OCH₃ | OCH₃ | CH | |
| 451 | CH₃ | | cycloheptanone | H | OCH₃ | CH₃ | CH | |
| 452 | CH₃ | | cycloheptanone | H | CH₃ | CH₃ | CH | |
| 453 | CH₃ | | cycloheptanone | H | Cl | OCH₃ | CH | |
| 454 | CH₃ | | cycloheptanone | H | OCH₃ | OCH₃ | N | |
| 455 | CH₃ | | cycloheptanone | H | OCH₃ | CH₃ | N | |
| 456 | CH₃ | | cycloheptanone | H | OCH₃ | CF₃ | N | |
| 457 | CH₃ | | cycloheptanone | CH₃ | OCH₃ | OCH₃ | CH | |

TABLE 1-continued

Compound of the formula (1a)

(Ia) structure: benzene ring with SO₂—R¹ (ortho), SO₂NH—CO—NR⁷—(pyrimidine with X, Y, Z), and CH(H)(H)—NR⁴R⁵ substituent; pyrimidine ring bearing X, Y, Z.

| No. | R¹ | R⁴ | R⁵ | R⁷ | X | Y | Z | mp.(°C.) |
|-----|-----|-----|-----|-----|-----|-----|-----|-----|
| 458 | CH₃ | | cycloheptanone (2-oxocycloheptyl) | CH₃ | OCH₃ | CH₃ | N | |
| 459 | CH₃ | | tetrahydrothiopyran-2-yl-1,1-dioxide | H | OCH₃ | OCH₃ | CH | |
| 460 | CH₃ | | tetrahydrothiopyran-2-yl-1,1-dioxide | H | OCH₃ | CH₃ | CH | |
| 461 | CH₃ | | tetrahydrothiopyran-2-yl-1,1-dioxide | H | CH₃ | CH₃ | CH | |
| 462 | CH₃ | | tetrahydrothiopyran-2-yl-1,1-dioxide | H | Cl | OCH₃ | CH | |
| 463 | CH₃ | | tetrahydrothiopyran-2-yl-1,1-dioxide | H | OCH₃ | OCH₃ | N | |
| 464 | CH₃ | | tetrahydrothiopyran-2-yl-1,1-dioxide | H | OCH₃ | CH₃ | N | |
| 465 | CH₃ | | tetrahydrothiopyran-2-yl-1,1-dioxide | H | OCH₃ | CF₃ | N | |
| 466 | CH₃ | | tetrahydrothiopyran-2-yl-1,1-dioxide | CH₃ | OCH₃ | OCH₃ | CH | |

TABLE 1-continued
Compound of the formula (1a)
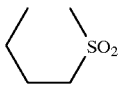
| No. | R¹ | R⁴ | R⁵ | R⁷ | X | Y | Z | mp.(°C.) |
|---|---|---|---|---|---|---|---|---|
| 467 | $CH_3$ | | 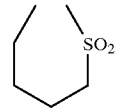 | $CH_3$ | $OCH_3$ | $CH_3$ | N | |
| 468 | $CH_3$ | | 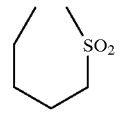 | H | $OCH_3$ | $OCH_3$ | CH | |
| 469 | $CH_3$ | | 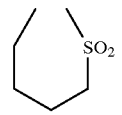 | H | $OCH_3$ | $CH_3$ | CH | |
| 470 | $CH_3$ | | 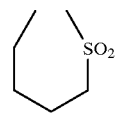 | H | $CH_3$ | $CH_3$ | CH | |
| 471 | $CH_3$ | | 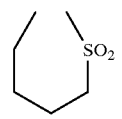 | H | Cl | $OCH_3$ | CH | |
| 472 | $CH_3$ | | 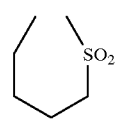 | H | $OCH_3$ | $OCH_3$ | N | |
| 473 | $CH_3$ | | 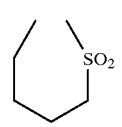 | H | $OCH_3$ | $CH_3$ | N | |
| 474 | $CH_3$ | |  | H | $OCH_3$ | $CF_3$ | N | |

TABLE 1-continued

Compound of the formula (1a)

$$\text{(Ia)}$$

Structure: benzene ring with $SO_2-R^1$ at one position, $SO_2NH-CO-NR^7$- connected to pyrimidine ring bearing X, Y, Z substituents, and $-CH_2-NR^4R^5$ group on benzene.

| No. | R¹ | R⁴ | R⁵ | R⁷ | X | Y | Z | mp.(°C.) |
|-----|-----|-----|-----|-----|-----|-----|-----|----------|
| 475 | CH₃ | | (cycloalkyl-SO₂) | CH₃ | OCH₃ | OCH₃ | CH | |
| 476 | CH₃ | | (cycloalkyl-SO₂) | CH₃ | OCH₃ | CH₃ | N | |
| 477 | CH₃ | | (tetrahydropyranyl, O) | H | OCH₃ | OCH₃ | CH | |
| 478 | CH₃ | | (tetrahydropyranyl, O) | H | OCH₃ | CH₃ | CH | |
| 479 | CH₃ | | (tetrahydropyranyl, O) | H | CH₃ | CH₃ | CH | |
| 480 | CH₃ | | (tetrahydropyranyl, O) | H | Cl | OCH₃ | CH | |
| 481 | CH₃ | | (tetrahydropyranyl, O) | H | OCH₃ | OCH₃ | N | |
| 482 | CH₃ | | (tetrahydropyranyl, O) | H | OCH₃ | CH₃ | N | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 483 | $CH_3$ | | tetrahydropyranyl | H | $OCH_3$ | $CF_3$ | N | |
| 484 | $CH_3$ | | tetrahydropyranyl | $CH_3$ | $OCH_3$ | $OCH_3$ | CH | |
| 485 | $CH_3$ | | tetrahydropyranyl | $CH_3$ | $OCH_3$ | $CH_3$ | N | |
| 486 | $CH_3$ | H | $COSCH_3$ | H | $OCH_3$ | $OCH_3$ | CH | |
| 487 | $CH_3$ | H | $COSCH_3$ | H | $OCH_3$ | $CH_3$ | CH | |
| 488 | $CH_3$ | H | $COSCH_3$ | H | $CH_3$ | $CH_3$ | CH | |
| 489 | $CH_3$ | H | $COSCH_3$ | H | Cl | $OCH_3$ | CH | |
| 490 | $CH_3$ | H | $COSCH_3$ | H | $OCH_3$ | $OCH_3$ | N | |
| 491 | $CH_3$ | H | $COSCH_3$ | H | $OCH_3$ | $CH_3$ | N | |
| 492 | $CH_3$ | H | $COSCH_3$ | H | $OCH_3$ | $CF_3$ | N | |
| 493 | $CH_3$ | H | $COSCH_3$ | $CH_3$ | $OCH_3$ | $OCH_3$ | CH | |
| 494 | $CH_3$ | H | $COSCH_3$ | $CH_3$ | $OCH_3$ | $CH_3$ | N | |
| 495 | $CH_3$ | H | $COSCH_3$ | H | $OCH_3$ | $OCH_3$ | CH | |
| 496 | $CH_3$ | H | $COSCH_3$ | H | $OCH_3$ | $CH_3$ | CH | |
| 497 | $CH_3$ | H | $COSCH_3$ | H | $CH_3$ | $CH_3$ | CH | |
| 498 | $CH_3$ | H | $COSCH_3$ | H | Cl | $OCH_3$ | CH | |
| 499 | $CH_3$ | H | $COSCH_3$ | H | $OCH_3$ | $OCH_3$ | N | |
| 500 | $CH_3$ | H | $COSCH_3$ | H | $OCH_3$ | $CH_3$ | N | |
| 501 | $CH_3$ | H | $COSCH_3$ | H | $OCH_3$ | $CF_3$ | N | |
| 502 | $CH_3$ | H | $CSOCH_3$ | $CH_3$ | $OCH_3$ | $OCH_3$ | CH | |
| 503 | $CH_3$ | H | $CSOCH_3$ | $CH_3$ | $OCH_3$ | $CH_3$ | N | |
| 504 | $CH_3$ | H | $CSSCH_3$ | H | $OCH_3$ | $OCH_3$ | CH | |
| 505 | $CH_3$ | H | $CSSCH_3$ | H | $OCH_3$ | $CH_3$ | CH | |
| 506 | $CH_3$ | H | $CSSCH_3$ | H | $CH_3$ | $CH_3$ | CH | |
| 507 | $CH_3$ | H | $CSSCH_3$ | H | Cl | $OCH_3$ | CH | |
| 508 | $CH_3$ | H | $CSSCH_3$ | H | $OCH_3$ | $OCH_3$ | N | |
| 509 | $CH_3$ | H | $CSSCH_3$ | H | $OCH_3$ | $CH_3$ | N | |
| 510 | $CH_3$ | H | $CSSCH_3$ | H | $OCH_3$ | $CF_3$ | N | |
| 511 | $CH_3$ | H | $CSSCH_3$ | $CH_3$ | $OCH_3$ | $OCH_3$ | CH | |
| 512 | $CH_3$ | H | $CSSCH_3$ | $CH_3$ | $OCH_3$ | $CH_3$ | N | |
| 513 | $CH_3$ | H | $COCOOCH_3$ | H | $OCH_3$ | $OCH_3$ | CH | |
| 514 | $CH_3$ | H | $COCOOCH_3$ | H | $OCH_3$ | $CH_3$ | CH | |
| 515 | $CH_3$ | H | $COCOOCH_3$ | H | $CH_3$ | $CH_3$ | CH | |
| 516 | $CH_3$ | H | $COCOOCH_3$ | H | Cl | $OCH_3$ | CH | |
| 517 | $CH_3$ | H | $COCOOCH_3$ | H | $OCH_3$ | $OCH_3$ | N | |
| 518 | $CH_3$ | H | $COCOOCH_3$ | H | $OCH_3$ | $CH_3$ | N | |
| 519 | $CH_3$ | H | $COCOOCH_3$ | H | $OCH_3$ | $CF_3$ | N | |
| 520 | $CH_3$ | H | $COCOOCH_3$ | $CH_3$ | $OCH_3$ | $OCH_3$ | CH | |
| 521 | $CH_3$ | H | $COCOOCH_3$ | $CH_3$ | $OCH_3$ | $CH_3$ | N | |
| 522 | $CH_3$ | H | $i-C_3H_7OCO$ | H | $OCH_3$ | $OCH_3$ | CH | |
| 523 | $CH_3$ | H | $i-C_3H_7OCO$ | H | $OCH_3$ | $CH_3$ | CH | |

TABLE 1-continued

Compound of the formula (1a)

$$\text{(Ia)}$$

| No. | $R^1$ | $R^4$ | $R^5$ | $R^7$ | X | Y | Z | mp.(°C.) |
|---|---|---|---|---|---|---|---|---|
| 524 | $CH_3$ | H | i-$C_3H_7$OCO | H | $CH_3$ | $CH_3$ | CH | |
| 525 | $CH_3$ | H | i-$C_3H_7$OCO | H | Cl | $OCH_3$ | CH | |
| 526 | $CH_3$ | H | i-$C_3H_7$OCO | H | $OCH_3$ | $OCH_3$ | N | |
| 527 | $CH_3$ | H | i-$C_3H_7$OCO | H | $OCH_3$ | $CH_3$ | N | |
| 528 | $CH_3$ | H | i-$C_3H_7$OCO | H | $OCH_3$ | $CF_3$ | N | |
| 529 | $CH_3$ | H | i-$C_3H_7$OCO | $CH_3$ | $OCH_3$ | $OCH_3$ | CH | |
| 530 | $CH_3$ | H | i-$C_3H_7$OCO | $CH_3$ | $OCH_3$ | $CH_3$ | N | |
| 531 | $CH_3$ | $CH_3$ | CHO | H | $OCH_3$ | $OCH_3$ | CH | 180–182 |
| 532 | $CH_3$ | $CH_3$ | CHO | H | $OCH_3$ | $CH_3$ | CH | |
| 533 | $CH_3$ | $CH_3$ | CHO | H | $CH_3$ | $CH_3$ | CH | |
| 534 | $CH_3$ | $CH_3$ | CHO | H | $CH_3$ | $OC_2H_5$ | CH | |
| 535 | $CH_3$ | $CH_3$ | CHO | H | $C_2H_5$ | $OCH_3$ | CH | |
| 536 | $CH_3$ | $CH_3$ | CHO | H | $OC_2H_5$ | $OC_2H_5$ | CH | |
| 537 | $CH_3$ | $CH_3$ | CHO | H | $OCHF_2$ | $OCHF_2$ | CH | |
| 538 | $CH_3$ | $CH_3$ | CHO | H | $CH_3$ | $OCHF_2$ | CH | |
| 539 | $CH_3$ | $CH_3$ | CHO | H | Cl | $OCH_3$ | CH | |
| 540 | $CH_3$ | $CH_3$ | CHO | H | $OCH_3$ | $OCH_3$ | N | |
| 541 | $CH_3$ | $CH_3$ | CHO | H | $OCH_3$ | $CH_3$ | N | |
| 542 | $CH_3$ | $CH_3$ | CHO | H | $CH_3$ | $CH_3$ | N | |
| 543 | $CH_3$ | $CH_3$ | CHO | H | $N(CH_3)_2$ | $OCH_2CF_3$ | N | |
| 544 | $CH_3$ | $CH_3$ | CHO | H | $OCH_3$ | $CF_3$ | N | |
| 545 | $CH_3$ | $CH_3$ | CHO | H | $OC_2H_5$ | $NHCH_3$ | N | |
| 546 | $CH_3$ | $CH_3$ | CHO | $CH_3$ | $OCH_3$ | $OCH_3$ | CH | |
| 547 | $CH_3$ | $CH_3$ | CHO | $CH_3$ | $OCH_3$ | $CH_3$ | N | |
| 548 | $CH_3$ | $CH_3$ | $COCH_3$ | H | $OCH_3$ | $OCH_3$ | CH | 133–136 |
| 549 | $CH_3$ | $CH_3$ | $COCH_3$ | H | $OCH_3$ | $CH_3$ | CH | |
| 550 | $CH_3$ | $CH_3$ | $COCH_3$ | H | $CH_3$ | $CH_3$ | CH | |
| 551 | $CH_3$ | $CH_3$ | $COCH_3$ | H | $CH_3$ | $OC_2H_5$ | CH | |
| 552 | $CH_3$ | $CH_3$ | $COCH_3$ | H | $C_2H_5$ | $OCH_3$ | CH | |
| 553 | $CH_3$ | $CH_3$ | $COCH_3$ | H | $OC_2H_5$ | $OC_2H_5$ | CH | |
| 554 | $CH_3$ | $CH_3$ | $COCH_3$ | H | $OCHF_2$ | $OCHF_2$ | CH | |
| 555 | $CH_3$ | $CH_3$ | $COCH_3$ | H | $CH_3$ | $OCHF_2$ | CH | |
| 556 | $CH_3$ | $CH_3$ | $COCH_3$ | H | Cl | $OCH_3$ | CH | |
| 557 | $CH_3$ | $CH_3$ | $COCH_3$ | H | $OCH_3$ | $OCH_3$ | N | |
| 558 | $CH_3$ | $CH_3$ | $COCH_3$ | H | $OCH_3$ | $CH_3$ | N | |
| 559 | $CH_3$ | $CH_3$ | $COCH_3$ | H | $CH_3$ | $CH_3$ | N | |
| 560 | $CH_3$ | $CH_3$ | $COCH_3$ | H | $N(CH_3)_2$ | $OCH_2CF_3$ | N | |
| 561 | $CH_3$ | $CH_3$ | $COCH_3$ | H | $OCH_3$ | $CF_3$ | N | |
| 562 | $CH_3$ | $CH_3$ | $COCH_3$ | H | $OC_2H_5$ | $NHCH_3$ | N | |
| 563 | $CH_3$ | $CH_3$ | $COCH_3$ | $CH_3$ | $OCH_3$ | $OCH_3$ | CH | |
| 564 | $CH_3$ | $CH_3$ | $COCH_3$ | $CH_3$ | $OCH_3$ | $CH_3$ | N | |
| 565 | $CH_3$ | $CH_3$ | $COC_2H_5$ | H | $OCH_3$ | $OCH_3$ | CH | 182–185 |
| 566 | $CH_3$ | $CH_3$ | $COC_2H_5$ | H | $OCH_3$ | $CH_3$ | CH | |
| 567 | $CH_3$ | $CH_3$ | $COC_2H_5$ | H | $CH_3$ | $CH_3$ | CH | |
| 568 | $CH_3$ | $CH_3$ | $COC_2H_5$ | H | $CH_3$ | $OC_2H_5$ | CH | |
| 569 | $CH_3$ | $CH_3$ | $COC_2H_5$ | H | $C_2H_5$ | $OCH_3$ | CH | |
| 570 | $CH_3$ | $CH_3$ | $COC_2H_5$ | H | $OC_2H_5$ | $OC_2H_5$ | CH | |
| 571 | $CH_3$ | $CH_3$ | $COC_2H_5$ | H | $OCHF_2$ | $OCHF_2$ | CH | |
| 572 | $CH_3$ | $CH_3$ | $COC_2H_5$ | H | $CH_3$ | $OCHF_2$ | CH | |
| 573 | $CH_3$ | $CH_3$ | $COC_2H_5$ | H | Cl | $OCH_3$ | CH | |
| 574 | $CH_3$ | $CH_3$ | $COC_2H_5$ | H | $OCH_3$ | $OCH_3$ | N | |
| 575 | $CH_3$ | $CH_3$ | $COC_2H_5$ | H | $OCH_3$ | $CH_3$ | N | |
| 576 | $CH_3$ | $CH_3$ | $COC_2H_5$ | H | $CH_3$ | $CH_3$ | N | |
| 577 | $CH_3$ | $CH_3$ | $COC_2H_5$ | H | $N(CH_3)_2$ | $OCH_2CF_3$ | N | |
| 578 | $CH_3$ | $CH_3$ | $COC_2H_5$ | H | $OCH_3$ | $CF_3$ | N | |
| 579 | $CH_3$ | $CH_3$ | $COC_2H_5$ | H | $OC_2H_5$ | $NHCH_3$ | N | |
| 580 | $CH_3$ | $CH_3$ | $COC_2H_5$ | $CH_3$ | $OCH_3$ | $OCH_3$ | CH | |
| 581 | $CH_3$ | $CH_3$ | $COC_2H_5$ | $CH_3$ | $OCH_3$ | $CH_3$ | N | |
| 582 | $CH_3$ | $CH_3$ | CO-n-$C_3H_7$ | H | $OCH_3$ | $OCH_3$ | CH | |
| 583 | $CH_3$ | $CH_3$ | CO-n-$C_3H_7$ | H | $OCH_3$ | $CH_3$ | CH | |
| 584 | $CH_3$ | $CH_3$ | CO-n-$C_3H_7$ | H | $CH_3$ | $CH_3$ | CH | |
| 585 | $CH_3$ | $CH_3$ | CO-n-$C_3H_7$ | H | $CH_3$ | $OC_2H_5$ | CH | |
| 586 | $CH_3$ | $CH_3$ | CO-n-$C_3H_7$ | H | $C_2H_5$ | $OCH_3$ | CH | |

TABLE 1-continued

Compound of the formula (1a)

$$\text{(Ia)}$$

Structure: benzene ring with SO$_2$–R$^1$ at one position, SO$_2$NH–CO–NR$^7$– linked to a pyrimidine ring bearing X, Y, Z substituents; and a CH$_2$NR$^4$R$^5$ group on the benzene ring.

| No. | R$^1$ | R$^4$ | R$^5$ | R$^7$ | X | Y | Z | mp.(°C.) |
|---|---|---|---|---|---|---|---|---|
| 587 | CH$_3$ | CH$_3$ | CO-n-C$_3$H$_7$ | H | OC$_2$H$_5$ | OC$_2$H$_5$ | CH | |
| 588 | CH$_3$ | CH$_3$ | CO-n-C$_3$H$_7$ | H | OCHF$_2$ | OCHF$_2$ | CH | |
| 589 | CH$_3$ | CH$_3$ | CO-n-C$_3$H$_7$ | H | CH$_3$ | OCHF$_2$ | CH | |
| 590 | CH$_3$ | CH$_3$ | CO-n-C$_3$H$_7$ | H | Cl | OCH$_3$ | CH | |
| 591 | CH$_3$ | CH$_3$ | CO-n-C$_3$H$_7$ | H | OCH$_3$ | OCH$_3$ | N | |
| 592 | CH$_3$ | CH$_3$ | CO-n-C$_3$H$_7$ | H | OCH$_3$ | CH$_3$ | N | |
| 593 | CH$_3$ | CH$_3$ | CO-n-C$_3$H$_7$ | H | CH$_3$ | CH$_3$ | N | |
| 594 | CH$_3$ | CH$_3$ | CO-n-C$_3$H$_7$ | H | N(CH$_3$)$_2$ | OCH$_2$CF$_3$ | N | |
| 595 | CH$_3$ | CH$_3$ | CO-n-C$_3$H$_7$ | H | OCH$_3$ | CF$_3$ | N | |
| 596 | CH$_3$ | CH$_3$ | CO-n-C$_3$H$_7$ | H | OC$_2$H$_5$ | NHCH$_3$ | N | |
| 597 | CH$_3$ | CH$_3$ | CO-n-C$_3$H$_7$ | CH$_3$ | OCH$_3$ | OCH$_3$ | CH | |
| 598 | CH$_3$ | CH$_3$ | CO-n-C$_3$H$_7$ | CH$_3$ | OCH$_3$ | CH$_3$ | N | |
| 599 | CH$_3$ | CH$_3$ | CO-i-C$_3$H$_7$ | H | OCH$_3$ | OCH$_3$ | CH | 186–188 |
| 600 | CH$_3$ | CH$_3$ | CO-i-C$_3$H$_7$ | H | OCH$_3$ | CH$_3$ | CH | |
| 601 | CH$_3$ | CH$_3$ | CO-i-C$_3$H$_7$ | H | CH$_3$ | CH$_3$ | CH | |
| 602 | CH$_3$ | CH$_3$ | CO-i-C$_3$H$_7$ | H | CH$_3$ | OC$_2$H$_5$ | CH | |
| 603 | CH$_3$ | CH$_3$ | CO-i-C$_3$H$_7$ | H | C$_2$H$_5$ | OCH$_3$ | CH | |
| 604 | CH$_3$ | CH$_3$ | CO-i-C$_3$H$_7$ | H | OC$_2$H$_5$ | OC$_2$H$_5$ | CH | |
| 605 | CH$_3$ | CH$_3$ | CO-i-C$_3$H$_7$ | H | OCHF$_2$ | OCHF$_2$ | CH | |
| 606 | CH$_3$ | CH$_3$ | CO-i-C$_3$H$_7$ | H | CH$_3$ | OCHF$_2$ | CH | |
| 607 | CH$_3$ | CH$_3$ | CO-i-C$_3$H$_7$ | H | Cl | OCH$_3$ | CH | |
| 608 | CH$_3$ | CH$_3$ | CO-i-C$_3$H$_7$ | H | OCH$_3$ | OCH$_3$ | N | |
| 609 | CH$_3$ | CH$_3$ | CO-i-C$_3$H$_7$ | H | OCH$_3$ | CH$_3$ | N | |
| 610 | CH$_3$ | CH$_3$ | CO-i-C$_3$H$_7$ | H | CH$_3$ | CH$_3$ | N | |
| 611 | CH$_3$ | CH$_3$ | CO-i-C$_3$H$_7$ | H | N(CH$_3$)$_2$ | OCH$_2$CF$_3$ | N | |
| 612 | CH$_3$ | CH$_3$ | CO-i-C$_3$H$_7$ | H | OCH$_3$ | CF$_3$ | N | |
| 613 | CH$_3$ | CH$_3$ | CO-i-C$_3$H$_7$ | H | OC$_2$H$_5$ | NHCH$_3$ | N | |
| 614 | CH$_3$ | CH$_3$ | CO-i-C$_3$H$_7$ | CH$_3$ | OCH$_3$ | OCH$_3$ | CH | |
| 615 | CH$_3$ | CH$_3$ | CO-i-C$_3$H$_7$ | CH$_3$ | OCH$_3$ | CH$_3$ | N | |
| 616 | CH$_3$ | CH$_3$ | COCF$_3$ | H | OCH$_3$ | OCH$_3$ | CH | 133–136 |
| 617 | CH$_3$ | CH$_3$ | COCF$_3$ | H | OCH$_3$ | CH$_3$ | CH | |
| 618 | CH$_3$ | CH$_3$ | COCF$_3$ | H | CH$_3$ | CH$_3$ | CH | |
| 619 | CH$_3$ | CH$_3$ | COCF$_3$ | H | CH$_3$ | OC$_2$H$_5$ | CH | |
| 620 | CH$_3$ | CH$_3$ | COCF$_3$ | H | C$_2$H$_5$ | OCH$_3$ | CH | |
| 621 | CH$_3$ | CH$_3$ | COCF$_3$ | H | OC$_2$H$_5$ | OC$_2$H$_5$ | CH | |
| 622 | CH$_3$ | CH$_3$ | COCF$_3$ | H | OCHF$_2$ | OCHF$_2$ | CH | |
| 623 | CH$_3$ | CH$_3$ | COCF$_3$ | H | CH$_3$ | OCHF$_2$ | CH | |
| 624 | CH$_3$ | CH$_3$ | COCF$_3$ | H | Cl | OCH$_3$ | CH | |
| 625 | CH$_3$ | CH$_3$ | COCF$_3$ | H | OCH$_3$ | OCH$_3$ | N | |
| 626 | CH$_3$ | CH$_3$ | COCF$_3$ | H | OCH$_3$ | CH$_3$ | N | |
| 627 | CH$_3$ | CH$_3$ | COCF$_3$ | H | CH$_3$ | CH$_3$ | N | |
| 628 | CH$_3$ | CH$_3$ | COCF$_3$ | H | N(CH$_3$)$_2$ | OCH$_2$CF$_3$ | N | |
| 629 | CH$_3$ | CH$_3$ | COCF$_3$ | H | OCH$_3$ | CF$_3$ | N | |
| 630 | CH$_3$ | CH$_3$ | COCF$_3$ | H | OC$_2$H$_5$ | NHCH$_3$ | N | |
| 631 | CH$_3$ | CH$_3$ | COCF$_3$ | CH$_3$ | OCH$_3$ | OCH$_3$ | CH | |
| 632 | CH$_3$ | CH$_3$ | COCF$_3$ | CH$_3$ | OCH$_3$ | CH$_3$ | N | |
| 633 | CH$_3$ | CH$_3$ | COOCH$_3$ | H | OCH$_3$ | OCH$_3$ | CH | 105–111 |
| 634 | CH$_3$ | CH$_3$ | COOCH$_3$ | H | OCH$_3$ | CH$_3$ | CH | |
| 635 | CH$_3$ | CH$_3$ | COOCH$_3$ | H | CH$_3$ | CH$_3$ | CH | |
| 636 | CH$_3$ | CH$_3$ | COOCH$_3$ | H | CH$_3$ | OC$_2$H$_5$ | CH | |
| 637 | CH$_3$ | CH$_3$ | COOCH$_3$ | H | C$_2$H$_5$ | OCH$_3$ | CH | |
| 638 | CH$_3$ | CH$_3$ | COOCH$_3$ | H | OC$_2$H$_5$ | OC$_2$H$_5$ | CH | |
| 639 | CH$_3$ | CH$_3$ | COOCH$_3$ | H | OCHF$_2$ | OCHF$_2$ | CH | |
| 640 | CH$_3$ | CH$_3$ | COOCH$_3$ | H | CH$_3$ | OCHF$_2$ | CH | |
| 641 | CH$_3$ | CH$_3$ | COOCH$_3$ | H | Cl | OCH$_3$ | CH | |
| 642 | CH$_3$ | CH$_3$ | COOCH$_3$ | H | OCH$_3$ | OCH$_3$ | N | |
| 643 | CH$_3$ | CH$_3$ | COOCH$_3$ | H | OCH$_3$ | CH$_3$ | N | |
| 644 | CH$_3$ | CH$_3$ | COOCH$_3$ | H | CH$_3$ | CH$_3$ | N | |
| 645 | CH$_3$ | CH$_3$ | COOCH$_3$ | H | N(CH$_3$)$_2$ | OCH$_2$CF$_3$ | N | |
| 646 | CH$_3$ | CH$_3$ | COOCH$_3$ | H | OCH$_3$ | CF$_3$ | N | |
| 647 | CH$_3$ | CH$_3$ | COOCH$_3$ | H | OC$_2$H$_5$ | NHCH$_3$ | N | |
| 648 | CH$_3$ | CH$_3$ | COOCH$_3$ | CH$_3$ | OCH$_3$ | OCH$_3$ | CH | |
| 649 | CH$_3$ | CH$_3$ | COOCH$_3$ | CH$_3$ | OCH$_3$ | CH$_3$ | N | |

TABLE 1-continued

Compound of the formula (1a)

$$\text{(Ia)}$$

| No. | $R^1$ | $R^4$ | $R^5$ | $R^7$ | X | Y | Z | mp.(°C.) |
|---|---|---|---|---|---|---|---|---|
| 650 | $CH_3$ | $CH_3$ | $COOC_2H_5$ | H | $OCH_3$ | $OCH_3$ | CH | 227–229 |
| 651 | $CH_3$ | $CH_3$ | $COOC_2H_5$ | H | $OCH_3$ | $CH_3$ | CH | |
| 652 | $CH_3$ | $CH_3$ | $COOC_2H_5$ | H | $CH_3$ | $CH_3$ | CH | |
| 653 | $CH_3$ | $CH_3$ | $COOC_2H_5$ | H | $CH_3$ | $OC_2H_5$ | CH | |
| 654 | $CH_3$ | $CH_3$ | $COOC_2H_5$ | H | $C_2H_5$ | $OCH_3$ | CH | |
| 655 | $CH_3$ | $CH_3$ | $COOC_2H_5$ | H | $OC_2H_5$ | $OC_2H_5$ | CH | |
| 656 | $CH_3$ | $CH_3$ | $COOC_2H_5$ | H | $OCHF_2$ | $OCHF_2$ | CH | |
| 657 | $CH_3$ | $CH_3$ | $COOC_2H_5$ | H | $CH_3$ | $OCHF_2$ | CH | |
| 658 | $CH_3$ | $CH_3$ | $COOC_2H_5$ | H | Cl | $OCH_3$ | CH | |
| 659 | $CH_3$ | $CH_3$ | $COOC_2H_5$ | H | $OCH_3$ | $OCH_3$ | N | |
| 660 | $CH_3$ | $CH_3$ | $COOC_2H_5$ | H | $OCH_3$ | $CH_3$ | N | |
| 661 | $CH_3$ | $CH_3$ | $COOC_2H_5$ | H | $CH_3$ | $CH_3$ | N | |
| 662 | $CH_3$ | $CH_3$ | $COOC_2H_5$ | H | $N(CH_3)_2$ | $OCH_2CF_3$ | N | |
| 663 | $CH_3$ | $CH_3$ | $COOC_2H_5$ | H | $OCH_3$ | $CF_3$ | N | |
| 664 | $CH_3$ | $CH_3$ | $COOC_2H_5$ | H | $OC_2H_5$ | $NHCH_3$ | N | |
| 665 | $CH_3$ | $CH_3$ | $COOC_2H_5$ | $CH_3$ | $OCH_3$ | $OCH_3$ | CH | |
| 666 | $CH_3$ | $CH_3$ | $COOC_2H_5$ | $CH_3$ | $OCH_3$ | $CH_3$ | N | |
| 667 | $CH_3$ | $CH_3$ | $SO_2CH_3$ | H | $OCH_3$ | $OCH_3$ | CH | 205–210 |
| 668 | $CH_3$ | $CH_3$ | $SO_2CH_3$ | H | $OCH_3$ | $CH_3$ | CH | |
| 669 | $CH_3$ | $CH_3$ | $SO_2CH_3$ | H | $CH_3$ | $CH_3$ | CH | |
| 670 | $CH_3$ | $CH_3$ | $SO_2CH_3$ | H | $CH_3$ | $OC_2H_5$ | CH | |
| 671 | $CH_3$ | $CH_3$ | $SO_2CH_3$ | H | $C_2H_5$ | $OCH_3$ | CH | |
| 672 | $CH_3$ | $CH_3$ | $SO_2CH_3$ | H | $OC_2H_5$ | $OC_2H_5$ | CH | |
| 673 | $CH_3$ | $CH_3$ | $SO_2CH_3$ | H | $OCHF_2$ | $OCHF_2$ | CH | |
| 674 | $CH_3$ | $CH_3$ | $SO_2CH_3$ | H | $CH_3$ | $OCHF_2$ | CH | |
| 675 | $CH_3$ | $CH_3$ | $SO_2CH_3$ | H | Cl | $OCH_3$ | CH | |
| 676 | $CH_3$ | $CH_3$ | $SO_2CH_3$ | H | $OCH_3$ | $OCH_3$ | N | |
| 677 | $CH_3$ | $CH_3$ | $SO_2CH_3$ | H | $OCH_3$ | $CH_3$ | N | |
| 678 | $CH_3$ | $CH_3$ | $SO_2CH_3$ | H | $CH_3$ | $CH_3$ | N | |
| 679 | $CH_3$ | $CH_3$ | $SO_2CH_3$ | H | $N(CH_3)_2$ | $OCH_2CF_3$ | N | |
| 680 | $CH_3$ | $CH_3$ | $SO_2CH_3$ | H | $OCH_3$ | $CF_3$ | N | |
| 681 | $CH_3$ | $CH_3$ | $SO_2CH_3$ | H | $OC_2H_5$ | $NHCH_3$ | N | |
| 682 | $CH_3$ | $CH_3$ | $SO_2CH_3$ | $CH_3$ | $OCH_3$ | $OCH_3$ | CH | |
| 683 | $CH_3$ | $CH_3$ | $SO_2CH_3$ | $CH_3$ | $OCH_3$ | $CH_3$ | N | |
| 684 | $CH_3$ | $CH_3$ | $SO_2C_2H_5$ | H | $OCH_3$ | $OCH_3$ | CH | 206–208 |
| 685 | $CH_3$ | $CH_3$ | $SO_2C_2H_5$ | H | $OCH_3$ | $CH_3$ | CH | |
| 686 | $CH_3$ | $CH_3$ | $SO_2C_2H_5$ | H | $CH_3$ | $CH_3$ | CH | |
| 687 | $CH_3$ | $CH_3$ | $SO_2C_2H_5$ | H | $CH_3$ | $OC_2H_5$ | CH | |
| 688 | $CH_3$ | $CH_3$ | $SO_2C_2H_5$ | H | $C_2H_5$ | $OCH_3$ | CH | |
| 689 | $CH_3$ | $CH_3$ | $SO_2C_2H_5$ | H | $OC_2H_5$ | $OC_2H_5$ | CH | |
| 690 | $CH_3$ | $CH_3$ | $SO_2C_2H_5$ | H | $OCHF_2$ | $OCHF_2$ | CH | |
| 691 | $CH_3$ | $CH_3$ | $SO_2C_2H_5$ | H | $CH_3$ | $OCHF_2$ | CH | |
| 692 | $CH_3$ | $CH_3$ | $SO_2C_2H_5$ | H | Cl | $OCH_3$ | CH | |
| 693 | $CH_3$ | $CH_3$ | $SO_2C_2H_5$ | H | $OCH_3$ | $OCH_3$ | N | |
| 694 | $CH_3$ | $CH_3$ | $SO_2C_2H_5$ | H | $OCH_3$ | $CH_3$ | N | |
| 695 | $CH_3$ | $CH_3$ | $SO_2C_2H_5$ | H | $CH_3$ | $CH_3$ | N | |
| 696 | $CH_3$ | $CH_3$ | $SO_2C_2H_5$ | H | $N(CH_3)_2$ | $OCH_2CF_3$ | N | |
| 697 | $CH_3$ | $CH_3$ | $SO_2C_2H_5$ | H | $OCH_3$ | $CF_3$ | N | |
| 698 | $CH_3$ | $CH_3$ | $SO_2C_2H_5$ | H | $OC_2H_5$ | $NHCH_3$ | N | |
| 699 | $CH_3$ | $CH_3$ | $SO_2C_2H_5$ | $CH_3$ | $OCH_3$ | $OCH_3$ | CH | |
| 700 | $CH_3$ | $CH_3$ | $SO_2C_2H_5$ | $CH_3$ | $OCH_3$ | $CH_3$ | N | |
| 701 | $CH_3$ | $CH_3$ | $SO_2$-n-$C_3H_7$ | H | $OCH_3$ | $OCH_3$ | CH | |
| 702 | $CH_3$ | $CH_3$ | $SO_2$-n-$C_3H_7$ | H | $OCH_3$ | $CH_3$ | CH | |
| 703 | $CH_3$ | $CH_3$ | $SO_2$-n-$C_3H_7$ | H | $CH_3$ | $CH_3$ | CH | |
| 704 | $CH_3$ | $CH_3$ | $SO_2$-n-$C_3H_7$ | H | $CH_3$ | $OC_2H_5$ | CH | |
| 705 | $CH_3$ | $CH_3$ | $SO_2$-n-$C_3H_7$ | H | $C_2H_5$ | $OCH_3$ | CH | |
| 706 | $CH_3$ | $CH_3$ | $SO_2$-n-$C_3H_7$ | H | $OC_2H_5$ | $OC_2H_5$ | CH | |
| 707 | $CH_3$ | $CH_3$ | $SO_2$-n-$C_3H_7$ | H | $OCHF_2$ | $OCHF_2$ | CH | |
| 708 | $CH_3$ | $CH_3$ | $SO_2$-n-$C_3H_7$ | H | $CH_3$ | $OCHF_2$ | CH | |
| 709 | $CH_3$ | $CH_3$ | $SO_2$-n-$C_3H_7$ | H | Cl | $OCH_3$ | CH | |
| 710 | $CH_3$ | $CH_3$ | $SO_2$-n-$C_3H_7$ | H | $OCH_3$ | $OCH_3$ | N | |
| 711 | $CH_3$ | $CH_3$ | $SO_2$-n-$C_3H_7$ | H | $OCH_3$ | $CH_3$ | N | |
| 712 | $CH_3$ | $CH_3$ | $SO_2$-n-$C_3H_7$ | H | $CH_3$ | $CH_3$ | N | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 713 | $CH_3$ | $CH_3$ | $SO_2$-n-$C_3H_7$ | H | $N(CH_3)_2$ | $OCH_2CF_3$ | N | |
| 714 | $CH_3$ | $CH_3$ | $SO_2$-n-$C_3H_7$ | H | $OCH_3$ | $CF_3$ | N | |
| 715 | $CH_3$ | $CH_3$ | $SO_2$-n-$C_3H_7$ | H | $OC_2H_5$ | $NHCH_3$ | N | |
| 716 | $CH_3$ | $CH_3$ | $SO_2$-n-$C_3H_7$ | $CH_3$ | $OCH_3$ | $OCH_3$ | CH | |
| 717 | $CH_3$ | $CH_3$ | $SO_2$-n-$C_3H_7$ | $CH_3$ | $OCH_3$ | $CH_3$ | N | |
| 718 | $CH_3$ | $CH_3$ | $SO_2$-i-$C_3H_7$ | H | $OCH_3$ | $OCH_3$ | CH | |
| 719 | $CH_3$ | $CH_3$ | $SO_2$-i-$C_3H_7$ | H | $OCH_3$ | $CH_3$ | CH | |
| 720 | $CH_3$ | $CH_3$ | $SO_2$-i-$C_3H_7$ | H | $CH_3$ | $CH_3$ | CH | |
| 721 | $CH_3$ | $CH_3$ | $SO_2$-i-$C_3H_7$ | H | $CH_3$ | $OC_2H_5$ | CH | |
| 722 | $CH_3$ | $CH_3$ | $SO_2$-i-$C_3H_7$ | H | $C_2H_5$ | $OCH_3$ | CH | |
| 723 | $CH_3$ | $CH_3$ | $SO_2$-i-$C_3H_7$ | H | $OC_2H_5$ | $OC_2H_5$ | CH | |
| 724 | $CH_3$ | $CH_3$ | $SO_2$-i-$C_3H_7$ | H | $OCHF_2$ | $OCHF_2$ | CH | |
| 725 | $CH_3$ | $CH_3$ | $SO_2$-i-$C_3H_7$ | H | $CH_3$ | $OCHF_2$ | CH | |
| 726 | $CH_3$ | $CH_3$ | $SO_2$-i-$C_3H_7$ | H | Cl | $OCH_3$ | CH | |
| 727 | $CH_3$ | $CH_3$ | $SO_2$-i-$C_3H_7$ | H | $OCH_3$ | $OCH_3$ | N | |
| 728 | $CH_3$ | $CH_3$ | $SO_2$-i-$C_3H_7$ | H | $OCH_3$ | $CH_3$ | N | |
| 729 | $CH_3$ | $CH_3$ | $SO_2$-i-$C_3H_7$ | H | $CH_3$ | $CH_3$ | N | |
| 730 | $CH_3$ | $CH_3$ | $SO_2$-i-$C_3H_7$ | H | $N(CH_3)_2$ | $OCH_2CF_3$ | N | |
| 731 | $CH_3$ | $CH_3$ | $SO_2$-i-$C_3H_7$ | H | $OCH_3$ | $CF_3$ | N | |
| 732 | $CH_3$ | $CH_3$ | $SO_2$-i-$C_3H_7$ | H | $OC_2H_5$ | $NHCH_3$ | N | |
| 733 | $CH_3$ | $CH_3$ | $SO_2$-i-$C_3H_7$ | $CH_3$ | $OCH_3$ | $OCH_3$ | CH | |
| 734 | $CH_3$ | $CH_3$ | $SO_2$-i-$C_3H_7$ | $CH_3$ | $OCH_3$ | $CH_3$ | N | |
| 735 | $CH_3$ | $CH_3$ | $ClCH_2CO$ | H | $OCH_3$ | $OCH_3$ | CH | |
| 736 | $CH_3$ | $CH_3$ | $ClCH_2CO$ | H | $OCH_3$ | $CH_3$ | CH | |
| 737 | $CH_3$ | $CH_3$ | $ClCH_2CO$ | H | $CH_3$ | $CH_3$ | CH | |
| 738 | $CH_3$ | $CH_3$ | $ClCH_2CO$ | H | Cl | $OCH_3$ | CH | |
| 739 | $CH_3$ | $CH_3$ | $ClCH_2CO$ | H | $OCH_3$ | $OCH_3$ | N | |
| 740 | $CH_3$ | $CH_3$ | $ClCH_2CO$ | H | $OCH_3$ | $CH_3$ | N | |
| 741 | $CH_3$ | $CH_3$ | $ClCH_2CO$ | H | $OCH_3$ | $CF_3$ | N | |
| 742 | $CH_3$ | $CH_3$ | $ClCH_2CO$ | $CH_3$ | $OCH_3$ | $OCH_3$ | CH | |
| 743 | $CH_3$ | $CH_3$ | $ClCH_2CO$ | $CH_3$ | $OCH_3$ | $CH_3$ | N | |
| 744 | $CH_3$ | $CH_3$ | $Cl_2CHCO$ | H | $OCH_3$ | $OCH_3$ | CH | |
| 745 | $CH_3$ | $CH_3$ | $Cl_2CHCO$ | H | $OCH_3$ | $CH_3$ | CH | |
| 746 | $CH_3$ | $CH_3$ | $Cl_2CHCO$ | H | $CH_3$ | $CH_3$ | CH | |
| 747 | $CH_3$ | $CH_3$ | $Cl_2CHCO$ | H | Cl | $OCH_3$ | CH | |
| 748 | $CH_3$ | $CH_3$ | $Cl_2CHCO$ | H | $OCH_3$ | $OCH_3$ | N | |
| 749 | $CH_3$ | $CH_3$ | $Cl_2CHCO$ | H | $OCH_3$ | $CH_3$ | N | |
| 750 | $CH_3$ | $CH_3$ | $Cl_2CHCO$ | H | $OCH_3$ | $CF_3$ | N | |
| 751 | $CH_3$ | $CH_3$ | $Cl_2CHCO$ | $CH_3$ | $OCH_3$ | $OCH_3$ | CH | |
| 752 | $CH_3$ | $CH_3$ | $Cl_2CHCO$ | $CH_3$ | $OCH_3$ | $CH_3$ | N | |
| 753 | $CH_3$ | $CH_3$ | $Cl_2CCO$ | H | $OCH_3$ | $OCH_3$ | CH | 144–146 |
| 754 | $CH_3$ | $CH_3$ | $Cl_2CCO$ | H | $OCH_3$ | $CH_3$ | CH | |
| 755 | $CH_3$ | $CH_3$ | $Cl_2CCO$ | H | $CH_3$ | $CH_3$ | CH | |
| 756 | $CH_3$ | $CH_3$ | $Cl_2CCO$ | H | Cl | $OCH_3$ | CH | |
| 757 | $CH_3$ | $CH_3$ | $Cl_2CCO$ | H | $OCH_3$ | $OCH_3$ | CH | |
| 758 | $CH_3$ | $CH_3$ | $Cl_2CCO$ | H | $OCH_3$ | $CH_3$ | N | |
| 759 | $CH_3$ | $CH_3$ | $Cl_2CCO$ | H | $OCH_3$ | $CF_3$ | N | |
| 760 | $CH_3$ | $CH_3$ | $Cl_2CCO$ | $CH_3$ | $OCH_3$ | $OCH_3$ | CH | |
| 761 | $CH_3$ | $CH_3$ | $Cl_2CCO$ | $CH_3$ | $OCH_3$ | $CH_3$ | N | |
| 762 | $CH_3$ | $CH_3$ | $CH_3OCH_2CO$ | H | $OCH_3$ | $OCH_3$ | CH | |
| 763 | $CH_3$ | $CH_3$ | $CH_3OCH_2CO$ | H | $OCH_3$ | $CH_3$ | CH | |
| 764 | $CH_3$ | $CH_3$ | $CH_3OCH_2CO$ | H | $CH_3$ | $CH_3$ | CH | |
| 765 | $CH_3$ | $CH_3$ | $CH_3OCH_2CO$ | H | Cl | $OCH_3$ | CH | |
| 766 | $CH_3$ | $CH_3$ | $CH_3OCH_2CO$ | H | $OCH_3$ | $OCH_3$ | N | |
| 767 | $CH_3$ | $CH_3$ | $CH_3OCH_2CO$ | H | $OCH_3$ | $CH_3$ | N | |
| 768 | $CH_3$ | $CH_3$ | $CH_3OCH_2CO$ | H | $OCH_3$ | $CF_3$ | N | |
| 769 | $CH_3$ | $CH_3$ | $CH_3OCH_2CO$ | $CH_3$ | $OCH_3$ | $OCH_3$ | CH | |
| 770 | $CH_3$ | $CH_3$ | $CH_3OCH_2CO$ | $CH_3$ | $OCH_3$ | $CH_3$ | N | |
| 771 | $CH_3$ | $CH_3$ | $CH_2=CHCO$ | H | $OCH_3$ | $OCH_3$ | CH | |
| 772 | $CH_3$ | $CH_3$ | $CH_2=CHCO$ | H | $OCH_3$ | $CH_3$ | CH | |
| 773 | $CH_3$ | $CH_3$ | $CH_2=CHCO$ | H | $CH_3$ | $CH_3$ | CH | |
| 774 | $CH_3$ | $CH_3$ | $CH_2=CHCO$ | H | Cl | $OCH_3$ | CH | |
| 775 | $CH_3$ | $CH_3$ | $CH_2=CHCO$ | H | $OCH_3$ | $OCH_3$ | N | |

TABLE 1-continued

Compound of the formula (1a)

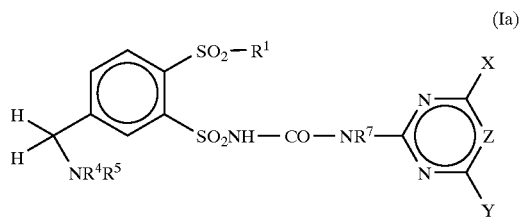

(Ia)

| No. | R¹ | R⁴ | R⁵ | R⁷ | X | Y | Z | mp.(°C.) |
|---|---|---|---|---|---|---|---|---|
| 776 | CH₃ | CH₃ | CH₂=CHCO | H | OCH₃ | CH₃ | N | |
| 777 | CH₃ | CH₃ | CH₂=CHCO | H | OCH₃ | CF₃ | N | |
| 778 | CH₃ | CH₃ | CH₂=CHCO | CH₃ | OCH₃ | OCH₃ | CH | |
| 779 | CH₃ | CH₃ | CH₂=CHCO | CH₃ | OCH₃ | CH₃ | N | |
| 780 | CH₃ | CH₃ | CH≡CCO | H | OCH₃ | OCH₃ | CH | |
| 781 | CH₃ | CH₃ | CH≡CCO | H | OCH₃ | CH₃ | CH | |
| 782 | CH₃ | CH₃ | CH≡CCO | H | CH₃ | CH₃ | CH | |
| 783 | CH₃ | CH₃ | CH≡CCO | H | Cl | OCH₃ | CH | |
| 784 | CH₃ | CH₃ | CH≡CCO | H | OCH₃ | OCH₃ | N | |
| 785 | CH₃ | CH₃ | CH≡CCO | H | OCH₃ | CH₃ | N | |
| 786 | CH₃ | CH₃ | CH≡CCO | H | OCH₃ | CF₃ | N | |
| 787 | CH₃ | CH₃ | CH≡CCO | CH₃ | OCH₃ | OCH₃ | CH | |
| 788 | CH₃ | CH₃ | CH≡CCO | CH₃ | OCH₃ | CH₃ | N | |
| 789 | CH₃ | CH₃ | CO—◁ | H | OCH₃ | OCH₃ | CH | |
| 790 | CH₃ | CH₃ | CO—◁ | H | OCH₃ | CH₃ | CH | |
| 791 | CH₃ | CH₃ | CO—◁ | H | CH₃ | CH₃ | CH | |
| 792 | CH₃ | CH₃ | CO—◁ | H | Cl | OCH₃ | CH | |
| 793 | CH₃ | CH₃ | CO—◁ | H | OCH₃ | OCH₃ | N | |
| 794 | CH₃ | CH₃ | CO—◁ | H | OCH₃ | CH₃ | N | |
| 795 | CH₃ | CH₃ | CO—◁ | H | OCH₃ | CF₃ | N | |
| 796 | CH₃ | CH₃ | CO—◁ | CH₃ | OCH₃ | OCH₃ | CH | |
| 797 | CH₃ | CH₃ | CO—◁ | CH₃ | OCH₃ | CH₃ | N | |

TABLE 1-continued

Compound of the formula (1a)

(Ia)

| No. | R¹ | R⁴ | R⁵ | R⁷ | X | Y | Z | mp.(°C.) |
|-----|-----|-----|-----|-----|-----|-----|-----|-----|
| 798 | CH₃ | CH₃ | CO—⬦ (cyclobutyl) | H | OCH₃ | OCH₃ | CH | |
| 799 | CH₃ | CH₃ | CO—⬦ | H | OCH₃ | CH₃ | CH | |
| 800 | CH₃ | CH₃ | CO—⬦ | H | CH₃ | CH₃ | CH | |
| 801 | CH₃ | CH₃ | CO—⬦ | H | Cl | OCH₃ | CH | |
| 802 | CH₃ | CH₃ | CO—⬦ | H | OCH₃ | OCH₃ | N | |
| 803 | CH₃ | CH₃ | CO—⬦ | H | OCH₃ | CH₃ | N | |
| 804 | CH₃ | CH₃ | CO—⬦ | H | OCH₃ | CF₃ | N | |
| 805 | CH₃ | CH₃ | CO—⬦ | CH₃ | OCH₃ | OCH₃ | CH | |
| 806 | CH₃ | CH₃ | CO—⬦ | CH₃ | OCH₃ | CH₃ | N | |
| 807 | CH₃ | CH₃ | CO—cyclopentyl | H | OCH₃ | OCH₃ | CH | |
| 808 | CH₃ | CH₃ | CO—cyclopentyl | H | OCH₃ | CH₃ | CH | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 809 | $CH_3$ | $CH_3$ | CO-cyclopentyl | H | $CH_3$ | $CH_3$ | CH | |
| 810 | $CH_3$ | $CH_3$ | CO-cyclopentyl | H | Cl | $OCH_3$ | CH | |
| 811 | $CH_3$ | $CH_3$ | CO-cyclopentyl | H | $OCH_3$ | $OCH_3$ | N | |
| 812 | $CH_3$ | $CH_3$ | CO-cyclopentyl | H | $OCH_3$ | $CH_3$ | N | |
| 813 | $CH_3$ | $CH_3$ | CO-cyclopentyl | H | $OCH_3$ | $CF_3$ | N | |
| 814 | $CH_3$ | $CH_3$ | CO-cyclopentyl | $CH_3$ | $OCH_3$ | $OCH_3$ | CH | |
| 815 | $CH_3$ | $CH_3$ | CO-cyclopentyl | $CH_3$ | $OCH_3$ | $CH_3$ | N | |
| 816 | $CH_3$ | $CH_3$ | CO-cyclohexyl | H | $OCH_3$ | $OCH_3$ | CH | |
| 817 | $CH_3$ | $CH_3$ | CO-cyclohexyl | H | $OCH_3$ | $CH_3$ | CH | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 818 | $CH_3$ | $CH_3$ | CO—cyclohexyl | H | $CH_3$ | $CH_3$ | CH | |
| 819 | $CH_3$ | $CH_3$ | CO—cyclohexyl | H | Cl | $OCH_3$ | CH | |
| 820 | $CH_3$ | $CH_3$ | CO—cyclohexyl | H | $OCH_3$ | $OCH_3$ | N | |
| 821 | $CH_3$ | $CH_3$ | CO—cyclohexyl | H | $OCH_3$ | $CH_3$ | N | |
| 822 | $CH_3$ | $CH_3$ | CO—cyclohexyl | H | $OCH_3$ | $CF_3$ | N | |
| 823 | $CH_3$ | $CH_3$ | CO—cyclohexyl | $CH_3$ | $OCH_3$ | $OCH_3$ | CH | |
| 824 | $CH_3$ | $CH_3$ | CO—cyclohexyl | $CH_3$ | $OCH_3$ | $CH_3$ | N | |
| 825 | $CH_3$ | $CH_3$ | $CF_3SO_2$ | H | $OCH_3$ | $OCH_3$ | CH | |
| 826 | $CH_3$ | $CH_3$ | $CF_3SO_2$ | H | $OCH_3$ | $CH_3$ | CH | |
| 827 | $CH_3$ | $CH_3$ | $CF_3SO_2$ | H | $CH_3$ | $CH_3$ | CH | |
| 828 | $CH_3$ | $CH_3$ | $CF_3SO_2$ | H | Cl | $OCH_3$ | CH | |
| 829 | $CH_3$ | $CH_3$ | $CF_3SO_2$ | H | $OCH_3$ | $OCH_3$ | N | |
| 830 | $CH_3$ | $CH_3$ | $CF_3SO_2$ | H | $OCH_3$ | $CH_3$ | N | |
| 831 | $CH_3$ | $CH_3$ | $CF_3SO_2$ | H | $OCH_3$ | $CF_3$ | N | |
| 832 | $CH_3$ | $CH_3$ | $CF_3SO_2$ | $CH_3$ | $OCH_3$ | $OCH_3$ | CH | |
| 833 | $CH_3$ | $CH_3$ | $CF_3SO_2$ | $CH_3$ | $OCH_3$ | $CH_3$ | N | |
| 834 | $CH_3$ | $CH_3$ | $FCH_2SO_2$ | $CH_3$ | $OCH_3$ | $OCH_3$ | CH | |
| 835 | $CH_3$ | $CH_3$ | $FCH_2SO_2$ | H | $OCH_3$ | $CH_3$ | CH | |
| 836 | $CH_3$ | $CH_3$ | $FCH_2SO_2$ | H | $CH_3$ | $CH_3$ | CH | |
| 837 | $CH_3$ | $CH_3$ | $FCH_2SO_2$ | H | Cl | $OCH_3$ | CH | |
| 838 | $CH_3$ | $CH_3$ | $FCH_2SO_2$ | H | $OCH_3$ | $OCH_3$ | N | |
| 839 | $CH_3$ | $CH_3$ | $FCH_2SO_2$ | H | $OCH_3$ | $CH_3$ | N | |

TABLE 1-continued

Compound of the formula (1a)

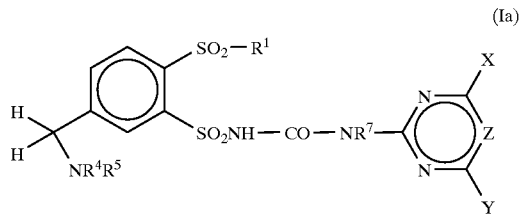

(Ia)

| No. | R$^1$ | R$^4$ | R$^5$ | R$^7$ | X | Y | Z | mp.(°C.) |
|---|---|---|---|---|---|---|---|---|
| 840 | CH$_3$ | CH$_3$ | FCH$_2$SO$_2$ | H | OCH$_3$ | CF$_3$ | N | |
| 841 | CH$_3$ | CH$_3$ | FCH$_2$SO$_2$ | H | OCH$_3$ | OCH$_3$ | CH | |
| 842 | CH$_3$ | CH$_3$ | FCH$_2$SO$_2$ | CH$_3$ | OCH$_3$ | CH$_3$ | N | |
| 843 | CH$_3$ | CH$_3$ | ClCH$_2$SO$_2$ | CH$_3$ | OCH$_3$ | OCH$_3$ | CH | |
| 844 | CH$_3$ | CH$_3$ | ClCH$_2$SO$_2$ | H | OCH$_3$ | CH$_3$ | CH | |
| 845 | CH$_3$ | CH$_3$ | ClCH$_2$SO$_2$ | H | CH$_3$ | CH$_3$ | CH | |
| 846 | CH$_3$ | CH$_3$ | ClCH$_2$SO$_2$ | H | Cl | OCH$_3$ | CH | |
| 847 | CH$_3$ | CH$_3$ | ClCH$_2$SO$_2$ | H | OCH$_3$ | OCH$_3$ | N | |
| 848 | CH$_3$ | CH$_3$ | ClCH$_2$SO$_2$ | H | OCH$_3$ | CH$_3$ | N | |
| 849 | CH$_3$ | CH$_3$ | ClCH$_2$SO$_2$ | H | OCH$_3$ | CF$_3$ | N | |
| 850 | CH$_3$ | CH$_3$ | ClCH$_2$SO$_2$ | CH$_3$ | OCH$_3$ | OCH$_3$ | CH | |
| 851 | CH$_3$ | CH$_3$ | ClCH$_2$SO$_2$ | CH$_3$ | OCH$_3$ | CH$_3$ | N | |
| 852 | CH$_3$ | CH$_3$ | ClCH$_2$SO$_2$ | H | OCH$_3$ | OCH$_3$ | CH | |
| 853 | CH$_3$ | CH$_3$ | ClCH$_2$SO$_2$ | H | OCH$_3$ | CH$_3$ | CH | |
| 854 | CH$_3$ | CH$_3$ | ClCH$_2$SO$_2$ | H | CH$_3$ | CH$_3$ | CH | |
| 855 | CH$_3$ | CH$_3$ | ClCH$_2$SO$_2$ | H | Cl | OCH$_3$ | CH | |
| 856 | CH$_3$ | CH$_3$ | ClCH$_2$SO$_2$ | H | OCH$_3$ | OCH$_3$ | N | |
| 857 | CH$_3$ | CH$_3$ | ClCH$_2$SO$_2$ | H | OCH$_3$ | CH$_3$ | N | |
| 858 | CH$_3$ | CH$_3$ | ClCH$_2$SO$_2$ | H | OCH$_3$ | CF$_3$ | N | |
| 859 | CH$_3$ | CH$_3$ | Cl$_2$CHSO$_2$ | CH$_3$ | OCH$_3$ | OCH$_3$ | CH | |
| 860 | CH$_3$ | CH$_3$ | Cl$_2$CHSO$_2$ | CH$_3$ | OCH$_3$ | CH$_3$ | N | |
| 861 | CH$_3$ | CH$_3$ | Cl$_3$CSO$_2$ | H | OCH$_3$ | OCH$_3$ | CH | |
| 862 | CH$_3$ | CH$_3$ | Cl$_3$CSO$_2$ | H | OCH$_3$ | CH$_3$ | CH | |
| 863 | CH$_3$ | CH$_3$ | Cl$_3$CSO$_2$ | H | CH$_3$ | CH$_3$ | CH | |
| 864 | CH$_3$ | CH$_3$ | Cl$_3$CSO$_2$ | H | Cl | OCH$_3$ | CH | |
| 865 | CH$_3$ | CH$_3$ | Cl$_3$CSO$_2$ | H | OCH$_3$ | OCH$_3$ | N | |
| 866 | CH$_3$ | CH$_3$ | Cl$_3$CSO$_2$ | H | OCH$_3$ | CH$_3$ | N | |
| 867 | CH$_3$ | CH$_3$ | Cl$_3$CSO$_2$ | H | OCH$_3$ | CF$_3$ | N | |
| 868 | CH$_3$ | CH$_3$ | Cl$_3$CSO$_2$ | CH$_3$ | OCH$_3$ | OCH$_3$ | CH | |
| 869 | CH$_3$ | CH$_3$ | Cl$_3$CSO$_2$ | CH$_3$ | OCH$_3$ | CH$_3$ | N | |
| 870 | CH$_3$ | CH$_3$ | n-C$_4$H$_9$SO$_2$ | H | OCH$_3$ | OCH$_3$ | CH | |
| 871 | CH$_3$ | CH$_3$ | n-C$_4$H$_9$SO$_2$ | H | OCH$_3$ | CH$_3$ | CH | |
| 872 | CH$_3$ | CH$_3$ | n-C$_4$H$_9$SO$_2$ | H | CH$_3$ | CH$_3$ | CH | |
| 873 | CH$_3$ | CH$_3$ | n-C$_4$H$_9$SO$_2$ | H | Cl | OCH$_3$ | CH | |
| 874 | CH$_3$ | CH$_3$ | n-C$_4$H$_9$SO$_2$ | H | OCH$_3$ | OCH$_3$ | N | |
| 875 | CH$_3$ | CH$_3$ | n-C$_4$H$_9$SO$_2$ | H | OCH$_3$ | CH$_3$ | N | |
| 876 | CH$_3$ | CH$_3$ | n-C$_4$H$_9$SO$_2$ | H | OCH$_3$ | CF$_3$ | N | |
| 877 | CH$_3$ | CH$_3$ | n-C$_4$H$_9$SO$_2$ | CH$_3$ | OCH$_3$ | OCH$_3$ | CH | |
| 878 | CH$_3$ | CH$_3$ | n-C$_4$H$_9$SO$_2$ | CH$_3$ | OCH$_3$ | CH$_3$ | N | |
| 879 | CH$_3$ | CH$_3$ | CF$_3$CH$_2$SO$_2$ | H | OCH$_3$ | OCH$_3$ | CH | |
| 880 | CH$_3$ | CH$_3$ | CF$_3$CH$_2$SO$_2$ | H | OCH$_3$ | CH$_3$ | CH | |
| 881 | CH$_3$ | CH$_3$ | CF$_3$CH$_2$SO$_2$ | H | CH$_3$ | CH$_3$ | CH | |
| 882 | CH$_3$ | CH$_3$ | CF$_3$CH$_2$SO$_2$ | H | Cl | OCH$_3$ | CH | |
| 883 | CH$_3$ | CH$_3$ | CF$_3$CH$_2$SO$_2$ | H | OCH$_3$ | OCH$_3$ | N | |
| 884 | CH$_3$ | CH$_3$ | CF$_3$CH$_2$SO$_2$ | H | OCH$_3$ | CH$_3$ | N | |
| 885 | CH$_3$ | CH$_3$ | CF$_3$CH$_2$SO$_2$ | H | OCH$_3$ | CF$_3$ | N | |
| 886 | CH$_3$ | CH$_3$ | CF$_3$CH$_2$SO$_2$ | CH$_3$ | OCH$_3$ | OCH$_3$ | CH | |
| 887 | CH$_3$ | CH$_3$ | CF$_3$CH$_2$SO$_2$ | CH$_3$ | OCH$_3$ | CH$_3$ | N | |
| 888 | CH$_3$ | CH$_3$ | CH$_3$NHSO$_2$ | H | OCH$_3$ | OCH$_3$ | CH | |
| 889 | CH$_3$ | CH$_3$ | CH$_3$NHSO$_2$ | H | OCH$_3$ | CH$_3$ | CH | |
| 890 | CH$_3$ | CH$_3$ | CH$_3$NHSO$_2$ | H | CH$_3$ | CH$_3$ | CH | |
| 891 | CH$_3$ | CH$_3$ | CH$_3$NHSO$_2$ | H | Cl | OCH$_3$ | CH | |
| 892 | CH$_3$ | CH$_3$ | CH$_3$NHSO$_2$ | H | OCH$_3$ | OCH$_3$ | N | |
| 893 | CH$_3$ | CH$_3$ | CH$_3$NHSO$_2$ | H | OCH$_3$ | CH$_3$ | N | |
| 894 | CH$_3$ | CH$_3$ | CH$_3$NHSO$_2$ | H | OCH$_3$ | CF$_3$ | N | |
| 895 | CH$_3$ | CH$_3$ | CH$_3$NHSO$_2$ | CH$_3$ | OCH$_3$ | OCH$_3$ | CH | |
| 896 | CH$_3$ | CH$_3$ | CH$_3$NHSO$_2$ | CH$_3$ | OCH$_3$ | CH$_3$ | N | |
| 897 | CH$_3$ | CH$_3$ | (CH$_3$)$_2$NSO$_2$ | H | OCH$_3$ | OCH$_3$ | CH | |
| 898 | CH$_3$ | CH$_3$ | (CH$_3$)$_2$NSO$_2$ | H | OCH$_3$ | CH$_3$ | CH | |
| 899 | CH$_3$ | CH$_3$ | (CH$_3$)$_2$NSO$_2$ | H | CH$_3$ | CH$_3$ | CH | |
| 900 | CH$_3$ | CH$_3$ | (CH$_3$)$_2$NSO$_2$ | H | Cl | OCH$_3$ | CH | |
| 901 | CH$_3$ | CH$_3$ | (CH$_3$)$_2$NSO$_2$ | H | OCH$_3$ | OCH$_3$ | N | |
| 902 | CH$_3$ | CH$_3$ | (CH$_3$)$_2$NSO$_2$ | H | OCH$_3$ | CH$_3$ | N | |

TABLE 1-continued

Compound of the formula (1a)

$$\text{(Ia)}$$

| No. | R$^1$ | R$^4$ | R$^5$ | R$^7$ | X | Y | Z | mp.(°C.) |
|---|---|---|---|---|---|---|---|---|
| 903 | CH$_3$ | CH$_3$ | (CH$_3$)$_2$NSO$_2$ | H | OCH$_3$ | CF$_3$ | N | |
| 904 | CH$_3$ | CH$_3$ | (CH$_3$)$_2$NSO$_2$ | CH$_3$ | OCH$_3$ | OCH$_3$ | CH | |
| 905 | CH$_3$ | CH$_3$ | (CH$_3$)$_2$NSO$_2$ | CH$_3$ | OCH$_3$ | CH$_3$ | N | |
| 906 | CH$_3$ | CH$_3$ | (CH$_3$)$_3$COCO | H | OCH$_3$ | OCH$_3$ | CH | |
| 907 | CH$_3$ | CH$_3$ | (CH$_3$)$_3$COCO | H | OCH$_3$ | CH$_3$ | CH | |
| 908 | CH$_3$ | CH$_3$ | (CH$_3$)$_3$COCO | H | CH$_3$ | CH$_3$ | CH | |
| 909 | CH$_3$ | CH$_3$ | (CH$_3$)$_3$COCO | H | Cl | OCH$_3$ | CH | |
| 910 | CH$_3$ | CH$_3$ | (CH$_3$)$_3$COCO | H | OCH$_3$ | OCH$_3$ | N | |
| 911 | CH$_3$ | CH$_3$ | (CH$_3$)$_3$COCO | H | OCH$_3$ | CH$_3$ | N | |
| 912 | CH$_3$ | CH$_3$ | (CH$_3$)$_3$COCO | H | OCH$_3$ | CF$_3$ | N | |
| 913 | CH$_3$ | CH$_3$ | (CH$_3$)$_3$COCO | CH$_3$ | OCH$_3$ | OCH$_3$ | CH | |
| 914 | CH$_3$ | CH$_3$ | (CH$_3$)$_3$COCO | CH$_3$ | OCH$_3$ | CH$_3$ | N | |
| 915 | CH$_3$ | CH$_3$ | PhCO | H | OCH$_3$ | OCH$_3$ | CH | |
| 916 | CH$_3$ | CH$_3$ | PhCO | H | OCH$_3$ | CH$_3$ | CH | |
| 917 | CH$_3$ | CH$_3$ | PhCO | H | CH$_3$ | CH$_3$ | CH | |
| 918 | CH$_3$ | CH$_3$ | PhCO | H | Cl | OCH$_3$ | CH | |
| 919 | CH$_3$ | CH$_3$ | PhCO | H | OCH$_3$ | OCH$_3$ | N | |
| 920 | CH$_3$ | CH$_3$ | PhCO | H | OCH$_3$ | CH$_3$ | N | |
| 921 | CH$_3$ | CH$_3$ | PhCO | H | OCH$_3$ | CF$_3$ | N | |
| 922 | CH$_3$ | CH$_3$ | PhCO | CH$_3$ | OCH$_3$ | OCH$_3$ | CH | |
| 923 | CH$_3$ | CH$_3$ | PhCO | CH$_3$ | OCH$_3$ | CH$_3$ | N | |
| 924 | CH$_3$ | CH$_3$ | PhSO$_2$ | H | OCH$_3$ | OCH$_3$ | CH | |
| 925 | CH$_3$ | CH$_3$ | PhSO$_2$ | H | OCH$_3$ | CH$_3$ | CH | |
| 926 | CH$_3$ | CH$_3$ | PhSO$_2$ | H | CH$_3$ | CH$_3$ | CH | |
| 927 | CH$_3$ | CH$_3$ | PhSO$_2$ | H | Cl | OCH$_3$ | CH | |
| 928 | CH$_3$ | CH$_3$ | PhSO$_2$ | H | OCH$_3$ | OCH$_3$ | N | |
| 929 | CH$_3$ | CH$_3$ | PhSO$_2$ | H | OCH$_3$ | CH$_3$ | N | |
| 930 | CH$_3$ | CH$_3$ | PhSO$_2$ | H | OCH$_3$ | CF$_3$ | N | |
| 931 | CH$_3$ | CH$_3$ | PhSO$_2$ | CH$_3$ | OCH$_3$ | OCH$_3$ | CH | |
| 932 | CH$_3$ | CH$_3$ | PhSO$_2$ | CH$_3$ | OCH$_3$ | CH$_3$ | N | |
| 933 | CH$_3$ | CH$_3$ | CH$_3$NHCO | H | OCH$_3$ | OCH$_3$ | CH | |
| 934 | CH$_3$ | CH$_3$ | CH$_3$NHCO | H | OCH$_3$ | CH$_3$ | CH | |
| 935 | CH$_3$ | CH$_3$ | CH$_3$NHCO | H | CH$_3$ | CH$_3$ | CH | |
| 936 | CH$_3$ | CH$_3$ | CH$_3$NHCO | H | Cl | OCH$_3$ | CH | |
| 937 | CH$_3$ | CH$_3$ | CH$_3$NHCO | H | OCH$_3$ | OCH$_3$ | N | |
| 938 | CH$_3$ | CH$_3$ | CH$_3$NHCO | H | OCH$_3$ | CH$_3$ | N | |
| 939 | CH$_3$ | CH$_3$ | CH$_3$NHCO | H | OCH$_3$ | CF$_3$ | N | |
| 940 | CH$_3$ | CH$_3$ | CH$_3$NHCO | CH$_3$ | OCH$_3$ | OCH$_3$ | CH | |
| 941 | CH$_3$ | CH$_3$ | CH$_3$NHCO | CH$_3$ | OCH$_3$ | CH$_3$ | N | |
| 942 | CH$_3$ | CH$_3$ | EtNHCO | H | OCH$_3$ | OCH$_3$ | CH | |
| 943 | CH$_3$ | CH$_3$ | EtNHCO | H | OCH$_3$ | CH$_3$ | CH | |
| 944 | CH$_3$ | CH$_3$ | EtNHCO | H | CH$_3$ | CH$_3$ | CH | |
| 945 | CH$_3$ | CH$_3$ | EtNHCO | H | Cl | OCH$_3$ | CH | |
| 946 | CH$_3$ | CH$_3$ | EtNHCO | H | OCH$_3$ | OCH$_3$ | N | |
| 947 | CH$_3$ | CH$_3$ | EtNHCO | H | OCH$_3$ | CH$_3$ | N | |
| 948 | CH$_3$ | CH$_3$ | EtNHCO | H | OCH$_3$ | CF$_3$ | N | |
| 949 | CH$_3$ | CH$_3$ | EtNHCO | CH$_3$ | OCH$_3$ | OCH$_3$ | CH | |
| 950 | CH$_3$ | CH$_3$ | EtNHCO | CH$_3$ | OCH$_3$ | CH$_3$ | N | |
| 951 | CH$_3$ | CH$_3$ | CH$_3$NHCS | H | OCH$_3$ | OCH$_3$ | CH | |
| 952 | CH$_3$ | CH$_3$ | CH$_3$NHCS | H | OCH$_3$ | CH$_3$ | CH | |
| 953 | CH$_3$ | CH$_3$ | CH$_3$NHCS | H | CH$_3$ | CH$_3$ | CH | |
| 954 | CH$_3$ | CH$_3$ | CH$_3$NHCS | H | Cl | OCH$_3$ | CH | |
| 955 | CH$_3$ | CH$_3$ | CH$_3$NHCS | H | OCH$_3$ | OCH$_3$ | N | |
| 956 | CH$_3$ | CH$_3$ | CH$_3$NHCS | H | OCH$_3$ | CH$_3$ | N | |
| 957 | CH$_3$ | CH$_3$ | CH$_3$NHCS | H | OCH$_3$ | CF$_3$ | N | |
| 958 | CH$_3$ | CH$_3$ | CH$_3$NHCS | CH$_3$ | OCH$_3$ | OCH$_3$ | CH | |
| 959 | CH$_3$ | CH$_3$ | CH$_3$NHCS | CH$_3$ | OCH$_3$ | CH$_3$ | N | |
| 960 | CH$_3$ | CH$_3$ | EtNHCS | H | OCH$_3$ | OCH$_3$ | CH | |
| 961 | CH$_3$ | CH$_3$ | EtNHCS | H | OCH$_3$ | CH$_3$ | CH | |
| 962 | CH$_3$ | CH$_3$ | EtNHCS | H | CH$_3$ | CH$_3$ | CH | |
| 963 | CH$_3$ | CH$_3$ | EtNHCS | H | Cl | OCH$_3$ | CH | |
| 964 | CH$_3$ | CH$_3$ | EtNHCS | H | OCH$_3$ | OCH$_3$ | N | |
| 965 | CH$_3$ | CH$_3$ | EtNHCS | H | OCH$_3$ | CH$_3$ | N | |

TABLE 1-continued

Compound of the formula (1a)

$$\text{(Ia)}$$

| No. | $R^1$ | $R^4$ | $R^5$ | $R^7$ | X | Y | Z | mp.(°C.) |
|---|---|---|---|---|---|---|---|---|
| 966 | $CH_3$ | $CH_3$ | EtNHCS | H | $OCH_3$ | $CF_3$ | N | |
| 967 | $CH_3$ | $CH_3$ | EtNHCS | $CH_3$ | $OCH_3$ | $OCH_3$ | CH | |
| 968 | $CH_3$ | $CH_3$ | EtNHCS | $CH_3$ | $OCH_3$ | $CH_3$ | N | |
| 969 | $CH_3$ | $CH_3$ | $COSCH_3$ | H | $OCH_3$ | $OCH_3$ | CH | |
| 970 | $CH_3$ | $CH_3$ | $COSCH_3$ | H | $OCH_3$ | $CH_3$ | CH | |
| 971 | $CH_3$ | $CH_3$ | $COSCH_3$ | H | $CH_3$ | $CH_3$ | CH | |
| 972 | $CH_3$ | $CH_3$ | $COSCH_3$ | H | Cl | $OCH_3$ | CH | |
| 973 | $CH_3$ | $CH_3$ | $COSCH_3$ | H | $OCH_3$ | $OCH_3$ | N | |
| 974 | $CH_3$ | $CH_3$ | $COSCH_3$ | H | $OCH_3$ | $CH_3$ | N | |
| 975 | $CH_3$ | $CH_3$ | $COSCH_3$ | H | $OCH_3$ | $CF_3$ | N | |
| 976 | $CH_3$ | $CH_3$ | $COSCH_3$ | $CH_3$ | $OCH_3$ | $OCH_3$ | CH | |
| 977 | $CH_3$ | $CH_3$ | $COSCH_3$ | $CH_3$ | $OCH_3$ | $CH_3$ | N | |
| 978 | $CH_3$ | $CH_3$ | $COSCH_3$ | H | $OCH_3$ | $OCH_3$ | CH | |
| 979 | $CH_3$ | $CH_3$ | $COSCH_3$ | H | $OCH_3$ | $CH_3$ | CH | |
| 980 | $CH_3$ | $CH_3$ | $COSCH_3$ | H | $CH_3$ | $CH_3$ | CH | |
| 981 | $CH_3$ | $CH_3$ | $COSCH_3$ | H | Cl | $OCH_3$ | CH | |
| 982 | $CH_3$ | $CH_3$ | $COSCH_3$ | H | $OCH_3$ | $OCH_3$ | N | |
| 983 | $CH_3$ | $CH_3$ | $COSCH_3$ | H | $OCH_3$ | $CH_3$ | N | |
| 984 | $CH_3$ | $CH_3$ | $COSCH_3$ | H | $OCH_3$ | $CF_3$ | N | |
| 985 | $CH_3$ | $CH_3$ | $CSOCH_3$ | $CH_3$ | $OCH_3$ | $OCH_3$ | CH | |
| 986 | $CH_3$ | $CH_3$ | $CSOCH_3$ | $CH_3$ | $OCH_3$ | $CH_3$ | N | |
| 987 | $CH_3$ | $CH_3$ | $CSSCH_2$ | H | $OCH_3$ | $OCH_3$ | CH | |
| 988 | $CH_3$ | $CH_3$ | $CSSCH_2$ | H | $OCH_3$ | $CH_3$ | CH | |
| 989 | $CH_3$ | $CH_3$ | $CSSCH_2$ | H | $CH_3$ | $CH_3$ | CH | |
| 990 | $CH_3$ | $CH_3$ | $CSSCH_2$ | H | Cl | $OCH_3$ | CH | |
| 991 | $CH_3$ | $CH_3$ | $CSSCH_2$ | H | $OCH_3$ | $OCH_3$ | N | |
| 992 | $CH_3$ | $CH_3$ | $CSSCH_2$ | H | $OCH_3$ | $CH_3$ | N | |
| 993 | $CH_3$ | $CH_3$ | $CSSCH_2$ | H | $OCH_3$ | $CF_3$ | N | |
| 994 | $CH_3$ | $CH_3$ | $CSSCH_2$ | $CH_3$ | $OCH_3$ | $OCH_3$ | CH | |
| 995 | $CH_3$ | $CH_3$ | $CSSCH_2$ | $CH_3$ | $OCH_3$ | $CH_3$ | N | |
| 996 | $CH_3$ | $CH_3$ | $COCOOCH_3$ | H | $OCH_3$ | $OCH_3$ | CH | |
| 997 | $CH_3$ | $CH_3$ | $COCOOCH_3$ | H | $OCH_3$ | $CH_3$ | CH | |
| 998 | $CH_3$ | $CH_3$ | $COCOOCH_3$ | H | $CH_3$ | $CH_3$ | CH | |
| 999 | $CH_3$ | $CH_3$ | $COCOOCH_3$ | H | Cl | $OCH_3$ | CH | |
| 1000 | $CH_3$ | $CH_3$ | $COCOOCH_3$ | H | $OCH_3$ | $OCH_3$ | N | |
| 1001 | $CH_3$ | $CH_3$ | $COCOOCH_3$ | H | $OCH_3$ | $CH_3$ | N | |
| 1002 | $CH_3$ | $CH_3$ | $COCOOCH_3$ | H | $OCH_3$ | $CF_3$ | N | |
| 1003 | $CH_3$ | $CH_3$ | $COCOOCH_3$ | $CH_3$ | $OCH_3$ | $OCH_3$ | CH | |
| 1004 | $CH_3$ | $CH_3$ | $COCOOCH_3$ | $CH_3$ | $OCH_3$ | $CH_3$ | N | |
| 1005 | $CH_3$ | $CH_3$ | $i\text{-}C_3H_7OCO$ | H | $OCH_3$ | $OCH_3$ | CH | |
| 1006 | $CH_3$ | $CH_3$ | $i\text{-}C_3H_7OCO$ | H | $OCH_3$ | $CH_3$ | CH | |
| 1007 | $CH_3$ | $CH_3$ | $i\text{-}C_3H_7OCO$ | H | $CH_3$ | $CH_3$ | CH | |
| 1008 | $CH_3$ | $CH_3$ | $i\text{-}C_3H_7OCO$ | H | Cl | $OCH_3$ | CH | |
| 1009 | $CH_3$ | $CH_3$ | $i\text{-}C_3H_7OCO$ | H | $OCH_3$ | $OCH_3$ | N | |
| 1010 | $CH_3$ | $CH_3$ | $i\text{-}C_3H_7OCO$ | H | $OCH_3$ | $CH_3$ | N | |
| 1011 | $CH_3$ | $CH_3$ | $i\text{-}C_3H_7OCO$ | H | $OCH_3$ | $CF_3$ | N | |
| 1012 | $CH_3$ | $CH_3$ | $i\text{-}C_3H_7OCO$ | $CH_3$ | $OCH_3$ | $OCH_3$ | CH | |
| 1013 | $CH_3$ | $CH_3$ | $i\text{-}C_3H_7OCO$ | $CH_3$ | $OCH_3$ | $CH_3$ | N | |
| 1014 | $CH_3$ | $C_2H_5$ | CHO | H | $OCH_3$ | $OCH_3$ | CH | |
| 1015 | $CH_3$ | $C_2H_5$ | CHO | H | $OCH_3$ | $CH_3$ | CH | |
| 1016 | $CH_3$ | $C_2H_5$ | CHO | H | $CH_3$ | $CH_3$ | CH | |
| 1017 | $CH_3$ | $C_2H_5$ | CHO | H | Cl | $OCH_3$ | CH | |
| 1018 | $CH_3$ | $C_2H_5$ | CHO | H | $OCH_3$ | $OCH_3$ | N | |
| 1019 | $CH_3$ | $C_2H_5$ | CHO | H | $OCH_3$ | $CH_3$ | N | |
| 1020 | $CH_3$ | $C_2H_5$ | CHO | H | $OCH_3$ | $CF_3$ | N | |
| 1021 | $CH_3$ | $C_2H_5$ | CHO | $CH_3$ | $OCH_3$ | $OCH_3$ | CH | |
| 1022 | $CH_3$ | $C_2H_5$ | CHO | $CH_3$ | $OCH_3$ | $CH_3$ | N | |
| 1023 | $CH_3$ | $C_2H_5$ | $COCH_3$ | H | $OCH_3$ | $OCH_3$ | CH | |
| 1024 | $CH_3$ | $C_2H_5$ | $COCH_3$ | H | $OCH_3$ | $CH_3$ | CH | |
| 1025 | $CH_3$ | $C_2H_5$ | $COCH_3$ | H | $CH_3$ | $CH_3$ | CH | |
| 1026 | $CH_3$ | $C_2H_5$ | $COCH_3$ | H | Cl | $OCH_3$ | CH | |
| 1027 | $CH_3$ | $C_2H_5$ | $COCH_3$ | H | $OCH_3$ | $OCH_3$ | N | |
| 1028 | $CH_3$ | $C_2H_5$ | $COCH_3$ | H | $OCH_3$ | $CH_3$ | N | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 1029 | $CH_3$ | $C_2H_5$ | $COCH_3$ | H | $OCH_3$ | $CF_3$ | N | |
| 1030 | $CH_3$ | $C_2H_5$ | $COCH_3$ | $CH_3$ | $OCH_3$ | $OCH_3$ | CH | |
| 1031 | $CH_3$ | $C_2H_5$ | $COCH_3$ | $CH_3$ | $OCH_3$ | $CH_3$ | N | |
| 1032 | $CH_3$ | $C_2H_5$ | $COOCH_3$ | H | $OCH_3$ | $OCH_3$ | CH | |
| 1033 | $CH_3$ | $C_2H_5$ | $COOCH_3$ | H | $OCH_3$ | $CH_3$ | CH | |
| 1034 | $CH_3$ | $C_2H_5$ | $COOCH_3$ | H | $CH_3$ | $CH_3$ | CH | |
| 1035 | $CH_3$ | $C_2H_5$ | $COOCH_3$ | H | Cl | $OCH_3$ | CH | |
| 1036 | $CH_3$ | $C_2H_5$ | $COOCH_3$ | H | $OCH_3$ | $OCH_3$ | N | |
| 1037 | $CH_3$ | $C_2H_5$ | $COOCH_3$ | H | $OCH_3$ | $CH_3$ | N | |
| 1038 | $CH_3$ | $C_2H_5$ | $COOCH_3$ | H | $OCH_3$ | $CF_3$ | N | |
| 1039 | $CH_3$ | $C_2H_5$ | $COOCH_3$ | $CH_3$ | $OCH_3$ | $OCH_3$ | CH | |
| 1040 | $CH_3$ | $C_2H_5$ | $COOCH_3$ | $CH_3$ | $OCH_3$ | $CH_3$ | N | |
| 1041 | $CH_3$ | $C_2H_5$ | $COOC_2H_5$ | H | $OCH_3$ | $OCH_3$ | CH | |
| 1042 | $CH_3$ | $C_2H_5$ | $COOC_2H_5$ | H | $OCH_3$ | $CH_3$ | CH | |
| 1043 | $CH_3$ | $C_2H_5$ | $COOC_2H_5$ | H | $CH_3$ | $CH_3$ | CH | |
| 1044 | $CH_3$ | $C_2H_5$ | $COOC_2H_5$ | H | Cl | $OCH_3$ | CH | |
| 1045 | $CH_3$ | $C_2H_5$ | $COOC_2H_5$ | H | $OCH_3$ | $OCH_3$ | N | |
| 1046 | $CH_3$ | $C_2H_5$ | $COOC_2H_5$ | H | $OCH_3$ | $CH_3$ | N | |
| 1047 | $CH_3$ | $C_2H_5$ | $COOC_2H_5$ | H | $OCH_3$ | $CF_3$ | N | |
| 1048 | $CH_3$ | $C_2H_5$ | $COOC_2H_5$ | $CH_3$ | $OCH_3$ | $OCH_3$ | CH | |
| 1049 | $CH_3$ | $C_2H_5$ | $COOC_2H_5$ | $CH_3$ | $OCH_3$ | $CH_3$ | N | |
| 1050 | $CH_3$ | $C_2H_5$ | $SO_2CH_3$ | H | $OCH_3$ | $OCH_3$ | CH | |
| 1051 | $CH_3$ | $C_2H_5$ | $SO_2CH_3$ | H | $OCH_3$ | $CH_3$ | CH | |
| 1052 | $CH_3$ | $C_2H_5$ | $SO_2CH_3$ | H | $CH_3$ | $CH_3$ | CH | |
| 1053 | $CH_3$ | $C_2H_5$ | $SO_2CH_3$ | H | Cl | $OCH_3$ | CH | |
| 1054 | $CH_3$ | $C_2H_5$ | $SO_2CH_3$ | H | $OCH_3$ | $OCH_3$ | N | |
| 1055 | $CH_3$ | $C_2H_5$ | $SO_2CH_3$ | H | $OCH_3$ | $CH_3$ | N | |
| 1056 | $CH_3$ | $C_2H_5$ | $SO_2CH_3$ | H | $OCH_3$ | $CF_3$ | N | |
| 1057 | $CH_3$ | $C_2H_5$ | $SO_2CH_3$ | $CH_3$ | $OCH_3$ | $OCH_3$ | CH | |
| 1058 | $CH_3$ | $C_2H_5$ | $SO_2CH_3$ | $CH_3$ | $OCH_3$ | $CH_3$ | N | |
| 1059 | $CH_3$ | $C_2H_5$ | $SO_2C_2H_5$ | H | $OCH_3$ | $OCH_3$ | CH | |
| 1060 | $CH_3$ | $C_2H_5$ | $SO_2C_2H_5$ | H | $OCH_3$ | $CH_3$ | CH | |
| 1061 | $CH_3$ | $C_2H_5$ | $SO_2C_2H_5$ | H | $CH_3$ | $CH_3$ | CH | |
| 1062 | $CH_3$ | $C_2H_5$ | $SO_2C_2H_5$ | H | Cl | $OCH_3$ | CH | |
| 1063 | $CH_3$ | $C_2H_5$ | $SO_2C_2H_5$ | H | $OCH_3$ | $OCH_3$ | N | |
| 1064 | $CH_3$ | $C_2H_5$ | $SO_2C_2H_5$ | H | $OCH_3$ | $CH_3$ | N | |
| 1065 | $CH_3$ | $C_2H_5$ | $SO_2C_2H_5$ | H | $OCH_3$ | $CF_3$ | N | |
| 1066 | $CH_3$ | $C_2H_5$ | $SO_2C_2H_5$ | $CH_3$ | $OCH_3$ | $OCH_3$ | CH | |
| 1067 | $CH_3$ | $C_2H_5$ | $SO_2C_2H_5$ | $CH_3$ | $OCH_3$ | $CH_3$ | N | |
| 1068 | $C_2H_5$ | H | CHO | H | $OCH_3$ | $OCH_3$ | CH | 146–147 |
| 1069 | $C_2H_5$ | H | CHO | H | $OCH_3$ | $CH_3$ | CH | |
| 1070 | $C_2H_5$ | H | CHO | H | $CH_3$ | $CH_3$ | CH | |
| 1071 | $C_2H_5$ | H | CHO | H | $CH_3$ | $OC_2H_5$ | CH | |
| 1072 | $C_2H_5$ | H | CHO | H | $C_2H_5$ | $OCH_3$ | CH | |
| 1073 | $C_2H_5$ | H | CHO | H | $OC_2H_5$ | $OC_2H_5$ | CH | |
| 1074 | $C_2H_5$ | H | CHO | H | $OCHF_2$ | $OCHF_2$ | CH | |
| 1075 | $C_2H_5$ | H | CHO | H | $CH_3$ | $OCHF_2$ | CH | |
| 1076 | $C_2H_5$ | H | CHO | H | Cl | $OCH_3$ | CH | |
| 1077 | $C_2H_5$ | H | CHO | H | $OCH_3$ | $OCH_3$ | N | |
| 1078 | $C_2H_5$ | H | CHO | H | $OCH_3$ | $CH_3$ | N | |
| 1079 | $C_2H_5$ | H | CHO | H | $CH_3$ | $CH_3$ | N | |
| 1080 | $C_2H_5$ | H | CHO | H | $N(CH_3)_2$ | $OCH_2CF_3$ | N | |
| 1081 | $C_2H_5$ | H | CHO | H | $OCH_3$ | $CF_3$ | N | |
| 1082 | $C_2H_5$ | H | CHO | H | $OC_2H_5$ | $NHCH_3$ | N | |
| 1083 | $C_2H_5$ | H | CHO | $CH_3$ | $OCH_3$ | $OCH_3$ | CH | |
| 1084 | $C_2H_5$ | H | CHO | $CH_3$ | $OCH_3$ | $CH_3$ | N | |
| 1085 | $C_2H_5$ | H | $COCH_3$ | H | $OCH_3$ | $OCH_3$ | CH | 126–128 |
| 1086 | $C_2H_5$ | H | $COCH_3$ | H | $OCH_3$ | $CH_3$ | CH | |
| 1087 | $C_2H_5$ | H | $COCH_3$ | H | $CH_3$ | $CH_3$ | CH | |
| 1088 | $C_2H_5$ | H | $COCH_3$ | H | $CH_3$ | $OC_2H_5$ | CH | |
| 1089 | $C_2H_5$ | H | $COCH_3$ | H | $C_2H_5$ | $OCH_3$ | CH | |
| 1090 | $C_2H_5$ | H | $COCH_3$ | H | $OC_2H_5$ | $OC_2H_5$ | CH | |
| 1091 | $C_2H_5$ | H | $COCH_3$ | H | $OCHF_2$ | $OCHF_2$ | CH | |

TABLE 1-continued

Compound of the formula (1a)

(Ia)

| No. | R$^1$ | R$^4$ | R$^5$ | R$^7$ | X | Y | Z | mp.(°C.) |
|---|---|---|---|---|---|---|---|---|
| 1092 | C$_2$H$_5$ | H | COCH$_3$ | H | CH$_3$ | OCHF$_2$ | CH | |
| 1093 | C$_2$H$_5$ | H | COCH$_3$ | H | Cl | OCH$_3$ | CH | |
| 1094 | C$_2$H$_5$ | H | COCH$_3$ | H | OCH$_3$ | OCH$_3$ | N | |
| 1095 | C$_2$H$_5$ | H | COCH$_3$ | H | OCH$_3$ | CH$_3$ | N | |
| 1096 | C$_2$H$_5$ | H | COCH$_3$ | H | CH$_3$ | CH$_3$ | N | |
| 1097 | C$_2$H$_5$ | H | COCH$_3$ | H | N(CH$_3$)$_2$ | OCH$_2$CF$_3$ | N | |
| 1098 | C$_2$H$_5$ | H | COCH$_3$ | H | OCH$_3$ | CF$_3$ | N | |
| 1099 | C$_2$H$_5$ | H | COCH$_3$ | H | OC$_2$H$_5$ | NHCH$_3$ | N | |
| 1100 | C$_2$H$_5$ | H | COCH$_3$ | CH$_3$ | OCH$_3$ | OCH$_3$ | CH | |
| 1101 | C$_2$H$_5$ | H | COCH$_3$ | CH$_3$ | OCH$_3$ | CH$_3$ | N | |
| 1102 | C$_2$H$_5$ | H | COC$_2$H$_5$ | H | OCH$_3$ | OCH$_3$ | CH | |
| 1103 | C$_2$H$_5$ | H | COC$_2$H$_5$ | H | OCH$_3$ | CH$_3$ | CH | |
| 1104 | C$_2$H$_5$ | H | COC$_2$H$_5$ | H | CH$_3$ | CH$_3$ | CH | |
| 1105 | C$_2$H$_5$ | H | COC$_2$H$_5$ | H | CH$_3$ | OC$_2$H$_5$ | CH | |
| 1106 | C$_2$H$_5$ | H | COC$_2$H$_5$ | H | C$_2$H$_5$ | OCH$_3$ | CH | |
| 1107 | C$_2$H$_5$ | H | COC$_2$H$_5$ | H | OC$_2$H$_5$ | OC$_2$H$_5$ | CH | |
| 1108 | C$_2$H$_5$ | H | COC$_2$H$_5$ | H | OCHF$_2$ | OCHF$_2$ | CH | |
| 1109 | C$_2$H$_5$ | H | COC$_2$H$_5$ | H | CH$_3$ | OCHF$_2$ | CH | |
| 1110 | C$_2$H$_5$ | H | COC$_2$H$_5$ | H | Cl | OCH$_3$ | CH | |
| 1111 | C$_2$H$_5$ | H | COC$_2$H$_5$ | H | OCH$_3$ | OCH$_3$ | N | |
| 1112 | C$_2$H$_5$ | H | COC$_2$H$_5$ | H | OCH$_3$ | CH$_3$ | N | |
| 1113 | C$_2$H$_5$ | H | COC$_2$H$_5$ | H | CH$_3$ | CH$_3$ | N | |
| 1114 | C$_2$H$_5$ | H | COC$_2$H$_5$ | H | N(CH$_3$)$_2$ | OCH$_2$CF$_3$ | N | |
| 1115 | C$_2$H$_5$ | H | COC$_2$H$_5$ | H | OCH$_3$ | CF$_3$ | N | |
| 1116 | C$_2$H$_5$ | H | COC$_2$H$_5$ | H | OC$_2$H$_5$ | NHCH$_3$ | N | |
| 1117 | C$_2$H$_5$ | H | COC$_2$H$_5$ | CH$_3$ | OCH$_3$ | OCH$_3$ | CH | |
| 1118 | C$_2$H$_5$ | H | COC$_2$H$_5$ | CH$_3$ | OCH$_3$ | CH$_3$ | N | |
| 1119 | C$_2$H$_5$ | H | CO-n-C$_3$H$_7$ | H | OCH$_3$ | OCH$_3$ | CH | |
| 1120 | C$_2$H$_5$ | H | CO-n-C$_3$H$_7$ | H | OCH$_3$ | CH$_3$ | CH | |
| 1121 | C$_2$H$_5$ | H | CO-n-C$_3$H$_7$ | H | CH$_3$ | CH$_3$ | CH | |
| 1122 | C$_2$H$_5$ | H | CO-n-C$_3$H$_7$ | H | CH$_3$ | OC$_2$H$_5$ | CH | |
| 1123 | C$_2$H$_5$ | H | CO-n-C$_3$H$_7$ | H | C$_2$H$_5$ | OCH$_3$ | CH | |
| 1124 | C$_2$H$_5$ | H | CO-n-C$_3$H$_7$ | H | OC$_2$H$_5$ | OC$_2$H$_5$ | CH | |
| 1125 | C$_2$H$_5$ | H | CO-n-C$_3$H$_7$ | H | OCHF$_2$ | OCHF$_2$ | CH | |
| 1126 | C$_2$H$_5$ | H | CO-n-C$_3$H$_7$ | H | CH$_3$ | OCHF$_2$ | CH | |
| 1127 | C$_2$H$_5$ | H | CO-n-C$_3$H$_7$ | H | Cl | OCH$_3$ | CH | |
| 1128 | C$_2$H$_5$ | H | CO-n-C$_3$H$_7$ | H | OCH$_3$ | OCH$_3$ | N | |
| 1129 | C$_2$H$_5$ | H | CO-n-C$_3$H$_7$ | H | OCH$_3$ | CH$_3$ | N | |
| 1130 | C$_2$H$_5$ | H | CO-n-C$_3$H$_7$ | H | CH$_3$ | CH$_3$ | N | |
| 1131 | C$_2$H$_5$ | H | CO-n-C$_3$H$_7$ | H | N(CH$_3$)$_2$ | OCH$_2$CF$_3$ | N | |
| 1132 | C$_2$H$_5$ | H | CO-n-C$_3$H$_7$ | H | OCH$_3$ | CF$_3$ | N | |
| 1133 | C$_2$H$_5$ | H | CO-n-C$_3$H$_7$ | H | OC$_2$H$_5$ | NHCH$_3$ | N | |
| 1134 | C$_2$H$_5$ | H | CO-n-C$_3$H$_7$ | CH$_3$ | OCH$_3$ | OCH$_3$ | CH | |
| 1135 | C$_2$H$_5$ | H | CO-n-C$_3$H$_7$ | CH$_3$ | OCH$_3$ | CH$_3$ | N | |
| 1136 | C$_2$H$_5$ | H | CO-i-C$_3$H$_7$ | H | OCH$_3$ | OCH$_3$ | CH | |
| 1137 | C$_2$H$_5$ | H | CO-i-C$_3$H$_7$ | H | OCH$_3$ | CH$_3$ | CH | |
| 1138 | C$_2$H$_5$ | H | CO-i-C$_3$H$_7$ | H | CH$_3$ | CH$_3$ | CH | |
| 1139 | C$_2$H$_5$ | H | CO-i-C$_3$H$_7$ | H | CH$_3$ | OC$_2$H$_5$ | CH | |
| 1140 | C$_2$H$_5$ | H | CO-i-C$_3$H$_7$ | H | C$_2$H$_5$ | OCH$_3$ | CH | |
| 1141 | C$_2$H$_5$ | H | CO-i-C$_3$H$_7$ | H | OC$_2$H$_5$ | OC$_2$H$_5$ | CH | |
| 1142 | C$_2$H$_5$ | H | CO-i-C$_3$H$_7$ | H | OCHF$_2$ | OCHF$_2$ | CH | |
| 1143 | C$_2$H$_5$ | H | CO-i-C$_3$H$_7$ | H | CH$_3$ | OCHF$_2$ | CH | |
| 1144 | C$_2$H$_5$ | H | CO-i-C$_3$H$_7$ | H | Cl | OCH$_3$ | CH | |
| 1145 | C$_2$H$_5$ | H | CO-i-C$_3$H$_7$ | H | OCH$_3$ | OCH$_3$ | N | |
| 1146 | C$_2$H$_5$ | H | CO-i-C$_3$H$_7$ | H | OCH$_3$ | CH$_3$ | N | |
| 1147 | C$_2$H$_5$ | H | CO-i-C$_3$H$_7$ | H | CH$_3$ | CH$_3$ | N | |
| 1148 | C$_2$H$_5$ | H | CO-i-C$_3$H$_7$ | H | N(CH$_3$)$_2$ | OCH$_2$CF$_3$ | N | |
| 1149 | C$_2$H$_5$ | H | CO-i-C$_3$H$_7$ | H | OCH$_3$ | CF$_3$ | N | |
| 1150 | C$_2$H$_5$ | H | CO-i-C$_3$H$_7$ | H | OC$_2$H$_5$ | NHCH$_3$ | N | |
| 1151 | C$_2$H$_5$ | H | CO-i-C$_3$H$_7$ | CH$_3$ | OCH$_3$ | OCH$_3$ | CH | |
| 1152 | C$_2$H$_5$ | H | CO-i-C$_3$H$_7$ | CH$_3$ | OCH$_3$ | CH$_3$ | N | |
| 1153 | C$_2$H$_5$ | H | COCF$_3$ | H | OCH$_3$ | OCH$_3$ | CH | |
| 1154 | C$_2$H$_5$ | H | COCF$_3$ | H | OCH$_3$ | CH$_3$ | CH | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 1155 | $C_2H_5$ | H | $COCF_3$ | H | $CH_3$ | $CH_3$ | CH | |
| 1156 | $C_2H_5$ | H | $COCF_3$ | H | $CH_3$ | $OC_2H_5$ | CH | |
| 1157 | $C_2H_5$ | H | $COCF_3$ | H | $C_2H_5$ | $OCH_3$ | CH | |
| 1158 | $C_2H_5$ | H | $COCF_3$ | H | $OC_2H_5$ | $OC_2H_5$ | CH | |
| 1159 | $C_2H_5$ | H | $COCF_3$ | H | $OCHF_2$ | $OCHF_2$ | CH | |
| 1160 | $C_2H_5$ | H | $COCF_3$ | H | $CH_3$ | $OCHF_2$ | CH | |
| 1161 | $C_2H_5$ | H | $COCF_3$ | H | Cl | $OCH_3$ | CH | |
| 1162 | $C_2H_5$ | H | $COCF_3$ | H | $OCH_3$ | $OCH_3$ | N | |
| 1163 | $C_2H_5$ | H | $COCF_3$ | H | $OCH_3$ | $CH_3$ | N | |
| 1164 | $C_2H_5$ | H | $COCF_3$ | H | $CH_3$ | $CH_3$ | N | |
| 1165 | $C_2H_5$ | H | $COCF_3$ | H | $N(CH_3)_2$ | $OCH_2CF_3$ | N | |
| 1166 | $C_2H_5$ | H | $COCF_3$ | H | $OCH_3$ | $CF_3$ | N | |
| 1167 | $C_2H_5$ | H | $COCF_3$ | H | $OC_2H_5$ | $NHCH_3$ | N | |
| 1168 | $C_2H_5$ | H | $COCF_3$ | $CH_3$ | $OCH_3$ | $OCH_3$ | CH | |
| 1169 | $C_2H_5$ | H | $COCF_3$ | $CH_3$ | $OCH_3$ | $CH_3$ | N | |
| 1170 | $C_2H_5$ | H | $COOCH_3$ | H | $OCH_3$ | $OCH_3$ | CH | 132–136 |
| 1170 a | $C_2H_5$ | H | $COOCH_3$ | H | $OCH_3$ | $CH_3$ | CH | |
| 1171 | $C_2H_5$ | H | $COOCH_3$ | H | $CH_3$ | $CH_3$ | CH | |
| 1172 | $C_2H_5$ | H | $COOCH_3$ | H | $CH_3$ | $OC_2H_5$ | CH | |
| 1173 | $C_2H_5$ | H | $COOCH_3$ | H | $C_2H_5$ | $OCH_3$ | CH | |
| 1174 | $C_2H_5$ | H | $COOCH_3$ | H | $OC_2H_5$ | $OC_2H_5$ | CH | |
| 1175 | $C_2H_5$ | H | $COOCH_3$ | H | $OCHF_2$ | $OCHF_2$ | CH | |
| 1176 | $C_2H_5$ | H | $COOCH_3$ | H | $CH_3$ | $OCHF_2$ | CH | |
| 1177 | $C_2H_5$ | H | $COOCH_3$ | H | Cl | $OCH_3$ | CH | |
| 1178 | $C_2H_5$ | H | $COOCH_3$ | H | $OCH_3$ | $OCH_3$ | N | |
| 1179 | $C_2H_5$ | H | $COOCH_3$ | H | $OCH_3$ | $CH_3$ | N | |
| 1180 | $C_2H_5$ | H | $COOCH_3$ | H | $CH_3$ | $CH_3$ | N | |
| 1181 | $C_2H_5$ | H | $COOCH_3$ | H | $N(CH_3)_2$ | $OCH_2CF_3$ | N | |
| 1182 | $C_2H_5$ | H | $COOCH_3$ | H | $OCH_3$ | $CF_3$ | N | |
| 1183 | $C_2H_5$ | H | $COOCH_3$ | H | $OC_2H_5$ | $NHCH_3$ | N | |
| 1184 | $C_2H_5$ | H | $COOCH_3$ | $CH_3$ | $OCH_3$ | $OCH_3$ | CH | |
| 1185 | $C_2H_5$ | H | $COOCH_3$ | $CH_3$ | $OCH_3$ | $CH_3$ | N | |
| 1186 | $C_2H_5$ | H | $COOC_2H_5$ | H | $OCH_3$ | $OCH_3$ | CH | |
| 1186 a | $C_2H_5$ | H | $COOC_2H_5$ | H | $OCH_3$ | $CH_3$ | CH | |
| 1187 | $C_2H_5$ | H | $COOC_2H_5$ | H | $CH_3$ | $CH_3$ | CH | |
| 1188 | $C_2H_5$ | H | $COOC_2H_5$ | H | $CH_3$ | $OC_2H_5$ | CH | |
| 1189 | $C_2H_5$ | H | $COOC_2H_5$ | H | $C_2H_5$ | $OCH_3$ | CH | |
| 1190 | $C_2H_5$ | H | $COOC_2H_5$ | H | $OC_2H_5$ | $OC_2H_5$ | CH | |
| 1191 | $C_2H_5$ | H | $COOC_2H_5$ | H | $OCHF_2$ | $OCHF_2$ | CH | |
| 1192 | $C_2H_5$ | H | $COOC_2H_5$ | H | $CH_3$ | $OCHF_2$ | CH | |
| 1193 | $C_2H_5$ | H | $COOC_2H_5$ | H | Cl | $OCH_3$ | CH | |
| 1194 | $C_2H_5$ | H | $COOC_2H_5$ | H | $OCH_3$ | $OCH_3$ | N | |
| 1195 | $C_2H_5$ | H | $COOC_2H_5$ | H | $OCH_3$ | $CH_3$ | N | |
| 1196 | $C_2H_5$ | H | $COOC_2H_5$ | H | $CH_3$ | $CH_3$ | N | |
| 1197 | $C_2H_5$ | H | $COOC_2H_5$ | H | $N(CH_3)_2$ | $OCH_2CF_3$ | N | |
| 1198 | $C_2H_5$ | H | $COOC_2H_5$ | H | $OCH_3$ | $CF_3$ | N | |
| 1199 | $C_2H_5$ | H | $COOC_2H_5$ | H | $OC_2H_5$ | $NHCH_3$ | N | |
| 1200 | $C_2H_5$ | H | $COOC_2H_5$ | $CH_3$ | $OCH_3$ | $OCH_3$ | CH | |
| 1201 | $C_2H_5$ | H | $COOC_2H_5$ | $CH_3$ | $OCH_3$ | $CH_3$ | N | |
| 1202 | $C_2H_5$ | H | $SO_2CH_3$ | H | $OCH_3$ | $OCH_3$ | CH | 130–132 |
| 1202 a | $C_2H_5$ | H | $SO_2CH_3$ | H | $OCH_3$ | $CH_3$ | CH | |
| 1203 | $C_2H_5$ | H | $SO_2CH_3$ | H | $CH_3$ | $CH_3$ | CH | |
| 1204 | $C_2H_5$ | H | $SO_2CH_3$ | H | $CH_3$ | $OC_2H_5$ | CH | |
| 1205 | $C_2H_5$ | H | $SO_2CH_3$ | H | $C_2H_5$ | $OCH_3$ | CH | |
| 1206 | $C_2H_5$ | H | $SO_2CH_3$ | H | $OC_2H_5$ | $OC_2H_5$ | CH | |
| 1207 | $C_2H_5$ | H | $SO_2CH_3$ | H | $OCHF_2$ | $OCHF_2$ | CH | |
| 1208 | $C_2H_5$ | H | $SO_2CH_3$ | H | $CH_3$ | $OCHF_2$ | CH | |
| 1209 | $C_2H_5$ | H | $SO_2CH_3$ | H | Cl | $OCH_3$ | CH | |
| 1210 | $C_2H_5$ | H | $SO_2CH_3$ | H | $OCH_3$ | $OCH_3$ | N | |
| 1211 | $C_2H_5$ | H | $SO_2CH_3$ | H | $OCH_3$ | $CH_3$ | N | |

TABLE 1-continued

Compound of the formula (1a)

$$\text{(Ia)}$$

| No. | $R^1$ | $R^4$ | $R^5$ | $R^7$ | X | Y | Z | mp.(°C.) |
|---|---|---|---|---|---|---|---|---|
| 1212 | $C_2H_5$ | H | $SO_2CH_3$ | H | $CH_3$ | $CH_3$ | N | |
| 1213 | $C_2H_5$ | H | $SO_2CH_3$ | H | $N(CH_3)_2$ | $OCH_2CF_3$ | N | |
| 1214 | $C_2H_5$ | H | $SO_2CH_3$ | H | $OCH_3$ | $CF_3$ | N | |
| 1215 | $C_2H_5$ | H | $SO_2CH_3$ | H | $OC_2H_5$ | $NHCH_3$ | N | |
| 1216 | $C_2H_5$ | H | $SO_2CH_3$ | $CH_3$ | $OCH_3$ | $OCH_3$ | CH | |
| 1217 | $C_2H_5$ | H | $SO_2CH_3$ | $CH_3$ | $OCH_3$ | $CH_3$ | N | |
| 1218 | $C_2H_5$ | H | $SO_2C_2H_5$ | H | $OCH_3$ | $OCH_3$ | CH | |
| 1218 a | $C_2H_5$ | H | $SO_2C_2H_5$ | H | $OCH_3$ | $CH_3$ | CH | |
| 1219 | $C_2H_5$ | H | $SO_2C_2H_5$ | H | $CH_3$ | $CH_3$ | CH | |
| 1220 | $C_2H_5$ | H | $SO_2C_2H_5$ | H | $CH_3$ | $OC_2H_5$ | CH | |
| 1221 | $C_2H_5$ | H | $SO_2C_2H_5$ | H | $C_2H_5$ | $OCH_3$ | CH | |
| 1222 | $C_2H_5$ | H | $SO_2C_2H_5$ | H | $OC_2H_5$ | $OC_2H_5$ | CH | |
| 1223 | $C_2H_5$ | H | $SO_2C_2H_5$ | H | $OCHF_2$ | $OCHF_2$ | CH | |
| 1224 | $C_2H_5$ | H | $SO_2C_2H_5$ | H | $CH_3$ | $OCHF_2$ | CH | |
| 1225 | $C_2H_5$ | H | $SO_2C_2H_5$ | H | Cl | $OCH_3$ | CH | |
| 1226 | $C_2H_5$ | H | $SO_2C_2H_5$ | H | $OCH_3$ | $OCH_3$ | N | |
| 1227 | $C_2H_5$ | H | $SO_2C_2H_5$ | H | $OCH_3$ | $CH_3$ | N | |
| 1228 | $C_2H_5$ | H | $SO_2C_2H_5$ | H | $CH_3$ | $CH_3$ | N | |
| 1229 | $C_2H_5$ | H | $SO_2C_2H_5$ | H | $N(CH_3)_2$ | $OCH_2CF_3$ | N | |
| 1230 | $C_2H_5$ | H | $SO_2C_2H_5$ | H | $OCH_2$ | $CF_3$ | N | |
| 1231 | $C_2H_5$ | H | $SO_2C_2H_5$ | H | $OC_2H_5$ | $NHCH_3$ | N | |
| 1232 | $C_2H_5$ | H | $SO_2C_2H_5$ | $CH_3$ | $OCH_3$ | $OCH_3$ | CH | |
| 1233 | $C_2H_5$ | H | $SO_2C_2H_5$ | $CH_3$ | $OCH_3$ | $CH_3$ | N | |
| 1234 | $C_2H_5$ | H | $SO_2$-n-$C_3H_7$ | H | $OCH_3$ | $OCH_3$ | CH | |
| 1234 a | $C_2H_5$ | H | $SO_2$-n-$C_3H_7$ | H | $OCH_3$ | $CH_3$ | CH | |
| 1235 | $C_2H_5$ | H | $SO_2$-n-$C_3H_7$ | H | $CH_3$ | $CH_3$ | CH | |
| 1236 | $C_2H_5$ | H | $SO_2$-n-$C_3H_7$ | H | $CH_3$ | $OC_2H_5$ | CH | |
| 1237 | $C_2H_5$ | H | $SO_2$-n-$C_3H_7$ | H | $C_2H_5$ | $OCH_3$ | CH | |
| 1238 | $C_2H_5$ | H | $SO_2$-n-$C_3H_7$ | H | $OC_2H_5$ | $OC_2H_5$ | CH | |
| 1239 | $C_2H_5$ | H | $SO_2$-n-$C_3H_7$ | H | $OCHF_2$ | $OCHF_2$ | CH | |
| 1240 | $C_2H_5$ | H | $SO_2$-n-$C_3H_7$ | H | $CH_3$ | $OCHF_2$ | CH | |
| 1241 | $C_2H_5$ | H | $SO_2$-n-$C_3H_7$ | H | Cl | $OCH_3$ | CH | |
| 1242 | $C_2H_5$ | H | $SO_2$-n-$C_3H_7$ | H | $OCH_3$ | $OCH_3$ | N | |
| 1243 | $C_2H_5$ | H | $SO_2$-n-$C_3H_7$ | H | $OCH_3$ | $CH_3$ | N | |
| 1244 | $C_2H_5$ | H | $SO_2$-n-$C_3H_7$ | H | $CH_3$ | $CH_3$ | N | |
| 1245 | $C_2H_5$ | H | $SO_2$-n-$C_3H_7$ | H | $N(CH_3)_2$ | $OCH_2CF_3$ | N | |
| 1246 | $C_2H_5$ | H | $SO_2$-n-$C_3H_7$ | H | $OCH_3$ | $CF_3$ | N | |
| 1247 | $C_2H_5$ | H | $SO_2$-n-$C_3H_7$ | H | $OC_2H_5$ | $NHCH_3$ | N | |
| 1248 | $C_2H_5$ | H | $SO_2$-n-$C_3H_7$ | $CH_3$ | $OCH_3$ | $OCH_3$ | CH | |
| 1249 | $C_2H_5$ | H | $SO_2$-n-$C_3H_7$ | $CH_3$ | $OCH_3$ | $CH_3$ | N | |
| 1250 | $C_2H_5$ | H | $SO_2$-i-$C_3H_7$ | H | $OCH_3$ | $OCH_3$ | CH | |
| 1250 a | $C_2H_5$ | H | $SO_2$-i-$C_3H_7$ | H | $OCH_3$ | $CH_3$ | CH | |
| 1251 | $C_2H_5$ | H | $SO_2$-i-$C_3H_7$ | H | $CH_3$ | $CH_3$ | CH | |
| 1252 | $C_2H_5$ | H | $SO_2$-i-$C_3H_7$ | H | $CH_3$ | $OC_2H_5$ | CH | |
| 1253 | $C_2H_5$ | H | $SO_2$-i-$C_3H_7$ | H | $C_2H_5$ | $OCH_3$ | CH | |
| 1254 | $C_2H_5$ | H | $SO_2$-i-$C_3H_7$ | H | $OC_2H_5$ | $OC_2H_5$ | CH | |
| 1255 | $C_2H_5$ | H | $SO_2$-i-$C_3H_7$ | H | $OCHF_2$ | $OCHF_2$ | CH | |
| 1256 | $C_2H_5$ | H | $SO_2$-i-$C_3H_7$ | H | $CH_3$ | $OCHF_2$ | CH | |
| 1257 | $C_2H_5$ | H | $SO_2$-i-$C_3H_7$ | H | Cl | $OCH_3$ | CH | |
| 1258 | $C_2H_5$ | H | $SO_2$-i-$C_3H_7$ | H | $OCH_3$ | $OCH_3$ | N | |
| 1259 | $C_2H_5$ | H | $SO_2$-i-$C_3H_7$ | H | $OCH_3$ | $CH_3$ | N | |
| 1260 | $C_2H_5$ | H | $SO_2$-i-$C_3H_7$ | H | $CH_3$ | $CH_3$ | N | |
| 1261 | $C_2H_5$ | H | $SO_2$-i-$C_3H_7$ | H | $N(CH_3)_2$ | $OCH_2CF_3$ | N | |
| 1262 | $C_2H_5$ | H | $SO_2$-i-$C_3H_7$ | H | $OCH_3$ | $CF_3$ | N | |
| 1263 | $C_2H_5$ | H | $SO_2$-i-$C_3H_7$ | H | $OC_2H_5$ | $NHCH_3$ | N | |
| 1264 | $C_2H_5$ | H | $SO_2$-i-$C_3H_7$ | $CH_3$ | $OCH_3$ | $OCH_3$ | CH | |
| 1265 | $C_2H_5$ | H | $SO_2$-i-$C_3H_7$ | $CH_3$ | $OCH_3$ | $CH_3$ | N | |
| 1266 | $C_2H_5$ | H | $ClCH_2CO$ | H | $OCH_3$ | $OCH_3$ | CH | |
| 1267 | $C_2H_5$ | H | $ClCH_2CO$ | H | $OCH_3$ | $CH_3$ | CH | |
| 1268 | $C_2H_5$ | H | $ClCH_2CO$ | H | $CH_3$ | $CH_3$ | CH | |

TABLE 1-continued

Compound of the formula (1a)

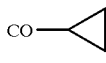

(Ia)

| No. | R¹ | R⁴ | R⁵ | R⁷ | X | Y | Z | mp.(°C.) |
|---|---|---|---|---|---|---|---|---|
| 1269 | C₂H₅ | H | ClCH₂CO | H | Cl | OCH₃ | CH | |
| 1270 | C₂H₅ | H | ClCH₂CO | H | OCH₃ | OCH₃ | N | |
| 1271 | C₂H₅ | H | ClCH₂CO | H | OCH₃ | CH₃ | N | |
| 1272 | C₂H₅ | H | ClCH₂CO | H | OCH₃ | CF₃ | N | |
| 1273 | C₂H₅ | H | ClCH₂CO | CH₃ | OCH₃ | OCH₃ | CH | |
| 1274 | C₂H₅ | H | ClCH₂CO | CH₃ | OCH₃ | CH₃ | N | |
| 1275 | C₂H₅ | H | Cl₂CHCO | H | OCH₃ | OCH₃ | CH | |
| 1276 | C₂H₅ | H | Cl₂CHCO | H | OCH₃ | CH₃ | CH | |
| 1277 | C₂H₅ | H | Cl₂CHCO | H | CH₃ | CH₃ | CH | |
| 1278 | C₂H₅ | H | Cl₂CHCO | H | Cl | OCH₃ | CH | |
| 1279 | C₂H₅ | H | Cl₂CHCO | H | OCH₃ | OCH₃ | N | |
| 1280 | C₂H₅ | H | Cl₂CHCO | H | OCH₃ | CH₃ | N | |
| 1281 | C₂H₅ | H | Cl₂CHCO | H | OCH₃ | CF₃ | N | |
| 1282 | C₂H₅ | H | Cl₂CHCO | CH₃ | OCH₃ | OCH₃ | CH | |
| 1283 | C₂H₅ | H | Cl₂CHCO | CH₃ | OCH₃ | CH₃ | N | |
| 1284 | C₂H₅ | H | Cl₃CCO | H | OCH₃ | OCH₃ | CH | |
| 1285 | C₂H₅ | H | Cl₃CCO | H | OCH₃ | CH₃ | CH | |
| 1286 | C₂H₅ | H | Cl₃CCO | H | CH₃ | CH₃ | CH | |
| 1287 | C₂H₅ | H | Cl₃CCO | H | Cl | OCH₃ | CH | |
| 1288 | C₂H₅ | H | Cl₃CCO | H | OCH₃ | OCH₃ | N | |
| 1289 | C₂H₅ | H | Cl₃CCO | H | OCH₃ | CH₃ | N | |
| 1290 | C₂H₅ | H | Cl₃CCO | H | OCH₃ | CF₃ | N | |
| 1291 | C₂H₅ | H | Cl₃CCO | CH₃ | OCH₃ | OCH₃ | CH | |
| 1292 | C₂H₅ | H | Cl₃CCO | CH₃ | OCH₃ | CH₃ | N | |
| 1293 | C₂H₅ | H | CH₃OCH₂CO | H | OCH₃ | OCH₃ | CH | |
| 1294 | C₂H₅ | H | CH₃OCH₂CO | H | OCH₃ | CH₃ | CH | |
| 1295 | C₂H₅ | H | CH₃OCH₂CO | H | CH₃ | CH₃ | CH | |
| 1296 | C₂H₅ | H | CH₃OCH₂CO | H | Cl | OCH₃ | CH | |
| 1297 | C₂H₅ | H | CH₃OCH₂CO | H | OCH₃ | OCH₃ | N | |
| 1298 | C₂H₅ | H | CH₃OCH₂CO | H | OCH₃ | CH₃ | N | |
| 1299 | C₂H₅ | H | CH₃OCH₂CO | H | OCH₃ | CF₃ | N | |
| 1300 | C₂H₅ | H | CH₃OCH₂CO | CH₃ | OCH₃ | OCH₃ | CH | |
| 1301 | C₂H₅ | H | CH₃OCH₂CO | CH₃ | OCH₃ | CH₃ | N | |
| 1302 | C₂H₅ | H | CH₂=CHCO | H | OCH₃ | OCH₃ | CH | |
| 1303 | C₂H₅ | H | CH₂=CHCO | H | OCH₃ | CH₃ | CH | |
| 1304 | C₂H₅ | H | CH₂=CHCO | H | CH₃ | CH₃ | CH | |
| 1305 | C₂H₅ | H | CH₂=CHCO | H | Cl | OCH₃ | CH | |
| 1306 | C₂H₅ | H | CH₂=CHCO | H | OCH₃ | OCH₃ | N | |
| 1307 | C₂H₅ | H | CH₂=CHCO | H | OCH₃ | CH₃ | N | |
| 1308 | C₂H₅ | H | CH₂=CHCO | H | OCH₃ | CF₃ | N | |
| 1309 | C₂H₅ | H | CH₂=CHCO | CH₃ | OCH₃ | OCH₃ | CH | |
| 1310 | C₂H₅ | H | CH₂=CHCO | CH₃ | OCH₃ | CH₃ | N | |
| 1311 | C₂H₅ | H | CH≡CCO | H | OCH₃ | OCH₃ | CH | |
| 1312 | C₂H₅ | H | CH≡CCO | H | OC₂H₅ | OCH₃ | CH | |
| 1313 | C₂H₅ | H | CH≡CCO | H | OCH₃ | CH₃ | CH | |
| 1314 | C₂H₅ | H | CH≡CCO | H | CH₃ | CH₃ | CH | |
| 1315 | C₂H₅ | H | CH≡CCO | H | Cl | OCH₃ | CH | |
| 1316 | C₂H₅ | H | CH≡CCO | H | OCH₃ | OCH₃ | N | |
| 1317 | C₂H₅ | H | CH≡CCO | H | OCH₃ | CH₃ | N | |
| 1318 | C₂H₅ | H | CH≡CCO | H | OCH₃ | CF₃ | N | |
| 1319 | C₂H₅ | H | CH≡CCO | CH₃ | OCH₃ | OCH₃ | CH | |
| 1320 | C₂H₅ | H | CH≡CCO | CH₃ | OCH₃ | CH₃ | N | |
| 1321 | C₂H₅ | H | 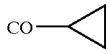 | H | OCH₃ | OCH₃ | CH | |
| 1322 | C₂H₅ | H | 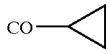 | H | OCH₃ | CH₃ | CH | |

TABLE 1-continued
Compound of the formula (1a)
(Ia)
| No. | R¹ | R⁴ | R⁵ | R⁷ | X | Y | Z | mp.(°C.) |
|-----|----|----|----|----|----|----|----|----------|
| 1323 | $C_2H_5$ | H |  | H | $CH_3$ | $CH_3$ | CH | |
| 1324 | $C_2H_5$ | H |  | H | Cl | $OCH_3$ | CH | |
| 1325 | $C_2H_5$ | H |  | H | $OCH_3$ | $OCH_3$ | N | |
| 1326 | $C_2H_5$ | H |  | H | $OCH_3$ | $CH_3$ | N | |
| 1327 | $C_2H_5$ | H |  | H | $OCH_3$ | $CF_3$ | N | |
| 1328 | $C_2H_5$ | H |  | $CH_3$ | $OCH_3$ | $OCH_3$ | CH | |
| 1329 | $C_2H_5$ | H |  | $CH_3$ | $OCH_3$ | $CH_3$ | N | |
| 1330 | $C_2H_5$ | H |  | H | $OCH_3$ | $OCH_3$ | CH | |
| 1331 | $C_2H_5$ | H |  | H | $OCH_3$ | $CH_3$ | CH | |
| 1332 | $C_2H_5$ | H |  | H | $CH_3$ | $CH_3$ | CH | |
| 1333 | $C_2H_5$ | H |  | H | Cl | $OCH_3$ | CH | |

TABLE 1-continued
Compound of the formula (1a)
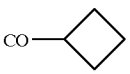
| No. | R¹ | R⁴ | R⁵ | R⁷ | X | Y | Z | mp.(°C.) |
|---|---|---|---|---|---|---|---|---|
| 1334 | $C_2H_5$ | H | 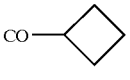 | H | $OCH_3$ | $OCH_3$ | N | |
| 1335 | $C_2H_5$ | H | 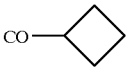 | H | $OCH_3$ | $CH_3$ | N | |
| 1336 | $C_2H_5$ | H | 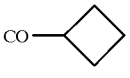 | H | $OCH_3$ | $CF_3$ | N | |
| 1337 | $C_2H_5$ | H | 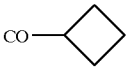 | $CH_3$ | $OCH_3$ | $OCH_3$ | CH | |
| 1338 | $C_2H_5$ | H | 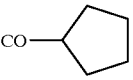 | $CH_3$ | $OCH_3$ | $CH_3$ | N | |
| 1339 | $C_2H_5$ | H | 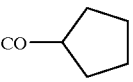 | H | $OCH_3$ | $OCH_3$ | CH | |
| 1340 | $C_2H_5$ | H | 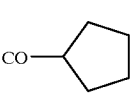 | H | $OCH_3$ | $CH_3$ | CH | |
| 1341 | $C_2H_5$ | H |  | H | $CH_3$ | $CH_3$ | CH | |
| 1342 | $C_2H_5$ | H | 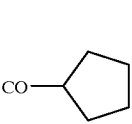 | H | Cl | $OCH_3$ | CH | |
| 1343 | $C_2H_5$ | H |  | H | $OCH_3$ | $OCH_3$ | N | |

TABLE 1-continued

Compound of the formula (1a)

(Ia)

| No. | R$^1$ | R$^4$ | R$^5$ | R$^7$ | X | Y | Z | mp.(°C.) |
|---|---|---|---|---|---|---|---|---|
| 1344 | C$_2$H$_5$ | H | CO-cyclopentyl | H | OCH$_3$ | OCH$_3$ | N | |
| 1345 | C$_2$H$_5$ | H | CO-cyclopentyl | H | OCH$_3$ | CF$_3$ | N | |
| 1346 | C$_2$H$_5$ | H | CO-cyclopentyl | CH$_3$ | OCH$_3$ | OCH$_3$ | CH | |
| 1347 | C$_2$H$_5$ | H | CO-cyclopentyl | CH$_3$ | OCH$_3$ | CH$_3$ | N | |
| 1348 | C$_2$H$_5$ | H | CO-cyclopentyl | H | OCH$_3$ | OCH$_3$ | CH | |
| 1349 | C$_2$H$_5$ | H | CO-cyclohexyl | H | OCH$_3$ | CH$_3$ | CH | |
| 1350 | C$_2$H$_5$ | H | CO-cyclohexyl | H | CH$_3$ | CH$_3$ | CH | |
| 1351 | C$_2$H$_5$ | H | CO-cyclohexyl | H | Cl | OCH$_3$ | CH | |
| 1352 | C$_2$H$_5$ | H | CO-cyclohexyl | H | OCH$_3$ | OCH$_3$ | N | |

TABLE 1-continued

Compound of the formula (1a)

| No. | R¹ | R⁴ | R⁵ | R⁷ | X | Y | Z | mp.(°C.) |
|---|---|---|---|---|---|---|---|---|
| 1353 | $C_2H_5$ | H | CO-cyclohexyl | H | $OCH_3$ | $CH_3$ | N | |
| 1354 | $C_2H_5$ | H | CO-cyclohexyl | H | $OCH_3$ | $CF_3$ | N | |
| 1355 | $C_2H_5$ | H | CO-cyclohexyl | $CH_3$ | $OCH_3$ | $OCH_3$ | CH | |
| 1356 | $C_2H_5$ | H | CO-cyclohexyl | $CH_3$ | $OCH_3$ | $CH_3$ | N | |
| 1357 | $C_2H_5$ | H | $CF_3SO_2$ | H | $OCH_3$ | $OCH_3$ | CH | |
| 1358 | $C_2H_5$ | H | $CF_3SO_2$ | H | $OCH_3$ | $CH_3$ | CH | |
| 1359 | $C_2H_5$ | H | $CF_3SO_2$ | H | $CH_3$ | $CH_3$ | CH | |
| 1360 | $C_2H_5$ | H | $CF_3SO_2$ | H | Cl | $OCH_3$ | CH | |
| 1361 | $C_2H_5$ | H | $CF_3SO_2$ | H | $OCH_3$ | $CH_3$ | N | |
| 1362 | $C_2H_5$ | H | $CF_3SO_2$ | H | $OCH_3$ | $CF_3$ | N | |
| 1363 | $C_2H_5$ | H | $CF_3SO_2$ | H | $OCH_3$ | $OCH_3$ | N | |
| 1364 | $C_2H_5$ | H | $CF_3SO_2$ | $CH_3$ | $OCH_3$ | $CH_3$ | CH | |
| 1365 | $C_2H_5$ | H | $CF_3SO_2$ | $CH_3$ | $OCH_3$ | $OCH_3$ | N | |
| 1366 | $C_2H_5$ | H | $FCH_2SO_2$ | H | $OCH_3$ | $OCH_3$ | CH | |
| 1367 | $C_2H_5$ | H | $FCH_2SO_2$ | H | $OCH_3$ | $CH_3$ | CH | |
| 1368 | $C_2H_5$ | H | $FCH_2SO_2$ | H | $CH_3$ | $CH_3$ | CH | |
| 1369 | $C_2H_5$ | H | $FCH_2SO_2$ | H | Cl | $OCH_3$ | CH | |
| 1370 | $C_2H_5$ | H | $FCH_2SO_2$ | H | $OCH_3$ | $OCH_3$ | N | |
| 1371 | $C_2H_5$ | H | $FCH_2SO_2$ | H | $OCH_3$ | $CH_3$ | N | |
| 1372 | $C_2H_5$ | H | $FCH_2SO_2$ | H | $OCH_3$ | $CF_3$ | N | |
| 1373 | $C_2H_5$ | H | $FCH_2SO_2$ | $CH_3$ | $OCH_3$ | $OCH_3$ | CH | |
| 1374 | $C_2H_5$ | H | $FCH_2SO_2$ | $CH_3$ | $OCH_3$ | $OCH_3$ | N | |
| 1375 | $C_2H_5$ | H | $ClCH_2SO_2$ | H | $OCH_3$ | $OCH_3$ | CH | |
| 1376 | $C_2H_5$ | H | $ClCH_2SO_2$ | H | $OCH_3$ | $CH_3$ | CH | |
| 1377 | $C_2H_5$ | H | $ClCH_2SO_2$ | H | $CH_3$ | $CH_3$ | CH | |
| 1378 | $C_2H_5$ | H | $ClCH_2SO_2$ | H | Cl | $OCH_3$ | CH | |
| 1379 | $C_2H_5$ | H | $ClCH_2SO_2$ | H | $OCH_3$ | $OCH_3$ | N | |
| 1380 | $C_2H_5$ | H | $ClCH_2SO_2$ | H | $OCH_3$ | $CH_3$ | N | |
| 1381 | $C_2H_5$ | H | $ClCH_2SO_2$ | H | $OCH_3$ | $CF_3$ | N | |
| 1382 | $C_2H_5$ | H | $ClCH_2SO_2$ | $CH_3$ | $OCH_3$ | $OCH_3$ | CH | |
| 1383 | $C_2H_5$ | H | $ClCH_2SO_2$ | $CH_3$ | $OCH_3$ | $CH_3$ | N | |
| 1384 | $C_2H_5$ | H | $Cl_2CHSO_2$ | H | $OCH_3$ | $OCH_3$ | CH | |
| 1385 | $C_2H_5$ | H | $Cl_2CHSO_2$ | H | $OCH_3$ | $CH_3$ | CH | |
| 1386 | $C_2H_5$ | H | $Cl_2CHSO_2$ | H | $CH_3$ | $CH_3$ | CH | |
| 1387 | $C_2H_5$ | H | $Cl_2CHSO_2$ | H | Cl | $OCH_3$ | CH | |
| 1388 | $C_2H_5$ | H | $Cl_2CHSO_2$ | H | $OCH_3$ | $OCH_3$ | N | |
| 1389 | $C_2H_5$ | H | $Cl_2CHSO_2$ | H | $OCH_3$ | $CH_3$ | N | |
| 1390 | $C_2H_5$ | H | $Cl_2CHSO_2$ | H | $OCH_3$ | $CF_3$ | N | |
| 1391 | $C_2H_5$ | H | $Cl_2CHSO_2$ | $CH_3$ | $OCH_3$ | $OCH_3$ | CH | |
| 1392 | $C_2H_5$ | H | $Cl_2CHSO_2$ | $CH_3$ | $OCH_3$ | $CH_3$ | N | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 1393 | $C_2H_5$ | H | $Cl_3CSO_2$ | H | $OCH_3$ | $OCH_3$ | CH | |
| 1394 | $C_2H_5$ | H | $Cl_3CSO_2$ | H | $OCH_3$ | $CH_3$ | CH | |
| 1395 | $C_2H_5$ | H | $Cl_3CSO_2$ | H | $CH_3$ | $CH_3$ | CH | |
| 1396 | $C_2H_5$ | H | $Cl_3CSO_2$ | H | Cl | $OCH_3$ | CH | |
| 1397 | $C_2H_5$ | H | $Cl_3CSO_2$ | H | $OCH_3$ | $OCH_3$ | N | |
| 1398 | $C_2H_5$ | H | $Cl_3CSO_2$ | H | $OCH_3$ | $CH_3$ | N | |
| 1399 | $C_2H_5$ | H | $Cl_3CSO_2$ | H | $OCH_3$ | $CF_3$ | N | |
| 1400 | $C_2H_5$ | H | $Cl_3CSO_2$ | $CH_3$ | $OCH_3$ | $OCH_3$ | CH | |
| 1401 | $C_2H_5$ | H | $Cl_3CSO_2$ | $CH_3$ | $OCH_3$ | $CH_3$ | N | |
| 1402 | $C_2H_5$ | H | $n-C_4H_9SO_2$ | H | $OCH_3$ | $OCH_3$ | CH | |
| 1403 | $C_2H_5$ | H | $n-C_4H_9SO_2$ | H | $OCH_3$ | $CH_3$ | CH | |
| 1404 | $C_2H_5$ | H | $n-C_4H_9SO_2$ | H | $CH_3$ | $CH_3$ | CH | |
| 1405 | $C_2H_5$ | H | $n-C_4H_9SO_2$ | H | Cl | $OCH_3$ | CH | |
| 1406 | $C_2H_5$ | H | $n-C_4H_9SO_2$ | H | $OCH_3$ | $OCH_3$ | N | |
| 1407 | $C_2H_5$ | H | $n-C_4H_9SO_2$ | H | $OCH_3$ | $CF_3$ | N | |
| 1408 | $C_2H_5$ | H | $n-C_4H_9SO_2$ | H | $OCH_3$ | $OCH_3$ | N | |
| 1409 | $C_2H_5$ | H | $n-C_4H_9SO_2$ | $CH_3$ | $OCH_3$ | $CH_3$ | CH | |
| 1410 | $C_2H_5$ | H | $n-C_4H_9SO_2$ | $CH_3$ | $OCH_3$ | $OCH_3$ | N | |
| 1411 | $C_2H_5$ | H | $CF_3CH_2SO_2$ | H | $OCH_3$ | $OCH_3$ | CH | |
| 1412 | $C_2H_5$ | H | $CF_3CH_2SO_2$ | H | $OCH_3$ | $CH_3$ | CH | |
| 1413 | $C_2H_5$ | H | $CF_3CH_2SO_2$ | H | $CH_3$ | $CH_3$ | CH | |
| 1414 | $C_2H_5$ | H | $CF_3CH_2SO_2$ | H | Cl | $OCH_3$ | CH | |
| 1415 | $C_2H_5$ | H | $CF_3CH_2SO_2$ | H | $OCH_3$ | $OCH_3$ | N | |
| 1416 | $C_2H_5$ | H | $CF_3CH_2SO_2$ | H | $OCH_3$ | $CH_3$ | N | |
| 1417 | $C_2H_5$ | H | $CF_3CH_2SO_2$ | H | $OCH_3$ | $CF_3$ | N | |
| 1418 | $C_2H_5$ | H | $CF_3CH_2SO_2$ | $CH_3$ | $OCH_3$ | $OCH_3$ | CH | |
| 1419 | $C_2H_5$ | H | $CF_3CH_2SO_2$ | $CH_3$ | $OCH_3$ | $OCH_3$ | N | |
| 1420 | $C_2H_5$ | H | $CH_3NHSO_2$ | H | $OCH_3$ | $OCH_3$ | CH | |
| 1421 | $C_2H_5$ | H | $CH_3NHSO_2$ | H | $OCH_3$ | $CH_3$ | CH | |
| 1422 | $C_2H_5$ | H | $CH_3NHSO_2$ | H | $CH_3$ | $CH_3$ | CH | |
| 1423 | $C_2H_5$ | H | $CH_3NHSO_2$ | H | Cl | $OCH_3$ | CH | |
| 1424 | $C_2H_5$ | H | $CH_3NHSO_2$ | H | $OCH_3$ | $OCH_3$ | N | |
| 1425 | $C_2H_5$ | H | $CH_3NHSO_2$ | H | $OCH_3$ | $CH_3$ | N | |
| 1426 | $C_2H_5$ | H | $CH_3NHSO_2$ | H | $OCH_3$ | $CF_3$ | N | |
| 1427 | $C_2H_5$ | H | $CH_3NHSO_2$ | $CH_3$ | $OCH_3$ | $OCH_3$ | CH | |
| 1428 | $C_2H_5$ | H | $CH_3NHSO_2$ | $CH_3$ | $OCH_3$ | $CH_3$ | N | |
| 1429 | $C_2H_5$ | H | $(CH_3)_2NSO_2$ | H | $OCH_3$ | $OCH_3$ | CH | |
| 1430 | $C_2H_5$ | H | $(CH_3)_2NSO_2$ | H | $OCH_3$ | $CH_3$ | CH | |
| 1431 | $C_2H_5$ | H | $(CH_3)_2NSO_2$ | H | $CH_3$ | $CH_3$ | CH | |
| 1432 | $C_2H_5$ | H | $(CH_3)_2NSO_2$ | H | Cl | $OCH_3$ | CH | |
| 1433 | $C_2H_5$ | H | $(CH_3)_2NSO_2$ | H | $OCH_3$ | $OCH_3$ | N | |
| 1434 | $C_2H_5$ | H | $(CH_3)_2NSO_2$ | H | $OCH_3$ | $CH_3$ | N | |
| 1435 | $C_2H_5$ | H | $(CH_3)_2NSO_2$ | H | $OCH_3$ | $CF_3$ | N | |
| 1436 | $C_2H_5$ | H | $(CH_3)_2NSO_2$ | $CH_3$ | $OCH_3$ | $OCH_3$ | CH | |
| 1437 | $C_2H_5$ | H | $(CH_3)_2NSO_2$ | $CH_3$ | $OCH_3$ | $CH_3$ | N | |
| 1438 | $C_2H_5$ | H | $(CH_3)_3C-OCO$ | H | $OCH_3$ | $OCH_3$ | CH | |
| 1439 | $C_2H_5$ | H | $(CH_3)_3C-OCO$ | H | $OCH_3$ | $CH_3$ | CH | |
| 1440 | $C_2H_5$ | H | $(CH_3)_3C-OCO$ | H | $CH_3$ | $CH_3$ | CH | |
| 1441 | $C_2H_5$ | H | $(CH_3)_3C-OCO$ | H | Cl | $OCH_3$ | CH | |
| 1442 | $C_2H_5$ | H | $(CH_3)_3C-OCO$ | H | $OCH_3$ | $OCH_3$ | N | |
| 1443 | $C_2H_5$ | H | $(CH_3)_3C-OCO$ | H | $OCH_3$ | $CH_3$ | N | |
| 1444 | $C_2H_5$ | H | $(CH_3)_3C-OCO$ | H | $OCH_3$ | $CF_3$ | N | |
| 1445 | $C_2H_5$ | H | $(CH_3)_3C-OCO$ | $CH_3$ | $OCH_3$ | $OCH_3$ | CH | |
| 1446 | $C_2H_5$ | H | $(CH_3)_3C-OCO$ | $CH_3$ | $OCH_3$ | $CH_3$ | N | |

TABLE 1-continued

Compound of the formula (1a)

$$\text{(Ia)}$$

| No. | R$^1$ | R$^4$ | R$^5$ | R$^7$ | X | Y | Z | mp.(°C.) |
|---|---|---|---|---|---|---|---|---|
| 1447 | C$_2$H$_5$ | H | PhCO | H | OCH$_3$ | OCH$_3$ | CH | |
| 1448 | C$_2$H$_5$ | H | PhCO | H | OCH$_3$ | CH$_3$ | CH | |
| 1449 | C$_2$H$_5$ | H | PhCO | H | CH$_3$ | CH$_3$ | CH | |
| 1450 | C$_2$H$_5$ | H | PhCO | H | Cl | OCH$_3$ | CH | |
| 1451 | C$_2$H$_5$ | H | PhCO | H | OCH$_3$ | OCH$_3$ | N | |
| 1452 | C$_2$H$_5$ | H | PhCO | H | OCH$_3$ | CH$_3$ | N | |
| 1453 | C$_2$H$_5$ | H | PhCO | H | OCH$_3$ | CF$_3$ | N | |
| 1454 | C$_2$H$_5$ | H | PhCO | CH$_3$ | OCH$_3$ | OCH$_3$ | CH | |
| 1455 | C$_2$H$_5$ | H | PhCO | CH$_3$ | OCH$_3$ | CH$_3$ | N | |
| 1456 | C$_2$H$_5$ | H | PhSO$_2$ | H | OCH$_3$ | OCH$_3$ | CH | |
| 1457 | C$_2$H$_5$ | H | PhSO$_2$ | H | OCH$_3$ | CH$_3$ | CH | |
| 1458 | C$_2$H$_5$ | H | PhSO$_2$ | H | CH$_3$ | CH$_3$ | CH | |
| 1459 | C$_2$H$_5$ | H | PhSO$_2$ | H | Cl | OCH$_3$ | CH | |
| 1460 | C$_2$H$_5$ | H | PhSO$_2$ | H | OCH$_3$ | OCH$_3$ | N | |
| 1461 | C$_2$H$_5$ | H | PhSO$_2$ | H | OCH$_3$ | CH$_3$ | N | |
| 1462 | C$_2$H$_5$ | H | PhSO$_2$ | H | OCH$_3$ | CF$_3$ | N | |
| 1463 | C$_2$H$_5$ | H | PhSO$_2$ | CH$_3$ | OCH$_3$ | OCH$_3$ | CH | |
| 1464 | C$_2$H$_5$ | H | PhSO$_2$ | CH$_3$ | OCH$_3$ | CH$_3$ | N | |
| 1465 | C$_2$H$_5$ | H | CH$_3$NHCO | H | OCH$_3$ | OCH$_3$ | CH | |
| 1466 | C$_2$H$_5$ | H | CH$_3$NHCO | H | OCH$_3$ | CH$_3$ | CH | |
| 1467 | C$_2$H$_5$ | H | CH$_3$NHCO | H | CH$_3$ | CH$_3$ | CH | |
| 1468 | C$_2$H$_5$ | H | CH$_3$NHCO | H | Cl | OCH$_3$ | CH | |
| 1469 | C$_2$H$_5$ | H | CH$_3$NHCO | H | OCH$_3$ | OCH$_3$ | N | |
| 1470 | C$_2$H$_5$ | H | CH$_3$NHCO | H | OCH$_3$ | CH$_3$ | N | |
| 1471 | C$_2$H$_5$ | H | CH$_3$NHCO | H | OCH$_3$ | CF$_3$ | N | |
| 1472 | C$_2$H$_5$ | H | CH$_3$NHCO | CH$_3$ | OCH$_3$ | OCH$_3$ | CH | |
| 1473 | C$_2$H$_5$ | H | CH$_3$NHCO | CH$_3$ | OCH$_3$ | CH$_3$ | N | |
| 1474 | C$_2$H$_5$ | H | C$_2$H$_5$NHCO | H | OCH$_3$ | OCH$_3$ | CH | |
| 1475 | C$_2$H$_5$ | H | C$_2$H$_5$NHCO | H | OCH$_3$ | CH$_3$ | CH | |
| 1476 | C$_2$H$_5$ | H | C$_2$H$_5$NHCO | H | CH$_3$ | CH$_3$ | CH | |
| 1477 | C$_2$H$_5$ | H | C$_2$H$_5$NHCO | H | Cl | OCH$_3$ | CH | |
| 1478 | C$_2$H$_5$ | H | C$_2$H$_5$NHCO | H | OCH$_3$ | OCH$_3$ | N | |
| 1479 | C$_2$H$_5$ | H | C$_2$H$_5$NHCO | H | OCH$_3$ | CH$_3$ | N | |
| 1480 | C$_2$H$_5$ | H | C$_2$H$_5$NHCO | H | OCH$_3$ | CF$_3$ | N | |
| 1481 | C$_2$H$_5$ | H | C$_2$H$_5$NHCO | CH$_3$ | OCH$_3$ | OCH$_3$ | CH | |
| 1482 | C$_2$H$_5$ | H | C$_2$H$_5$NHCO | CH$_3$ | OCH$_3$ | CH$_3$ | N | |
| 1483 | C$_2$H$_5$ | H | CH$_3$NHCS | H | OCH$_3$ | OCH$_3$ | CH | |
| 1484 | C$_2$H$_5$ | H | CH$_3$NHCS | H | OCH$_3$ | CH$_3$ | CH | |
| 1485 | C$_2$H$_5$ | H | CH$_3$NHCS | H | CH$_3$ | CH$_3$ | CH | |
| 1486 | C$_2$H$_5$ | H | CH$_3$NHCS | H | Cl | OCH$_3$ | CH | |
| 1487 | C$_2$H$_5$ | H | CH$_3$NHCS | H | OCH$_3$ | OCH$_3$ | N | |
| 1488 | C$_2$H$_5$ | H | CH$_3$NHCS | H | OCH$_3$ | CH$_3$ | N | |
| 1489 | C$_2$H$_5$ | H | CH$_3$NHCS | H | OCH$_3$ | CF$_3$ | N | |
| 1490 | C$_2$H$_5$ | H | CH$_3$NHCS | CH$_3$ | OCH$_3$ | OCH$_3$ | CH | |
| 1491 | C$_2$H$_5$ | H | CH$_3$NHCS | CH$_3$ | OCH$_3$ | CH$_3$ | N | |
| 1492 | C$_2$H$_5$ | H | C$_2$H$_5$NHCS | H | OCH$_3$ | OCH$_3$ | CH | |
| 1493 | C$_2$H$_5$ | H | C$_2$H$_5$NHCS | H | OCH$_3$ | CH$_3$ | CH | |
| 1494 | C$_2$H$_5$ | H | C$_2$H$_5$NHCS | H | CH$_3$ | CH$_3$ | CH | |
| 1495 | C$_2$H$_5$ | H | C$_2$H$_5$NHCS | H | Cl | OCH$_3$ | CH | |
| 1496 | C$_2$H$_5$ | H | C$_2$H$_5$NHCS | H | OCH$_3$ | CH$_3$ | N | |
| 1497 | C$_2$H$_5$ | H | C$_2$H$_5$NHCS | H | OCH$_3$ | CF$_3$ | N | |
| 1498 | C$_2$H$_5$ | H | C$_2$H$_5$NHCS | H | OCH$_3$ | OCH$_3$ | N | |
| 1499 | C$_2$H$_5$ | H | C$_2$H$_5$NHCS | CH$_3$ | OCH$_3$ | CH$_3$ | CH | |
| 1500 | C$_2$H$_5$ | H | C$_2$H$_5$NHCS | CH$_3$ | OCH$_3$ | OCH$_3$ | N | |
| 1501 | C$_2$H$_5$ | (cyclohexylidene =O on N) | | H | OCH$_3$ | OCH$_3$ | CH | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 1502 | C₂H₅ | | cyclohexanone-yl | H | OCH₃ | CH₃ | CH | |
| 1503 | C₂H₅ | | cyclohexanone-yl | H | CH₃ | CH₃ | CH | |
| 1504 | C₂H₅ | | cyclohexanone-yl | H | Cl | OCH₃ | CH | |
| 1505 | C₂H₅ | | cyclohexanone-yl | H | OCH₃ | OCH₃ | N | |
| 1506 | C₂H₅ | | cyclohexanone-yl | H | OCH₃ | CH₃ | N | |
| 1507 | C₂H₅ | | cyclohexanone-yl | H | OCH₃ | CF₃ | N | |
| 1508 | C₂H₅ | | cyclohexanone-yl | CH₃ | OCH₃ | OCH₃ | CH | |
| 1509 | C₂H₅ | | cyclohexanone-yl | H | OCH₃ | OCH₃ | CH | |
| 1510 | C₂H₅ | | cycloheptanone-yl | H | OCH₃ | OCH₃ | CH | |

TABLE 1-continued

Compound of the formula (1a)

(Ia)

[Structure: benzene ring with SO₂-R¹ group, SO₂NH-CO-NR⁷ linked to pyrimidine ring with X, Y, Z substituents, and CH₂-NR⁴R⁵ group]

| No. | R¹ | R⁴ | R⁵ | R⁷ | X | Y | Z | mp.(°C.) |
|---|---|---|---|---|---|---|---|---|
| 1511 | C₂H₅ | | cycloheptanone | H | OCH₃ | CH₃ | CH | |
| 1512 | C₂H₅ | | cycloheptanone | H | CH₃ | CH₃ | CH | |
| 1513 | C₂H₅ | | cycloheptanone | H | Cl | OCH₃ | CH | |
| 1514 | C₂H₅ | | cycloheptanone | H | OCH₃ | OCH₃ | N | |
| 1515 | C₂H₅ | | cycloheptanone | H | OCH₃ | CH₃ | N | |
| 1516 | C₂H₅ | | cycloheptanone | H | OCH₃ | CF₃ | N | |
| 1517 | C₂H₅ | | cycloheptanone | CH₃ | OCH₃ | OCH₃ | CH | |
| 1518 | C₂H₅ | | cycloheptanone | CH₃ | OCH₃ | CH₃ | N | |

TABLE 1-continued
Compound of the formula (1a)
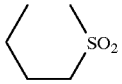
(Ia)
| No. | R¹ | R⁴ | R⁵ | R⁷ | X | Y | Z | mp.(°C.) |
|---|---|---|---|---|---|---|---|---|
| 1519 | C₂H₅ | | 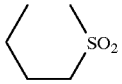 | H | OCH₃ | OCH₃ | CH | |
| 1520 | C₂H₅ | | 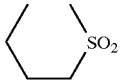 | H | OCH₃ | CH₃ | CH | |
| 1521 | C₂H₅ | |  | H | CH₃ | CH₃ | CH | |
| 1522 | C₂H₅ | | 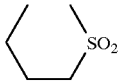 | H | Cl | OCH₃ | CH | |
| 1523 | C₂H₅ | | 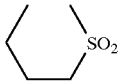 | H | OCH₃ | OCH₃ | N | |
| 1524 | C₂H₅ | | 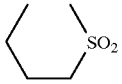 | H | OCH₃ | CH₃ | N | |
| 1525 | C₂H₅ | | 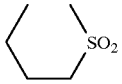 | H | OCH₃ | CF₃ | N | |
| 1526 | C₂H₅ | | 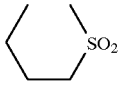 | CH₃ | OCH₃ | OCH₃ | CH | |
| 1527 | C₂H₅ | | 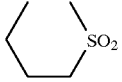 | CH₃ | OCH₃ | CH₃ | N | |

TABLE 1-continued

Compound of the formula (1a)

(Ia)

| No. | R¹ | R⁴ | R⁵ | R⁷ | X | Y | Z | mp.(°C.) |
|---|---|---|---|---|---|---|---|---|
| 1528 | $C_2H_5$ | | (CH₂)₅SO₂ ring | H | $OCH_3$ | $OCH_3$ | CH | |
| 1529 | $C_2H_5$ | | (CH₂)₅SO₂ ring | H | $OCH_3$ | $CH_3$ | CH | |
| 1530 | $C_2H_5$ | | (CH₂)₅SO₂ ring | H | $CH_3$ | $CH_3$ | CH | |
| 1531 | $C_2H_5$ | | (CH₂)₅SO₂ ring | H | Cl | $OCH_3$ | CH | |
| 1532 | $C_2H_5$ | | (CH₂)₅SO₂ ring | H | $OCH_3$ | $OCH_3$ | N | |
| 1533 | $C_2H_5$ | | (CH₂)₅SO₂ ring | H | $OCH_3$ | $CH_3$ | N | |
| 1534 | $C_2H_5$ | | (CH₂)₅SO₂ ring | H | $OCH_3$ | $CF_3$ | N | |
| 1535 | $C_2H_5$ | | (CH₂)₅SO₂ ring | $CH_3$ | $OCH_3$ | $OCH_3$ | CH | |

TABLE 1-continued

Compound of the formula (1a)

(Ia)

Structure: benzene ring with SO₂—R¹ substituent, SO₂NH—CO—NR⁷— linked to pyrimidine bearing X, Y, Z; and CH₂—NR⁴R⁵ group.

| No. | R¹ | R⁴ | R⁵ | R⁷ | X | Y | Z | mp.(°C.) |
|---|---|---|---|---|---|---|---|---|
| 1536 | $C_2H_5$ | | (cyclic -SO₂- ring) | $CH_3$ | $OCH_3$ | $CH_3$ | N | |
| 1537 | $C_2H_5$ | | (cyclic -O- ring) | H | $OCH_3$ | $OCH_3$ | CH | |
| 1538 | $C_2H_5$ | | (cyclic -O- ring) | H | $OCH_3$ | $CH_3$ | CH | |
| 1539 | $C_2H_5$ | | (cyclic -O- ring) | H | $CH_3$ | $CH_3$ | CH | |
| 1540 | $C_2H_5$ | | (cyclic -O- ring) | H | Cl | $OCH_3$ | CH | |
| 1541 | $C_2H_5$ | | (cyclic -O- ring) | H | $OCH_3$ | $CH_3$ | N | |
| 1542 | $C_2H_5$ | | (cyclic -O- ring) | H | $OCH_3$ | $CF_3$ | N | |
| 1543 | $C_2H_5$ | | (cyclic -O- ring) | H | $OCH_3$ | $OCH_3$ | N | |

TABLE 1-continued

Compound of the formula (1a)

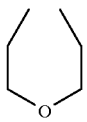

(Ia)

| No. | R¹ | R⁴ | R⁵ | R⁷ | X | Y | Z | mp.(°C.) |
|---|---|---|---|---|---|---|---|---|
| 1544 | C₂H₅ | | 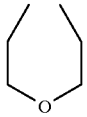 | CH₃ | OCH₃ | CH₃ | CH | |
| 1545 | C₂H₅ | | (tetrahydropyran) | CH₃ | OCH₃ | OCH₃ | N | |
| 1546 | C₂H₅ | H | COSCH₃ | H | OCH₃ | OCH₃ | CH | |
| 1547 | C₂H₅ | H | COSCH₃ | H | OCH₃ | CH₃ | CH | |
| 1548 | C₂H₅ | H | COSCH₃ | H | CH₃ | CH₃ | CH | |
| 1549 | C₂H₅ | H | COSCH₃ | H | Cl | OCH₃ | CH | |
| 1550 | C₂H₅ | H | COSCH₃ | H | OCH₃ | OCH₃ | N | |
| 1551 | C₂H₅ | H | COSCH₃ | H | OCH₃ | CH₃ | N | |
| 1552 | C₂H₅ | H | COSCH₃ | H | OCH₃ | CF₃ | N | |
| 1553 | C₂H₅ | H | COSCH₃ | CH₃ | OCH₃ | OCH₃ | CH | |
| 1554 | C₂H₅ | H | COSCH₃ | CH₃ | OCH₃ | CH₃ | N | |
| 1555 | C₂H₅ | H | CSOCH₃ | H | OCH₃ | OCH₃ | CH | |
| 1556 | C₂H₅ | H | CSOCH₃ | H | OCH₃ | CH₃ | CH | |
| 1557 | C₂H₅ | H | CSOCH₃ | H | CH₃ | CH₃ | CH | |
| 1558 | C₂H₅ | H | CSOCH₃ | H | Cl | OCH₃ | CH | |
| 1559 | C₂H₅ | H | CSOCH₃ | H | OCH₃ | OCH₃ | N | |
| 1560 | C₂H₅ | H | CSOCH₃ | H | OCH₃ | CH₃ | N | |
| 1561 | C₂H₅ | H | CSOCH₃ | H | OCH₃ | CF₃ | N | |
| 1562 | C₂H₅ | H | CSOCH₃ | CH₃ | OCH₃ | OCH₃ | CH | |
| 1563 | C₂H₅ | H | CSOCH₃ | CH₃ | OCH₃ | CH₃ | N | |
| 1564 | C₂H₅ | H | CSSCH₃ | H | OCH₃ | OCH₃ | CH | |
| 1565 | C₂H₅ | H | CSSCH₃ | H | OCH₃ | CH₃ | CH | |
| 1566 | C₂H₅ | H | CSSCH₃ | H | CH₃ | CH₃ | CH | |
| 1567 | C₂H₅ | H | CSSCH₃ | H | Cl | OCH₃ | CH | |
| 1568 | C₂H₅ | H | CSSCH₃ | H | OCH₃ | OCH₃ | N | |
| 1569 | C₂H₅ | H | CSSCH₃ | H | OCH₃ | CH₃ | N | |
| 1570 | C₂H₅ | H | CSSCH₃ | H | OCH₃ | CF₃ | N | |
| 1571 | C₂H₅ | H | CSSCH₃ | CH₃ | OCH₃ | OCH₃ | CH | |
| 1572 | C₂H₅ | H | CSSCH₃ | CH₃ | OCH₃ | CH₃ | N | |
| 1573 | C₂H₅ | H | COCOOCH₃ | H | OCH₃ | OCH₃ | CH | |
| 1574 | C₂H₅ | H | COCOOCH₃ | H | OCH₃ | CH₃ | CH | |
| 1575 | C₂H₅ | H | COCOOCH₃ | H | CH₃ | CH₃ | CH | |
| 1576 | C₂H₅ | H | COCOOCH₃ | H | Cl | OCH₃ | CH | |
| 1577 | C₂H₅ | H | COCOOCH₃ | H | OCH₃ | OCH₃ | N | |
| 1578 | C₂H₅ | H | COCOOCH₃ | H | OCH₃ | CH₃ | N | |
| 1579 | C₂H₅ | H | COCOOCH₃ | H | OCH₃ | CF₃ | N | |
| 1580 | C₂H₅ | H | COCOOCH₃ | CH₃ | OCH₃ | OCH₃ | CH | |
| 1581 | C₂H₅ | H | COCOOCH₃ | CH₃ | OCH₃ | CH₃ | N | |
| 1582 | C₂H₅ | H | i-C₃H₇OCO | H | OCH₃ | OCH₃ | CH | |
| 1583 | C₂H₅ | H | i-C₃H₇OCO | H | OCH₃ | CH₃ | CH | |
| 1584 | C₂H₅ | H | i-C₃H₇OCO | H | CH₃ | CH₃ | CH | |
| 1585 | C₂H₅ | H | i-C₃H₇OCO | H | Cl | OCH₃ | CH | |
| 1586 | C₂H₅ | H | i-C₃H₇OCO | H | OCH₃ | OCH₃ | N | |
| 1587 | C₂H₅ | H | i-C₃H₇OCO | H | OCH₃ | CH₃ | N | |
| 1588 | C₂H₅ | H | i-C₃H₇OCO | H | OCH₃ | OCH₃ | N | |
| 1589 | C₂H₅ | H | i-C₃H₇OCO | CH₃ | OCH₃ | CH₃ | CH | |
| 1590 | C₂H₅ | H | i-C₃H₇OCO | CH₃ | OCH₃ | OCH₃ | N | |
| 1591 | C₂H₅ | CH₃ | CHO | H | OCH₃ | OCH₃ | CH | 212–213 |

TABLE 1-continued

Compound of the formula (1a)

$$\text{(Ia)}$$

| No. | $R^1$ | $R^4$ | $R^5$ | $R^7$ | X | Y | Z | mp.(°C.) |
|---|---|---|---|---|---|---|---|---|
| 1592 | $C_2H_5$ | $CH_3$ | CHO | H | $OCH_3$ | $CH_3$ | CH | |
| 1593 | $C_2H_5$ | $CH_3$ | CHO | H | $CH_3$ | $CH_3$ | CH | |
| 1594 | $C_2H_5$ | $CH_3$ | CHO | H | $CH_3$ | $OC_2H_5$ | CH | |
| 1595 | $C_2H_5$ | $CH_3$ | CHO | H | $C_2H_5$ | $OCH_3$ | CH | |
| 1596 | $C_2H_5$ | $CH_3$ | CHO | H | $OC_2H_5$ | $OC_2H_5$ | CH | |
| 1597 | $C_2H_5$ | $CH_3$ | CHO | H | $OCHF_2$ | $OCHF_2$ | CH | |
| 1598 | $C_2H_5$ | $CH_3$ | CHO | H | $CH_3$ | $OCHF_2$ | CH | |
| 1599 | $C_2H_5$ | $CH_3$ | CHO | H | Cl | $OCH_3$ | CH | |
| 1600 | $C_2H_5$ | $CH_3$ | CHO | H | $OCH_3$ | $OCH_3$ | N | |
| 1601 | $C_2H_5$ | $CH_3$ | CHO | H | $OCH_3$ | $CH_3$ | N | |
| 1602 | $C_2H_5$ | $CH_3$ | CHO | H | $CH_3$ | $CH_3$ | N | |
| 1603 | $C_2H_5$ | $CH_3$ | CHO | H | $N(CH_3)_2$ | $OCH_2CF_3$ | N | |
| 1604 | $C_2H_5$ | $CH_3$ | CHO | H | $OCH_3$ | $CF_3$ | N | |
| 1605 | $C_2H_5$ | $CH_3$ | CHO | H | $OC_2H_5$ | $NHCH_3$ | N | |
| 1606 | $C_2H_5$ | $CH_3$ | CHO | $CH_3$ | $OCH_3$ | $OCH_3$ | CH | |
| 1607 | $C_2H_5$ | $CH_3$ | CHO | $CH_3$ | $OCH_3$ | $CH_3$ | N | |
| 1608 | $C_2H_5$ | $CH_3$ | $COCH_3$ | H | $OCH_3$ | $OCH_3$ | CH | 174–176 |
| 1609 | $C_2H_5$ | $CH_3$ | $COCH_3$ | H | $OCH_3$ | $CH_3$ | CH | |
| 1610 | $C_2H_5$ | $CH_3$ | $COCH_3$ | H | $CH_3$ | $CH_3$ | CH | |
| 1611 | $C_2H_5$ | $CH_3$ | $COCH_3$ | H | $CH_3$ | $OC_2H_5$ | CH | |
| 1612 | $C_2H_5$ | $CH_3$ | $COCH_3$ | H | $C_2H_5$ | $OCH_3$ | CH | |
| 1613 | $C_2H_5$ | $CH_3$ | $COCH_3$ | H | $OC_2H_5$ | $OC_2H_5$ | CH | |
| 1614 | $C_2H_5$ | $CH_3$ | $COCH_3$ | H | $OCHF_2$ | $OCHF_2$ | CH | |
| 1615 | $C_2H_5$ | $CH_3$ | $COCH_3$ | H | $CH_3$ | $OCHF_2$ | CH | |
| 1616 | $C_2H_5$ | $CH_3$ | $COCH_3$ | H | Cl | $OCH_3$ | CH | |
| 1617 | $C_2H_5$ | $CH_3$ | $COCH_3$ | H | $OCH_3$ | $OCH_3$ | N | |
| 1618 | $C_2H_5$ | $CH_3$ | $COCH_3$ | H | $OCH_3$ | $CH_3$ | N | |
| 1619 | $C_2H_5$ | $CH_3$ | $COCH_3$ | H | $CH_3$ | $CH_3$ | N | |
| 1620 | $C_2H_5$ | $CH_3$ | $COCH_3$ | H | $N(CH_3)_2$ | $OCH_2CF_3$ | N | |
| 1621 | $C_2H_5$ | $CH_3$ | $COCH_3$ | H | $OCH_3$ | $CF_3$ | N | |
| 1622 | $C_2H_5$ | $CH_3$ | $COCH_3$ | H | $OC_2H_5$ | $NHCH_3$ | N | |
| 1623 | $C_2H_5$ | $CH_3$ | $COCH_3$ | $CH_3$ | $OCH_3$ | $OCH_3$ | CH | |
| 1624 | $C_2H_5$ | $CH_3$ | $COCH_3$ | $CH_3$ | $OCH_3$ | $CH_3$ | N | |
| 1625 | $C_2H_5$ | $CH_3$ | $COC_2H_5$ | H | $OCH_3$ | $OCH_3$ | CH | |
| 1626 | $C_2H_5$ | $CH_3$ | $COC_2H_5$ | H | $OCH_3$ | $CH_3$ | CH | |
| 1627 | $C_2H_5$ | $CH_3$ | $COC_2H_5$ | H | $CH_3$ | $CH_3$ | CH | |
| 1628 | $C_2H_5$ | $CH_3$ | $COC_2H_5$ | H | $CH_3$ | $OC_2H_5$ | CH | |
| 1629 | $C_2H_5$ | $CH_3$ | $COC_2H_5$ | H | $C_2H_5$ | $OCH_3$ | CH | |
| 1630 | $C_2H_5$ | $CH_3$ | $COC_2H_5$ | H | $OC_2H_5$ | $OC_2H_5$ | CH | |
| 1631 | $C_2H_5$ | $CH_3$ | $COC_2H_5$ | H | $OCHF_2$ | $OCHF_2$ | CH | |
| 1632 | $C_2H_5$ | $CH_3$ | $COC_2H_5$ | H | $CH_3$ | $OCHF_2$ | CH | |
| 1633 | $C_2H_5$ | $CH_3$ | $COC_2H_5$ | H | Cl | $OCH_3$ | CH | |
| 1634 | $C_2H_5$ | $CH_3$ | $COC_2H_5$ | H | $OCH_3$ | $OCH_3$ | N | |
| 1635 | $C_2H_5$ | $CH_3$ | $COC_2H_5$ | H | $OCH_3$ | $CH_3$ | N | |
| 1636 | $C_2H_5$ | $CH_3$ | $COC_2H_5$ | H | $CH_3$ | $CH_3$ | N | |
| 1637 | $C_2H_5$ | $CH_3$ | $COC_2H_5$ | H | $N(CH_3)_2$ | $OCH_2CF_3$ | N | |
| 1638 | $C_2H_5$ | $CH_3$ | $COC_2H_5$ | H | $OCH_3$ | $CF_3$ | N | |
| 1639 | $C_2H_5$ | $CH_3$ | $COC_2H_5$ | H | $OC_2H_5$ | $NHCH_3$ | N | |
| 1640 | $C_2H_5$ | $CH_3$ | $COC_2H_5$ | $CH_3$ | $OCH_3$ | $OCH_3$ | CH | |
| 1641 | $C_2H_5$ | $CH_3$ | $COC_2H_5$ | $CH_3$ | $OCH_3$ | $CH_3$ | N | |
| 1642 | $C_2H_5$ | $CH_3$ | CO-n-$C_3H_7$ | H | $OCH_3$ | $OCH_3$ | CH | |
| 1643 | $C_2H_5$ | $CH_3$ | CO-n-$C_3H_7$ | H | $OCH_3$ | $CH_3$ | CH | |
| 1644 | $C_2H_5$ | $CH_3$ | CO-n-$C_3H_7$ | H | $CH_3$ | $CH_3$ | CH | |
| 1645 | $C_2H_5$ | $CH_3$ | CO-n-$C_3H_7$ | H | $CH_3$ | $OC_2H_5$ | CH | |
| 1646 | $C_2H_5$ | $CH_3$ | CO-n-$C_3H_7$ | H | $C_2H_5$ | $OCH_3$ | CH | |
| 1647 | $C_2H_5$ | $CH_3$ | CO-n-$C_3H_7$ | H | $OC_2H_5$ | $OC_2H_5$ | CH | |
| 1648 | $C_2H_5$ | $CH_3$ | CO-n-$C_3H_7$ | H | $OCHF_2$ | $OCHF_2$ | CH | |
| 1649 | $C_2H_5$ | $CH_3$ | CO-n-$C_3H_7$ | H | $CH_3$ | $OCHF_2$ | CH | |
| 1650 | $C_2H_5$ | $CH_3$ | CO-n-$C_3H_7$ | H | Cl | $OCH_3$ | CH | |
| 1651 | $C_2H_5$ | $CH_3$ | CO-n-$C_3H_7$ | H | $OCH_3$ | $OCH_3$ | N | |
| 1652 | $C_2H_5$ | $CH_3$ | CO-n-$C_3H_7$ | H | $OCH_3$ | $CH_3$ | N | |
| 1653 | $C_2H_5$ | $CH_3$ | CO-n-$C_3H_7$ | H | $CH_3$ | $CH_3$ | N | |
| 1654 | $C_2H_5$ | $CH_3$ | CO-n-$C_3H_7$ | H | $N(CH_3)_2$ | $OCH_2CF_3$ | N | |

TABLE 1-continued

Compound of the formula (1a)

$$\text{(Ia)}$$

| No. | $R^1$ | $R^4$ | $R^5$ | $R^7$ | X | Y | Z | mp.(°C.) |
|---|---|---|---|---|---|---|---|---|
| 1655 | $C_2H_5$ | $CH_3$ | $CO$-n-$C_3H_7$ | H | $OCH_3$ | $CF_3$ | N | |
| 1656 | $C_2H_5$ | $CH_3$ | $CO$-n-$C_3H_7$ | H | $OC_2H_5$ | $NHCH_3$ | N | |
| 1657 | $C_2H_5$ | $CH_3$ | $CO$-n-$C_3H_7$ | $CH_3$ | $OCH_3$ | $OCH_3$ | CH | |
| 1658 | $C_2H_5$ | $CH_3$ | $CO$-n-$C_3H_7$ | $CH_3$ | $OCH_3$ | $CH_3$ | N | |
| 1659 | $C_2H_5$ | $CH_3$ | $CO$-i-$C_3H_7$ | H | $OCH_3$ | $OCH_3$ | CH | |
| 1660 | $C_2H_5$ | $CH_3$ | $CO$-i-$C_3H_7$ | H | $OCH_3$ | $CH_3$ | CH | |
| 1661 | $C_2H_5$ | $CH_3$ | $CO$-i-$C_3H_7$ | H | $CH_3$ | $CH_3$ | CH | |
| 1662 | $C_2H_5$ | $CH_3$ | $CO$-i-$C_3H_7$ | H | $CH_3$ | $OC_2H_5$ | CH | |
| 1663 | $C_2H_5$ | $CH_3$ | $CO$-i-$C_3H_7$ | H | $C_2H_5$ | $OCH_3$ | CH | |
| 1664 | $C_2H_5$ | $CH_3$ | $CO$-i-$C_3H_7$ | H | $OC_2H_5$ | $OC_2H_5$ | CH | |
| 1665 | $C_2H_5$ | $CH_3$ | $CO$-i-$C_3H_7$ | H | $OCHF_2$ | $OCHF_2$ | CH | |
| 1666 | $C_2H_5$ | $CH_3$ | $CO$-i-$C_3H_7$ | H | $CH_3$ | $OCHF_2$ | CH | |
| 1667 | $C_2H_5$ | $CH_3$ | $CO$-i-$C_3H_7$ | H | Cl | $OCH_3$ | CH | |
| 1668 | $C_2H_5$ | $CH_3$ | $CO$-i-$C_3H_7$ | H | $OCH_3$ | $OCH_3$ | N | |
| 1669 | $C_2H_5$ | $CH_3$ | $CO$-i-$C_3H_7$ | H | $OCH_3$ | $CH_3$ | N | |
| 1670 | $C_2H_5$ | $CH_3$ | $CO$-i-$C_3H_7$ | H | $CH_3$ | $CH_3$ | N | |
| 1671 | $C_2H_5$ | $CH_3$ | $CO$-i-$C_3H_7$ | H | $N(CH_3)_2$ | $OCH_2CF_3$ | N | |
| 1672 | $C_2H_5$ | $CH_3$ | $CO$-i-$C_3H_7$ | H | $OCH_3$ | $CF_3$ | N | |
| 1673 | $C_2H_5$ | $CH_3$ | $CO$-i-$C_3H_7$ | H | $OC_2H_5$ | $NHCH_3$ | N | |
| 1674 | $C_2H_5$ | $CH_3$ | $CO$-i-$C_3H_7$ | $CH_3$ | $OCH_3$ | $OCH_3$ | CH | |
| 1675 | $C_2H_5$ | $CH_3$ | $CO$-i-$C_3H_7$ | $CH_3$ | $OCH_3$ | $CH_3$ | N | |
| 1676 | $C_2H_5$ | $CH_3$ | $COCF_3$ | H | $OCH_3$ | $OCH_3$ | CH | 201–202 |
| 1677 | $C_2H_5$ | $CH_3$ | $COCF_3$ | H | $OCH_3$ | $CH_3$ | CH | |
| 1678 | $C_2H_5$ | $CH_3$ | $COCF_3$ | H | $CH_3$ | $CH_3$ | CH | |
| 1679 | $C_2H_5$ | $CH_3$ | $COCF_3$ | H | $CH_3$ | $OC_2H_5$ | CH | |
| 1680 | $C_2H_5$ | $CH_3$ | $COCF_3$ | H | $C_2H_5$ | $OCH_3$ | CH | |
| 1681 | $C_2H_5$ | $CH_3$ | $COCF_3$ | H | $OC_2H_5$ | $OC_2H_5$ | CH | |
| 1682 | $C_2H_5$ | $CH_3$ | $COCF_3$ | H | $OCHF_2$ | $OCHF_2$ | CH | |
| 1683 | $C_2H_5$ | $CH_3$ | $COCF_3$ | H | $CH_3$ | $OCHF_2$ | CH | |
| 1684 | $C_2H_5$ | $CH_3$ | $COCF_3$ | H | Cl | $OCH_3$ | CH | |
| 1685 | $C_2H_5$ | $CH_3$ | $COCF_3$ | H | $OCH_3$ | $OCH_3$ | N | |
| 1686 | $C_2H_5$ | $CH_3$ | $COCF_3$ | H | $OCH_3$ | $CH_3$ | N | |
| 1687 | $C_2H_5$ | $CH_3$ | $COCF_3$ | H | $CH_3$ | $CH_3$ | N | |
| 1688 | $C_2H_5$ | $CH_3$ | $COCF_3$ | H | $N(CH_3)_2$ | $OCH_2CF_3$ | N | |
| 1689 | $C_2H_5$ | $CH_3$ | $COCF_3$ | H | $OCH_3$ | $CF_3$ | N | |
| 1690 | $C_2H_5$ | $CH_3$ | $COCF_3$ | H | $OC_2H_5$ | $NHCH_3$ | N | |
| 1691 | $C_2H_5$ | $CH_3$ | $COCF_3$ | $CH_3$ | $OCH_3$ | $OCH_3$ | CH | |
| 1692 | $C_2H_5$ | $CH_3$ | $COCF_3$ | $CH_3$ | $OCH_3$ | $CH_3$ | N | |
| 1693 | $C_2H_5$ | $CH_3$ | $COOCH_3$ | H | $OCH_3$ | $OCH_3$ | CH | |
| 1694 | $C_2H_5$ | $CH_3$ | $COOCH_3$ | H | $OCH_3$ | $CH_3$ | CH | |
| 1695 | $C_2H_5$ | $CH_3$ | $COOCH_3$ | H | $CH_3$ | $CH_3$ | CH | |
| 1696 | $C_2H_5$ | $CH_3$ | $COOCH_3$ | H | $CH_3$ | $OC_2H_5$ | CH | |
| 1697 | $C_2H_5$ | $CH_3$ | $COOCH_3$ | H | $C_2H_5$ | $OCH_3$ | CH | |
| 1698 | $C_2H_5$ | $CH_3$ | $COOCH_3$ | H | $OC_2H_5$ | $OC_2H_5$ | CH | |
| 1699 | $C_2H_5$ | $CH_3$ | $COOCH_3$ | H | $OCHF_2$ | $OCHF_2$ | CH | |
| 1700 | $C_2H_5$ | $CH_3$ | $COOCH_3$ | H | $CH_3$ | $OCHF_2$ | CH | |
| 1701 | $C_2H_5$ | $CH_3$ | $COOCH_3$ | H | Cl | $OCH_3$ | CH | |
| 1702 | $C_2H_5$ | $CH_3$ | $COOCH_3$ | H | $OCH_3$ | $OCH_3$ | N | |
| 1703 | $C_2H_5$ | $CH_3$ | $COOCH_3$ | H | $OCH_3$ | $CH_3$ | N | |
| 1704 | $C_2H_5$ | $CH_3$ | $COOCH_3$ | H | $CH_3$ | $CH_3$ | N | |
| 1705 | $C_2H_5$ | $CH_3$ | $COOCH_3$ | H | $N(CH_3)_2$ | $OCH_2CF_3$ | N | |
| 1706 | $C_2H_5$ | $CH_3$ | $COOCH_3$ | H | $OCH_3$ | $CF_3$ | N | |
| 1707 | $C_2H_5$ | $CH_3$ | $COOCH_3$ | H | $OC_2H_5$ | $NHCH_3$ | N | |
| 1708 | $C_2H_5$ | $CH_3$ | $COOCH_3$ | $CH_3$ | $OCH_3$ | $OCH_3$ | CH | |
| 1709 | $C_2H_5$ | $CH_3$ | $COOCH_3$ | $CH_3$ | $OCH_3$ | $CH_3$ | N | |
| 1710 | $C_2H_5$ | $CH_3$ | $COOC_2H_5$ | H | $OCH_3$ | $OCH_3$ | CH | |
| 1711 | $C_2H_5$ | $CH_3$ | $COOC_2H_5$ | H | $OCH_3$ | $CH_3$ | CH | |
| 1712 | $C_2H_5$ | $CH_3$ | $COOC_2H_5$ | H | $CH_3$ | $CH_3$ | CH | |
| 1713 | $C_2H_5$ | $CH_3$ | $COOC_2H_5$ | H | $CH_3$ | $OC_2H_5$ | CH | |
| 1714 | $C_2H_5$ | $CH_3$ | $COOC_2H_5$ | H | $C_2H_5$ | $OCH_3$ | CH | |
| 1715 | $C_2H_5$ | $CH_3$ | $COOC_2H_5$ | H | $OC_2H_5$ | $OC_2H_5$ | CH | |
| 1716 | $C_2H_5$ | $CH_3$ | $COOC_2H_5$ | H | $OCHF_2$ | $OCHF_2$ | CH | |
| 1717 | $C_2H_5$ | $CH_3$ | $COOC_2H_5$ | H | $CH_3$ | $OCHF_2$ | CH | |

TABLE 1-continued

Compound of the formula (1a)

$$\text{(Ia)}$$

| No. | $R^1$ | $R^4$ | $R^5$ | $R^7$ | X | Y | Z | mp.(°C.) |
|---|---|---|---|---|---|---|---|---|
| 1718 | $C_2H_5$ | $CH_3$ | $COOC_2H_5$ | H | Cl | $OCH_3$ | CH | |
| 1719 | $C_2H_5$ | $CH_3$ | $COOC_2H_5$ | H | $OCH_3$ | $OCH_3$ | N | |
| 1720 | $C_2H_5$ | $CH_3$ | $COOC_2H_5$ | H | $OCH_3$ | $CH_3$ | N | |
| 1721 | $C_2H_5$ | $CH_3$ | $COOC_2H_5$ | H | $CH_3$ | $CH_3$ | N | |
| 1722 | $C_2H_5$ | $CH_3$ | $COOC_2H_5$ | H | $N(CH_3)_2$ | $OCH_2CF_3$ | N | |
| 1723 | $C_2H_5$ | $CH_3$ | $COOC_2H_5$ | H | $OCH_3$ | $CF_3$ | N | |
| 1724 | $C_2H_5$ | $CH_3$ | $COOC_2H_5$ | H | $OC_2H_5$ | $NHCH_3$ | N | |
| 1725 | $C_2H_5$ | $CH_3$ | $COOC_2H_5$ | $CH_3$ | $OCH_3$ | $OCH_3$ | CH | |
| 1726 | $C_2H_5$ | $CH_3$ | $COOC_2H_5$ | $CH_3$ | $OCH_3$ | $CH_3$ | N | |
| 1727 | $C_2H_5$ | $CH_3$ | $SO_2CH_3$ | H | $OCH_3$ | $OCH_3$ | CH | 195–196 |
| 1728 | $C_2H_5$ | $CH_3$ | $SO_2CH_3$ | H | $OCH_3$ | $CH_3$ | CH | |
| 1729 | $C_2H_5$ | $CH_3$ | $SO_2CH_3$ | H | $CH_3$ | $CH_3$ | CH | |
| 1730 | $C_2H_5$ | $CH_3$ | $SO_2CH_3$ | H | $CH_3$ | $OC_2H_5$ | CH | |
| 1731 | $C_2H_5$ | $CH_3$ | $SO_2CH_3$ | H | $C_2H_5$ | $OCH_3$ | CH | |
| 1732 | $C_2H_5$ | $CH_3$ | $SO_2CH_3$ | H | $OC_2H_5$ | $OC_2H_5$ | CH | |
| 1733 | $C_2H_5$ | $CH_3$ | $SO_2CH_3$ | H | $OCHF_2$ | $OCHF_2$ | CH | |
| 1734 | $C_2H_5$ | $CH_3$ | $SO_2CH_3$ | H | $CH_3$ | $OCHF_2$ | CH | |
| 1735 | $C_2H_5$ | $CH_3$ | $SO_2CH_3$ | H | Cl | $OCH_3$ | CH | |
| 1736 | $C_2H_5$ | $CH_3$ | $SO_2CH_3$ | H | $OCH_3$ | $OCH_3$ | N | |
| 1737 | $C_2H_5$ | $CH_3$ | $SO_2CH_3$ | H | $OCH_3$ | $CH_3$ | N | |
| 1738 | $C_2H_5$ | $CH_3$ | $SO_2CH_3$ | H | $CH_3$ | $CH_3$ | N | |
| 1739 | $C_2H_5$ | $CH_3$ | $SO_2CH_3$ | H | $N(CH_3)_2$ | $OCH_2CF_3$ | N | |
| 1740 | $C_2H_5$ | $CH_3$ | $SO_2CH_3$ | H | $OCH_3$ | $CF_3$ | N | |
| 1741 | $C_2H_5$ | $CH_3$ | $SO_2CH_3$ | H | $OC_2H_5$ | $NHCH_3$ | N | |
| 1742 | $C_2H_5$ | $CH_3$ | $SO_2CH_3$ | $CH_3$ | $OCH_3$ | $OCH_3$ | CH | |
| 1743 | $C_2H_5$ | $CH_3$ | $SO_2CH_3$ | $CH_3$ | $OCH_3$ | $CH_3$ | N | |
| 1744 | $C_2H_5$ | $CH_3$ | $SO_2C_2H_5$ | H | $OCH_3$ | $OCH_3$ | CH | |
| 1745 | $C_2H_5$ | $CH_3$ | $SO_2C_2H_5$ | H | $OCH_3$ | $CH_3$ | CH | |
| 1746 | $C_2H_5$ | $CH_3$ | $SO_2C_2H_5$ | H | $CH_3$ | $CH_3$ | CH | |
| 1747 | $C_2H_5$ | $CH_3$ | $SO_2C_2H_5$ | H | $CH_3$ | $OC_2H_5$ | CH | |
| 1748 | $C_2H_5$ | $CH_3$ | $SO_2C_2H_5$ | H | $C_2H_5$ | $OCH_3$ | CH | |
| 1749 | $C_2H_5$ | $CH_3$ | $SO_2C_2H_5$ | H | $OC_2H_5$ | $OC_2H_5$ | CH | |
| 1750 | $C_2H_5$ | $CH_3$ | $SO_2C_2H_5$ | H | $OCHF_2$ | $OCHF_2$ | CH | |
| 1751 | $C_2H_5$ | $CH_3$ | $SO_2C_2H_5$ | H | $CH_3$ | $OCHF_2$ | CH | |
| 1752 | $C_2H_5$ | $CH_3$ | $SO_2C_2H_5$ | H | Cl | $OCH_3$ | CH | |
| 1753 | $C_2H_5$ | $CH_3$ | $SO_2C_2H_5$ | H | $OCH_3$ | $OCH_3$ | N | |
| 1754 | $C_2H_5$ | $CH_3$ | $SO_2C_2H_5$ | H | $OCH_3$ | $CH_3$ | N | |
| 1755 | $C_2H_5$ | $CH_3$ | $SO_2C_2H_5$ | H | $CH_3$ | $CH_3$ | N | |
| 1756 | $C_2H_5$ | $CH_3$ | $SO_2C_2H_5$ | H | $N(CH_3)_2$ | $OCH_2CF_3$ | N | |
| 1757 | $C_2H_5$ | $CH_3$ | $SO_2C_2H_5$ | H | $OCH_3$ | $CF_3$ | N | |
| 1758 | $C_2H_5$ | $CH_3$ | $SO_2C_2H_5$ | H | $OC_2H_5$ | $NHCH_3$ | N | |
| 1759 | $C_2H_5$ | $CH_3$ | $SO_2C_2H_5$ | $CH_3$ | $OCH_3$ | $OCH_3$ | CH | |
| 1760 | $C_2H_5$ | $CH_3$ | $SO_2C_2H_5$ | $CH_3$ | $OCH_3$ | $CH_3$ | N | |
| 1761 | $C_2H_5$ | $CH_3$ | $SO_2$-n-$C_3H_7$ | H | $OCH_3$ | $OCH_3$ | CH | |
| 1762 | $C_2H_5$ | $CH_3$ | $SO_2$-n-$C_3H_7$ | H | $OCH_3$ | $CH_3$ | CH | |
| 1763 | $C_2H_5$ | $CH_3$ | $SO_2$-n-$C_3H_7$ | H | $CH_3$ | $CH_3$ | CH | |
| 1764 | $C_2H_5$ | $CH_3$ | $SO_2$-n-$C_3H_7$ | H | $CH_3$ | $OC_2H_5$ | CH | |
| 1765 | $C_2H_5$ | $CH_3$ | $SO_2$-n-$C_3H_7$ | H | $C_2H_5$ | $OCH_3$ | CH | |
| 1766 | $C_2H_5$ | $CH_3$ | $SO_2$-n-$C_3H_7$ | H | $OC_2H_5$ | $OC_2H_5$ | CH | |
| 1767 | $C_2H_5$ | $CH_3$ | $SO_2$-n-$C_3H_7$ | H | $OCHF_2$ | $OCHF_2$ | CH | |
| 1768 | $C_2H_5$ | $CH_3$ | $SO_2$-n-$C_3H_7$ | H | $CH_3$ | $OCHF_2$ | CH | |
| 1769 | $C_2H_5$ | $CH_3$ | $SO_2$-n-$C_3H_7$ | H | Cl | $OCH_3$ | CH | |
| 1770 | $C_2H_5$ | $CH_3$ | $SO_2$-n-$C_3H_7$ | H | $OCH_3$ | $OCH_3$ | N | |
| 1771 | $C_2H_5$ | $CH_3$ | $SO_2$-n-$C_3H_7$ | H | $OCH_3$ | $CH_3$ | N | |
| 1772 | $C_2H_5$ | $CH_3$ | $SO_2$-n-$C_3H_7$ | H | $CH_3$ | $CH_3$ | N | |
| 1773 | $C_2H_5$ | $CH_3$ | $SO_2$-n-$C_3H_7$ | H | $N(CH_3)_2$ | $OCH_2CF_3$ | N | |
| 1774 | $C_2H_5$ | $CH_3$ | $SO_2$-n-$C_3H_7$ | H | $OCH_3$ | $CF_3$ | N | |
| 1775 | $C_2H_5$ | $CH_3$ | $SO_2$-n-$C_3H_7$ | H | $OC_2H_5$ | $NHCH_3$ | N | |
| 1776 | $C_2H_5$ | $CH_3$ | $SO_2$-n-$C_3H_7$ | $CH_3$ | $OCH_3$ | $OCH_3$ | CH | |
| 1777 | $C_2H_5$ | $CH_3$ | $SO_2$-n-$C_3H_7$ | $CH_3$ | $OCH_3$ | $CH_3$ | N | |
| 1778 | $C_2H_5$ | $CH_3$ | $SO_2$-i-$C_3H_7$ | H | $OCH_3$ | $OCH_3$ | CH | |
| 1779 | $C_2H_5$ | $CH_3$ | $SO_2$-i-$C_3H_7$ | H | $OCH_3$ | $CH_3$ | CH | |
| 1780 | $C_2H_5$ | $CH_3$ | $SO_2$-i-$C_3H_7$ | H | $CH_3$ | $CH_3$ | CH | |

TABLE 1-continued

Compound of the formula (1a)

(Ia)

| No. | R$^1$ | R$^4$ | R$^5$ | R$^7$ | X | Y | Z | mp.(°C.) |
|---|---|---|---|---|---|---|---|---|
| 1781 | C$_2$H$_5$ | CH$_3$ | SO$_2$-i-C$_3$H$_7$ | H | CH$_3$ | OC$_2$H$_5$ | CH | |
| 1782 | C$_2$H$_5$ | CH$_3$ | SO$_2$-i-C$_3$H$_7$ | H | C$_2$H$_5$ | OCH$_3$ | CH | |
| 1783 | C$_2$H$_5$ | CH$_3$ | SO$_2$-i-C$_3$H$_7$ | H | OC$_2$H$_5$ | OC$_2$H$_5$ | CH | |
| 1784 | C$_2$H$_5$ | CH$_3$ | SO$_2$-i-C$_3$H$_7$ | H | OCHF$_2$ | OCHF$_2$ | CH | |
| 1785 | C$_2$H$_5$ | CH$_3$ | SO$_2$-i-C$_3$H$_7$ | H | CH$_3$ | OCHF$_2$ | CH | |
| 1786 | C$_2$H$_5$ | CH$_3$ | SO$_2$-i-C$_3$H$_7$ | H | Cl | OCH$_3$ | CH | |
| 1787 | C$_2$H$_5$ | CH$_3$ | SO$_2$-i-C$_3$H$_7$ | H | OCH$_3$ | OCH$_3$ | N | |
| 1788 | C$_2$H$_5$ | CH$_3$ | SO$_2$-i-C$_3$H$_7$ | H | OCH$_3$ | CH$_3$ | N | |
| 1789 | C$_2$H$_5$ | CH$_3$ | SO$_2$-i-C$_3$H$_7$ | H | CH$_3$ | CH$_3$ | N | |
| 1790 | C$_2$H$_5$ | CH$_3$ | SO$_2$-i-C$_3$H$_7$ | H | N(CH$_3$)$_2$ | OCH$_2$CF$_3$ | N | |
| 1791 | C$_2$H$_5$ | CH$_3$ | SO$_2$-i-C$_3$H$_7$ | H | OCH$_3$ | CF$_3$ | N | |
| 1792 | C$_2$H$_5$ | CH$_3$ | SO$_2$-i-C$_3$H$_7$ | H | OC$_2$H$_5$ | NHCH$_3$ | N | |
| 1793 | C$_2$H$_5$ | CH$_3$ | SO$_2$-i-C$_3$H$_7$ | CH$_3$ | OCH$_3$ | OCH$_3$ | CH | |
| 1794 | C$_2$H$_5$ | CH$_3$ | SO$_2$-i-C$_3$H$_7$ | CH$_3$ | OCH$_3$ | CH$_3$ | N | |
| 1795 | C$_2$H$_5$ | CH$_3$ | ClCH$_2$CO | H | OCH$_3$ | OCH$_3$ | CH | |
| 1796 | C$_2$H$_5$ | CH$_3$ | ClCH$_2$CO | H | OCH$_3$ | CH$_3$ | CH | |
| 1797 | C$_2$H$_5$ | CH$_3$ | ClCH$_2$CO | H | CH$_3$ | CH$_3$ | CH | |
| 1798 | C$_2$H$_5$ | CH$_3$ | ClCH$_2$CO | H | Cl | OCH$_3$ | CH | |
| 1799 | C$_2$H$_5$ | CH$_3$ | ClCH$_2$CO | H | OCH$_3$ | OCH$_3$ | N | |
| 1800 | C$_2$H$_5$ | CH$_3$ | ClCH$_2$CO | H | OCH$_3$ | CH$_3$ | N | |
| 1801 | C$_2$H$_5$ | CH$_3$ | ClCH$_2$CO | H | OCH$_3$ | CF$_3$ | N | |
| 1802 | C$_2$H$_5$ | CH$_3$ | ClCH$_2$CO | CH$_3$ | OCH$_3$ | OCH$_3$ | CH | |
| 1803 | C$_2$H$_5$ | CH$_3$ | ClCH$_2$CO | CH$_3$ | OCH$_3$ | CH$_3$ | N | |
| 1804 | C$_2$H$_5$ | CH$_3$ | Cl$_2$CHCO | H | OCH$_3$ | OCH$_3$ | CH | |
| 1805 | C$_2$H$_5$ | CH$_3$ | Cl$_2$CHCO | H | OCH$_3$ | CH$_3$ | CH | |
| 1806 | C$_2$H$_5$ | CH$_3$ | Cl$_2$CHCO | H | CH$_3$ | CH$_3$ | CH | |
| 1807 | C$_2$H$_5$ | CH$_3$ | Cl$_2$CHCO | H | Cl | OCH$_3$ | CH | |
| 1808 | C$_2$H$_5$ | CH$_3$ | Cl$_2$CHCO | H | OCH$_3$ | OCH$_3$ | N | |
| 1809 | C$_2$H$_5$ | CH$_3$ | Cl$_2$CHCO | H | OCH$_3$ | CH$_3$ | N | |
| 1810 | C$_2$H$_5$ | CH$_3$ | Cl$_2$CHCO | H | OCH$_3$ | CF$_3$ | N | |
| 1811 | C$_2$H$_5$ | CH$_3$ | Cl$_2$CHCO | CH$_3$ | OCH$_3$ | OCH$_3$ | CH | |
| 1812 | C$_2$H$_5$ | CH$_3$ | Cl$_2$CHCO | CH$_3$ | OCH$_3$ | OCH$_3$ | N | |
| 1813 | C$_2$H$_5$ | CH$_3$ | Cl$_3$CCO | H | OCH$_3$ | OCH$_3$ | CH | |
| 1814 | C$_2$H$_5$ | CH$_3$ | Cl$_3$CCO | H | OCH$_3$ | CH$_3$ | CH | |
| 1815 | C$_2$H$_5$ | CH$_3$ | Cl$_3$CCO | H | CH$_3$ | CH$_3$ | CH | |
| 1816 | C$_2$H$_5$ | CH$_3$ | Cl$_3$CCO | H | Cl | OCH$_3$ | CH | |
| 1817 | C$_2$H$_5$ | CH$_3$ | Cl$_3$CCO | H | OCH$_3$ | OCH$_3$ | N | |
| 1818 | C$_2$H$_5$ | CH$_3$ | Cl$_3$CCO | H | OCH$_3$ | CH$_3$ | N | |
| 1819 | C$_2$H$_5$ | CH$_3$ | Cl$_3$CCO | H | OCH$_3$ | CF$_3$ | N | |
| 1820 | C$_2$H$_5$ | CH$_3$ | Cl$_3$CCO | CH$_3$ | OCH$_3$ | OCH$_3$ | CH | |
| 1821 | C$_2$H$_5$ | CH$_3$ | Cl$_3$CCO | CH$_3$ | OCH$_3$ | CH$_3$ | N | |
| 1822 | C$_2$H$_5$ | CH$_3$ | CH$_3$OCH$_2$CO | H | OCH$_3$ | OCH$_3$ | CH | |
| 1823 | C$_2$H$_5$ | CH$_3$ | CH$_3$OCH$_2$CO | H | OCH$_3$ | CH$_3$ | CH | |
| 1824 | C$_2$H$_5$ | CH$_3$ | CH$_3$OCH$_2$CO | H | CH$_3$ | CH$_3$ | CH | |
| 1825 | C$_2$H$_5$ | CH$_3$ | CH$_3$OCH$_2$CO | H | Cl | OCH$_3$ | CH | |
| 1826 | C$_2$H$_5$ | CH$_3$ | CH$_3$OCH$_2$CO | H | OCH$_3$ | OCH$_3$ | N | |
| 1827 | C$_2$H$_5$ | CH$_3$ | CH$_3$OCH$_2$CO | H | OCH$_3$ | CH$_3$ | N | |
| 1828 | C$_2$H$_5$ | CH$_3$ | CH$_3$OCH$_2$CO | H | OCH$_3$ | CF$_3$ | N | |
| 1829 | C$_2$H$_5$ | CH$_3$ | CH$_3$OCH$_2$CO | CH$_3$ | OCH$_3$ | OCH$_3$ | CH | |
| 1830 | C$_2$H$_5$ | CH$_3$ | CH$_3$OCH$_2$CO | CH$_3$ | OCH$_3$ | CH$_3$ | N | |
| 1831 | C$_2$H$_5$ | CH$_3$ | CH$_2$=CHCO | H | OCH$_3$ | OCH$_3$ | CH | |
| 1832 | C$_2$H$_5$ | CH$_3$ | CH$_2$=CHCO | H | OCH$_3$ | CH$_3$ | CH | |
| 1833 | C$_2$H$_5$ | CH$_3$ | CH$_2$=CHCO | H | CH$_3$ | CH$_3$ | CH | |
| 1834 | C$_2$H$_5$ | CH$_3$ | CH$_2$=CHCO | H | Cl | OCH$_3$ | CH | |
| 1835 | C$_2$H$_5$ | CH$_3$ | CH$_2$=CHCO | H | OCH$_3$ | OCH$_3$ | N | |
| 1836 | C$_2$H$_5$ | CH$_3$ | CH$_2$=CHCO | H | OCH$_3$ | CH$_3$ | N | |
| 1837 | C$_2$H$_5$ | CH$_3$ | CH$_2$=CHCO | H | OCH$_3$ | CF$_3$ | N | |
| 1838 | C$_2$H$_5$ | CH$_3$ | CH$_2$=CHCO | CH$_3$ | OCH$_3$ | OCH$_3$ | CH | |
| 1839 | C$_2$H$_5$ | CH$_3$ | CH$_2$=CHCO | CH$_3$ | OCH$_3$ | CH$_3$ | N | |
| 1840 | C$_2$H$_5$ | CH$_3$ | CH≡CCO | H | OCH$_3$ | OCH$_3$ | CH | |
| 1841 | C$_2$H$_5$ | CH$_3$ | CH≡CCO | H | OCH$_3$ | CH$_3$ | CH | |
| 1842 | C$_2$H$_5$ | CH$_3$ | CH≡CCO | H | CH$_3$ | CH$_3$ | CH | |
| 1843 | C$_2$H$_5$ | CH$_3$ | CH≡CCO | H | Cl | OCH$_3$ | CH | |

TABLE 1-continued

Compound of the formula (1a)

(Ia)

| No. | R$^1$ | R$^4$ | R$^5$ | R$^7$ | X | Y | Z | mp.(°C.) |
|---|---|---|---|---|---|---|---|---|
| 1844 | C$_2$H$_5$ | CH$_3$ | CH≡CCO | H | OCH$_3$ | CH$_3$ | N | |
| 1845 | C$_2$H$_5$ | CH$_3$ | CH≡CCO | H | OCH$_3$ | CF$_3$ | N | |
| 1846 | C$_2$H$_5$ | CH$_3$ | CH≡CCO | H | OCH$_3$ | OCH$_3$ | N | |
| 1847 | C$_2$H$_5$ | CH$_3$ | CH≡CCO | CH$_3$ | OCH$_3$ | OCH$_3$ | CH | |
| 1848 | C$_2$H$_5$ | CH$_3$ | CH≡CCO | CH$_3$ | OCH$_3$ | CH$_3$ | N | |
| 1849 | C$_2$H$_5$ | CH$_3$ | CO-cyclopropyl | H | OCH$_3$ | OCH$_3$ | CH | |
| 1850 | C$_2$H$_5$ | CH$_3$ | CO-cyclopropyl | H | OCH$_3$ | CH$_3$ | CH | |
| 1851 | C$_2$H$_5$ | CH$_3$ | CO-cyclopropyl | H | CH$_3$ | CH$_3$ | CH | |
| 1852 | C$_2$H$_5$ | CH$_3$ | CO-cyclopropyl | H | Cl | OCH$_3$ | CH | |
| 1853 | C$_2$H$_5$ | CH$_3$ | CO-cyclopropyl | H | OCH$_3$ | OCH$_3$ | N | |
| 1854 | C$_2$H$_5$ | CH$_3$ | CO-cyclopropyl | H | OCH$_3$ | CH$_3$ | N | |
| 1855 | C$_2$H$_5$ | CH$_3$ | CO-cyclopropyl | H | OCH$_3$ | CF$_3$ | N | |
| 1856 | C$_2$H$_5$ | CH$_3$ | CO-cyclopropyl | CH$_3$ | OCH$_3$ | OCH$_3$ | CH | |
| 1857 | C$_2$H$_5$ | CH$_3$ | CO-cyclopropyl | CH$_3$ | OCH$_3$ | OCH$_3$ | CH | |
| 1858 | C$_2$H$_5$ | CH$_3$ | CO-cyclobutyl | H | OCH$_3$ | OCH$_3$ | CH | |
| 1859 | C$_2$H$_5$ | CH$_3$ | CO-cyclobutyl | H | OCH$_3$ | CH$_3$ | CH | |

TABLE 1-continued
Compound of the formula (1a)
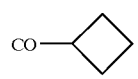
| No. | R¹ | R⁴ | R⁵ | R⁷ | X | Y | Z | mp.(°C.) |
|---|---|---|---|---|---|---|---|---|
| 1860 | $C_2H_5$ | $CH_3$ | 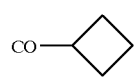 | H | $CH_3$ | $CH_3$ | CH | |
| 1861 | $C_2H_5$ | $CH_3$ | 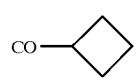 | H | Cl | $OCH_3$ | CH | |
| 1862 | $C_2H_5$ | $CH_3$ | 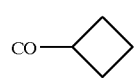 | H | $OCH_3$ | $OCH_3$ | N | |
| 1863 | $C_2H_5$ | $CH_3$ | 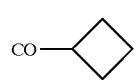 | H | $OCH_3$ | $CH_3$ | N | |
| 1864 | $C_2H_5$ | $CH_3$ | 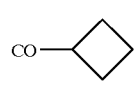 | H | $OCH_3$ | $CF_3$ | N | |
| 1865 | $C_2H_5$ | $CH_3$ | 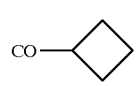 | $CH_3$ | $OCH_3$ | $OCH_3$ | CH | |
| 1866 | $C_2H_5$ | $CH_3$ | 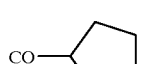 | $CH_3$ | $OCH_3$ | $CH_3$ | N | |
| 1867 | $C_2H_5$ | $CH_3$ | 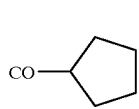 | H | $OCH_3$ | $OCH_3$ | CH | |
| 1868 | $C_2H_5$ | $CH_3$ |  | H | $OCH_3$ | $CH_3$ | CH | |
| 1869 | $C_2H_5$ | $CH_3$ | | H | $CH_3$ | $CH_3$ | CH | |

TABLE 1-continued

Compound of the formula (1a)

(Ia)

[Structure: benzene ring with SO$_2$—R$^1$ and SO$_2$NH—CO—NR$^7$— substituents, CH(H)(H)NR$^4$R$^5$ group, linked to pyrimidine ring with X, Y, Z substituents]

| No. | R$^1$ | R$^4$ | R$^5$ | R$^7$ | X | Y | Z | mp.(°C.) |
|---|---|---|---|---|---|---|---|---|
| 1870 | C$_2$H$_5$ | CH$_3$ | CO-cyclopentyl | H | Cl | OCH$_3$ | CH | |
| 1871 | C$_2$H$_5$ | CH$_3$ | CO-cyclopentyl | H | OCH$_3$ | OCH$_3$ | N | |
| 1872 | C$_2$H$_5$ | CH$_3$ | CO-cyclopentyl | H | OCH$_3$ | CH$_3$ | N | |
| 1873 | C$_2$H$_5$ | CH$_3$ | CO-cyclopentyl | H | OCH$_3$ | CF$_3$ | N | |
| 1874 | C$_2$H$_5$ | CH$_3$ | CO-cyclopentyl | CH$_3$ | OCH$_3$ | OCH$_3$ | CH | |
| 1875 | C$_2$H$_5$ | CH$_3$ | CO-cyclopentyl | CH$_3$ | OCH$_3$ | CH$_3$ | N | |
| 1876 | C$_2$H$_5$ | CH$_3$ | CO-cyclohexyl | H | OCH$_3$ | OCH$_3$ | CH | |
| 1877 | C$_2$H$_5$ | CH$_3$ | CO-cyclohexyl | H | OCH$_3$ | CH$_3$ | CH | |
| 1878 | C$_2$H$_5$ | CH$_3$ | CO-cyclohexyl | H | CH$_3$ | CH$_3$ | CH | |

TABLE 1-continued

Compound of the formula (1a)

| No. | R¹ | R⁴ | R⁵ | R⁷ | X | Y | Z | mp.(°C.) |
|---|---|---|---|---|---|---|---|---|
| 1879 | $C_2H_5$ | $CH_3$ | CO-cyclohexyl | H | Cl | $OCH_3$ | CH | |
| 1880 | $C_2H_5$ | $CH_3$ | CO-cyclohexyl | H | $OCH_3$ | $OCH_3$ | N | |
| 1881 | $C_2H_5$ | $CH_3$ | CO-cyclohexyl | H | $OCH_3$ | $CH_3$ | N | |
| 1882 | $C_2H_5$ | $CH_3$ | CO-cyclohexyl | H | $OCH_3$ | $CF_3$ | N | |
| 1883 | $C_2H_5$ | $CH_3$ | CO-cyclohexyl | $CH_3$ | $OCH_3$ | $OCH_3$ | CH | |
| 1884 | $C_2H_5$ | $CH_3$ | CO-cyclohexyl | $CH_3$ | $OCH_3$ | $CH_3$ | N | |
| 1885 | $C_2H_5$ | $CH_3$ | $CF_3SO_2$ | H | $OCH_3$ | $OCH_3$ | CH | |
| 1886 | $C_2H_5$ | $CH_3$ | $CF_3SO_2$ | H | $OCH_3$ | $CH_3$ | CH | |
| 1887 | $C_2H_5$ | $CH_3$ | $CF_3SO_2$ | H | $CH_3$ | $CH_3$ | CH | |
| 1888 | $C_2H_5$ | $CH_3$ | $CF_3SO_2$ | H | Cl | $OCH_3$ | CH | |
| 1889 | $C_2H_5$ | $CH_3$ | $CF_3SO_2$ | H | $OCH_3$ | $OCH_3$ | N | |
| 1890 | $C_2H_5$ | $CH_3$ | $CF_3SO_2$ | H | $OCH_3$ | $CH_3$ | N | |
| 1891 | $C_2H_5$ | $CH_3$ | $CF_3SO_2$ | H | $OCH_3$ | $CF_3$ | N | |
| 1892 | $C_2H_5$ | $CH_3$ | $CF_3SO_2$ | $CH_3$ | $OCH_3$ | $OCH_3$ | CH | |
| 1893 | $C_2H_5$ | $CH_3$ | $CF_3SO_2$ | $CH_3$ | $OCH_3$ | $CH_3$ | N | |
| 1894 | $C_2H_5$ | $CH_3$ | $FCH_2SO_2$ | H | $OCH_3$ | $OCH_3$ | CH | |
| 1895 | $C_2H_5$ | $CH_3$ | $FCH_2SO_2$ | H | $OCH_3$ | $CH_3$ | CH | |
| 1896 | $C_2H_5$ | $CH_3$ | $FCH_2SO_2$ | H | $CH_3$ | $CH_3$ | CH | |
| 1897 | $C_2H_5$ | $CH_3$ | $FCH_2SO_2$ | H | Cl | $OCH_3$ | CH | |
| 1898 | $C_2H_5$ | $CH_3$ | $FCH_2SO_2$ | H | $OCH_3$ | $OCH_3$ | N | |
| 1899 | $C_2H_5$ | $CH_3$ | $FCH_2SO_2$ | H | $OCH_3$ | $CH_3$ | N | |
| 1900 | $C_2H_5$ | $CH_3$ | $FCH_2SO_2$ | H | $OCH_3$ | $CF_3$ | N | |
| 1901 | $C_2H_5$ | $CH_3$ | $FCH_2SO_2$ | $CH_3$ | $OCH_3$ | $OCH_3$ | CH | |
| 1902 | $C_2H_5$ | $CH_3$ | $FCH_2SO_2$ | $CH_3$ | $OCH_3$ | $CH_3$ | N | |
| 1903 | $C_2H_5$ | $CH_3$ | $ClCH_2SO_2$ | H | $OCH_3$ | $OCH_3$ | CH | |
| 1904 | $C_2H_5$ | $CH_3$ | $ClCH_2SO_2$ | H | $OCH_3$ | $CH_3$ | CH | |
| 1905 | $C_2H_5$ | $CH_3$ | $ClCH_2SO_2$ | H | $CH_3$ | $CH_3$ | CH | |
| 1906 | $C_2H_5$ | $CH_3$ | $ClCH_2SO_2$ | H | Cl | $OCH_3$ | CH | |
| 1907 | $C_2H_5$ | $CH_3$ | $ClCH_2SO_2$ | H | $OCH_3$ | $OCH_3$ | N | |

TABLE 1-continued

Compound of the formula (1a)

(Ia)

| No. | R$^1$ | R$^4$ | R$^5$ | R$^7$ | X | Y | Z | mp.(°C.) |
|---|---|---|---|---|---|---|---|---|
| 1908 | C$_2$H$_5$ | CH$_3$ | ClCH$_2$SO$_2$ | H | OCH$_3$ | CH$_3$ | N | |
| 1909 | C$_2$H$_5$ | CH$_3$ | ClCH$_2$SO$_2$ | H | OCH$_3$ | CF$_3$ | N | |
| 1910 | C$_2$H$_5$ | CH$_3$ | ClCH$_2$SO$_2$ | CH$_3$ | OCH$_3$ | OCH$_3$ | CH | |
| 1911 | C$_2$H$_5$ | CH$_3$ | ClCH$_2$SO$_2$ | CH$_3$ | OCH$_3$ | CH$_3$ | N | |
| 1912 | C$_2$H$_5$ | CH$_3$ | Cl$_2$CHSO$_2$ | H | OCH$_3$ | OCH$_3$ | CH | |
| 1913 | C$_2$H$_5$ | CH$_3$ | Cl$_2$CHSO$_2$ | H | OCH$_3$ | CH$_3$ | CH | |
| 1914 | C$_2$H$_5$ | CH$_3$ | Cl$_2$CHSO$_2$ | H | CH$_3$ | CH$_3$ | CH | |
| 1915 | C$_2$H$_5$ | CH$_3$ | Cl$_2$CHSO$_2$ | H | Cl | OCH$_3$ | CH | |
| 1916 | C$_2$H$_5$ | CH$_3$ | Cl$_2$CHSO$_2$ | H | OCH$_3$ | OCH$_3$ | N | |
| 1917 | C$_2$H$_5$ | CH$_3$ | Cl$_2$CHSO$_2$ | H | OCH$_3$ | CH$_3$ | N | |
| 1918 | C$_2$H$_5$ | CH$_3$ | Cl$_2$CHSO$_2$ | H | OCH$_3$ | CF$_3$ | N | |
| 1919 | C$_2$H$_5$ | CH$_3$ | Cl$_2$CHSO$_2$ | CH$_3$ | OCH$_3$ | OCH$_3$ | CH | |
| 1920 | C$_2$H$_5$ | CH$_3$ | Cl$_2$CHSO$_2$ | CH$_3$ | OCH$_3$ | CH$_3$ | N | |
| 1921 | C$_2$H$_5$ | CH$_3$ | Cl$_3$CSO$_2$ | H | OCH$_3$ | OCH$_3$ | CH | |
| 1922 | C$_2$H$_5$ | CH$_3$ | Cl$_3$CSO$_2$ | H | OCH$_3$ | CH$_3$ | CH | |
| 1923 | C$_2$H$_5$ | CH$_3$ | Cl$_3$CSO$_2$ | H | CH$_3$ | CH$_3$ | CH | |
| 1924 | C$_2$H$_5$ | CH$_3$ | Cl$_3$CSO$_2$ | H | Cl | OCH$_3$ | CH | |
| 1925 | C$_2$H$_5$ | CH$_3$ | Cl$_3$CSO$_2$ | H | OCH$_3$ | OCH$_3$ | N | |
| 1926 | C$_2$H$_5$ | CH$_3$ | Cl$_3$CSO$_2$ | H | OCH$_3$ | CH$_3$ | N | |
| 1927 | C$_2$H$_5$ | CH$_3$ | Cl$_3$CSO$_2$ | H | OCH$_3$ | CF$_3$ | N | |
| 1928 | C$_2$H$_5$ | CH$_3$ | Cl$_3$CSO$_2$ | CH$_3$ | OCH$_3$ | OCH$_3$ | CH | |
| 1929 | C$_2$H$_5$ | CH$_3$ | Cl$_3$CSO$_2$ | CH$_3$ | OCH$_3$ | CH$_3$ | N | |
| 1930 | C$_2$H$_5$ | CH$_3$ | nC$_4$H$_9$SO$_2$ | H | OCH$_3$ | OCH$_3$ | CH | |
| 1931 | C$_2$H$_5$ | CH$_3$ | nC$_4$H$_9$SO$_2$ | H | OCH$_3$ | CH$_3$ | CH | |
| 1932 | C$_2$H$_5$ | CH$_3$ | nC$_4$H$_9$SO$_2$ | H | CH$_3$ | CH$_3$ | CH | |
| 1933 | C$_2$H$_5$ | CH$_3$ | nC$_4$H$_9$SO$_2$ | H | Cl | OCH$_3$ | CH | |
| 1934 | C$_2$H$_5$ | CH$_3$ | nC$_4$H$_9$SO$_2$ | H | OCH$_3$ | CH$_3$ | N | |
| 1935 | C$_2$H$_5$ | CH$_3$ | nC$_4$H$_9$SO$_2$ | H | OCH$_3$ | CF$_3$ | N | |
| 1936 | C$_2$H$_5$ | CH$_3$ | nC$_4$H$_9$SO$_2$ | H | OCH$_3$ | OCH$_3$ | N | |
| 1937 | C$_2$H$_5$ | CH$_3$ | nC$_4$H$_9$SO$_2$ | CH$_3$ | OCH$_3$ | OCH$_3$ | CH | |
| 1938 | C$_2$H$_5$ | CH$_3$ | nC$_4$H$_9$SO$_2$ | CH$_3$ | OCH$_3$ | CH$_3$ | N | |
| 1939 | C$_2$H$_5$ | CH$_3$ | CF$_3$CH$_2$SO$_2$ | H | OCH$_3$ | OCH$_3$ | CH | |
| 1940 | C$_2$H$_5$ | CH$_3$ | CF$_3$CH$_2$SO$_2$ | H | OCH$_3$ | CH$_3$ | CH | |
| 1941 | C$_2$H$_5$ | CH$_3$ | CF$_3$CH$_2$SO$_2$ | H | CH$_3$ | CH$_3$ | CH | |
| 1942 | C$_2$H$_5$ | CH$_3$ | CF$_3$CH$_2$SO$_2$ | H | Cl | OCH$_3$ | CH | |
| 1943 | C$_2$H$_5$ | CH$_3$ | CF$_3$CH$_2$SO$_2$ | H | OCH$_3$ | CH$_3$ | N | |
| 1944 | C$_2$H$_5$ | CH$_3$ | CF$_3$CH$_2$SO$_2$ | H | OCH$_3$ | CF$_3$ | N | |
| 1945 | C$_2$H$_5$ | CH$_3$ | CF$_3$CH$_2$SO$_2$ | H | OCH$_3$ | OCH$_3$ | N | |
| 1946 | C$_2$H$_5$ | CH$_3$ | CF$_3$CH$_2$SO$_2$ | CH$_3$ | OCH$_3$ | OCH$_3$ | CH | |
| 1947 | C$_2$H$_5$ | CH$_3$ | CF$_3$CH$_2$SO$_2$ | CH$_3$ | OCH$_3$ | CH$_3$ | N | |
| 1948 | C$_2$H$_5$ | CH$_3$ | CH$_3$NHSO$_2$ | H | OCH$_3$ | OCH$_3$ | CH | |
| 1949 | C$_2$H$_5$ | CH$_3$ | CH$_3$NHSO$_2$ | H | OCH$_3$ | CH$_3$ | CH | |
| 1950 | C$_2$H$_5$ | CH$_3$ | CH$_3$NHSO$_2$ | H | CH$_3$ | CH$_3$ | CH | |
| 1951 | C$_2$H$_5$ | CH$_3$ | CH$_3$NHSO$_2$ | H | Cl | OCH$_3$ | CH | |
| 1952 | C$_2$H$_5$ | CH$_3$ | CH$_3$NHSO$_2$ | H | OCH$_3$ | OCH$_3$ | N | |
| 1953 | C$_2$H$_5$ | CH$_3$ | CH$_3$NHSO$_2$ | H | OCH$_3$ | CH$_3$ | N | |
| 1954 | C$_2$H$_5$ | CH$_3$ | CH$_3$NHSO$_2$ | H | OCH$_3$ | CF$_3$ | N | |
| 1955 | C$_2$H$_5$ | CH$_3$ | CH$_3$NHSO$_2$ | CH$_3$ | OCH$_3$ | OCH$_3$ | CH | |
| 1956 | C$_2$H$_5$ | CH$_3$ | CH$_3$NHSO$_2$ | CH$_3$ | OCH$_3$ | CH$_3$ | N | |
| 1957 | C$_2$H$_5$ | CH$_3$ | (CH$_3$)$_2$NSO$_2$ | H | OCH$_3$ | OCH$_3$ | CH | |
| 1958 | C$_2$H$_5$ | CH$_3$ | (CH$_3$)$_2$NSO$_2$ | H | OCH$_3$ | CH$_3$ | CH | |
| 1959 | C$_2$H$_5$ | CH$_3$ | (CH$_3$)$_2$NSO$_2$ | H | CH$_3$ | CH$_3$ | CH | |
| 1960 | C$_2$H$_5$ | CH$_3$ | (CH$_3$)$_2$NSO$_2$ | H | Cl | OCH$_3$ | CH | |
| 1961 | C$_2$H$_5$ | CH$_3$ | (CH$_3$)$_2$NSO$_2$ | H | OCH$_3$ | OCH$_3$ | N | |
| 1962 | C$_2$H$_5$ | CH$_3$ | (CH$_3$)$_2$NSO$_2$ | H | OCH$_3$ | CH$_3$ | N | |
| 1963 | C$_2$H$_5$ | CH$_3$ | (CH$_3$)$_2$NSO$_2$ | H | OCH$_3$ | CF$_3$ | N | |
| 1964 | C$_2$H$_5$ | CH$_3$ | (CH$_3$)$_2$NSO$_2$ | CH$_3$ | OCH$_3$ | OCH$_3$ | CH | |
| 1965 | C$_2$H$_5$ | CH$_3$ | (CH$_3$)$_2$NSO$_2$ | CH$_3$ | OCH$_3$ | CH$_3$ | N | |
| 1966 | C$_2$H$_5$ | CH$_3$ | (CH$_3$)$_3$C—OCO | H | OCH$_3$ | OCH$_3$ | CH | |
| 1967 | C$_2$H$_5$ | CH$_3$ | (CH$_3$)$_3$C—OCO | H | OCH$_3$ | CH$_3$ | CH | |
| 1968 | C$_2$H$_5$ | CH$_3$ | (CH$_3$)$_3$C— | H | CH$_3$ | CH$_3$ | CH | |

TABLE 1-continued

Compound of the formula (1a)

(Ia)

| No. | R$^1$ | R$^4$ | R$^5$ | R$^7$ | X | Y | Z | mp.(°C.) |
|---|---|---|---|---|---|---|---|---|
| 1969 | C$_2$H$_5$ | CH$_3$ | (CH$_3$)$_3$C—OCO | H | Cl | OCH$_3$ | CH | |
| 1970 | C$_2$H$_5$ | CH$_3$ | (CH$_3$)$_3$C—OCO | H | OCH$_3$ | OCH$_3$ | N | |
| 1971 | C$_2$H$_5$ | CH$_3$ | (CH$_3$)$_3$C—OCO | H | OCH$_3$ | CH$_3$ | N | |
| 1972 | C$_2$H$_5$ | CH$_3$ | (CH$_3$)$_3$C—OCO | H | OCH$_3$ | CF$_3$ | N | |
| 1973 | C$_2$H$_5$ | CH$_3$ | (CH$_3$)$_3$C—OCO | CH$_3$ | OCH$_3$ | OCH$_3$ | CH | |
| 1974 | C$_2$H$_5$ | CH$_3$ | (CH$_3$)$_3$C—OCO | CH$_3$ | OCH$_3$ | CH$_3$ | N | |
| 1975 | C$_2$H$_5$ | CH$_3$ | PhCO | H | OCH$_3$ | OCH$_3$ | CH | |
| 1976 | C$_2$H$_5$ | CH$_3$ | PhCO | H | OCH$_3$ | CH$_3$ | CH | |
| 1977 | C$_2$H$_5$ | CH$_3$ | PhCO | H | CH$_3$ | CH$_3$ | CH | |
| 1978 | C$_2$H$_5$ | CH$_3$ | PhCO | H | Cl | OCH$_3$ | CH | |
| 1979 | C$_2$H$_5$ | CH$_3$ | PhCO | H | OCH$_3$ | OCH$_3$ | N | |
| 1980 | C$_2$H$_5$ | CH$_3$ | PhCO | H | OCH$_3$ | CH$_3$ | N | |
| 1981 | C$_2$H$_5$ | CH$_3$ | PhCO | H | OCH$_3$ | CF$_3$ | N | |
| 1982 | C$_2$H$_5$ | CH$_3$ | PhCO | CH$_3$ | OCH$_3$ | OCH$_3$ | CH | |
| 1983 | C$_2$H$_5$ | CH$_3$ | PhCO | CH$_3$ | OCH$_3$ | CH$_3$ | N | |
| 1984 | C$_2$H$_5$ | CH$_3$ | PhSO$_2$ | H | OCH$_3$ | OCH$_3$ | CH | |
| 1985 | C$_2$H$_5$ | CH$_3$ | PhSO$_2$ | H | OCH$_3$ | CH$_3$ | CH | |
| 1986 | C$_2$H$_5$ | CH$_3$ | PhSO$_2$ | H | CH$_3$ | CH$_3$ | CH | |
| 1987 | C$_2$H$_5$ | CH$_3$ | PhSO$_2$ | H | Cl | OCH$_3$ | CH | |
| 1988 | C$_2$H$_5$ | CH$_3$ | PhSO$_2$ | H | OCH$_3$ | CH$_3$ | N | |
| 1989 | C$_2$H$_5$ | CH$_3$ | PhSO$_2$ | H | OCH$_3$ | CF$_3$ | N | |
| 1990 | C$_2$H$_5$ | CH$_3$ | PhSO$_2$ | H | OCH$_3$ | OCH$_3$ | N | |
| 1991 | C$_2$H$_5$ | CH$_3$ | PhSO$_2$ | CH$_3$ | OCH$_3$ | CH$_3$ | CH | |
| 1992 | C$_2$H$_5$ | CH$_3$ | PhSO$_2$ | CH$_3$ | OCH$_3$ | OCH$_3$ | N | |
| 1993 | C$_2$H$_5$ | CH$_3$ | CH$_3$NHCO | H | OCH$_3$ | OCH$_3$ | CH | |
| 1994 | C$_2$H$_5$ | CH$_3$ | CH$_3$NHCO | H | OCH$_3$ | CH$_3$ | CH | |
| 1995 | C$_2$H$_5$ | CH$_3$ | CH$_3$NHCO | H | CH$_3$ | CH$_3$ | CH | |
| 1996 | C$_2$H$_5$ | CH$_3$ | CH$_3$NHCO | H | Cl | OCH$_3$ | CH | |
| 1997 | C$_2$H$_5$ | CH$_3$ | CH$_3$NHCO | H | OCH$_3$ | OCH$_3$ | N | |
| 1998 | C$_2$H$_5$ | CH$_3$ | CH$_3$NHCO | H | OCH$_3$ | CH$_3$ | N | |
| 1999 | C$_2$H$_5$ | CH$_3$ | CH$_3$NHCO | H | OCH$_3$ | CF$_3$ | N | |
| 2000 | C$_2$H$_5$ | CH$_3$ | CH$_3$NHCO | CH$_3$ | OCH$_3$ | CH$_3$ | N | |
| 2001 | C$_2$H$_5$ | CH$_3$ | CH$_3$NHCO | CH$_3$ | OCH$_3$ | OCH$_3$ | CH | |
| 2002 | C$_2$H$_5$ | CH$_3$ | C$_2$H$_5$NHCO | H | OCH$_3$ | OCH$_3$ | CH | |
| 2003 | C$_2$H$_5$ | CH$_3$ | C$_2$H$_5$NHCO | H | OCH$_3$ | CH$_3$ | CH | |
| 2004 | C$_2$H$_5$ | CH$_3$ | C$_2$H$_5$NHCO | H | CH$_3$ | CH$_3$ | CH | |
| 2005 | C$_2$H$_5$ | CH$_3$ | C$_2$H$_5$NHCO | H | Cl | OCH$_3$ | CH | |
| 2006 | C$_2$H$_5$ | CH$_3$ | C$_2$H$_5$NHCO | H | OCH$_3$ | OCH$_3$ | N | |
| 2007 | C$_2$H$_5$ | CH$_3$ | C$_2$H$_5$NHCO | H | OCH$_3$ | CH$_3$ | N | |
| 2008 | C$_2$H$_5$ | CH$_3$ | C$_2$H$_5$NHCO | H | OCH$_3$ | CF$_3$ | N | |
| 2009 | C$_2$H$_5$ | CH$_3$ | C$_2$H$_5$NHCO | CH$_3$ | OCH$_3$ | OCH$_3$ | CH | |
| 2010 | C$_2$H$_5$ | CH$_3$ | C$_2$H$_5$NHCO | CH$_3$ | OCH$_3$ | CH$_3$ | N | |
| 2011 | C$_2$H$_5$ | CH$_3$ | CH$_3$NHCS | H | OCH$_3$ | OCH$_3$ | CH | |
| 2012 | C$_2$H$_5$ | CH$_3$ | CH$_3$NHCS | H | OCH$_3$ | CH$_3$ | CH | |
| 2013 | C$_2$H$_5$ | CH$_3$ | CH$_3$NHCS | H | CH$_3$ | CH$_3$ | CH | |
| 2014 | C$_2$H$_5$ | CH$_3$ | CH$_3$NHCS | H | Cl | OCH$_3$ | CH | |
| 2015 | C$_2$H$_5$ | CH$_3$ | CH$_3$NHCS | H | OCH$_3$ | OCH$_3$ | N | |
| 2016 | C$_2$H$_5$ | CH$_3$ | CH$_3$NHCS | H | OCH$_3$ | CH$_3$ | N | |
| 2017 | C$_2$H$_5$ | CH$_3$ | CH$_3$NHCS | H | OCH$_3$ | CF$_3$ | N | |
| 2018 | C$_2$H$_5$ | CH$_3$ | CH$_3$NHCS | CH$_3$ | OCH$_3$ | OCH$_3$ | CH | |
| 2019 | C$_2$H$_5$ | CH$_3$ | CH$_3$NHCS | CH$_3$ | OCH$_3$ | CH$_3$ | N | |
| 2020 | C$_2$H$_5$ | CH$_3$ | C$_2$H$_5$NHCS | H | OCH$_3$ | OCH$_3$ | CH | |
| 2021 | C$_2$H$_5$ | CH$_3$ | C$_2$H$_5$NHCS | H | OCH$_3$ | CH$_3$ | CH | |
| 2022 | C$_2$H$_5$ | CH$_3$ | C$_2$H$_5$NHCS | H | CH$_3$ | CH$_3$ | CH | |
| 2023 | C$_2$H$_5$ | CH$_3$ | C$_2$H$_5$NHCS | H | Cl | OCH$_3$ | CH | |
| 2024 | C$_2$H$_5$ | CH$_3$ | C$_2$H$_5$NHCS | H | OCH$_3$ | OCH$_3$ | N | |

TABLE 1-continued

Compound of the formula (1a)

$$\text{(Ia)}$$

| No. | R$^1$ | R$^4$ | R$^5$ | R$^7$ | X | Y | Z | mp.(°C.) |
|---|---|---|---|---|---|---|---|---|
| 2025 | C$_2$H$_5$ | CH$_3$ | C$_2$H$_5$NHCS | H | OCH$_3$ | CH$_3$ | N | |
| 2026 | C$_2$H$_5$ | CH$_3$ | C$_2$H$_5$NHCS | H | OCH$_3$ | CF$_3$ | N | |
| 2027 | C$_2$H$_5$ | CH$_3$ | C$_2$H$_5$NHCS | CH$_3$ | OCH$_3$ | OCH$_3$ | CH | |
| 2028 | C$_2$H$_5$ | CH$_3$ | C$_2$H$_5$NHCS | CH$_3$ | OCH$_3$ | CH$_3$ | N | |
| 2029 | C$_2$H$_5$ | CH$_3$ | COSCH$_3$ | H | OCH$_3$ | OCH$_3$ | CH | |
| 2030 | C$_2$H$_5$ | CH$_3$ | COSCH$_3$ | H | OCH$_3$ | CH$_3$ | CH | |
| 2031 | C$_2$H$_5$ | CH$_3$ | COSCH$_3$ | H | CH$_3$ | CH$_3$ | CH | |
| 2032 | C$_2$H$_5$ | CH$_3$ | COSCH$_3$ | H | Cl | OCH$_3$ | CH | |
| 2033 | C$_2$H$_5$ | CH$_3$ | COSCH$_3$ | H | OCH$_3$ | OCH$_3$ | N | |
| 2034 | C$_2$H$_5$ | CH$_3$ | COSCH$_3$ | H | OCH$_3$ | CH$_3$ | N | |
| 2035 | C$_2$H$_5$ | CH$_3$ | COSCH$_3$ | H | OCH$_3$ | CF$_3$ | N | |
| 2036 | C$_2$H$_5$ | CH$_3$ | COSCH$_3$ | CH$_3$ | OCH$_3$ | OCH$_3$ | CN | |
| 2037 | C$_2$H$_5$ | CH$_3$ | COSCH$_3$ | CH$_3$ | OCH$_3$ | CH$_3$ | N | |
| 2038 | C$_2$H$_5$ | CH$_3$ | CSOCH$_3$ | H | OCH$_3$ | OCH$_3$ | CH | |
| 2039 | C$_2$H$_5$ | CH$_3$ | CSOCH$_3$ | H | OCH$_3$ | CH$_3$ | CH | |
| 2040 | C$_2$H$_5$ | CH$_3$ | CSOCH$_3$ | H | CH$_3$ | CH$_3$ | CH | |
| 2041 | C$_2$H$_5$ | CH$_3$ | CSOCH$_3$ | H | Cl | OCH$_3$ | CH | |
| 2042 | C$_2$H$_5$ | CH$_3$ | CSOCH$_3$ | H | OCH$_3$ | OCH$_3$ | N | |
| 2043 | C$_2$H$_5$ | CH$_3$ | CSOCH$_3$ | H | OCH$_3$ | CH$_3$ | N | |
| 2044 | C$_2$H$_5$ | CH$_3$ | CSOCH$_3$ | H | OCH$_3$ | CF$_3$ | N | |
| 2045 | C$_2$H$_5$ | CH$_3$ | CSOCH$_3$ | CH$_3$ | OCH$_3$ | OCH$_3$ | CH | |
| 2046 | C$_2$H$_5$ | CH$_3$ | CSOCH$_3$ | CH$_3$ | OCH$_3$ | CH$_3$ | N | |
| 2047 | C$_2$H$_5$ | CH$_3$ | CSSCH$_3$ | H | OCH$_3$ | OCH$_3$ | CH | |
| 2048 | C$_2$H$_5$ | CH$_3$ | CSSCH$_3$ | H | OCH$_3$ | CH$_3$ | CH | |
| 2049 | C$_2$H$_5$ | CH$_3$ | CSSCH$_3$ | H | CH$_3$ | CH$_3$ | CH | |
| 2050 | C$_2$H$_5$ | CH$_3$ | CSSCH$_3$ | H | Cl | OCH$_3$ | CH | |
| 2051 | C$_2$H$_5$ | CH$_3$ | CSSCH$_3$ | H | OCH$_3$ | OCH$_3$ | N | |
| 2052 | C$_2$H$_5$ | CH$_3$ | CSSCH$_3$ | H | OCH$_3$ | CH$_3$ | N | |
| 2053 | C$_2$H$_5$ | CH$_3$ | CSSCH$_3$ | H | OCH$_3$ | CF$_3$ | N | |
| 2054 | C$_2$H$_5$ | CH$_3$ | CSSCH$_3$ | CH$_3$ | OCH$_3$ | OCH$_3$ | CH | |
| 2055 | C$_2$H$_5$ | CH$_3$ | CSSCH$_3$ | CH$_3$ | OCH$_3$ | CH$_3$ | N | |
| 2056 | C$_2$H$_5$ | CH$_3$ | COCOOCH$_3$ | H | OCH$_3$ | OCH$_3$ | CH | |
| 2057 | C$_2$H$_5$ | CH$_3$ | COCOOCH$_3$ | H | OCH$_3$ | CH$_3$ | CH | |
| 2058 | C$_2$H$_5$ | CH$_3$ | COCOOCH$_3$ | H | CH$_3$ | CH$_3$ | CH | |
| 2059 | C$_2$H$_5$ | CH$_3$ | COCOOCH$_3$ | H | Cl | OCH$_3$ | CH | |
| 2060 | C$_2$H$_5$ | CH$_3$ | COCOOCH$_3$ | H | OCH$_3$ | OCH$_3$ | N | |
| 2061 | C$_2$H$_5$ | CH$_3$ | COCOOCH$_3$ | H | OCH$_3$ | CH$_3$ | N | |
| 2062 | C$_2$H$_5$ | CH$_3$ | COCOOCH$_3$ | H | OCH$_3$ | CF$_3$ | N | |
| 2063 | C$_2$H$_5$ | CH$_3$ | COCOOCH$_3$ | CH$_3$ | OCH$_3$ | OCH$_3$ | CH | |
| 2064 | C$_2$H$_5$ | CH$_3$ | COCOOCH$_3$ | CH$_3$ | OCH$_3$ | CH$_3$ | N | |
| 2065 | C$_2$H$_5$ | CH$_3$ | i-C$_3$H$_7$OCO | H | OCH$_3$ | OCH$_3$ | CH | |
| 2066 | C$_2$H$_5$ | CH$_3$ | i-C$_3$H$_7$OCO | H | OCH$_3$ | CH$_3$ | CH | |
| 2067 | C$_2$H$_5$ | CH$_3$ | i-C$_3$H$_7$OCO | H | CH$_3$ | CH$_3$ | CH | |
| 2068 | C$_2$H$_5$ | CH$_3$ | i-C$_3$H$_7$OCO | H | Cl | OCH$_3$ | CH | |
| 2069 | C$_2$H$_5$ | CH$_3$ | i-C$_3$H$_7$OCO | H | OCH$_3$ | OCH$_3$ | N | |
| 2070 | C$_2$H$_5$ | CH$_3$ | i-C$_3$H$_7$OCO | H | OCH$_3$ | CH$_3$ | N | |
| 2071 | C$_2$H$_5$ | CH$_3$ | i-C$_3$H$_7$OCO | H | OCH$_3$ | CF$_3$ | N | |
| 2072 | C$_2$H$_5$ | CH$_3$ | i-C$_3$H$_7$OCO | CH$_3$ | OCH$_3$ | OCH$_3$ | CH | |
| 2073 | C$_2$H$_5$ | CH$_3$ | i-C$_3$H$_7$OCO | CH$_3$ | OCH$_3$ | CH$_3$ | N | |
| 2074 | C$_2$H$_5$ | C$_2$H$_5$ | CHO | H | OCH$_3$ | OCH$_3$ | CH | 161–165 |
| 2075 | C$_2$H$_5$ | C$_2$H$_5$ | CHO | H | OCH$_3$ | CH$_3$ | CH | |
| 2076 | C$_2$H$_5$ | C$_2$H$_5$ | CHO | H | CH$_3$ | CH$_3$ | CH | |
| 2077 | C$_2$H$_5$ | C$_2$H$_5$ | CHO | H | Cl | OCH$_3$ | CH | |
| 2078 | C$_2$H$_5$ | C$_2$H$_5$ | CHO | H | OCH$_3$ | CH$_3$ | N | |
| 2079 | C$_2$H$_5$ | C$_2$H$_5$ | CHO | H | OCH$_3$ | CF$_3$ | N | |
| 2080 | C$_2$H$_5$ | C$_2$H$_5$ | CHO | H | OCH$_3$ | OCH$_3$ | N | |
| 2081 | C$_2$H$_5$ | C$_2$H$_5$ | CHO | CH$_3$ | OCH$_3$ | OCH$_3$ | CH | |
| 2082 | C$_2$H$_5$ | C$_2$H$_5$ | CHO | CH$_3$ | OCH$_3$ | CH$_3$ | N | |
| 2083 | C$_2$H$_5$ | C$_2$H$_5$ | COCH$_3$ | H | OCH$_3$ | OCH$_3$ | CH | 173–179 |
| 2084 | C$_2$H$_5$ | C$_2$H$_5$ | COCH$_3$ | H | OCH$_3$ | CH$_3$ | CH | |
| 2085 | C$_2$H$_5$ | C$_2$H$_5$ | COCH$_3$ | H | CH$_3$ | CH$_3$ | CH | |
| 2086 | C$_2$H$_5$ | C$_2$H$_5$ | COCH$_3$ | H | Cl | OCH$_3$ | CH | |
| 2087 | C$_2$H$_5$ | C$_2$H$_5$ | COCH$_3$ | H | OCH$_3$ | CH$_3$ | N | |

TABLE 1-continued

Compound of the formula (1a)

$$\text{(Ia)}$$

Structure: benzene ring with $-SO_2-R^1$ and $-SO_2NH-CO-NR^7-$ (connected to pyrimidine/triazine ring with X, Y, Z substituents), and $-CH_2-NR^4R^5$ group.

| No. | $R^1$ | $R^4$ | $R^5$ | $R^7$ | X | Y | Z | mp.(°C.) |
|---|---|---|---|---|---|---|---|---|
| 2088 | $C_2H_5$ | $C_2H_5$ | $COCH_3$ | H | $OCH_3$ | $CF_3$ | N | |
| 2089 | $C_2H_5$ | $C_2H_5$ | $COCH_3$ | H | $OCH_3$ | $OCH_3$ | N | |
| 2090 | $C_2H_5$ | $C_2H_5$ | $COCH_3$ | $CH_3$ | $OCH_3$ | $CH_3$ | CH | |
| 2091 | $C_2H_5$ | $C_2H_5$ | $COCH_3$ | $CH_3$ | $OCH_3$ | $OCH_3$ | N | |
| 2092 | $C_2H_5$ | $C_2H_5$ | $COOCH_3$ | H | $OCH_3$ | $OCH_3$ | CH | 158–160 |
| 2093 | $C_2H_5$ | $C_2H_5$ | $COOCH_3$ | H | $OCH_3$ | $CH_3$ | CH | |
| 2094 | $C_2H_5$ | $C_2H_5$ | $COOCH_3$ | H | $CH_3$ | $CH_3$ | CH | |
| 2095 | $C_2H_5$ | $C_2H_5$ | $COOCH_3$ | H | Cl | $OCH_3$ | CH | |
| 2096 | $C_2H_5$ | $C_2H_5$ | $COOCH_3$ | H | $OCH_3$ | $CH_3$ | N | |
| 2097 | $C_2H_5$ | $C_2H_5$ | $COOCH_3$ | H | $OCH_3$ | $CF_3$ | N | |
| 2098 | $C_2H_5$ | $C_2H_5$ | $COOCH_3$ | H | $OCH_3$ | $OCH_3$ | N | |
| 2099 | $C_2H_5$ | $C_2H_5$ | $COOCH_3$ | $CH_3$ | $OCH_3$ | $OCH_3$ | CH | |
| 2100 | $C_2H_5$ | $C_2H_5$ | $COOCH_3$ | $CH_3$ | $OCH_3$ | $CH_3$ | N | |
| 2101 | $C_2H_5$ | $C_2H_5$ | $COOC_2H_5$ | H | $OCH_3$ | $OCH_3$ | CH | |
| 2102 | $C_2H_5$ | $C_2H_5$ | $COOC_2H_5$ | H | $OCH_3$ | $CH_3$ | CH | |
| 2103 | $C_2H_5$ | $C_2H_5$ | $COOC_2H_5$ | H | $CH_3$ | $CH_3$ | CH | |
| 2104 | $C_2H_5$ | $C_2H_5$ | $COOC_2H_5$ | H | Cl | $OCH_3$ | CH | |
| 2105 | $C_2H_5$ | $C_2H_5$ | $COOC_2H_5$ | H | $OCH_3$ | $CH_3$ | N | |
| 2106 | $C_2H_5$ | $C_2H_5$ | $COOC_2H_5$ | H | $OCH_3$ | $CF_3$ | N | |
| 2107 | $C_2H_5$ | $C_2H_5$ | $COOC_2H_5$ | H | $OCH_3$ | $OCH_3$ | N | |
| 2108 | $C_2H_5$ | $C_2H_5$ | $COOC_2H_5$ | $CH_3$ | $OCH_3$ | $OCH_3$ | CH | |
| 2109 | $C_2H_5$ | $C_2H_5$ | $COOC_2H_5$ | $CH_3$ | $OCH_3$ | $CH_3$ | N | |
| 2110 | $C_2H_5$ | $C_2H_5$ | $SO_2CH_3$ | H | $OCH_3$ | $OCH_3$ | CH | 98–101 |
| 2111 | $C_2H_5$ | $C_2H_5$ | $SO_2CH_3$ | H | $OCH_3$ | $CH_3$ | CH | |
| 2112 | $C_2H_5$ | $C_2H_5$ | $SO_2CH_3$ | H | $CH_3$ | $CH_3$ | CH | |
| 2113 | $C_2H_5$ | $C_2H_5$ | $SO_2CH_3$ | H | Cl | $OCH_3$ | CH | |
| 2114 | $C_2H_5$ | $C_2H_5$ | $SO_2CH_3$ | H | $OCH_3$ | $CH_3$ | N | |
| 2115 | $C_2H_5$ | $C_2H_5$ | $SO_2CH_3$ | H | $OCH_3$ | $CF_3$ | N | |
| 2116 | $C_2H_5$ | $C_2H_5$ | $SO_2CH_3$ | H | $OCH_3$ | $OCH_3$ | N | |
| 2117 | $C_2H_5$ | $C_2H_5$ | $SO_2CH_3$ | $CH_3$ | $OCH_3$ | $OCH_3$ | CH | |
| 2118 | $C_2H_5$ | $C_2H_5$ | $SO_2CH_3$ | $CH_3$ | $OCH_3$ | $CH_3$ | N | |
| 2119 | $C_2H_5$ | $C_2H_5$ | $SO_2C_2H_5$ | H | $OCH_3$ | $OCH_3$ | CH | |
| 2120 | $C_2H_5$ | $C_2H_5$ | $SO_2C_2H_5$ | H | $OCH_3$ | $CH_3$ | CH | |
| 2121 | $C_2H_5$ | $C_2H_5$ | $SO_2C_2H_5$ | H | $CH_3$ | $CH_3$ | CH | |
| 2122 | $C_2H_5$ | $C_2H_5$ | $SO_2C_2H_5$ | H | Cl | $OCH_3$ | CH | |
| 2123 | $C_2H_5$ | $C_2H_5$ | $SO_2C_2H_5$ | H | $OCH_3$ | $CH_3$ | N | |
| 2124 | $C_2H_5$ | $C_2H_5$ | $SO_2C_2H_5$ | H | $OCH_3$ | $CF_3$ | N | |
| 2125 | $C_2H_5$ | $C_2H_5$ | $SO_2C_2H_5$ | H | $OCH_3$ | $OCH_3$ | N | |
| 2126 | $C_2H_5$ | $C_2H_5$ | $SO_2C_2H_5$ | $CH_3$ | $OCH_3$ | $OCH_3$ | CH | |
| 2127 | $C_2H_5$ | $C_2H_5$ | $SO_2C_2H_5$ | $CH_3$ | $OCH_3$ | $CH_3$ | N | |
| 2128 | $C_2H_5$ | $C_2H_5$ | $COCF_3$ | H | $OCH_3$ | $OCH_3$ | CH | 143–146 |
| 2129 | $C_2H_5$ | $C_2H_5$ | $COCF_3$ | H | $OCH_3$ | $CH_3$ | CH | |
| 2130 | $C_2H_5$ | $C_2H_5$ | $COCF_3$ | H | $CH_3$ | $CH_3$ | CH | |
| 2131 | $C_2H_5$ | $C_2H_5$ | $COCF_3$ | H | Cl | $OCH_3$ | CH | |
| 2132 | $C_2H_5$ | $C_2H_5$ | $COCF_3$ | H | $OCH_3$ | $CH_3$ | N | |
| 2133 | $C_2H_5$ | $C_2H_5$ | $COCF_3$ | H | $OCH_3$ | $CF_3$ | N | |
| 2134 | $C_2H_5$ | $C_2H_5$ | $COCF_3$ | H | $OCH_3$ | $OCH_3$ | N | |
| 2135 | $C_2H_5$ | $C_2H_5$ | $COCF_3$ | $CH_3$ | $OCH_3$ | $OCH_3$ | CH | |
| 2136 | $C_2H_5$ | $C_2H_5$ | $COCF_3$ | $CH_3$ | $OCH_3$ | $CH_3$ | N | |
| 2137 | $nC_3H_7$ | H | CHO | H | $OCH_3$ | $OCH_3$ | CH | 148–154 |
| 2138 | $nC_3H_7$ | H | CHO | H | $OCH_3$ | $CH_3$ | N | |
| 2139 | $nC_3H_7$ | H | $COCH_3$ | H | $OCH_3$ | $OCH_3$ | CH | 106–110 |
| 2140 | $nC_3H_7$ | H | $COCH_3$ | H | $OCH_3$ | $CH_3$ | N | |
| 2141 | $nC_3H_7$ | H | $COC_2H_5$ | H | $OCH_3$ | $OCH_3$ | CH | |
| 2142 | $nC_3H_7$ | H | $COC_2H_5$ | H | $OCH_3$ | $CH_3$ | N | |
| 2143 | $nC_3H_7$ | H | $COCF_3$ | H | $OCH_3$ | $OCH_3$ | CH | 194–197 |
| 2144 | $nC_3H_7$ | H | $COCF_3$ | H | $OCH_3$ | $CH_3$ | N | |
| 2145 | $nC_3H_7$ | H | $COOCH_3$ | H | $OCH_3$ | $OCH_3$ | CH | 142–147 |
| 2146 | $nC_3H_7$ | H | $COOCH_3$ | H | $OCH_3$ | $CH_3$ | N | |
| 2147 | $nC_3H_7$ | H | $COOC_2H_5$ | H | $OCH_3$ | $OCH_3$ | CH | |
| 2148 | $nC_3H_7$ | H | $COOC_2H_5$ | H | $OCH_3$ | $CH_3$ | N | |
| 2149 | $nC_3H_7$ | H | $SO_2CH_3$ | H | $OCH_3$ | $OCH_3$ | CH | 199–205 |
| 2150 | $nC_3H_7$ | H | $SO_2CH_3$ | H | $OCH_3$ | $CH_3$ | N | |

TABLE 1-continued

Compound of the formula (1a)

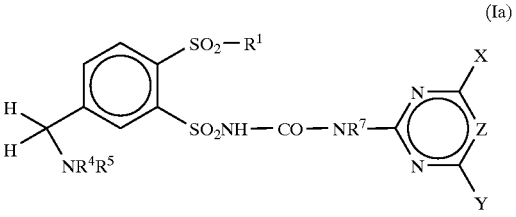

(Ia)

| No. | R$^1$ | R$^4$ | R$^5$ | R$^7$ | X | Y | Z | mp.(°C.) |
|---|---|---|---|---|---|---|---|---|
| 2151 | nC$_3$H$_7$ | H | SO$_2$C$_2$H$_5$ | H | OCH$_3$ | OCH$_3$ | CH | 128–133 |
| 2152 | nC$_3$H$_7$ | H | SO$_2$C$_2$H$_5$ | H | OCH$_3$ | CH$_3$ | N | |
| 2153 | nC$_3$H$_7$ | CH$_3$ | CHO | H | OCH$_3$ | OCH$_3$ | CH | 139–145 |
| 2154 | nC$_3$H$_7$ | CH$_3$ | CHO | H | OCH$_3$ | CH$_3$ | N | |
| 2155 | nC$_3$H$_7$ | CH$_3$ | COCH$_3$ | H | OCH$_3$ | OCH$_3$ | CH | 138–141 |
| 2156 | nC$_3$H$_7$ | CH$_3$ | COCH$_3$ | H | OCH$_3$ | CH$_3$ | N | |
| 2157 | nC$_3$H$_7$ | CH$_3$ | COC$_2$H$_5$ | H | OCH$_3$ | OCH$_3$ | CH | |
| 2158 | nC$_3$H$_7$ | CH$_3$ | COC$_2$H$_5$ | H | OCH$_3$ | CH$_3$ | N | |
| 2159 | nC$_3$H$_7$ | CH$_3$ | COCF$_3$ | H | OCH$_3$ | OCH$_3$ | CH | 172–175 |
| 2160 | nC$_3$H$_7$ | CH$_3$ | COCF$_3$ | H | OCH$_3$ | CH$_3$ | N | |
| 2161 | nC$_3$H$_7$ | CH$_3$ | COOCH$_3$ | H | OCH$_3$ | OCH$_3$ | CH | 182–185 |
| 2162 | nC$_3$H$_7$ | CH$_3$ | COOCH$_3$ | H | OCH$_3$ | CH$_3$ | N | |
| 2163 | nC$_3$H$_7$ | CH$_3$ | COOC$_2$H$_5$ | H | OCH$_3$ | OCH$_3$ | CH | |
| 2164 | nC$_3$H$_7$ | CH$_3$ | COOC$_2$H$_5$ | H | OCH$_3$ | CH$_3$ | N | |
| 2165 | nC$_3$H$_7$ | CH$_3$ | SO$_2$CH$_3$ | H | OCH$_3$ | OCH$_3$ | CH | 168–176 |
| 2166 | nC$_3$H$_7$ | CH$_3$ | SO$_2$CH$_3$ | H | OCH$_3$ | CH$_3$ | N | |
| 2167 | nC$_3$H$_7$ | CH$_3$ | SO$_2$C$_2$H$_5$ | H | OCH$_3$ | OCH$_3$ | CH | 129–132 |
| 2168 | nC$_3$H$_7$ | CH$_3$ | SO$_2$C$_2$H$_5$ | H | OCH$_3$ | CH$_3$ | N | |
| 2169 | nC$_3$H$_7$ | C$_2$H$_5$ | CHO | H | OCH$_3$ | OCH$_3$ | CH | 142–145 |
| 2170 | nC$_3$H$_7$ | C$_2$H$_5$ | CHO | H | OCH$_3$ | CH$_3$ | N | |
| 2171 | nC$_3$H$_7$ | C$_2$H$_5$ | COCH$_3$ | H | OCH$_3$ | OCH$_3$ | CH | |
| 2172 | nC$_3$H$_7$ | C$_2$H$_5$ | COCH$_3$ | H | OCH$_3$ | CH$_3$ | N | |
| 2173 | nC$_3$H$_7$ | C$_2$H$_5$ | COC$_2$H$_5$ | H | OCH$_3$ | OCH$_3$ | CH | |
| 2174 | nC$_3$H$_7$ | C$_2$H$_5$ | COC$_2$H$_5$ | H | OCH$_3$ | CH$_3$ | N | |
| 2175 | nC$_3$H$_7$ | C$_2$H$_5$ | COCF$_3$ | H | OCH$_3$ | OCH$_3$ | CH | |
| 2176 | nC$_3$H$_7$ | C$_2$H$_5$ | COCF$_3$ | H | OCH$_3$ | CH$_3$ | N | |
| 2177 | nC$_3$H$_7$ | C$_2$H$_5$ | COOCH$_3$ | H | OCH$_3$ | OCH$_3$ | CH | 173–177 |
| 2178 | nC$_3$H$_7$ | C$_2$H$_5$ | COOCH$_3$ | H | OCH$_3$ | CH$_3$ | N | |
| 2179 | nC$_3$H$_7$ | C$_2$H$_5$ | COOC$_2$H$_5$ | H | OCH$_3$ | OCH$_3$ | CH | |
| 2180 | nC$_3$H$_7$ | C$_2$H$_5$ | COOC$_2$H$_5$ | H | OCH$_3$ | CH$_3$ | N | |
| 2181 | nC$_3$H$_7$ | C$_2$H$_5$ | SO$_2$CH$_3$ | H | OCH$_3$ | OCH$_3$ | CH | 173–179 |
| 2182 | nC$_3$H$_7$ | C$_2$H$_5$ | SO$_2$CH$_3$ | H | OCH$_3$ | CH$_3$ | N | |
| 2183 | nC$_3$H$_7$ | C$_2$H$_5$ | SO$_2$C$_2$H$_5$ | H | OCH$_3$ | OCH$_3$ | CH | |
| 2184 | nC$_3$H$_7$ | C$_2$H$_5$ | SO$_2$C$_2$H$_5$ | H | OCH$_3$ | CH$_3$ | N | |
| 2185 | N(CH$_3$)$_2$ | H | CHO | H | OCH$_3$ | OCH$_3$ | CH | 143–144 |
| 2186 | N(CH$_3$)$_2$ | H | CHO | H | OCH$_3$ | CH$_3$ | N | |
| 2187 | N(CH$_3$)$_2$ | H | COCH$_3$ | H | OCH$_3$ | OCH$_3$ | CH | |
| 2188 | N(CH$_3$)$_2$ | H | COCH$_3$ | H | OCH$_3$ | CH$_3$ | N | |
| 2189 | N(CH$_3$)$_2$ | H | COC$_2$H$_5$ | H | OCH$_3$ | OCH$_3$ | CH | |
| 2190 | N(CH$_3$)$_2$ | H | COC$_2$H$_5$ | H | OCH$_3$ | CH$_3$ | N | |
| 2191 | N(CH$_3$)$_2$ | H | COCF$_3$ | H | OCH$_3$ | OCH$_3$ | CH | |
| 2192 | N(CH$_3$)$_2$ | H | COCF$_3$ | H | OCH$_3$ | CH$_3$ | N | |
| 2193 | N(CH$_3$)$_2$ | H | COOCH$_3$ | H | OCH$_3$ | OCH$_3$ | CH | |
| 2194 | N(CH$_3$)$_2$ | H | COOCH$_3$ | H | OCH$_3$ | CH$_3$ | N | |
| 2195 | N(CH$_3$)$_2$ | H | COOC$_2$H$_5$ | H | OCH$_3$ | OCH$_3$ | CH | |
| 2196 | N(CH$_3$)$_2$ | H | COOC$_2$H$_5$ | H | OCH$_3$ | CH$_3$ | N | |
| 2197 | N(CH$_3$)$_2$ | H | SO$_2$CH$_3$ | H | OCH$_3$ | OCH$_3$ | CH | |
| 2198 | N(CH$_3$)$_2$ | H | SO$_2$CH$_3$ | H | OCH$_3$ | CH$_3$ | N | |
| 2199 | N(CH$_3$)$_2$ | H | SO$_2$C$_2$H$_5$ | H | OCH$_3$ | OCH$_3$ | CH | |
| 2200 | N(CH$_3$)$_2$ | H | SO$_2$C$_2$H$_5$ | H | OCH$_3$ | CH$_3$ | N | |
| 2201 | N(CH$_3$)$_2$ | CH$_3$ | CHO | H | OCH$_3$ | OCH$_3$ | CH | 201–203 |
| 2202 | N(CH$_3$)$_2$ | CH$_3$ | CHO | H | OCH$_3$ | CH$_3$ | N | |
| 2203 | N(CH$_3$)$_2$ | CH$_3$ | COCH$_3$ | H | OCH$_3$ | OCH$_3$ | CH | 176–179 |
| 2204 | N(CH$_3$)$_2$ | CH$_3$ | COCH$_3$ | H | OCH$_3$ | CH$_3$ | N | |
| 2205 | N(CH$_3$)$_2$ | CH$_3$ | COC$_2$H$_5$ | H | OCH$_3$ | OCH$_3$ | CH | |
| 2206 | N(CH$_3$)$_2$ | CH$_3$ | COC$_2$H$_5$ | H | OCH$_3$ | CH$_3$ | N | |
| 2207 | N(CH$_3$)$_2$ | CH$_3$ | COCF$_3$ | H | OCH$_3$ | OCH$_3$ | CH | |
| 2208 | N(CH$_3$)$_2$ | CH$_3$ | COCF$_3$ | H | OCH$_3$ | CH$_3$ | N | |
| 2209 | N(CH$_3$)$_2$ | CH$_3$ | COOCH$_3$ | H | OCH$_3$ | OCH$_3$ | CH | 192–194 |
| 2210 | N(CH$_3$)$_2$ | CH$_3$ | COOCH$_3$ | H | OCH$_3$ | CH$_3$ | N | |
| 2211 | N(CH$_3$)$_2$ | CH$_3$ | COOC$_2$H$_5$ | H | OCH$_3$ | OCH$_3$ | CH | |
| 2212 | N(CH$_3$)$_2$ | CH$_3$ | COOC$_2$H$_5$ | H | OCH$_3$ | CH$_3$ | N | |
| 2213 | N(CH$_3$)$_2$ | CH$_3$ | SO$_2$CH$_3$ | H | OCH$_3$ | OCH$_3$ | CH | 144–146 |

TABLE 1-continued

Compound of the formula (Ia)

$$\text{(Ia)}$$

| No. | R¹ | R⁴ | R⁵ | R⁷ | X | Y | Z | mp.(°C.) |
|---|---|---|---|---|---|---|---|---|
| 2214 | N(CH₃)₂ | CH₃ | SO₂CH₃ | H | OCH₃ | CH₃ | N | |
| 2215 | N(CH₃)₂ | CH₃ | SO₂C₂H₅ | H | OCH₃ | OCH₃ | CH | |
| 2216 | N(CH₃)₂ | CH₃ | SO₂C₂H₅ | H | OCH₃ | CH₃ | N | |
| 2217 | N(CH₃)₂ | C₂H₅ | CHO | H | OCH₃ | OCH₃ | CH | 143–146 |
| 2218 | N(CH₃)₂ | C₂H₅ | CHO | H | OCH₃ | CH₃ | N | |
| 2219 | N(CH₃)₂ | C₂H₅ | COCH₃ | H | OCH₃ | OCH₃ | CH | 116–118 |
| 2220 | N(CH₃)₂ | C₂H₅ | COCH₃ | H | OCH₃ | CH₃ | N | |
| 2221 | N(CH₃)₂ | C₂H₅ | COC₂H₅ | H | OCH₃ | OCH₃ | CH | |
| 2222 | N(CH₃)₂ | C₂H₅ | COC₂H₅ | H | OCH₃ | CH₃ | N | |
| 2223 | N(CH₃)₂ | C₂H₅ | COCF₃ | H | OCH₃ | OCH₃ | CH | |
| 2224 | N(CH₃)₂ | C₂H₅ | COCF₃ | H | OCH₃ | CH₃ | N | |
| 2225 | N(CH₃)₂ | C₂H₅ | COOCH₃ | H | OCH₃ | OCH₃ | CH | 201–203 |
| 2226 | N(CH₃)₂ | C₂H₅ | COOCH₃ | H | OCH₃ | CH₃ | N | |
| 2227 | N(CH₃)₂ | C₂H₅ | COOC₂H₅ | H | OCH₃ | OCH₃ | CH | |
| 2228 | N(CH₃)₂ | C₂H₅ | COOC₂H₅ | H | OCH₃ | CH₃ | N | |
| 2229 | N(CH₃)₂ | C₂H₅ | SO₂CH₃ | H | OCH₃ | OCH₃ | CH | 125–128 |
| 2230 | N(CH₃)₂ | C₂H₅ | SO₂CH₃ | H | OCH₃ | CH₃ | N | |
| 2231 | N(CH₃)₂ | C₂H₅ | SO₂C₂H₅ | H | OCH₃ | OCH₃ | CH | |
| 2232 | N(CH₃)₂ | C₂H₅ | SO₂C₂H₅ | H | OCH₃ | CH₃ | N | |

TABLE 2

Compounds of the formula (Ib)

$$\text{(Ib)}$$

| No. | R¹ | R⁴ | R⁵ | X | Y | Z | mp.(° C.) |
|---|---|---|---|---|---|---|---|
| 2-1 | CH₃ | H | CHO | OCH₃ | OCH₃ | CH | |
| 2-2 | CH₃ | H | CHO | OCH₃ | CH₃ | N | |
| 2-3 | CH₃ | H | COOCH₃ | OCH₃ | OCH₃ | CH | |
| 2-4 | CH₃ | H | COOCH₃ | OCH₃ | CH₃ | N | |
| 2-5 | CH₃ | H | SO₂CH₃ | OCH₃ | OCH₃ | CH | |
| 2-6 | CH₃ | H | SO₂CH₃ | OCH₃ | CH₃ | N | |
| 2-7 | CH₃ | CH₃ | CHO | OCH₃ | OCH₃ | CH | |
| 2-8 | CH₃ | CH₃ | CHO | OCH₃ | CH₃ | N | |
| 2-9 | CH₃ | CH₃ | COOCH₃ | OCH₃ | OCH₃ | CH | |
| 2-10 | CH₃ | CH₃ | COOCH₃ | OCH₃ | CH₃ | N | |
| 2-11 | CH₃ | CH₃ | SO₂CH₃ | OCH₃ | OCH₃ | CH | |
| 2-12 | CH₃ | CH₃ | SO₂CH₃ | OCH₃ | CH₃ | N | |
| 2-13 | C₂H₅ | H | CHO | OCH₃ | OCH₃ | CH | |
| 2-14 | C₂H₅ | H | CHO | OCH₃ | CH₃ | N | |
| 2-15 | C₂H₅ | H | COOCH₃ | OCH₃ | OCH₃ | CH | |
| 2-16 | C₂H₅ | H | COOCH₃ | OCH₃ | CH₃ | N | |
| 2-17 | C₂H₅ | H | SO₂CH₃ | OCH₃ | OCH₃ | CH | |
| 2-18 | C₂H₅ | H | SO₂CH₃ | OCH₃ | CH₃ | N | |
| 2-19 | C₂H₅ | CH₃ | CHO | OCH₃ | OCH₃ | CH | |
| 2-20 | C₂H₅ | CH₃ | CHO | OCH₃ | CH₃ | N | |
| 2-21 | C₂H₅ | CH₃ | COOCH₃ | OCH₃ | OCH₃ | CH | |
| 2-22 | C₂H₅ | CH₃ | COOCH₃ | OCH₃ | CH₃ | N | |
| 2-23 | C₂H₅ | CH₃ | SO₂CH₃ | OCH₃ | OCH₃ | CH | |
| 2-24 | C₂H₅ | C₂H₅ | SO₂CH₃ | OCH₃ | CH₃ | N | |
| 2-25 | C₂H₅ | C₂H₅ | CHO | OCH₃ | CH₃ | N | |
| 2-26 | C₂H₅ | C₂H₅ | CHO | OCH₃ | CH₃ | N | |
| 2-27 | C₂H₅ | C₂H₅ | COOCH₃ | OCH₃ | OCH₃ | CH | |
| 2-28 | C₂H₅ | C₂H₅ | COOCH₃ | OCH₃ | CH₃ | N | |
| 2-29 | C₂H₅ | C₂H₅ | SO₂CH₃ | OCH₃ | OCH₃ | CH | |
| 2-30 | C₂H₅ | C₂H₅ | SO₂CH₃ | OCH₃ | CH₃ | N | |

TABLE 3

Compounds of the formula (Ic)

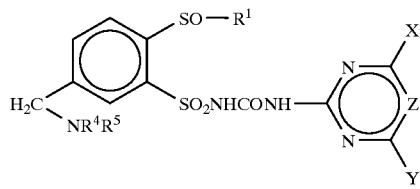

| No. | R¹ | R⁴ | R⁵ | X | Y | Z | mp.(° C.) |
|---|---|---|---|---|---|---|---|
| 3-1 | $CH_3$ | H | CHO | $OCH_3$ | $OCH_3$ | CH | |
| 3-2 | $CH_3$ | H | CHO | $OCH_3$ | $CH_3$ | N | |
| 3-3 | $CH_3$ | H | $COOCH_3$ | $OCH_3$ | $OCH_3$ | CH | |
| 3-4 | $CH_3$ | H | $COOCH_3$ | $OCH_3$ | $CH_3$ | N | |
| 3-5 | $CH_3$ | H | $SO_2CH_3$ | $OCH_3$ | $OCH_3$ | CH | |
| 3-6 | $CH_3$ | H | $SO_2CH_3$ | $OCH_3$ | $CH_3$ | N | |
| 3-7 | $CH_3$ | $CH_3$ | CHO | $OCH_3$ | $OCH_3$ | CH | |
| 3-8 | $CH_3$ | $CH_3$ | CHO | $OCH_3$ | $CH_3$ | N | |
| 3-9 | $CH_3$ | $CH_3$ | $COOCH_3$ | $OCH_3$ | $OCH_3$ | CH | |
| 3-10 | $CH_3$ | $CH_3$ | $COOCH_3$ | $OCH_3$ | $CH_3$ | N | |
| 3-11 | $CH_3$ | $CH_3$ | $SO_2CH_3$ | $OCH_3$ | $OCH_3$ | CH | |
| 3-12 | $CH_3$ | $CH_3$ | $SO_2CH_3$ | $OCH_3$ | $CH_3$ | N | |
| 3-13 | $C_2H_5$ | H | CHO | $OCH_3$ | $OCH_3$ | CH | 118–120 |
| 3-14 | $C_2H_5$ | H | CHO | $OCH_3$ | $CH_3$ | N | |
| 3-15 | $C_2H_5$ | H | $COOCH_3$ | $OCH_3$ | $OCH_3$ | CH | |
| 3-16 | $C_2H_5$ | H | $COOCH_3$ | $OCH_3$ | $CH_3$ | N | |
| 3-17 | $C_2H_5$ | H | $SO_2CH_3$ | $OCH_3$ | $OCH_3$ | CH | |

TABLE 3-continued

Compounds of the formula (Ic)

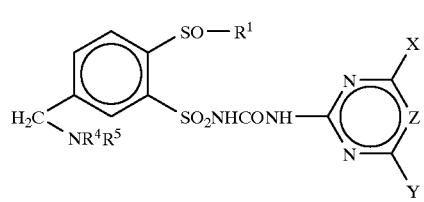

| No. | R¹ | R⁴ | R⁵ | X | Y | Z | mp.(° C.) |
|---|---|---|---|---|---|---|---|
| 3-18 | $C_2H_5$ | H | $SO_2CH_3$ | $OCH_3$ | $CH_3$ | N | |
| 3-19 | $C_2H_5$ | $CH_3$ | CHO | $OCH_3$ | $OCH_3$ | CH | 138–140 |
| 3-20 | $C_2H_5$ | $CH_3$ | CHO | $OCH_3$ | $CH_3$ | N | |
| 3-21 | $C_2H_5$ | $CH_3$ | $COOCH_3$ | $OCH_3$ | $OCH_3$ | CH | 116–117 |
| 3-22 | $C_2H_5$ | $CH_3$ | $COOCH_3$ | $OCH_3$ | $CH_3$ | N | |
| 3-23 | $C_2H_5$ | $CH_3$ | $SO_2CH_3$ | $OCH_3$ | $OCH_3$ | CH | 179–180 |
| 3-24 | $C_2H_5$ | $C_2H_5$ | $SO_2CH_3$ | $OCH_3$ | $CH_3$ | N | |
| 3-25 | $C_2H_5$ | $C_2H_5$ | CHO | $OCH_3$ | $OCH_3$ | CH | 173–174 |
| 3-26 | $C_2H_5$ | $C_2H_5$ | CHO | $OCH_3$ | $CH_3$ | N | |
| 3-27 | $C_2H_5$ | $C_2H_5$ | $COOCH_3$ | $OCH_3$ | $OCH_3$ | CH | 130–131 |
| 3-28 | $C_2H_5$ | $C_2H_5$ | $COOCH_3$ | $OCH_3$ | $CH_3$ | N | |
| 3-29 | $C_2H_5$ | $C_2H_5$ | $SO_2CH_3$ | $OCH_3$ | $OCH_3$ | CH | 130–131 |
| 3-30 | $C_2H_5$ | $C_2H_5$ | $SO_2CH_3$ | $OCH_3$ | $CH_3$ | N | |

TABLE 4

Na⁺ salts
Compounds of the formula (Id)

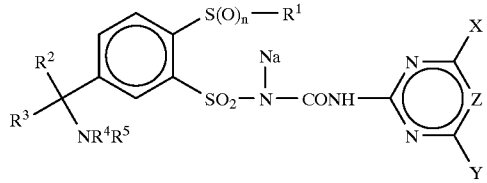

| No. | n | R¹ | R⁴ | R⁵ | X | Y | Z | mp.(° C.) |
|---|---|---|---|---|---|---|---|---|
| 4-1 | 2 | $CH_3$ | H | CHO | $OCH_3$ | $OCH_3$ | CH | 204–209 |
| 4-2 | 2 | $CH_3$ | H | $COCH_3$ | $OCH_3$ | $OCH_3$ | CH | 190–193 |
| 4-3 | 2 | $CH_3$ | H | $COC_2H_5$ | $OCH_3$ | $OCH_3$ | CH | 125–135 |
| 4-4 | 2 | $CH_3$ | H | $CO-i-C_3H_7$ | $OCH_3$ | $OCH_3$ | CH | 198–201 |
| 4-5 | 2 | $CH_3$ | H | $COCCl_3$ | $OCH_3$ | $OCH_3$ | CH | 256–260 |
| 4-6 | 2 | $CH_3$ | H | $COOC_2H_5$ | $OCH_3$ | $OCH_3$ | CH | 189–193 |
| 4-7 | 2 | $CH_3$ | H | $SO_2CH_3$ | $OCH_3$ | $OCH_3$ | CH | 188–192 |
| 4-8 | 2 | $CH_3$ | H | $SO_2C_2H_5$ | $OCH_3$ | $OCH_3$ | CH | 194–198 |
| 4-9 | 2 | $CH_3$ | H | CHO | $OCH_3$ | $OCH_3$ | CH | 178–182 |
| 4-10 | 2 | $CH_3$ | $CH_3$ | $COCH_3$ | $OCH_3$ | $OCH_3$ | CH | 181–190 |
| 4-11 | 2 | $CH_3$ | $CH_3$ | $COC_2H_5$ | $OCH_3$ | $OCH_3$ | CH | 187–195 |
| 4-12 | 2 | $CH_3$ | $CH_3$ | $COCF_3$ | $OCH_3$ | $OCH_3$ | CH | 189–198 |
| 4-13 | 2 | $CH_3$ | $CH_3$ | $COCCl_3$ | $OCH_3$ | $OCH_3$ | CH | 181–188 |
| 4-14 | 2 | $CH_3$ | $CH_3$ | $CO-i-C_3H_7$ | $OCH_3$ | $OCH_3$ | CH | 175–180 |
| 4-15 | 2 | $CH_3$ | $CH_3$ | $COOCH_3$ | $OCH_3$ | $OCH_3$ | CH | 142–150 |
| 4-16 | 2 | $CH_3$ | $CH_3$ | $COOC_2H_5$ | $OCH_3$ | $OCH_3$ | CH | 138–145 |
| 4-17 | 2 | $CH_3$ | $CH_3$ | $SO_2CH_3$ | $OCH_3$ | $OCH_3$ | CH | 191–194 |
| 4-18 | 2 | $CH_3$ | $CH_3$ | $SO_2C_2H_5$ | $OCH_3$ | $OCH_3$ | CH | 187–191 |
| 4-19 | 2 | $C_2H_5$ | H | CHO | $OCH_3$ | $OCH_3$ | CH | 191–198 |
| 4-20 | 2 | $C_2H_5$ | H | $COCH_3$ | $OCH_3$ | $OCH_3$ | CH | 172–180 |
| 4-21 | 2 | $C_2H_5$ | H | $COOCH_3$ | $OCH_3$ | $OCH_3$ | CH | 184–189 |
| 4-22 | 2 | $C_2H_5$ | H | $SO_2CH_3$ | $OCH_3$ | $OCH_3$ | CH | 172–180 |

TABLE 4-continued

Na⁺ salts
Compounds of the formula (Id)

$$\text{(Id)}$$

Structure: benzene ring with $S(O)_n-R^1$ at one position, $R^2$ and $R^3$ with $NR^4R^5$ group, and $SO_2-N(Na)-CONH-$ pyrimidine (with X, Y, Z substituents).

| No. | n | R¹ | R⁴ | R⁵ | X | Y | Z | mp.(° C.) |
|---|---|---|---|---|---|---|---|---|
| 4-23 | 2 | C₂H₅ | CH₃ | CHO | OCH₃ | OCH₃ | CH | 182–185 |
| 4-24 | 2 | C₂H₅ | CH₃ | COCH₃ | OCH₃ | OCH₃ | CH | 184–187 |
| 4-25 | 2 | C₂H₅ | CH₃ | SO₂CH₃ | OCH₃ | OCH₃ | CH | 228–229 |
| 4-26 | 2 | C₂H₅ | C₂H₅ | CHO | OCH₃ | OCH₃ | CH | 184–189 |
| 4-27 | 2 | C₂H₅ | C₂H₅ | COCH₃ | OCH₃ | OCH₃ | CH | 173–179 |
| 4-28 | 2 | C₂H₅ | C₂H₅ | COCF₃ | OCH₃ | OCH₃ | CH | 182–186 |
| 4-29 | 2 | C₂H₅ | C₂H₅ | COOCH₃ | OCH₃ | OCH₃ | CH | 155–162 |
| 4-30 | 2 | C₂H₅ | C₂H₅ | SO₂CH₃ | OCH₃ | OCH₃ | CH | 225–227 |
| 4-31 | 2 | nC₃H₇ | H | CHO | OCH₃ | OCH₃ | CH | 177–183 |
| 4-32 | 2 | nC₃H₇ | H | COCH₃ | OCH₃ | OCH₃ | CH | 178–182 |
| 4-33 | 2 | nC₃H₇ | H | COCF₃ | OCH₃ | OCH₃ | CH | 240–246 |
| 4-34 | 2 | nC₃H₇ | H | COOCH₃ | OCH₃ | OCH₃ | CH | 192–200 |
| 4-35 | 2 | nC₃H₇ | H | SO₂Cl₃ | OCH₃ | OCH₃ | CH | 247–250 |
| 4-36 | 2 | nC₃H₇ | H | SO₂C₂H₅ | OCH₃ | OCH₃ | CH | 183–187 |
| 4-37 | 2 | nC₃H₇ | CH₃ | CHO | OCH₃ | OCH₃ | CH | 194–202 |
| 4-38 | 2 | nC₃H₇ | CH₃ | COCH₃ | OCH₃ | OCH₃ | CH | 175–178 |
| 4-39 | 2 | nC₃H₇ | CH₃ | COCF₃ | OCH₃ | OCH₃ | CH | 155–161 |
| 4-40 | 2 | nC₃H₇ | CH₃ | COOCH₃ | OCH₃ | OCH₃ | CH | 213–216 |
| 4-41 | 2 | nC₃H₇ | CH₃ | SO₂CH₃ | OCH₃ | OCH₃ | CH | 213–216 |
| 4-42 | 2 | nC₃H₇ | CH₃ | SO₂C₂H₅ | OCH₃ | OCH₃ | CH | 168–174 |
| 4-43 | 2 | nC₃H₇ | C₂H₅ | CHO | OCH₃ | OCH₃ | CH | 170–176 |
| 4-44 | 2 | nC₃H₇ | C₂H₅ | COOCH₃ | OCH₃ | OCH₃ | CH | 150–155 |
| 4-45 | 2 | nC₃H₇ | C₂H₅ | SO₂CH₃ | OCH₃ | OCH₃ | CH | 167–173 |
| 4-46 | 2 | N(CH₃)₂ | H | CHO | OCH₃ | OCH₃ | CH | 188–192 |
| 4-47 | 2 | N(CH₃)₂ | H | SO₂CH₃ | OCH₃ | OCH₃ | CH | 192–197 |
| 4-48 | 2 | N(CH₃)₂ | CH₃ | CHO | OCH₃ | OCH₃ | CH | 180–184 |
| 4-49 | 2 | N(CH₃)₂ | CH₃ | COCH₃ | OCH₃ | OCH₃ | CH | 140–145 |
| 4-50 | 2 | N(CH₃)₂ | CH₃ | COOCH₃ | OCH₃ | OCH₃ | CH | 116 |
| 4-51 | 2 | N(CH₃)₂ | CH₃ | SO₂CH₃ | OCH₃ | OCH₃ | CH | 172–180 |
| 4-52 | 2 | N(CH₃)₂ | C₂H₅ | CHO | OCH₃ | OCH₃ | CH | 167–171 |
| 4-53 | 2 | N(CH₃)₂ | C₂H₅ | COCH₃ | OCH₃ | OCH₃ | CH | 128–133 |
| 4-54 | 2 | N(CH₃)₂ | C₂H₅ | COOCH₃ | OCH₃ | OCH₃ | CH | 163–168 |
| 4-55 | 2 | N(CH₃)₂ | C₂H₅ | SO₂CH₃ | OCH₃ | OCH₃ | CH | 178–182 |
| 4-56 | 1 | C₂H₅ | H | CHO | OCH₃ | OCH₃ | CH | 197–199 |
| 4-57 | 1 | C₂H₅ | CH₃ | CHO | OCH₃ | OCH₃ | CH | 112–115 |
| 4-58 | 1 | C₂H₅ | CH₃ | COOCH₃ | OCH₃ | OCH₃ | CH | 160–164 |
| 4-59 | 1 | C₂H₅ | CH₃ | SO₂CH₃ | OCH₃ | OCH₃ | CH | 180–183 |
| 4-60 | 1 | C₂H₅ | C₂H₅ | CHO | OCH₃ | OCH₃ | CH | 166–172 |
| 4-61 | 1 | C₂H₅ | C₂H₅ | SO₂CH₃ | OCH₃ | OCH₃ | CH | 221–222 |

B. Formulation examples a) A dust is obtained by mixing 10 parts by weight of a compound of the formula (I) and 90 parts by weight of talc as inert substance and comminuting the mixture in a hammer mill.

b) A wettable power which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A dispersion concentrate which is readily dispersible in water is obtained by mixing 20 parts by weight of a compound of the formula (I) with 6 parts by weight of akylphenyl polyglycol ether (®Triton X207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Granules which are dispersible in water are obtained by mixing 75 parts by weight of a compound of the formula (I),
10 " of calcium lignosulfonate,
5 " of sodium lauryl sulfate,
3 " of polyvinyl alcohol and
7 " of kaolin, grinding the mixture on a pinned-disk mill and granulating the powder in a fluidized bed by spraying on water as granulation liquid.

f) Water-dispersible granules are also obtained by homogenizing, on a colloid 25 parts by weight of a compound of the formula (I),
5 " of sodium 2,2'-dinaphthylmethane,6,6'-disulfonate,
2 " of sodium oleoylmethyltaurate,
1 part by weight of polyvinyl alcohol,
17 parts by weight of calcium carbonate and
50 " of water,
precomminuting the mixture, subsequently grinding it on a bead mill and atomizing and drying the resulting suspension in a spray tower by means of a single-substance nozzle.

C. Biological examples

1. Pre-emergence effect on weeds

Seeds or rhizome pieces of monocotyledonous and dicotyledonous weed plants are placed in sandy loam soil in plastic pots and covered with soil. The compounds of the formula (I) or salts thereof according to the invention which have been formulated in the form of wettable powders or emulsion concentrates are then applied to the surface of the soil cover in the form of aqueous suspensions or emulsions at an application rate of 600 to 800 l of water/ha (converted), in various dosages.

After the treatment, the pots are placed in a greenhouse and kept under good growth conditions for the weeds. After the test plants have emerged after a period of 3 to 4 weeks, the damage to the plants or the negative effect on the emergence i5 scored visually by comparison with untreated controls. As shown by the test results, the compounds according to the invention have a good herbicidal pre-emergence activity against a broad spectrum of grass weeds and broad-leaved weeds. For example, the compounds of Examples Nos. 1, 18, 35, 69, 86, 103, 120, 138, 155, 225, 531, 548, 565, 599, 616, 633, 650, 667, 684, 753, 1068, 1085, 1170, 1202, 1591, 1608, 1676, 1727, 2074, 2068, 2092, 2110, 2128, 2137, 2139,2144, 2145, 2149, 2151, 2153, 2155, 2159, 2161, 2165, 2167, 2169, 2177, 2181, 2185, 2201, 2203, 2209, 2213, 2217, 2219, 2225, 2229, 3–13, 3–19, 3–21, 3–23, 3–25, 3–27, 3–29 (see Section A) and their sodium salts show a very good herbicidal activity in the test against harmful plants such as *Sinapis alba, Stellaria media, Chrysanthemum segetum,* and *Lolium multiflorum* when applied pre-emergence at a rate of application of 0.3 kg to 0.005 kg of active ingredient per hectare.

2. Post-emergence effect on weeds

Seeds or rhizome pieces of monocotyledonous and diotyledonous weeds are placed in sandy loam soil in plastic pots, covered with soil and grown in a greenhouse under good growth conditions. Three weeks after sowing, the test plants are treated in the three-leaf stage. The compounds of the formula (I) or salts thereof according to the invention which have been formulated as wettable powders or as emulsion concentrates are sprayed in various dosages onto the green parts of the plants at an application rate of 600 to 800 l of water/ha (converted). After the test plants have remained in the greenhouse for about 3 to 4 weeks under ideal growth conditions, the effect of the preparations is scored visually by comparison with untreated controls. The agents according to the invention also have a good herbicidal post-emergence activity against a broad range of economically important grass weeds and broad-leaved weeds. For example, Examples Nos. 1, 18, 35, 69, 86, 103, 120, 138, 155, 225, 531, 548, 565, 599, 616, 633, 650, 667, 684, 753, 1068, 1085, 1170, 1202, 1591, 1608, 1676, 1727, 2074, 2068, 2092, 2110, 2128, 2137, 2139, 2144, 2145, 2149, 2151, 2153, 2155, 2159, 2161, 2165, 2167, 2169, 2177, 2181, 2185, 2201, 2203, 2209, 2213, 2217, 2219, 2225, 2229, 3–13, 3–19, 3–21, 3–23, 3–25, 3–27, 3–29 (see Section A) and their sodium salts show a very good herbicidal activity in the test against harmful plants such as *Sinapis alba, Stellaria media, Chrysanthemum segetum,* and *Lolium murlifflorum* when applied post-emergence at an application rate of 0.3 kg to 0.005 kg of active ingredient per hectare.

3. Tolerance by crop plants

In further greenhouse experiments, seeds of a substantial number of crop plants and weeds were placed in sandy loam substrate and covered with soil.

Some of the pots were treated immediately as described in Section 1, and the remaining pots were placed in a greenhouse until the plants had developed two to three true leaves and then sprayed with various dosages of the substances of the formula (I) or salts thereof according to the invention as described in Section 2.

Visual scoring four to five weeks after application and after the plants had remained in the greenhouse revealed that the compounds according to the invention did not inflict any damage to dicotyledonous crops such as soy beans, cotton, oil seed rape, sugar beet and potatoes when used pre- and post-emergence, even when high dosages of active substance were used. Moreover, some substances also left Gramineae crops such as barley, wheat, rye, Sorghum species, maize or rice unharmed. The compounds of the formula (I) or their salts therefore have a high selectivity when used for controlling undesirable vegetation in agricultural crops.

We claim:

1. A compound of the formula (I) or a salt thereof

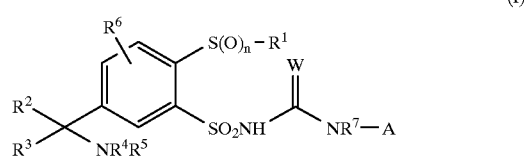

(I)

where $R^1$ is $NR^8R^9$ or an unsubstituted or substituted hydrocarbon radical, n is 0, 1 or 2, excluding n=0 or 1 if $R^1=NR^8R^9$, $R^2$ and $R^3$ are each independently of the other H or (1–4)alkyl, $R^4$ is H, OH, formyl, or a radical of the formula R, R—O—, R—CO— or R—SO$_2$—, R being an unsubstituted or substituted hydrocarbon radical, $R^5$ is an acyl radical or $NR^4R^5$ together are an unsubstituted or substituted heterocyclic radical, W is an oxygen or sulfur atom, $R^6$ is H, (1–4)alkyl, (1–4)alkoxy, (1–4)alkylthio, [(1–4)alkyl]-carbonyl, or [(1–4)alkoxy]carbonyl, each of the last radicals being unsubstituted or substituted by one or more halogen atoms, or halogen, NO$_2$, CN or mono- or disubstituted amino, $R^7$ is H or (1–4)alkyl, $R^8$ and $R^9$ are each independently of the other H, (1–4)alkyl, (1–4)alkoxy, [(1–4)alkyl]carbonyl or (1–4)alkylsulfonyl, A is a radical of the formula

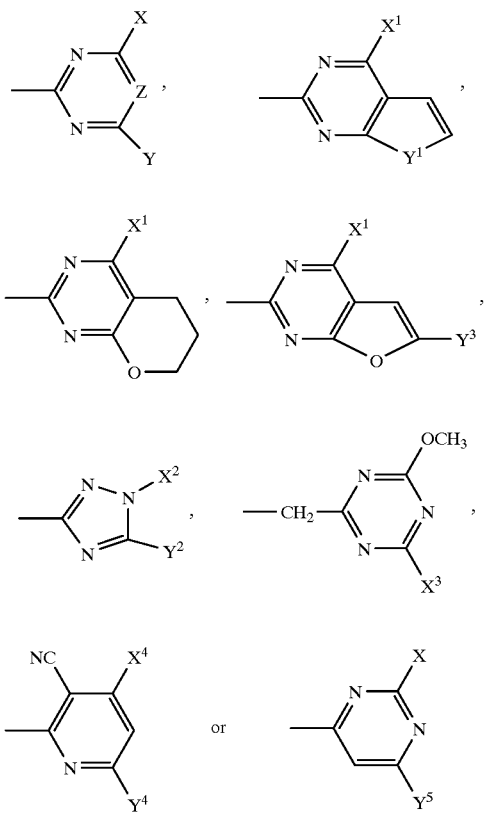

one of the radicals X and Y being hydrogen, (1–3)alkyl or (1–3)alkoxy, the last two radicals being unsubstituted or mono- or polysubstituted by halogen or monosubstituted by (1–3)alkoxy, and the other of the radicals X and Y being hydrogen, halogen, (1–3)alkyl, (1–3)alkoxy or (1–3)alkyithio, the last three alkyl-containing radicals being unsubstituted or mono- or polysubstituted by halogen or mono- or disubstituted by (1–3)alkoxy or (1–3)alkylthio, or a radical of the formula $NR^aR^b$, where $R^a$ and $R^b$, independently of each other, are H, (1–3)alkyl or (1–3)alkenyl, or (3–6)cycloalkyl, (2–4)alkenyl, (2–4)alkynyl, (3–4)-alkenyloxy or (3–4)alkynyloxy, Z is CH or N, $X^1$ is $CH_3$, $OCH_3$, $OC_2H_5$ or $OCHF_2$, $Y^1$ is —O— or —$CH_2$—, $X^2$ is $CH_3$, $C_2H_5$ or $CH_2CF_3$, $Y^2$ is $OCH_3$, $OC_2H_5$, $SCH_3$, $SCH_2CH_3$, $CH_3$ or $C_2H_5$, $X^3$ is $CH_3$ or $OCH_3$, $Y^3$ is H or $CH_3$, $X^4$ is $CH_3$, $OCH_3$, $OC_2H_5$, $CH_2OCH_3$ or Cl, $Y^4$ is $CH_3$, $OCH_3$, $OC_2H_5$ or Cl and $Y^5$ is $CH_3$, $C_2H_5$, $OCH_3$ or Cl.

2. A compound or a salt thereof as claimed in claim 1, wherein $R^1$ is $NR^8R^9$, (1–6)alkyl, (2–6)alkenyl, (2–6)alkynyl, (3–6)cycloalkyl, (3–6)cycloalkenyl or phenyl, each of the last 6 radicals being unsubstituted or substituted by one or more radicals from the group consisting of halogen, CN, (1–4)alkoxy, (1–4)haloalkoxy, (1–4)alkoxy(1–4)alkoxy, (1–4)alkylthio, (1–4)alkylsulfinyl, (1–4)-alkylsulfony, formyl, [(1–4)alkyl]-carbonyl, [(1–4)alkoxy]carbonyl, [(1–4)alkyl]carbonyloxy and in the case of cyclic radicals also (1–4)alkyl, (1–4) haloalkyl and (1–4)alkoxy-(1–4)alkyl, n is 0, 1 or 2, excluding n=0 or 1 if $R^1=NR^8R^9$, $R^2$ and $R^3$ are each independently of the other H or (1–4)alkyl, $R^4$ is H, OH, formyl, (1–6)alkyl, (2–6)alkenyl, (2–6) alkynyl, (1–6)alkoxy, (2–5)alkenyloxy, (2–5) alkynyloxy, [(1–6)alkyl]-carbonyl, (1–6)alkylsulfonyl, [(2–6)alkenyl]carbonyl, (2–6)alkenylsulfonyl, [(2–6) alkynyl]carbonyl, (2–6)-alkynyl-sulfonyl, (3–6) cycloalkyl, [(3–6)cycloalkenyl, [(3–6)cycloalkyl]-carbonyl, (3–6)cycloalkylsulfonyl, [(3–6)cycloalkenyl] carbonyl or (3–6)cycloalkenylsulfonyl, each of the last 18 radicals being unsubstituted or substituted by one or more radicals from the group consisting of halogen, (1–4)alkoxy, (1–4)alkylthio, (1–4)alkylsulfinyl, (1–4) alkylsulfonyl, [(1–4)alkoxy]carbonyl, [(1–4)alkyl] carbonyl, [(1–4)alkyl]carbonyloxy and CN and in the case of cyclic radicals also (1–4)alkyl and (1–4) haloalkyl, or phenylcarbonyl or phenylsulfonyl, the phenyl ring in the last two radicals being unsubstituted or substituted by one or more radicals from the group consisting of halogen, CN, $NO_2$, (1–4)alkyl, (1–4) haloalkyl, (1–4)alkoxy and (1–4)haloalkoxy, and $R^5$ is CHO, [(1–6)alkyl]carbonyl, [(2–6)alkenyl]carbonyl, [(2–6)alkynyl]carbonyl, (1–6)alkylsulfonyl, (2–6) alkenylsulfonyl, (2–6)alkynylsulfonyl, ](3–6) cycloalkyl]carbonyl, [(3–6)cycloalkenylsulfonyl, each of the last 10 radicals being unsubstituted or substituted by one or more radicals from the group consisting of halogen, (1–4)alkyl]-carbonyl, [(1–4)alkoxy]carbonyl, [(1–4)alkyl]carbonyloxy and CN and in the case of cyclic radicals also (1–4)alkyl and (1–4)haloalkyl, or phenylcarbonyl or phenylsulfonyl, each of the last two radicals being unsubstituted in the phenyl ring or substituted by one or more radicals from the group consisting of halogen, CN, $NO_2$, (1–4)alkyl, (1–4) haloalkyl, (1–4)alkoxy and (1–4)haloalkoxy, or mono- or di-[(1–4)alkyl]aminosulfonyl which is unsubstituted in the alkyl moiety or substituted by one or more radicals from the group consisting of halogen, (1–4) alkoxy, (1–4)alkylthio, (1–4)alkylsulfinyl, [(1–4) alkyl]-carbonyl, [(1–4)alkyl]carbonyloxy, [(1–4) alkoxy]carbonyl and CN or a group of the formula COCOR' where R'=H, OH, (1–4)alkoxy or (1–4)alkyl, or a group of the formula 1290

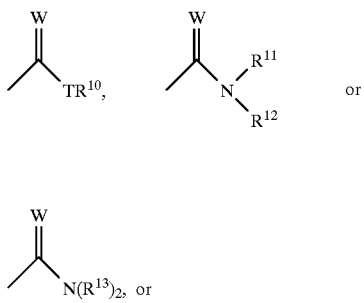

$R^4$ and $R^5$ together are a chain of the formula (—$CH_2$)$_{m1}B^1$— or —$B^1$—($CH_2$)$_{m2}B^2$ where individual groups $CH_2$ may be replaced by oxygen atoms and where the chain is unsubstituted or substituted by one or more (1–3)alkyl radicals or halogen and m1=3, 4 or 5 or m2=2, 3 or 4, and W is O or S, B$^1$ and B$^2$ are each independently of the other SO$_2$ or CO, T is O or S, R$^6$ is H, (1–4)alkyl, (1–4)alkoxy, (1–4)alkylthio, [(1–4)alkyl]-carbonyl or [(1–4)alkoxy]carbonyl, each of the last 5 radicals being unsubstituted or substituted in the alkyl moiety by one or more halogen atoms, or halogen, NO$_2$, CN or mono- or di-[(1–4)alkyl]amino, R$^7$ is H or (1–4)alkyl, R$^8$ is (1–4)alkyl, (1–4)alkoxy, (3–6)cycloalkyl or (3–6)cycloalkenyl, R$^9$ is H or (1–4)alkyl, R$^{10}$ is (1–4)alkyl, (3–4)alkenyl or (3–4)alkynyl, each of the last three radicals being unsubstituted or substituted by one or more radicals from the group consisting of halogen, (1–4)alkoxy, (1–4)alkylthio, [(1–4)alkyl]carbonyl and [(1–4)alkoxy]carbonyl, R$^{11}$ and R$^{12}$ are each independently of the other H, (1–4)alkyl, (3–4)alkenyl or (3–4)alkynyl, each of the last three radicals being unsubstituted or substituted by one or more radicals from the group consisting of halogen, (1–4)alkoxy, (1–4)alkylthio, [(1–4)alkyl]carbonyl and [(1–4)alkoxy]carbonyl, the radicals R$^{13}$ together with the nitrogen atom are a 5- to 6-membered heterocyclic ring which may contain further hetero atoms from the group consisting of N, O and S in the possible oxidation states and is unsubstituted or substituted by (1–4)alkyl or the oxo group or is benzo-fused.

3. A compound or a salt thereof as claimed in claim 1, wherein

R$^1$ is NR$^8$R$^9$, (1–4)alkyl, (3–6)cycloalkyl or phenyl, each of the last 3 radicals being unsubstituted or substituted by one or more radicals from the group consisting of halogen, CN, (1–4)alkoxy, (1–4)haloalkoxy, (1–4)alkylthio, (1–4)-alkylsulfonyl, formyl, [(1–4)alkoxy]carbonyl, [(1–4)alkyl]carbonyloxy and in the case of cyclic radicals also (1–4)alkyl, (1–4)haloalkyl and (1–4)alkoxy-(1–4)alkyl, or (2–4)alkenyl or (2–4)alkynyl, n is 0, 1 or 2, excluding n=0 or 1 if R$^1$=NR$^8$R$^9$, R$^2$ and R$^3$ are each independently of the other H or (1–4)alkyl, R$^4$ is H, OH, formyl, (1–4)alkyl, (2–4)alkenyl, (2–4)alkynyl, (1–4)alkoxy, [(1–4)alkyl]carbonyl, (1–4)alkylsulfony, each of the last 6 radicals being unsubstituted or substituted by one or more radicals from the group consisting of halogen and (1–4)alkoxy, or phenylcarbonyl or phenysulfonyl, the phanyl ring of the last two radicals being unsubstituted or substituted by one or more radicals from the group consisting of halogen, (1–4)alkyl, (1–4)haloalkyl, (1–4)alkoxy and (1–4)haloalkoxy, and R$^5$ is CHO, [(1–4)alkyl]carbonyl, [(2–4)alkenyl]carbonyl, [(2–4)alkynyl]carbonyl, (1–4)alkylsulfonyl, (2–4)alkenylsulfonyl, (2–4)alkynylsulfonyl, [(3–6)cycloalkyl]carbonyl, each of the last 7 radicals being unsubstituted or substituted by one or more radicals from the group consisting of halogen, (1–4)alkoxy, (1–4)alkylthio, [(1–4)alkoxy]carbonyl, [(1–4)alkyl]-carbonyloxy and CN and in the case of cyclic radicals also (1–4)alkyl and (1–4)haloalkyl, or phenylcarbonyl or phenylsulfonyl, each of the last two radicals being unsubstituted in the phenyl ring or substituted by one or more radicals from the group consisting of halogen, CN, NO$_2$, (1–4)alkyl, (1–4)haloalkyl, (1–4)alkoxy and (1–4)haloalkoxy, or mono- or di-[(1–4)alkyl]aminosulfonyl which is unsubstituted in the alkyl moiety or substituted by one or more halogen atoms, or a group of the formula COCOR' where R'=H, OH, (1–4)alkoxy or (1–4)alkyl, or a group of the formula

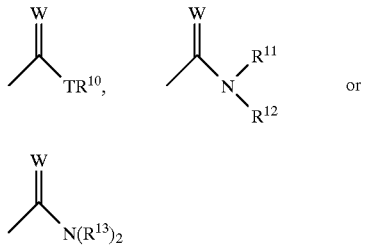

or

R$^4$ and R$^5$ together are a chain of the formula (—CH$_2$)$_{m1}$B$^1$— or —B$^1$—(CH$_2$)$_{m2}$B$^2$—, where individual groups CH$_2$ may be replaced by oxygen atoms and where the chain is unsubstituted or substituted by one or more (1–3)alkyl radicals or halogen and m1=3, 4 or 5 or m2=2, 3 or 4, and W is O or S, B$^1$ and B$^2$ are each independently of the other SO$_2$ or CO, are each independently of the other SO$_2$ or CO, T is O or S, R$^6$ is H, (1–4)alkyl, (1–4)alkoxy or halogen, R$^7$ is H or CH$_3$, R$^8$ is (1–4)alkyl, R$^9$ is H or (1–4)alkyl, R$^{10}$ is (1–4)alkyl, (1–4)haloalkyl, (3–4)alkenyl or (3–4)alkynyl, R$^{11}$ and R$^{12}$ are each independently of the other H or (1–4)alkyl, the radicals R$^{13}$ together are an alkylene chain having 4 or 5 carbon atoms, A is a radical of the formula

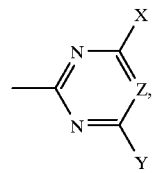

one of the radicals X and Y being (1–3)alkyl, halo(1–3)alkyl, (1–3)alkoxy or halo(1–3)alkoxy and the other of the radicals X and Y being (1–3)alkyl, halo(1–3)alkyl, (1–3)alkoxy, halo(1–3)alkoxy, halogen, mono- or di-[(1–3)alkyl]amino and Z is CH or N.

4. A compound or a salt thereof as claimed in claim 1, wherein

R$^1$ is mono- or di-[(1–4)alkyl]amino or (1–4)alkyl, n is 2,

R$^2$ and R$^3$ are each hydrogen,

R$^4$ is H or (1–4)alkyl,

R$^5$ is CHO, [(1–4)alkyl]carbonyl, [(1–4)haloalkyl]carbonyl, (1–4)alkylsulfonyl, (1–4)haloalkylsulfonyl,

[(1–4)alkoxy]-carbonyl, mono- or di-[(1–4)alkyl]aminocarbonyl, mono- or di-[(1–4)alkyl]aminosulfonyl or $R^4$ and $R^5$ together are a chain of the formula $(-CH_2)_{m_1}B^1-$ or $-B^1-(CH_2)_{m_2}B^2-$ where $B^1$ and $B^2$ independently of each other are $SO_2$ or CO, W and T are each O, $R^6$ is H and $R^7$ is H or $CH_3$.

5. A process for preparing compounds of the formula (I) or salts thereof as defined in claim 1, which comprises a) reacting a compound of the formula (II)

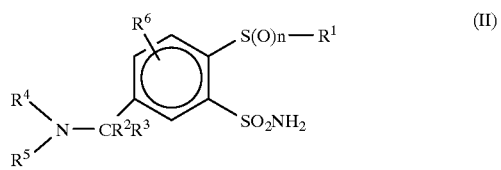

with a heterocyclic carbamate of the formula (III),

where R* is unsubstituted or substituted phenyl or (1–4) alkyl, or b) reacting an arylsulfonylcarbamate of the formula (IV)

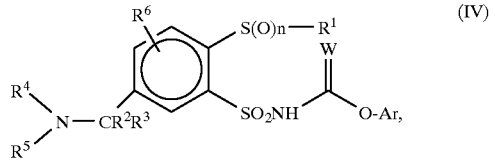

where Ar is an aryl radical, with an amino heterocycle of the formula (V)

or c) reacting a sulfonyl isocyanate of the formula (VI)

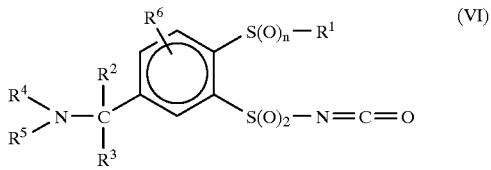

with an amino heterocycle of the formula $H-NR^7-A$ (V), or d) reacting in a one-pot reaction first an amino heterocycle of the formula $H-NR^7-A$ (V) in the presence of a base with phosgene and then the intermediate formed with a phenylsulfonamide of the formula (II), or e) reacting a sulfonyl chloride of the formula (VII)

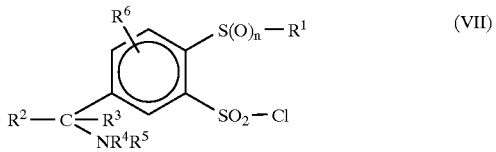

with a cyanate M—OCN where M=a cation and with an amino heterocycle of the formula $H-R^7-A$ (V) in the presence of a base, or f) reacting a sulfonamide of the formula (II) mentioned with a (thio)isocyanate of the formula (V')

in the presence of a base, where the radicals or symbols $R^1$ to $R^7$, A, W and n in the formulae (II)–(VII) and (V') are as defined in formula (I) and where the compounds initially obtained in variants a) and c)–e) are compounds of the formula (I) where W=O.

6. A herbicidal or plant growth regulating composition, which comprises one or more compounds of the formula (I) or a salt thereof as claimed in claim 1 and formulation auxiliaries customary in crop protection.

7. A method for controlling harmful plants or for regulating the growth of plants, which comprises applying an active amount of one or more compounds of the formula (I) or a salt thereof as claimed in claim 1 to the plants, plant seeds or to the area cultivated.

* * * * *